(12) United States Patent
Fangrow et al.

(10) Patent No.: US 9,126,029 B2
(45) Date of Patent: Sep. 8, 2015

(54) MEDICAL CONNECTOR

(71) Applicant: ICU MEDICAL, INC., San Clemente, CA (US)

(72) Inventors: Thomas F. Fangrow, Mission Viejo, CA (US); George A. Lopez, Laguna Beach, CA (US)

(73) Assignee: ICU Medical, Inc., San Clemente, CA (US)

(*) Notice: Subject to any disclaimer, the term of this patent is extended or adjusted under 35 U.S.C. 154(b) by 0 days.

(21) Appl. No.: 13/942,604

(22) Filed: Jul. 15, 2013

(65) Prior Publication Data

US 2013/0304037 A1    Nov. 14, 2013

Related U.S. Application Data

(63) Continuation of application No. 13/210,261, filed on Aug. 15, 2011, which is a continuation of application No. 12/117,568, filed on May 8, 2008, now Pat. No. 7,998,134.

(Continued)

(51) Int. Cl.
*A61M 25/18* (2006.01)
*A61M 39/10* (2006.01)
(Continued)

(52) U.S. Cl.
CPC ........... *A61M 39/1011* (2013.01); *A61M 39/10* (2013.01); *A61M 39/14* (2013.01);
(Continued)

(58) Field of Classification Search
CPC . A61M 39/1011; A61M 39/10; A61M 39/26; A61M 2205/14; A61M 2039/267; A61M 2039/261; A61M 2039/263; A61M 39/20; A61M 2039/1077; A61M 2039/1083; A61M 2039/1061; A61M 2039/1027; A61M 2039/262; A61M 25/0014; A61M 5/34; A61M 5/5086
USPC .................................................. 604/533–539
See application file for complete search history.

(56) References Cited

U.S. PATENT DOCUMENTS 2,842,382 A   7/1958   Franck
2,931,668 A   4/1960   Baley
(Continued)

FOREIGN PATENT DOCUMENTS

CA   2747283 A1   7/2002
EP   0368473 A2   5/1990
(Continued)

OTHER PUBLICATIONS

U.S. Appl. No. 10/584,920, filed Dec. 28, 2006, including its prosecution history.
(Continued)

*Primary Examiner* — Kami A Bosworth
*Assistant Examiner* — Brandy S Lee
(74) *Attorney, Agent, or Firm* — Knobbe Martens Olson & Bear, LLP

(57) ABSTRACT

Some embodiments comprise a connector including a rigid housing having a first end and a second end. A second member can be positioned at a second end portion of the housing and be engageable with a second device. The second member can have a body portion having a first body portion, a second body portion, and a flow lumen extending axially through the body portion, an annular covering portion extending in a radial direction away from the body portion, a receiving portion extending away from the covering portion in an axial direction, and at least one protrusion extending radially away from an outside surface of the body portion. In some embodiments, the second member can be supported by the housing such that, in an assembled state, the first body portion is positioned within the housing and such that the annular covering portion and the second body portion are positioned outside the housing.

19 Claims, 87 Drawing Sheets

Related U.S. Application Data

(60) Provisional application No. 61/042,016, filed on Apr. 3, 2008, provisional application No. 60/978,697, filed on Oct. 9, 2007, provisional application No. 60/938,428, filed on May 16, 2007.

(51) Int. Cl.
*A61M 39/26* (2006.01)
*A61M 39/22* (2006.01)
*A61M 39/14* (2006.01)

(52) U.S. Cl.
CPC .............. *A61M 39/22* (2013.01); *A61M 39/26* (2013.01); *A61M 39/143* (2013.01); *A61M 2039/1033* (2013.01); *A61M 2039/1038* (2013.01); *A61M 2039/1044* (2013.01); *A61M 2039/1061* (2013.01); *A61M 2039/261* (2013.01); *A61M 2039/268* (2013.01)

(56) References Cited

U.S. PATENT DOCUMENTS

| | | |
|---|---|---|
| 2,968,497 A | 1/1961 | Treleman |
| 3,127,892 A | 4/1964 | Bellamy, Jr. et al. |
| 3,304,047 A | 2/1967 | Martin |
| 3,334,860 A | 8/1967 | Bolton, Jr. |
| 3,707,972 A | 1/1973 | Villari et al. |
| 3,729,031 A | 4/1973 | Baldwin |
| 3,824,556 A | 7/1974 | Berkovits et al. |
| 3,986,508 A | 10/1976 | Barrington |
| 4,055,179 A | 10/1977 | Manschot et al. |
| 4,066,067 A | 1/1978 | Micheli |
| 4,076,285 A | 2/1978 | Martinez |
| 4,080,965 A | 3/1978 | Phillips |
| 4,084,606 A | 4/1978 | Mittleman |
| 4,121,585 A | 10/1978 | Becker, Jr. |
| 4,133,441 A | 1/1979 | Mittleman et al. |
| 4,143,853 A | 3/1979 | Abramson |
| 4,150,845 A | 4/1979 | Kopacz et al. |
| 4,187,848 A | 2/1980 | Taylor |
| 4,195,632 A | 4/1980 | Parker et al. |
| 4,233,982 A | 11/1980 | Bauer et al. |
| 4,245,635 A | 1/1981 | Kontos |
| 4,324,239 A | 4/1982 | Gordon et al. |
| 4,334,551 A | 6/1982 | Pfister |
| 4,340,049 A | 7/1982 | Munsch |
| 4,379,458 A | 4/1983 | Bauer et al. |
| 4,387,879 A | 6/1983 | Tauschinski |
| 4,397,442 A | 8/1983 | Larkin |
| 4,430,073 A | 2/1984 | Bemis et al. |
| 4,436,125 A | 3/1984 | Blenkush |
| 4,452,473 A | 6/1984 | Ruschke |
| 4,457,749 A | 7/1984 | Bellotti et al. |
| 4,511,359 A | 4/1985 | Vaillancourt |
| 4,538,836 A | 9/1985 | Kruetten |
| 4,610,469 A | 9/1986 | Wolff-Mooij |
| 4,619,640 A | 10/1986 | Potolsky et al. |
| 4,623,332 A | 11/1986 | Lindmayer et al. |
| 4,629,159 A | 12/1986 | Wellenstam |
| 4,660,803 A | 4/1987 | Johnston et al. |
| 4,662,878 A | 5/1987 | Lindmayer |
| 4,673,400 A | 6/1987 | Martin |
| 4,700,744 A | 10/1987 | Rutter et al. |
| 4,723,603 A | 2/1988 | Plummer |
| 4,723,948 A | 2/1988 | Clark et al. |
| 4,728,075 A | 3/1988 | Paradis |
| 4,745,950 A | 5/1988 | Mathieu |
| 4,758,023 A | 7/1988 | Vermillion |
| 4,774,964 A | 10/1988 | Bonaldo |
| 4,774,965 A | 10/1988 | Rodriguez et al. |
| 4,781,702 A | 11/1988 | Herrli |
| 4,804,015 A | 2/1989 | Albinsson |
| 4,816,024 A | 3/1989 | Sitar et al. |
| 4,834,271 A | 5/1989 | Litwin |
| 4,844,512 A | 7/1989 | Gahwiler |
| 4,862,913 A | 9/1989 | Wildfang |
| 4,883,483 A | 11/1989 | Lindmayer |
| 4,915,687 A | 4/1990 | Sivert |
| 4,917,669 A | 4/1990 | Bonaldo |
| 4,935,010 A | 6/1990 | Cox et al. |
| 4,950,260 A | 8/1990 | Bonaldo |
| 4,969,879 A | 11/1990 | Lichte |
| D313,277 S | 12/1990 | Haining |
| D314,050 S | 1/1991 | Sone |
| 5,006,114 A | 4/1991 | Rogers et al. |
| 5,021,059 A | 6/1991 | Kensey et al. |
| 5,047,021 A | 9/1991 | Utterberg |
| 5,053,015 A | 10/1991 | Gross |
| 5,065,783 A | 11/1991 | Ogle, II |
| 5,066,286 A | 11/1991 | Ryan |
| 5,070,885 A | 12/1991 | Bonaldo |
| 5,083,819 A | 1/1992 | Bynum |
| 5,098,385 A | 3/1992 | Walsh |
| 5,108,376 A | 4/1992 | Bonaldo |
| 5,122,123 A | 6/1992 | Vaillancourt |
| 5,139,483 A | 8/1992 | Ryan |
| 5,147,333 A | 9/1992 | Raines |
| 5,154,703 A | 10/1992 | Bonaldo |
| 5,176,406 A | 1/1993 | Straghan |
| RE34,223 E | 4/1993 | Bonaldo |
| 5,199,948 A | 4/1993 | McPhee |
| 5,201,717 A | 4/1993 | Wyatt et al. |
| 5,201,725 A | 4/1993 | Kling |
| 5,203,775 A | 4/1993 | Frank et al. |
| 5,211,634 A | 5/1993 | Vaillancourt |
| 5,215,537 A | 6/1993 | Lynn et al. |
| 5,215,538 A | 6/1993 | Larkin |
| 5,224,939 A | 7/1993 | Holman et al. |
| 5,242,393 A | 9/1993 | Brimhall et al. |
| 5,242,425 A | 9/1993 | White et al. |
| 5,251,873 A | 10/1993 | Atkinson et al. |
| 5,269,771 A | 12/1993 | Thomas et al. |
| 5,273,533 A | 12/1993 | Bonaldo |
| 5,279,571 A | 1/1994 | Larkin |
| 5,281,206 A | 1/1994 | Lopez |
| 5,284,475 A | 2/1994 | Mackal |
| 5,295,657 A | 3/1994 | Atkinson |
| 5,301,686 A | 4/1994 | Newman |
| 5,306,243 A | 4/1994 | Bonaldo |
| 5,312,377 A | 5/1994 | Dalton |
| 5,322,518 A | 6/1994 | Schneider et al. |
| 5,324,270 A | 6/1994 | Kayan et al. |
| 5,330,450 A | 7/1994 | Lopez |
| 5,334,159 A | 8/1994 | Turkel |
| 5,344,414 A | 9/1994 | Lopez et al. |
| 5,360,413 A | 11/1994 | Leason et al. |
| 5,370,636 A | 12/1994 | Von Witzleben |
| 5,380,306 A | 1/1995 | Brinon |
| 5,385,372 A | 1/1995 | Utterberg |
| 5,390,898 A | 2/1995 | Smedley et al. |
| 5,391,150 A | 2/1995 | Richmond |
| 5,395,348 A | 3/1995 | Ryan |
| 5,397,314 A | 3/1995 | Farley et al. |
| 5,400,500 A | 3/1995 | Behnke et al. |
| 5,401,245 A | 3/1995 | Haining |
| 5,402,826 A | 4/1995 | Molnar et al. |
| 5,402,982 A | 4/1995 | Atkinson et al. |
| 5,405,323 A | 4/1995 | Rogers et al. |
| 5,405,331 A | 4/1995 | Behnke et al. |
| 5,405,333 A | 4/1995 | Richmond |
| 5,411,499 A | 5/1995 | Dudar et al. |
| 5,417,673 A | 5/1995 | Gordon |
| 5,423,791 A | 6/1995 | Bartlett |
| 5,425,465 A | 6/1995 | Healy |
| 5,433,330 A | 7/1995 | Yatsko et al. |
| 5,439,451 A | 8/1995 | Collinson et al. |
| 5,441,487 A | 8/1995 | Vedder |
| 5,445,623 A | 8/1995 | Richmond |
| 5,456,668 A | 10/1995 | Ogle, II |
| 5,456,675 A | 10/1995 | Wolbring et al. |
| 5,462,255 A | 10/1995 | Rosen et al. |
| 5,464,399 A | 11/1995 | Boettger |
| 5,470,319 A | 11/1995 | Mayer |
| 5,470,327 A | 11/1995 | Helgren et al. |

(56) References Cited

U.S. PATENT DOCUMENTS

| | | |
|---|---|---|
| 5,474,536 A | 12/1995 | Bonaldo |
| 5,480,393 A | 1/1996 | Bommarito |
| 5,492,147 A | 2/1996 | Challender et al. |
| 5,501,426 A | 3/1996 | Atkinson et al. |
| 5,507,744 A | 4/1996 | Tay et al. |
| 5,514,177 A | 5/1996 | Kurz et al. |
| 5,518,026 A | 5/1996 | Benjey |
| 5,520,665 A | 5/1996 | Fleetwood |
| 5,520,666 A | 5/1996 | Choudhury et al. |
| 5,527,284 A | 6/1996 | Ohnemus et al. |
| 5,533,708 A | 7/1996 | Atkinson et al. |
| 5,533,983 A | 7/1996 | Haining |
| 5,535,785 A | 7/1996 | Werge et al. |
| 5,540,661 A | 7/1996 | Tomisaka et al. |
| 5,549,566 A | 8/1996 | Elias et al. |
| 5,549,577 A | 8/1996 | Siegel et al. |
| 5,549,651 A | 8/1996 | Lynn |
| 5,552,118 A | 9/1996 | Mayer |
| 5,555,908 A | 9/1996 | Edwards et al. |
| 5,569,235 A | 10/1996 | Ross et al. |
| 5,573,516 A | 11/1996 | Tyner |
| 5,575,769 A | 11/1996 | Vaillancourt |
| 5,578,059 A | 11/1996 | Patzer |
| 5,584,819 A | 12/1996 | Kopfer |
| 5,591,137 A | 1/1997 | Stevens |
| 5,591,143 A | 1/1997 | Trombley, III et al. |
| 5,597,536 A | 1/1997 | Mayer |
| 5,616,129 A | 4/1997 | Mayer |
| 5,616,130 A | 4/1997 | Mayer |
| RE35,539 E | 6/1997 | Bonaldo |
| 5,643,224 A | 7/1997 | Szapiro et al. |
| 5,645,538 A | 7/1997 | Richmond |
| 5,651,776 A | 7/1997 | Appling et al. |
| 5,658,260 A | 8/1997 | Desecki et al. |
| 5,674,206 A | 10/1997 | Allton et al. |
| 5,676,346 A | 10/1997 | Leinsing |
| 5,685,866 A | 11/1997 | Lopez |
| 5,685,868 A | 11/1997 | Lundquist |
| 5,699,821 A | 12/1997 | Paradis |
| 5,700,248 A | 12/1997 | Lopez |
| 5,702,374 A | 12/1997 | Johnson |
| 5,709,243 A | 1/1998 | Wells et al. |
| 5,735,826 A | 4/1998 | Richmond |
| 5,738,144 A | 4/1998 | Rogers |
| 5,741,084 A | 4/1998 | Del Rio et al. |
| 5,749,861 A | 5/1998 | Guala et al. |
| RE35,841 E | 7/1998 | Frank et al. |
| 5,782,816 A | 7/1998 | Werschmidt et al. |
| 5,784,750 A | 7/1998 | Sankovic et al. |
| 5,785,693 A | 7/1998 | Haining |
| 5,788,215 A | 8/1998 | Ryan |
| 5,806,831 A | 9/1998 | Paradis |
| 5,810,398 A | 9/1998 | Matkovich |
| 5,814,024 A | 9/1998 | Thompson et al. |
| 5,820,601 A | 10/1998 | Mayer |
| 5,820,614 A | 10/1998 | Erskine et al. |
| 5,830,189 A | 11/1998 | Chang |
| 5,830,195 A | 11/1998 | Peters et al. |
| 5,839,715 A | 11/1998 | Leinsing |
| 5,848,994 A | 12/1998 | Richmond |
| 5,855,568 A | 1/1999 | Battiato et al. |
| 5,947,954 A | 9/1999 | Bonaldo |
| 5,984,373 A | 11/1999 | Fitoussi et al. |
| 6,029,946 A | 2/2000 | Doyle |
| 6,036,171 A | 3/2000 | Weinheimer et al. |
| 6,050,978 A | 4/2000 | Orr et al. |
| 6,063,062 A | 5/2000 | Paradis |
| 6,068,011 A | 5/2000 | Paradis |
| 6,068,617 A | 5/2000 | Richmond |
| 6,079,432 A | 6/2000 | Paradis |
| 6,106,502 A | 8/2000 | Richmond |
| 6,113,068 A | 9/2000 | Ryan |
| 6,142,446 A | 11/2000 | Leinsing |
| 6,152,913 A | 11/2000 | Feith et al. |
| 6,168,137 B1 | 1/2001 | Paradis |
| 6,171,287 B1 | 1/2001 | Lynn et al. |
| 6,183,464 B1 | 2/2001 | Sharp et al. |
| 6,189,859 B1 | 2/2001 | Rohrbough et al. |
| 6,206,860 B1 | 3/2001 | Richmond |
| 6,221,029 B1 | 4/2001 | Mathis et al. |
| 6,224,578 B1 | 5/2001 | Davis et al. |
| 6,224,588 B1 | 5/2001 | Jentzen |
| 6,231,552 B1 | 5/2001 | Jentzen |
| 6,242,393 B1 | 6/2001 | Ishida et al. |
| 6,245,048 B1 | 6/2001 | Fangrow et al. |
| 6,290,206 B1 | 9/2001 | Doyle |
| 6,299,132 B1 | 10/2001 | Weinheimer et al. |
| 6,332,633 B1 | 12/2001 | Fitoussi et al. |
| 6,402,207 B1 | 6/2002 | Segal et al. |
| 6,428,520 B1 | 8/2002 | Lopez |
| 6,431,219 B1 | 8/2002 | Redler et al. |
| 6,485,472 B1 | 11/2002 | Richmond |
| 6,499,719 B1 | 12/2002 | Clancy et al. |
| 6,508,792 B2 | 1/2003 | Szames et al. |
| 6,508,807 B1 | 1/2003 | Peters |
| 6,541,802 B2 | 4/2003 | Doyle |
| 6,543,745 B1 | 4/2003 | Enerson |
| 6,581,906 B2 | 6/2003 | Pott et al. |
| 6,585,229 B2 | 7/2003 | Cote et al. |
| 6,595,964 B2 | 7/2003 | Finley et al. |
| 6,595,981 B2 | 7/2003 | Huet |
| 6,609,696 B2 | 8/2003 | Enerson |
| 6,612,624 B1 | 9/2003 | Segal et al. |
| 6,666,852 B2 | 12/2003 | Niedospial, Jr. |
| 6,673,059 B2 | 1/2004 | Guala |
| 6,695,817 B1 | 2/2004 | Fangrow |
| 6,745,998 B2 | 6/2004 | Doyle |
| 6,840,501 B2 | 1/2005 | Doyle |
| 6,843,513 B2 | 1/2005 | Guala |
| 6,869,426 B2 | 3/2005 | Ganem |
| 6,875,205 B2 | 4/2005 | Leinsing |
| 6,893,056 B2 | 5/2005 | Guala |
| 6,899,315 B2 | 5/2005 | Maiville et al. |
| 6,911,025 B2 * | 6/2005 | Miyahara .................. 604/415 |
| 6,955,669 B2 | 10/2005 | Curutcharry |
| 6,964,406 B2 | 11/2005 | Doyle |
| 6,991,608 B2 | 1/2006 | Young et al. |
| 7,004,934 B2 | 2/2006 | Vaillancourt |
| 7,037,302 B2 | 5/2006 | Vaillancourt |
| 7,040,598 B2 | 5/2006 | Raybuck |
| 7,044,441 B2 | 5/2006 | Doyle |
| 7,100,891 B2 | 9/2006 | Doyle |
| 7,125,396 B2 | 10/2006 | Leinsing et al. |
| 7,137,654 B2 | 11/2006 | Segal et al. |
| 7,140,592 B2 | 11/2006 | Phillips |
| 7,182,313 B2 | 2/2007 | Doyle |
| 7,195,228 B2 | 3/2007 | Tiberghien et al. |
| 7,244,249 B2 | 7/2007 | Leinsing et al. |
| 7,306,197 B2 | 12/2007 | Parrino et al. |
| 7,306,198 B2 | 12/2007 | Doyle |
| 7,306,566 B2 | 12/2007 | Raybuck |
| 7,316,679 B2 | 1/2008 | Bierman |
| 7,347,458 B2 | 3/2008 | Rome et al. |
| 7,350,764 B2 | 4/2008 | Raybuck |
| 7,361,164 B2 | 4/2008 | Simpson et al. |
| 7,497,484 B2 | 3/2009 | Ziman |
| 7,559,530 B2 | 7/2009 | Korogi et al. |
| 7,588,563 B2 | 9/2009 | Guala |
| 7,600,515 B2 | 10/2009 | Matlock |
| 7,628,781 B2 | 12/2009 | Roy et al. |
| 7,645,274 B2 | 1/2010 | Whitley |
| 7,651,481 B2 | 1/2010 | Raybuck |
| 7,666,170 B2 | 2/2010 | Guala |
| 7,717,874 B2 | 5/2010 | Landau et al. |
| 7,722,090 B2 | 5/2010 | Burton et al. |
| 7,758,566 B2 | 7/2010 | Simpson et al. |
| 7,762,524 B2 | 7/2010 | Cawthon et al. |
| 7,766,304 B2 | 8/2010 | Phillips |
| 7,766,897 B2 | 8/2010 | Ramsey et al. |
| 7,803,139 B2 | 9/2010 | Fangrow, Jr. |
| 7,803,140 B2 | 9/2010 | Fangrow, Jr. |
| 7,815,614 B2 | 10/2010 | Fangrow, Jr. |
| 7,837,568 B1 | 11/2010 | Glaze |
| 7,857,805 B2 | 12/2010 | Raines |

(56) References Cited

U.S. PATENT DOCUMENTS

| | | | |
|---|---|---|---|
| 7,875,019 B2 | 1/2011 | Barron et al. |
| 7,976,532 B2 | 7/2011 | Kitani et al. |
| 7,998,134 B2 | 8/2011 | Fangrow et al. |
| 8,066,692 B2 | 11/2011 | Simpson et al. |
| 8,211,069 B2 | 7/2012 | Fangrow, Jr. |
| 8,251,346 B2 | 8/2012 | Stroup |
| 8,262,628 B2 | 9/2012 | Fangrow, Jr. |
| 8,286,936 B2 | 10/2012 | Kitani et al. |
| 8,287,513 B2 | 10/2012 | Ellstrom et al. |
| 8,287,518 B2 | 10/2012 | Kitani et al. |
| 8,372,059 B2 | 2/2013 | Ziman |
| 8,408,226 B2 | 4/2013 | Raines et al. |
| 8,414,542 B2 | 4/2013 | Stroup |
| 8,556,868 B2 | 10/2013 | Simpson et al. |
| 8,647,310 B2 | 2/2014 | Fangrow, Jr. et al. |
| 8,667,997 B2 | 3/2014 | Costanzo |
| 8,679,090 B2 | 3/2014 | Anderson et al. |
| 8,721,628 B2 | 5/2014 | Ziman |
| 8,777,908 B2 | 7/2014 | Fangrow, Jr. |
| 8,777,909 B2 | 7/2014 | Fangrow, Jr. |
| 8,777,931 B2 | 7/2014 | Davis et al. |
| 2001/0029355 A1 | 10/2001 | Szames et al. |
| 2002/0066715 A1 | 6/2002 | Niedospial, Jr. |
| 2003/0060804 A1 | 3/2003 | Vaillancourt |
| 2003/0066978 A1 | 4/2003 | Enerson |
| 2003/0111623 A1 | 6/2003 | Enerson |
| 2003/0136932 A1 | 7/2003 | Doyle |
| 2003/0208165 A1 | 11/2003 | Christensen et al. |
| 2004/0124388 A1 | 7/2004 | Kiehne |
| 2004/0124389 A1 | 7/2004 | Phillips |
| 2004/0238776 A1 | 12/2004 | Peters et al. |
| 2005/0015075 A1 | 1/2005 | Wright et al. |
| 2005/0033268 A1 | 2/2005 | Decaria |
| 2005/0124942 A1 | 6/2005 | Richmond |
| 2005/0212292 A1 | 9/2005 | Parrino et al. |
| 2005/0228362 A1 | 10/2005 | Vaillancourt |
| 2005/0245872 A1 | 11/2005 | Simpson et al. |
| 2006/0025751 A1 | 2/2006 | Roy et al. |
| 2006/0058734 A1 | 3/2006 | Phillips |
| 2006/0129109 A1* | 6/2006 | Shaw et al. ............... 604/246 |
| 2006/0142730 A1 | 6/2006 | Proulx et al. |
| 2006/0142735 A1 | 6/2006 | Whitley |
| 2006/0149213 A1 | 7/2006 | Raybuck |
| 2006/0157984 A1 | 7/2006 | Rome et al. |
| 2006/0161115 A1 | 7/2006 | Fangrow |
| 2006/0192164 A1 | 8/2006 | Korogi et al. |
| 2006/0202146 A1 | 9/2006 | Doyle |
| 2006/0211996 A1 | 9/2006 | Trinchera et al. |
| 2006/0253084 A1 | 11/2006 | Nordgren |
| 2007/0073270 A1 | 3/2007 | Christensen et al. |
| 2007/0088292 A1 | 4/2007 | Fangrow |
| 2007/0088293 A1 | 4/2007 | Fangrow |
| 2007/0088294 A1 | 4/2007 | Fangrow |
| 2007/0088324 A1 | 4/2007 | Fangrow, Jr. |
| 2007/0088327 A1 | 4/2007 | Guala |
| 2007/0179453 A1 | 8/2007 | Lim et al. |
| 2007/0179454 A1 | 8/2007 | Ziman et al. |
| 2008/0103485 A1 | 5/2008 | Kruger |
| 2008/0125756 A1 | 5/2008 | Dicarlo et al. |
| 2008/0140020 A1 | 6/2008 | Shirley |
| 2008/0190485 A1 | 8/2008 | Guala |
| 2008/0200900 A1 | 8/2008 | Aeschlimann et al. |
| 2008/0287920 A1 | 11/2008 | Fangrow et al. |
| 2009/0001720 A1 | 1/2009 | Cheon et al. |
| 2010/0174242 A1 | 7/2010 | Anderson et al. |
| 2010/0211019 A1 | 8/2010 | Greco |
| 2010/0249723 A1 | 9/2010 | Fangrow, Jr. |
| 2011/0046572 A1 | 2/2011 | Fangrow |
| 2011/0074148 A1 | 3/2011 | Imai |
| 2011/0276035 A1 | 11/2011 | Fangrow, Jr. |
| 2011/0306931 A1 | 12/2011 | Kamen et al. |
| 2012/0041391 A1 | 2/2012 | Fangrow et al. |
| 2012/0089101 A1 | 4/2012 | Carlyon et al. |
| 2012/0271244 A1 | 10/2012 | Simpson et al. |
| 2012/0330247 A1 | 12/2012 | Fangrow, Jr. |
| 2013/0035668 A1 | 2/2013 | Kitani et al. |
| 2013/0150806 A1 | 6/2013 | Fangrow, Jr. |
| 2013/0197453 A1 | 8/2013 | Yeh |
| 2013/0231616 A1 | 9/2013 | Fangrow, Jr. |
| 2013/0317483 A1 | 11/2013 | Reichart et al. |
| 2014/0246616 A1 | 9/2014 | Fangrow |
| 2014/0303601 A1 | 10/2014 | Fangrow |

FOREIGN PATENT DOCUMENTS

| | | |
|---|---|---|
| EP | 0 791 371 | 8/1997 |
| EP | 1 917 996 | 5/2008 |
| EP | 1 946 792 | 7/2008 |
| GB | 2 116 277 | 9/1983 |
| GB | 2 118 440 | 11/1983 |
| GB | 2 353 078 | 2/2001 |
| JP | 11-311234 | 11/1999 |
| WO | WO 95/32748 | 12/1995 |
| WO | WO 01/03756 | 1/2001 |
| WO | WO 01/23026 A1 | 4/2001 |
| WO | WO 02096500 A1 | 12/2002 |
| WO | WO 2004/060474 | 7/2004 |
| WO | WO 2004/082756 | 9/2004 |
| WO | WO 2006/076656 | 7/2006 |
| WO | WO 2006/088858 | 8/2006 |
| WO | WO 2006/124756 | 11/2006 |
| WO | WO 2013/036854 | 3/2013 |

OTHER PUBLICATIONS

U.S. Appl. No. 11/417,604, filed May 3, 2006, including its prosecution history.
U.S. Appl. No. 11/417,836, filed May 3, 2006, including its prosecution history.
U.S. Appl. No. 11/482,176, filed Jul. 6, 2006, including its prosecution history.
U.S. Appl. No. 12/117,568, filed May 8, 2008, including its prosecution history.
U.S. Appl. No. 12/789,255, filed May 27, 2010, including its prosecution history.
U.S. Appl. No. 12/893,789, filed Sep. 29, 2010, including its prosecution history.
U.S. Appl. No. 11/417,923, filed May 3, 2006, and its prosecution history, Gustus et al.
U.S. Appl. No. 11/417,671, filed May 3, 2006, and its prosecution history, Gustus et al.
U.S. Appl. No. 11/417,648, filed May 3, 2006, and its prosecution history, Gustus et al.
U.S. Appl. No. 11/417,909, filed May 3, 2006, and its prosecution history, Gustus et al.
U.S. Appl. No. 11/417,882, filed May 3, 2006, and its prosecution history, Gustus et al.
U.S. Appl. No. 11/417,556, filed May 3, 2006, including its prosecution history.
U.S. Appl. No. 11/417,567, filed May 3, 2006, including its prosecution history.
U.S. Appl. No. 11/418,155, filed May 3, 2006, including its prosecution history.
U.S. Appl. No. 12/651,283, filed Dec. 17, 2009, including its prosecution history.
U.S. Appl. No. 13/100,508, filed May 4, 2011, including its prosecution history.
U.S. Appl. No. 13/210,261, filed Aug. 15, 2011, including its prosecution history.
U.S. Appl. No. 13/305,663, filed Nov. 28, 2011, including its prosecution history (U.S. Pat. No. 8,556,868).
U.S. Appl. No. 12/534,663, filed Jun. 27, 2012, including its prosecution history.
U.S. Appl. No. 13/606,520, filed Sep. 7, 2012, including its prosecution history.
U.S. Appl. No. 13/865,147, filed Apr. 17, 2013, including its prosecution history.
EPO Search Report re EP Application No. 08 755 612.2, dated Feb. 23, 2012.

(56) References Cited

OTHER PUBLICATIONS

EPO Examination Report re EP Application No. 08 755 612.2, dated Nov. 20, 2013.
EPO Examination Report regarding EP Application No. 08 755 612.2, dated Dec. 5, 2012 in 6 pages.
Search Report for PCT/US2006/026124, dated Mar. 13, 2007 in 5 pgs.
Written Opinion for PCT/US2006/026124, dated Jul. 6, 2006 in 11 pgs.
International Search Report and Written Opinion of International Application No. PCT/US2008/063797 mailed on Dec. 30, 2008 in 17 pages.
International Preliminary Report on Patentability, International Application No. PCT/US2008/063797 mailed on Nov. 17, 2009 in 11 pages.
Air Embolism and Exsanguination from Separation of Two-Piece Side Port/Hemostasis Valve Cardiac Catheter Introducers, ECRI Institute, Jan. 1995, http://www.mdsr.ecri.org/summary/detail.aspx?doc_id=8098.
Injection Site, Molded Products, Inc., Apr. 2, 2004, https://web.archive.org/web/20040402123354/http://www.moldedproducts.com/injectionsite.htm.
U.S. Appl. No. 14/199,836, filed Mar. 6, 2014, and its prosecution history, Fangrow.
U.S. Appl. No. 14/470,647, filed Aug. 27, 2014, and its prosecution history, Fangrow, Jr. et al.

\* cited by examiner

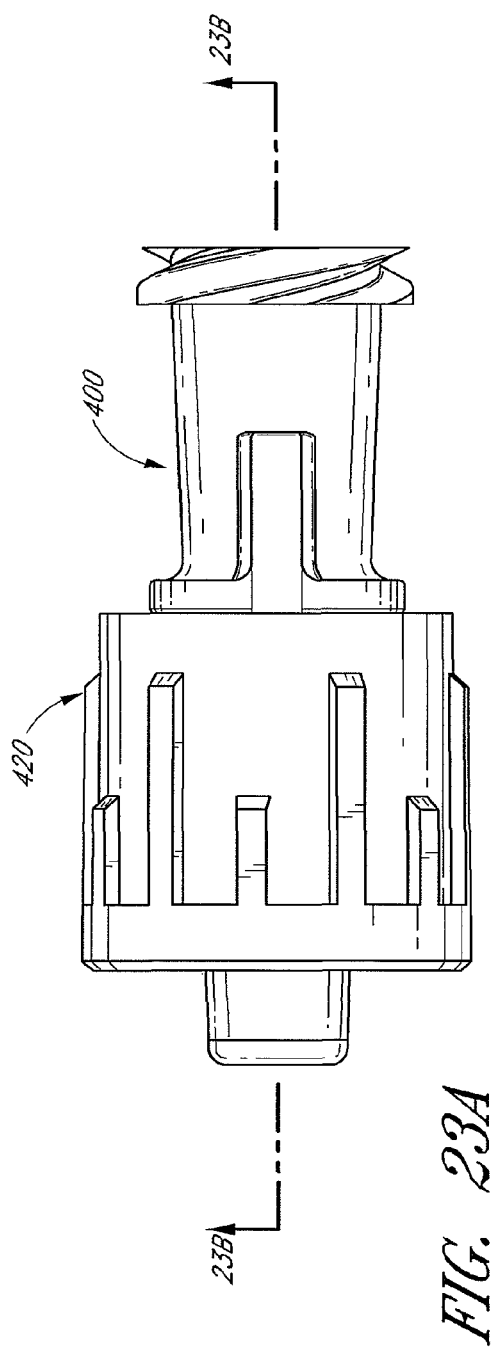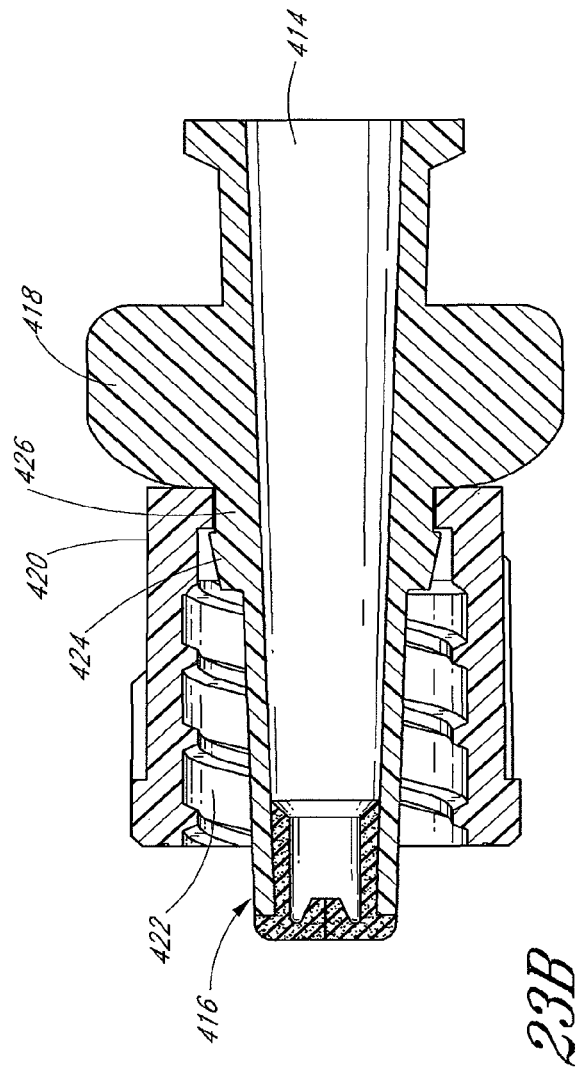
FIG. 23A
FIG. 23B

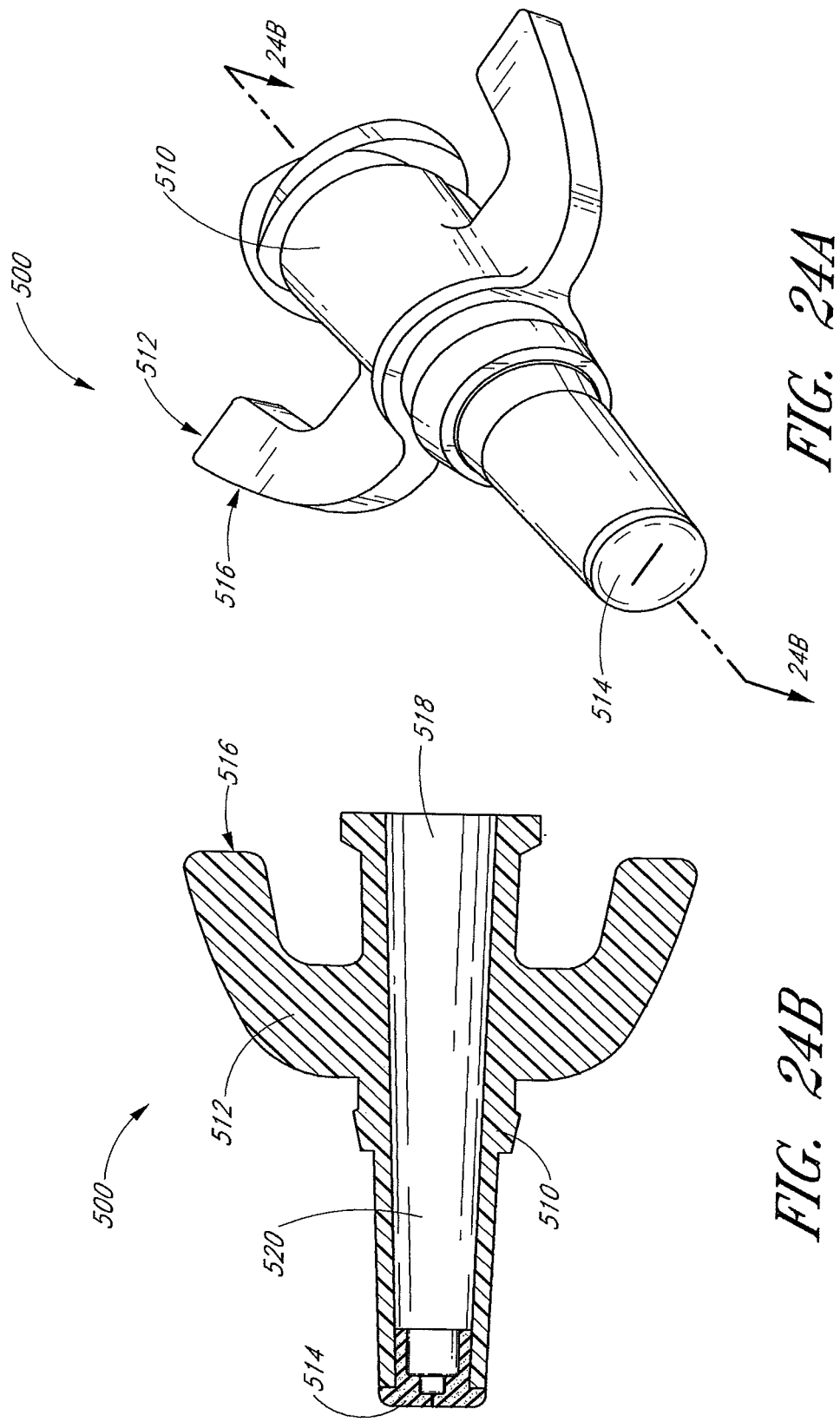

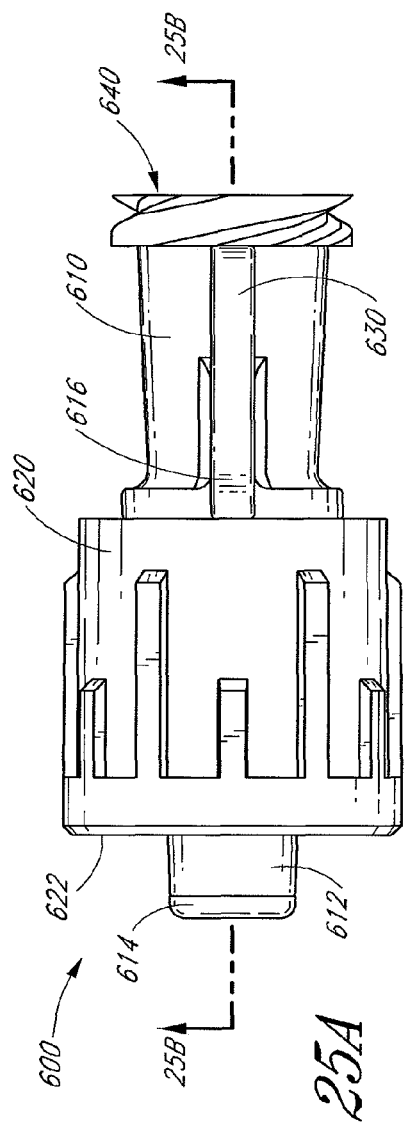
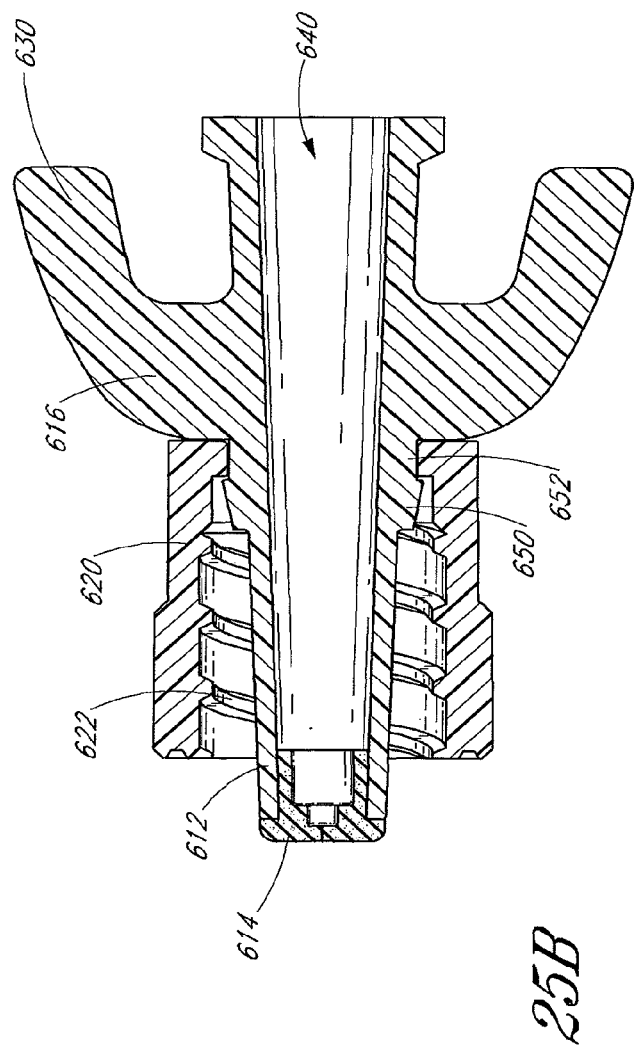
FIG. 25A
FIG. 25B

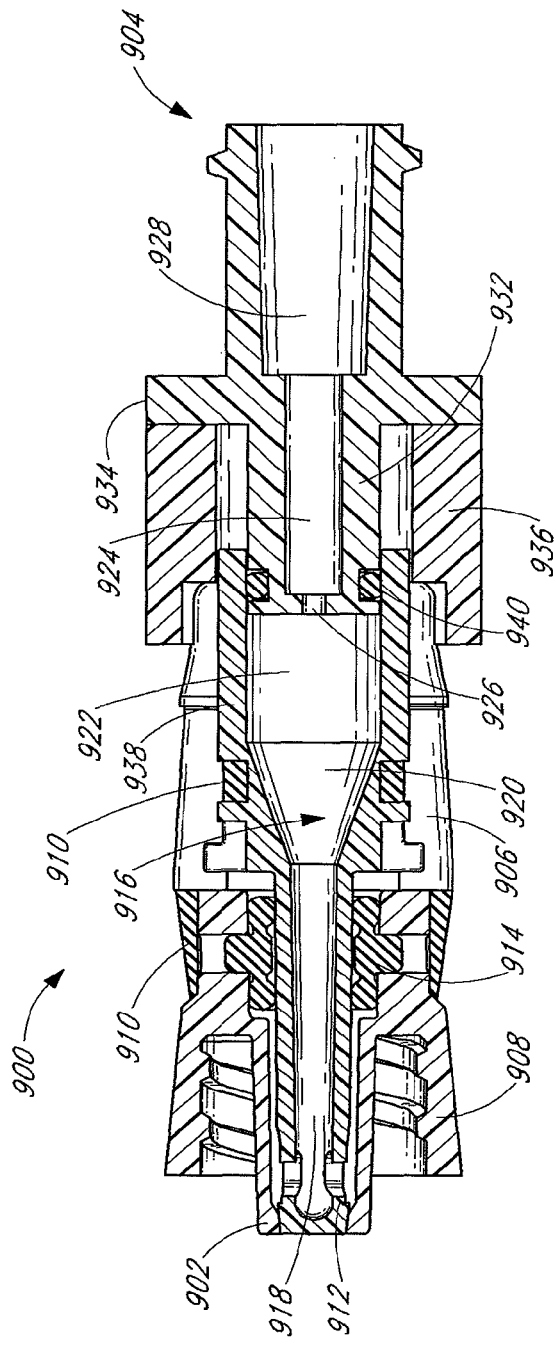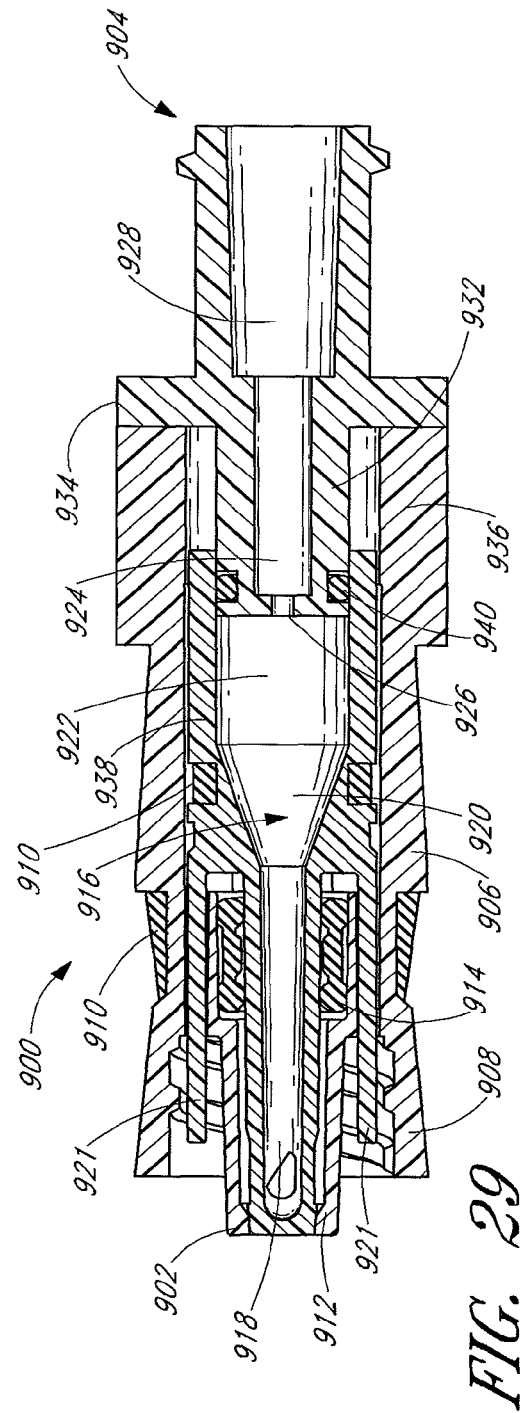

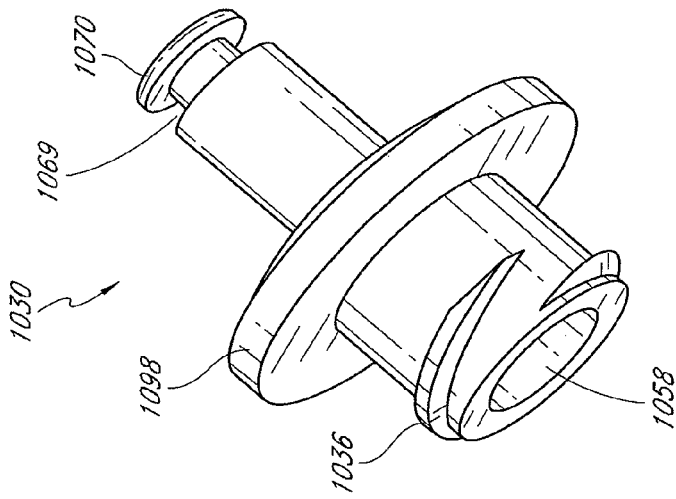
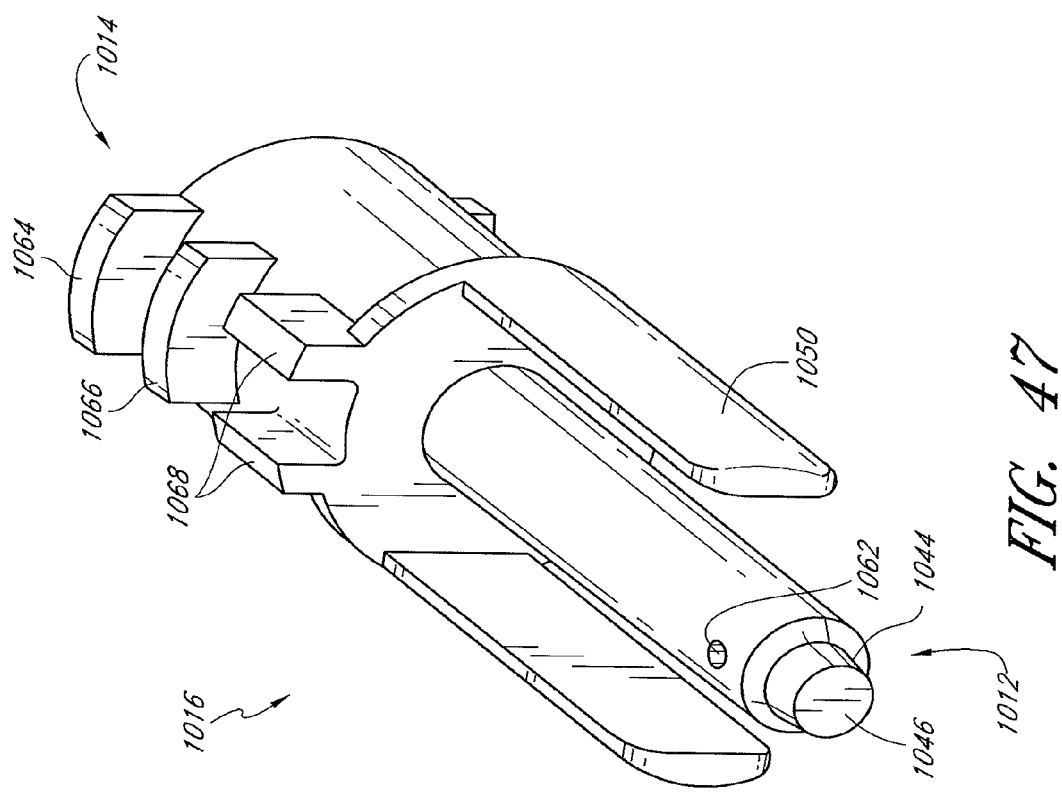

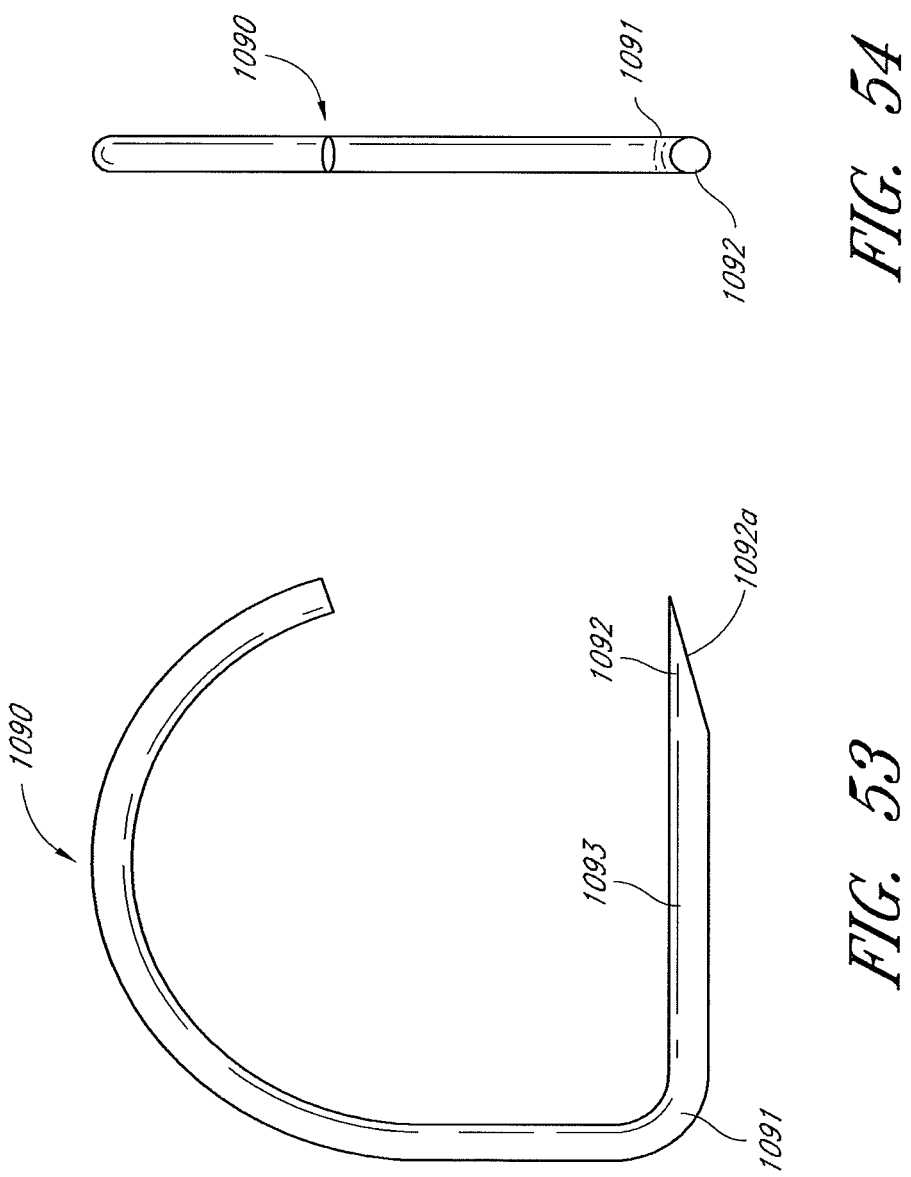

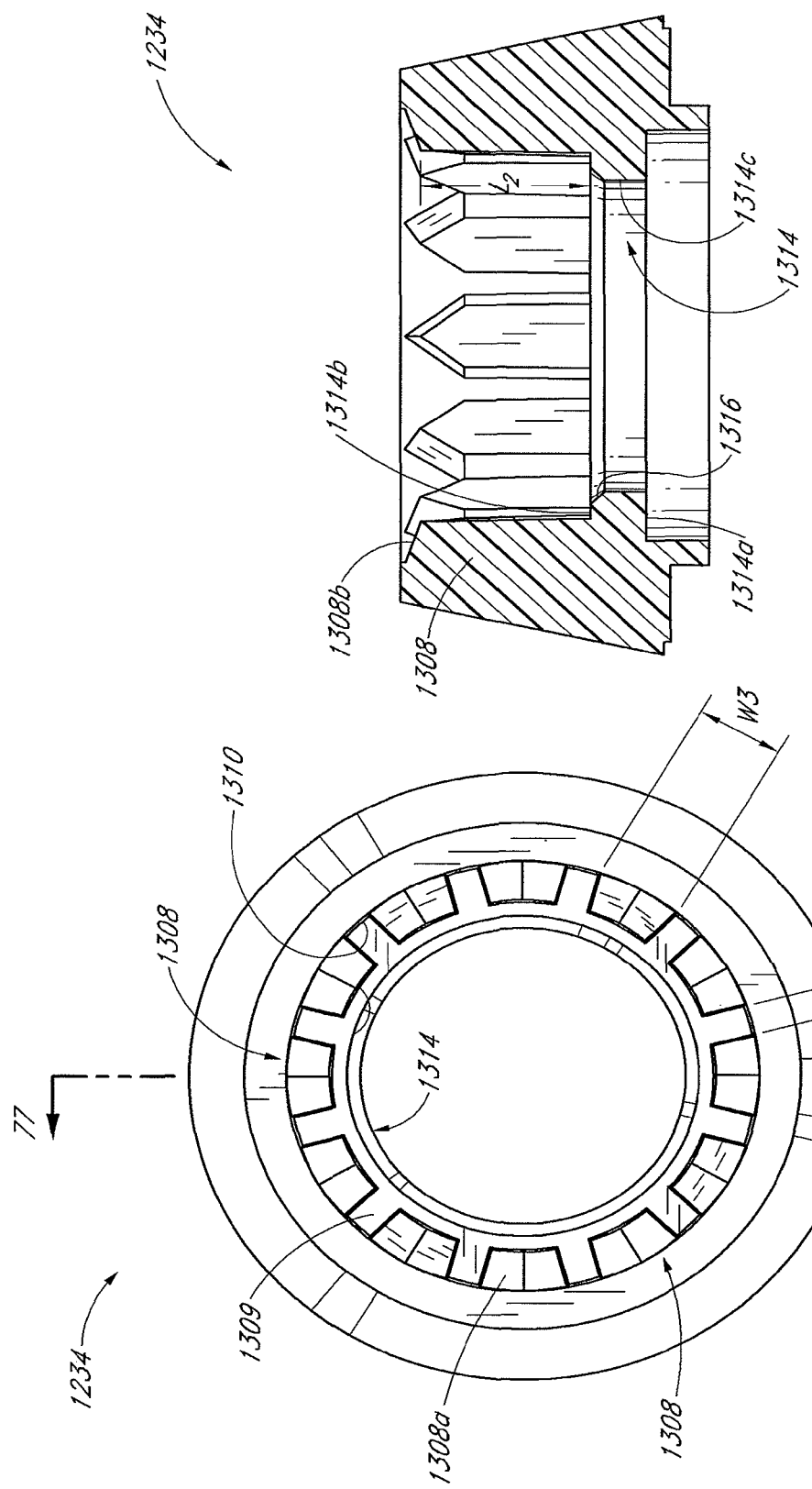

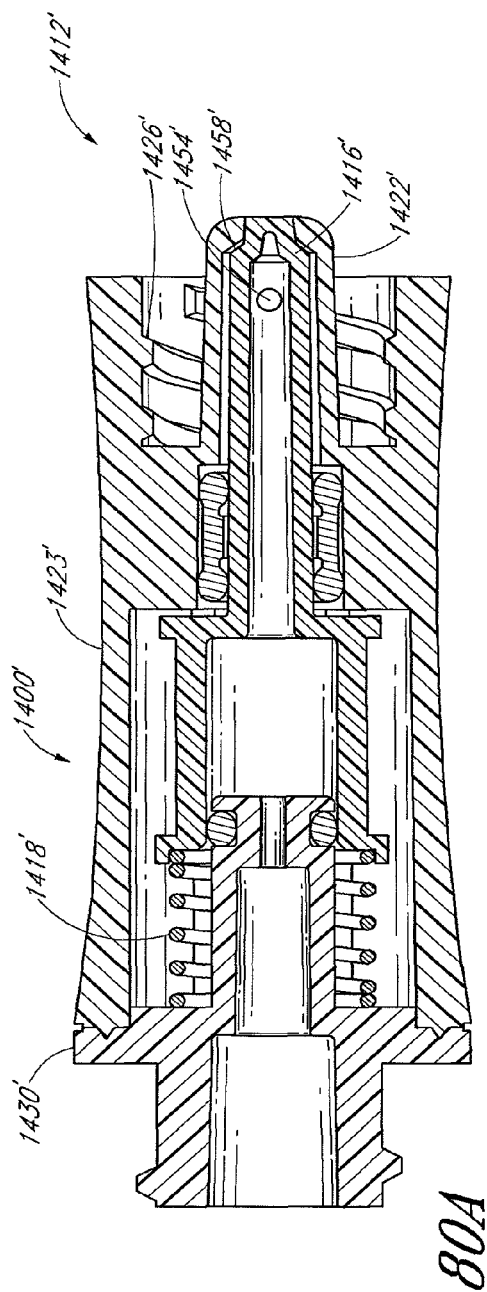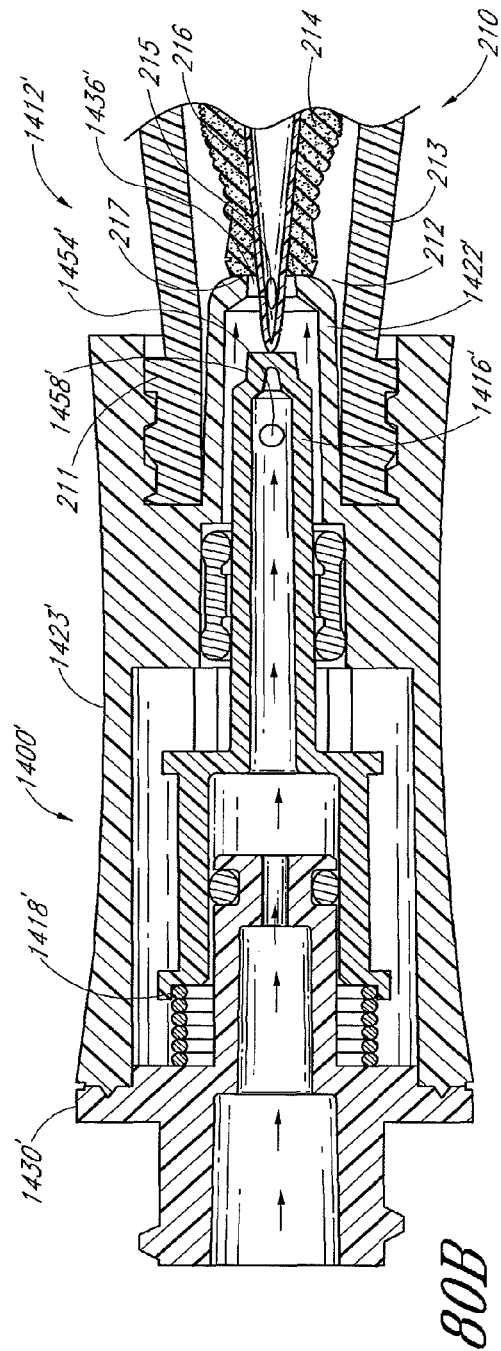
FIG. 80A
FIG. 80B

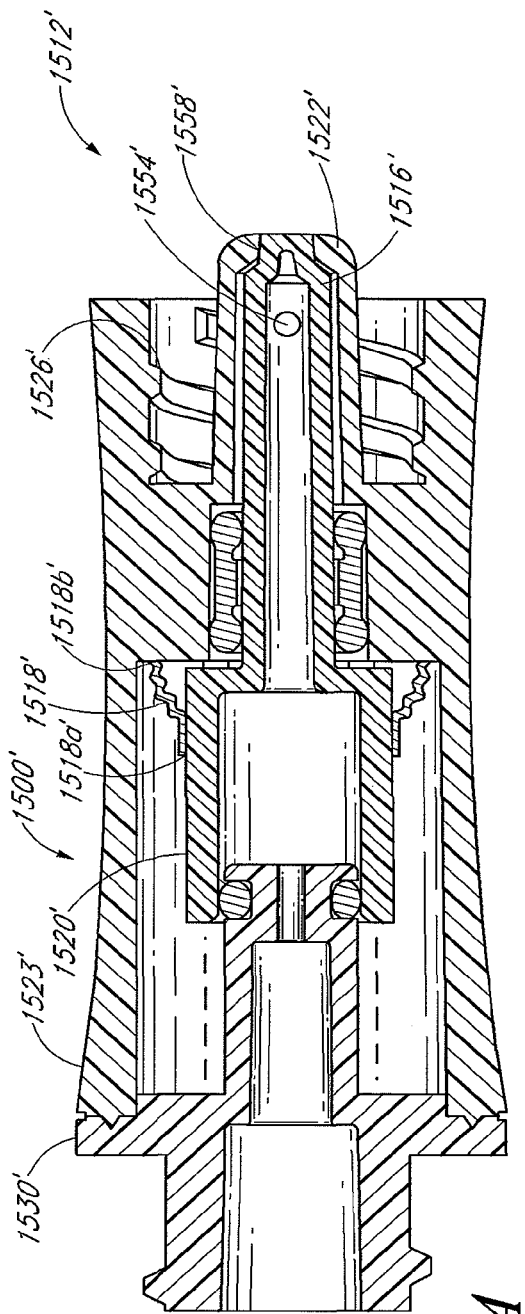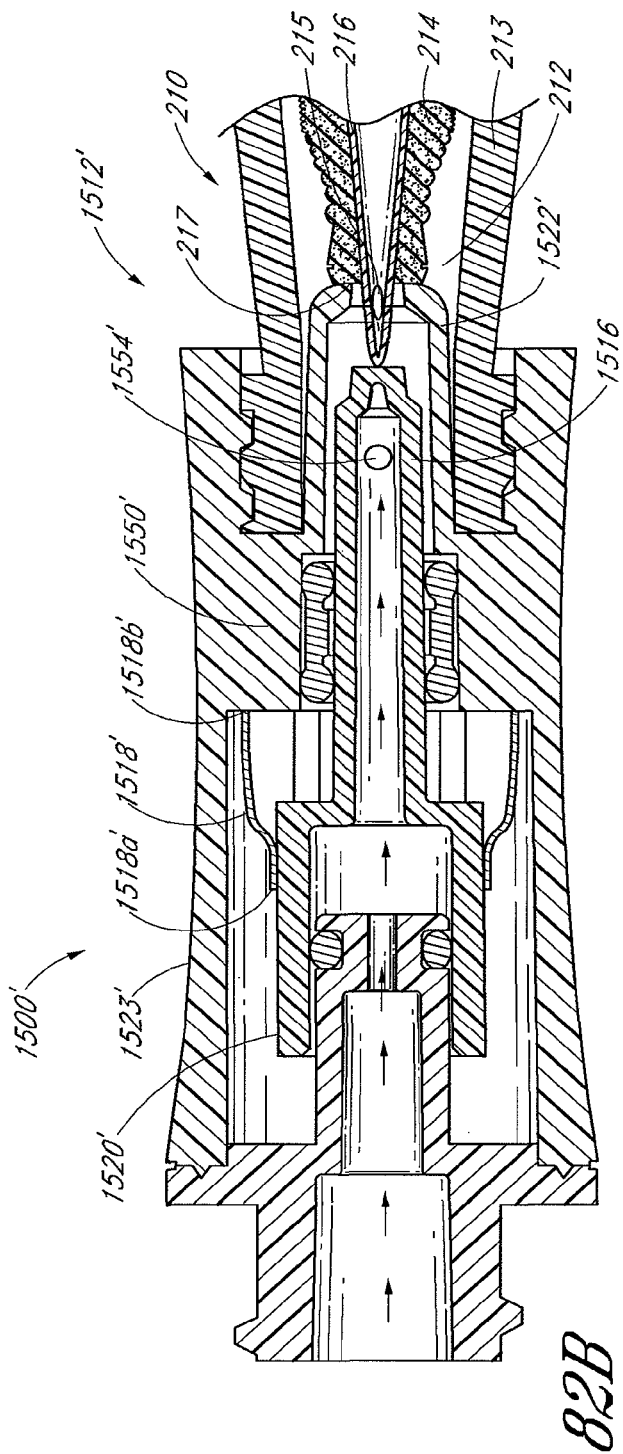

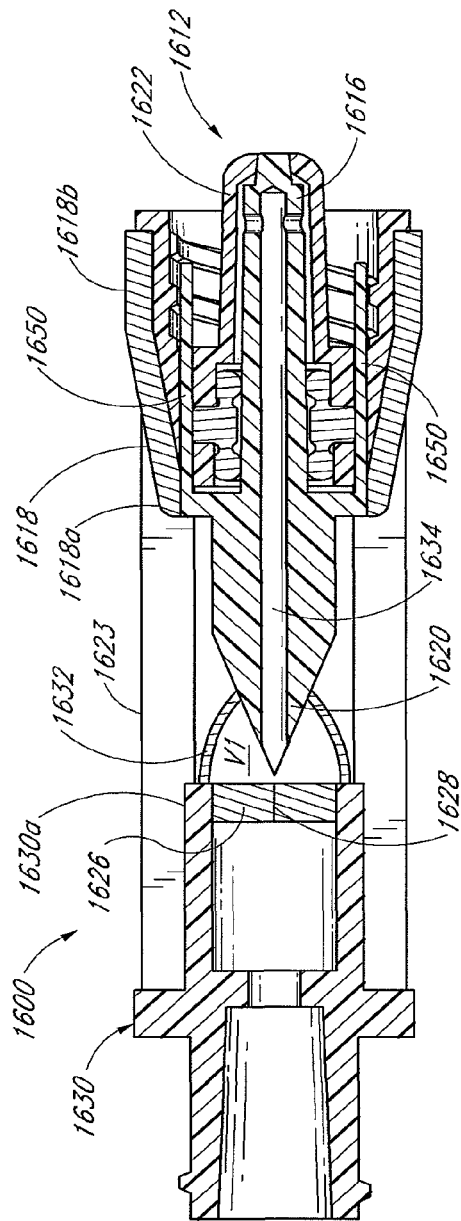
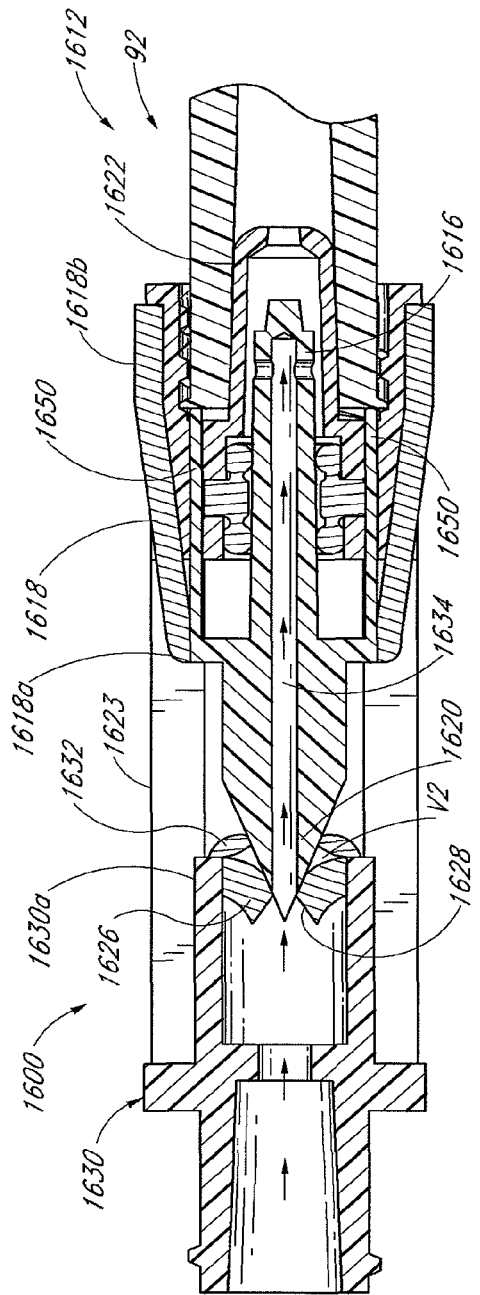
FIG. 83A
FIG. 83B

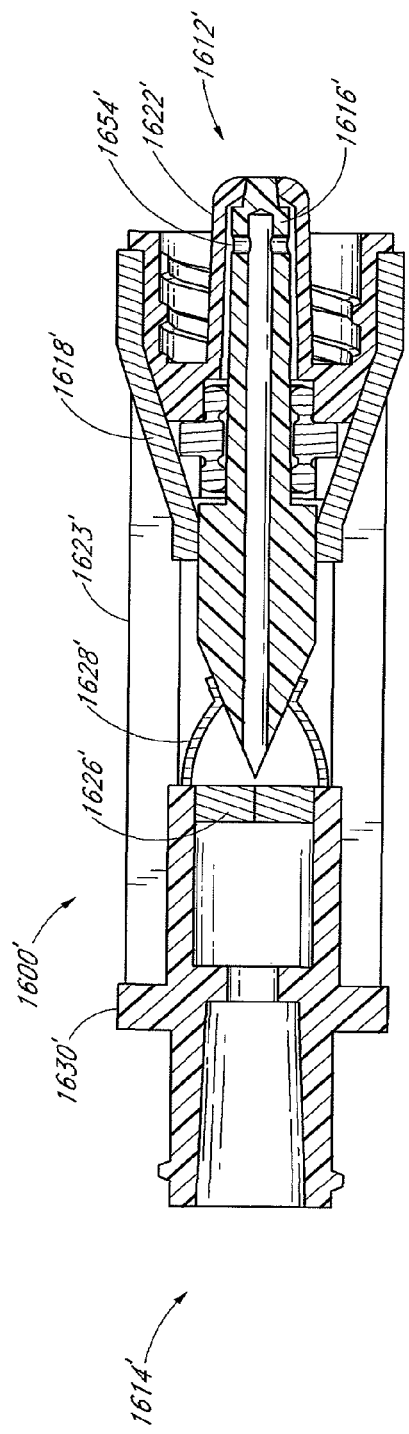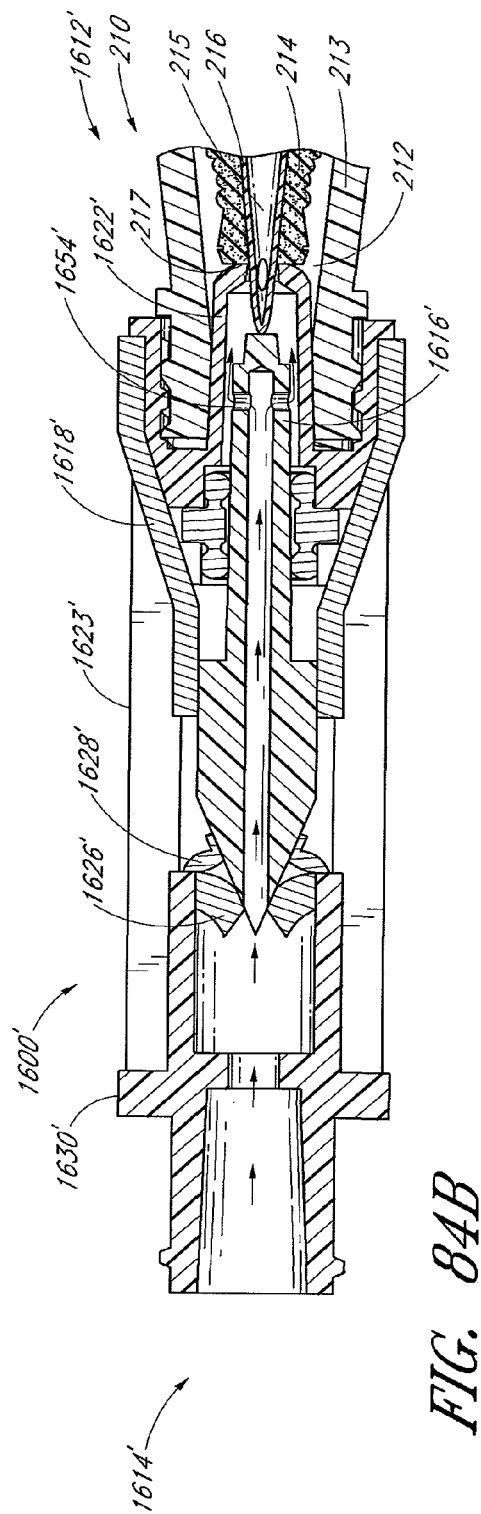
FIG. 84A
FIG. 84B

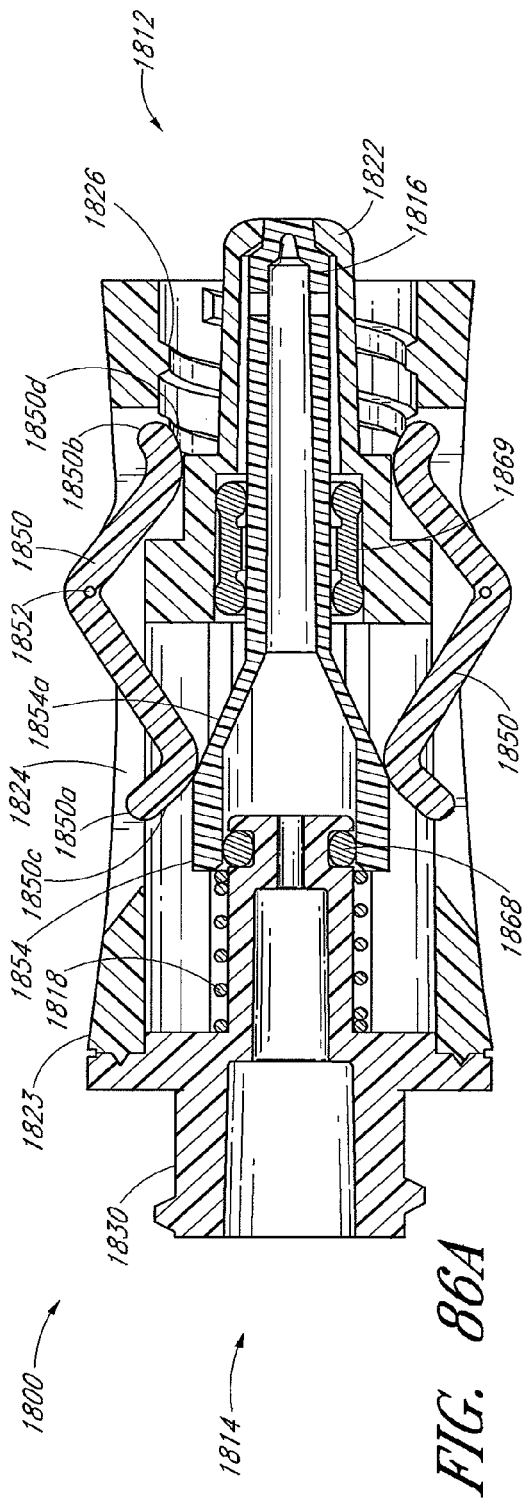
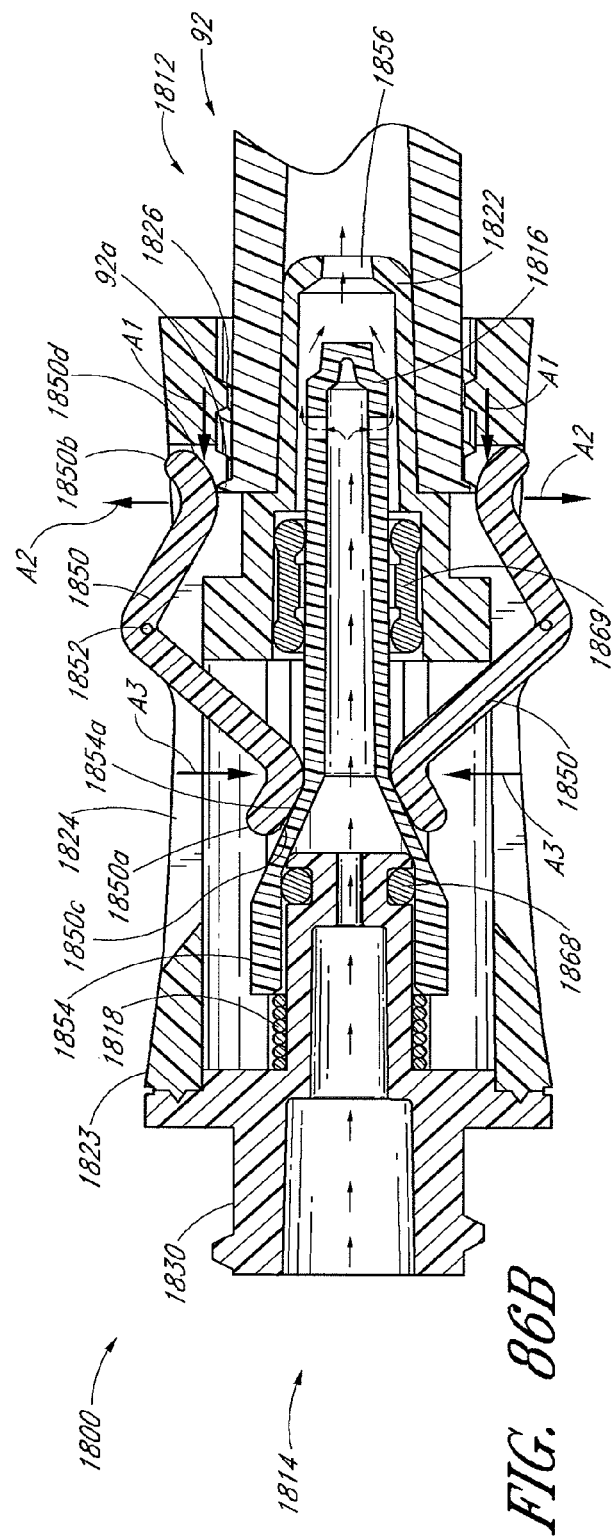
FIG. 86A
FIG. 86B

MEDICAL CONNECTOR

CROSS-REFERENCE TO RELATED APPLICATIONS AND INCORPORATION BY REFERENCE

This application is a continuation of U.S. patent application Ser. No. 13/210,261, filed on Aug. 15, 2011, which is a continuation of U.S. patent application Ser. No. 12/117,568, filed on May 8, 2008, which is related to, claims the benefit of, and is the non-provisional of U.S. Provisional Patent Application No. 60/938,428, filed on May 16, 2007, U.S. Provisional Patent Application No. 60/978,697, filed on Oct. 9, 2007, and U.S. Provisional Patent Application No. 61/042,016, filed Apr. 3, 2008, all of which are incorporated by reference in its entirety herein. This application also incorporates by reference in their entireties U.S. Provisional Patent Application No. 60/696,894, filed on Jul. 6, 2005, U.S. Provisional Patent Application No. 60/707,319, filed on Aug. 11, 2005, U.S. patent application Ser. No. 11/417,604, filed on May 3, 2006, and U.S. patent application Ser. No. 11/482,176, filed on Jul. 6, 2006.

BACKGROUND OF THE INVENTIONS

1. Field of the Inventions

These inventions relate generally to medical connectors through which fluids flow, and in particular, to medical connectors with male luers.

2. Description of the Related Art

Systems of connectors, valves, and tubing are routinely used in hospitals and other medical settings for facilitating the transfer of fluids to and from patients. It is often a challenge to keep such systems sterile and to prevent leakage of fluids when the various components are engaged and disengaged.

In order to maintain a barrier to bacteria, debris, and fluid leakage, female connectors often have been provided with closures, such as septa, flexible seals, or other impediments, at their mating ends. When a male luer connector is engaged with the female connector, the closure of the female connector is temporarily opened, pierced, or moved to allow fluid to flow between the two connectors. Male connectors typically employ needles or luers to open, pierce, or move the closure on the female connectors.

In many systems, only the female connectors are automatically blocked from the external environment when disengaged. Male luer connectors are generally not provided with automatic closing mechanisms. Male luer connectors sometimes employ additional components, such as caps, to stop the flow of fluid and impede the entry of bacteria and debris. Because such closure mechanisms are not automatic (or not used at all), male luer connectors are sometimes left unsealed, allowing fluid to drip out. This may increase the risk of unsanitary conditions inside and outside of the fluid transfer system. In addition, in some medical applications such as certain chemotherapy treatments, the fluids in the tubing and connectors can be harmful if released.

Moreover, in the busy environment of hospitals and other medical settings, health care providers must often quickly manipulate multiple medical implements with one hand, making it difficult to retrieve male luer caps and rapidly attach them upon disengagement of male connectors. In addition, male luer connectors are often employed at the downstream end of gravity-fed fluid sources such as IV bags. When the connectors and tubing are initially connected to such sources, they are generally empty (i.e., filled with air) and must be primed with fluid before they can be connected to a patient. During the priming procedure, fluid is allowed to flow from the upstream end of the tubing toward the male luer connector on the downstream end. As the fluid flows through the tubing, the air in the tubing escapes through the male connector on the downstream end into the environment. Once the fluid itself reaches the male connector, it can also escape and spill out. Because male luer connectors do not usually close automatically after priming, the male luer often drips out a small amount of fluid as the male connector is rapidly moved into mating engagement with a female connector. For this reason, the male luer is generally held over a sink or trash can at the end of the priming procedure to contain the dripping fluid.

There is a need for a closeable male luer connector that automatically opens when engaged with a female connector and automatically closes when disengaged from such connector to minimize or eliminate dripping during priming and other procedures and to improve the barrier of the fluid transfer system against bacteria and other debris. There is also a need for a closeable male luer connector with a female connector having a locking arrangement or other arrangement that permits the female portion of the male luer connector to be coupled with a corresponding male connecting portion of a male connector or other medical device such as a syringe, but inhibits the ability of, or substantially prevents, the female portion of the male luer connector from becoming decoupled from the corresponding male luer portion of the coupled component.

SUMMARY OF SOME EMBODIMENTS

Disclosed are various embodiments of medical connectors with closeable male luers. It is contemplated that the features of the various embodiments disclosed herein are combinable to form additional embodiments. Such combinations are within the scope of this disclosure.

In an exemplary embodiment, a male luer connector has a main housing with first and second ends. The second end of the housing comprises a male luer and a shroud surrounding at least a portion of the male luer. The shroud has screw threads disposed on an internal wall thereof. A tubular valve member with a fluid pathway is disposed within the housing. The valve member has a tip on its second end. In the region near the tip, a pair of fluid holes is positioned on opposite sides of the valve member. The tip is configured to abut snugly against an internal wall of the male luer in a region at or near the second end of the male luer. The valve member also has a pair of struts directed towards the second end. The struts extend axially through a portion of the housing, and the ends of the struts towards the second end are positioned within a space between the male luer and the shroud on the second end of the housing. A length of medical tubing is connected to the connector. An end of the tubing is attached to the first end of the valve member by adhesive, welding, or some other means. A resilient, elastomeric member extends from a mid-section region on the outside of the housing to a region at or near the first end of the valve member within the housing.

In a substantially closed state, the resilient member is configured to pull the housing and the tubular valve member together along their respective axes. In this state, the tip of the valve member is pressed into close contact with a portion of the internal wall on the second end of the male luer, and fluid flow from the medical tubing through the tubular valve member is impeded. Fluid generally cannot escape through the opening on the second end of the male luer because such opening is blocked by the tip of the valve member.

When a force is applied to separate the valve member from the housing, the resilient member is stretched and the tip of the valve member is displaced in the direction of the first end from the second end of the male luer. This separating force can be applied manually, for example, by grasping the external wall of the housing with two fingers and grasping the tubing adhered to the first end of the valve member with two other fingers, and then moving the fingers in opposite direction. The separating force can also be applied automatically by a different manual action. For example, the action of connecting the male luer to a female end of another medical implement can automatically separate the valve member from the housing. As the advancing end of the female connector proceeds up the screw threads on the second end of the housing of the male luer connector, the female connector makes contact with and exerts a force directed towards the first end against the struts of the valve member. This force moves the valve member towards the first end against the biasing force directed towards the second end exerted by the resilient member. In this opened state, fluid is permitted to flow through the opposing holes, around the tip of the valve member, and out of the connector through the gap between the tip of the valve member and the internal wall on the second end of the male luer. In some embodiments, the valve member is automatically advanced in the direction of the first end when the valve member contacts a fluid conduit (e.g., a spike positioned within a female connector) as the male and female connectors are brought together.

When the separating force is removed, for example, by releasing the manual grip on the housing and the tubing, or by detaching the female connector from the second end of the housing, the resilient member once again draws the housing and the valve member together. This causes the tip on the second end of the valve member to abut closely against a portion of the internal wall in a region near the second end of the male luer, and impedes fluid flow out of the valve.

One embodiment that prevents the decoupling of the female portion of the male luer connector from the corresponding male luer portion of the coupled component is described herein. In brief, without limitation, this embodiment of a luer connector can comprise a rigid housing having a first end and a second end. The housing can further comprise a rigid tubular male portion at the first end, a rigid tubular female portion comprising a locking arrangement at the second end, and a longitudinal opening therethrough. The male portion is configured to be engageable with a female connector. The female portion is configured to be engageable with a male connector. The locking arrangement is configured to substantially allow rotation of the luer connector relative to the male connector in a first direction so as to allow the female portion to threadably engage an internal thread of the male connector, and is configured to substantially prevent rotation of the luer connector relative to the male connector in a second direction.

Another embodiment that can prevent the decoupling of the female portion of the male luer connector from the corresponding male connecting portion of the coupled component is described herein. In brief, without limitation, this embodiment of a luer connector can comprise a rigid housing having a first end and a second end. The housing further can comprise a rigid tubular male portion at a first end, a rigid tubular female portion comprising a breakaway arrangement at a second end, and a longitudinal opening therethrough. The male portion can be configured to be engageable with a female connector. The female portion can be configured to be engageable with a male connector. The breakaway arrangement can substantially prevent the removal of the corresponding male connector portion of the coupled component from the female portion of the luer connector.

In more detail, but without limitation, the breakaway arrangement can be configured to allow a threaded male connector portion of the coupled component to rotate relative to a threaded female portion of the luer connector in a first, tightening direction until the male connector portion of the coupled component is substantially completely threadedly engaged with the female portion of the luer connector. Additionally, without limitation, the breakaway arrangement can be configured to prevent the male connector portion of the coupled component from rotating relative to the female portion of the luer connector in a second, loosening direction after the male connector portion of the coupled component has been substantially completely engaged with the female portion of the luer connector, thus preventing the coupled component from easily decoupling from the luer connector.

In some embodiments, this is accomplished as follows. As will be described in greater detail below, the female portion of the luer connector can comprise an end cap between the main housing body and the female connector. The end cap can comprise a first end cap component and a second end cap component. The second end cap component can be supported by a housing member, and the first end cap component can be supported by the second end cap component and can be partially positioned on the inside of the second end cap component. The first end cap component of the luer connector can comprise one or more tabs protruding radially outwardly from an outside surface thereof that can engage with complementary tabs protruding radially inwardly from an inside surface of the second end cap component. In a first state, the engagement of the tabs can prevent the first end cap component of the luer connector from rotating freely within the second end cap component. The tabs protruding outwardly from the first end cap component of the luer connector can be configured to shear or break off when a predetermined level of torque is applied to the first end cap component of the luer connector, which, in some embodiments, can occur when a male luer portion of the coupled component is substantially fully threadably engaged with the first end cap component of the luer connector. Once the tabs on the first end cap component of the luer connector have sheared or broken off, the first end cap component of the luer connector then can rotate substantially freely within the second end cap component so that the male portion of the coupled component cannot be rotated relative to the first end cap component. In other words, when the male portion of the coupled component is rotated relative to the luer connector, the first end cap component can rotates in unison with the male portion of the coupled component so that the male portion of the coupled component is substantially prevented from decoupling from the first end cap component, hence, the luer connector.

In some embodiments, a method of engaging a medical implement with a connector is provided, the method comprising the steps of connecting a first end of a medical implement with a first end of a connector The connector can comprise a rigid housing with a first end configured to threadingly engage the first end of the medical implement. The first end can comprise a first portion comprising at least one engaging surface and a second portion co-axially aligned with the first portion and comprising at least one engaging surface. The first and second portions can be configured to be in a first, locked configuration wherein the respective engaging surfaces of the first and second portions cooperate to prevent or impede the first and second portions from rotating relative to each other and a second, substantially unimpeded position wherein the first and second portions are able to rotate relative to each other. The method further comprising twisting the medical implement relative to the connector to threadingly advance the first end of the medical implement past the first end of the connector until the medical implement and the connector reach a substantially fully theadingly engaged point. Further twisting the medical implement relative to the connector in the advancing direction beyond the substantially fully threadedly engaged point disengages the cooperating engaging surfaces of the first and second portions to permit the first portion to rotate relative to the second portion without disengaging the medical implement from the connector.

Also disclosed herein are other features and configurations for the foregoing embodiments, as well as additional embodiments for other connectors with closeable male luers. Such embodiments generally include means for permitting or impeding fluid flow through a male luer on a connector, preferably automatically upon connection with a corresponding female connector. Such embodiments can also include features and configurations that permit the female portion of the male luer connector to be coupled with a corresponding male connector portion of another connector or medical device such as a syringe, while inhibiting or substantially preventing the decoupling of the female portion of the male luer connector from the corresponding male connector portion of the coupled component.

BRIEF DESCRIPTION OF THE DRAWINGS

Certain embodiments of this inventions will now be discussed in detail with reference to the following figures. These figures are provided for illustrative purposes only, and the inventions are not limited to the subject matter illustrated in the figures.

FIG. 23A is a side view of another embodiment of a closeable male luer connector with a shroud.

FIG. 23B is a cross-sectional view of the connector of FIG. 23A.

FIG. 24A is a perspective view of another embodiment of a closeable male luer connector.

FIG. 24B is a cross-sectional view of the connector of FIG. 24A.

FIG. 25A is a side view of another embodiment of a closeable male luer connector with a shroud.

FIG. 25B is a cross-sectional view of the connector of FIG. 25A.

FIG. 28 is a cross-sectional view of the connector of FIG. 27.

FIG. 29 is another cross-sectional view of the connector of FIG. 27.

FIG. 47 is a perspective view of the valve member component of the closeable male luer connector of FIG. 42.

FIG. 48 is a perspective view of the female connector component of the closeable male luer connector of FIG. 42.

FIG. 53 is a side view of an embodiment of a component of a non-reversible closeable male luer connector.

FIG. 54 is a side view of the component of FIG. 53.

FIG. 76 is an end view of the component shown in FIG. 75.

FIG. 77 is a cross-sectional view of the component shown in FIG. 75, taken along the line 77-77 in FIG. 76.

FIG. 80A is a cross-sectional view of another embodiment of a luer connector in a closed position.

FIG. 80B is a cross-sectional view of the embodiment of the luer connector shown in FIG. 80A in an open position.

FIG. 82A is a cross-sectional view of another embodiment of a luer connector in a closed position.

FIG. 82B is a cross-sectional view of the embodiment of the luer connector shown in FIG. 82A in an open position.

FIG. 83A is a cross-sectional view of another embodiment of a luer connector in a closed position.

FIG. 83B is a cross-sectional view of the embodiment of the luer connector shown in FIG. 83A in an open position.

FIG. 84A is a cross-sectional view of another embodiment of a luer connector in a closed position.

FIG. 84B is a cross-sectional view of the embodiment of the luer connector shown in FIG. 84A in an open position.

FIG. 86A is a cross-sectional view of another embodiment of a luer connector in a closed position.

FIG. 86B is a cross-sectional view of the embodiment of the luer connector shown in FIG. 86A in an open position.

DETAILED DESCRIPTION OF SOME EXEMPLIFYING EMBODIMENTS

The following detailed description is now directed to certain specific embodiments of the disclosure.

In some aspects of the embodiments described herein, a variety of means are shown for closing the second end of a male luer connector. In some embodiments, these closing mechanisms function to prevent and/or impede fluid from escaping from or entering into the male luer, while allowing fluid flow when the male luer is manually opened or engaged with a corresponding female luer. As used herein, terms such as "closed" or "sealed" should be understood as obstructions or barriers to fluid flow. These terms should not be understood to require that a particular structure or configuration achieves a complete fluid closure in all circumstances.

Figure 1A:
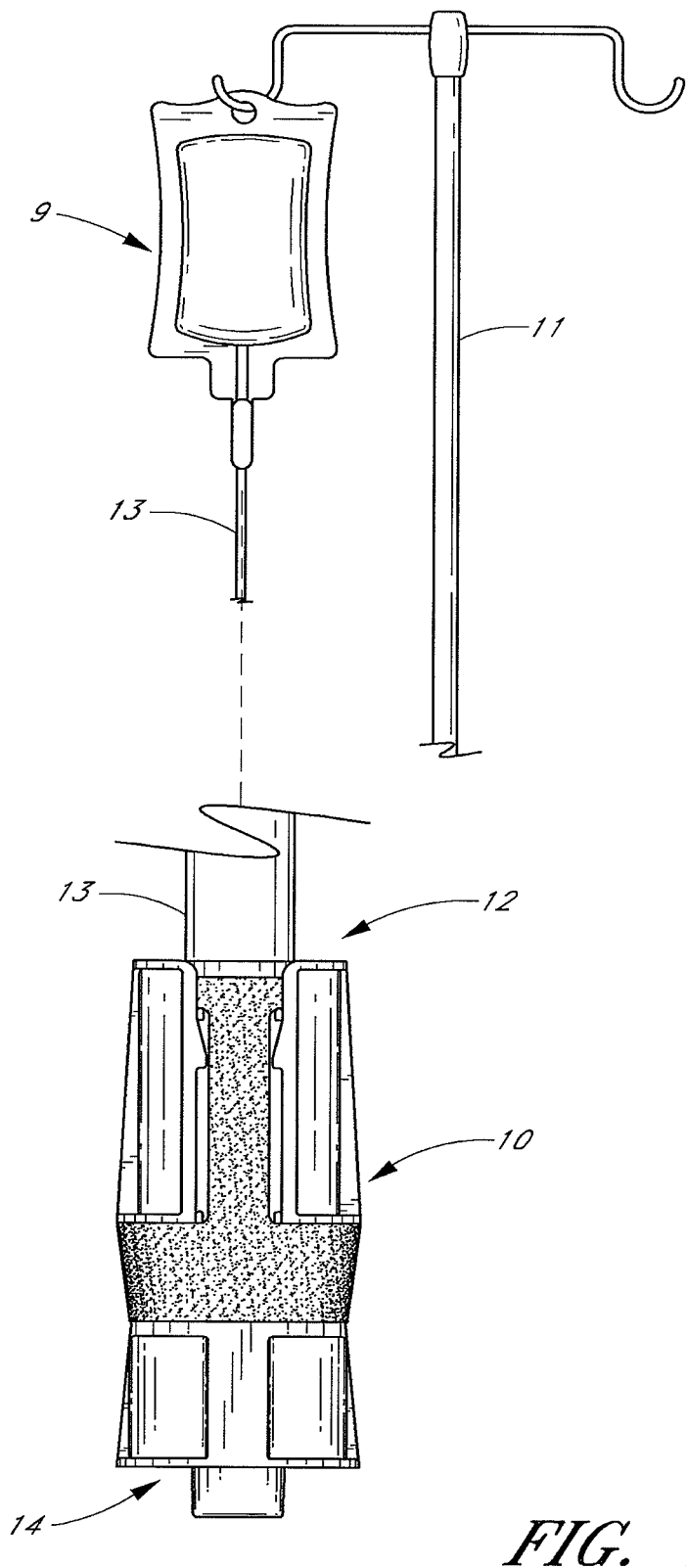
FIG. 1A shows a perspective view of an embodiment of a male luer connector attached to tubing configured to receive fluid from a hanging gravity-fed IV bag. In this and other figures, the relative size of the connector and attached tubing is increased in comparison to other objects to facilitate viewing certain details.

In FIG. 1A, an embodiment of a closeable male luer connector 10 is shown in a closed position. The luer connector 10 is attached to a gravity-fed IV bag 9 filled with fluid hanging from a pole stand 11. At the bottom of the bag 9, a section of tubing 13 is attached. The opposite end of the tubing 13 is connected to the first end 12 of the luer connector 10. A closing mechanism on the interior of the second end 14 of the luer connector 10 prevents the fluid contained within the bag 9 from flowing through the tubing 13 and leaking out of the luer connector 10, as long as the luer connector 10 remains in a closed configuration.

Figure 1B:
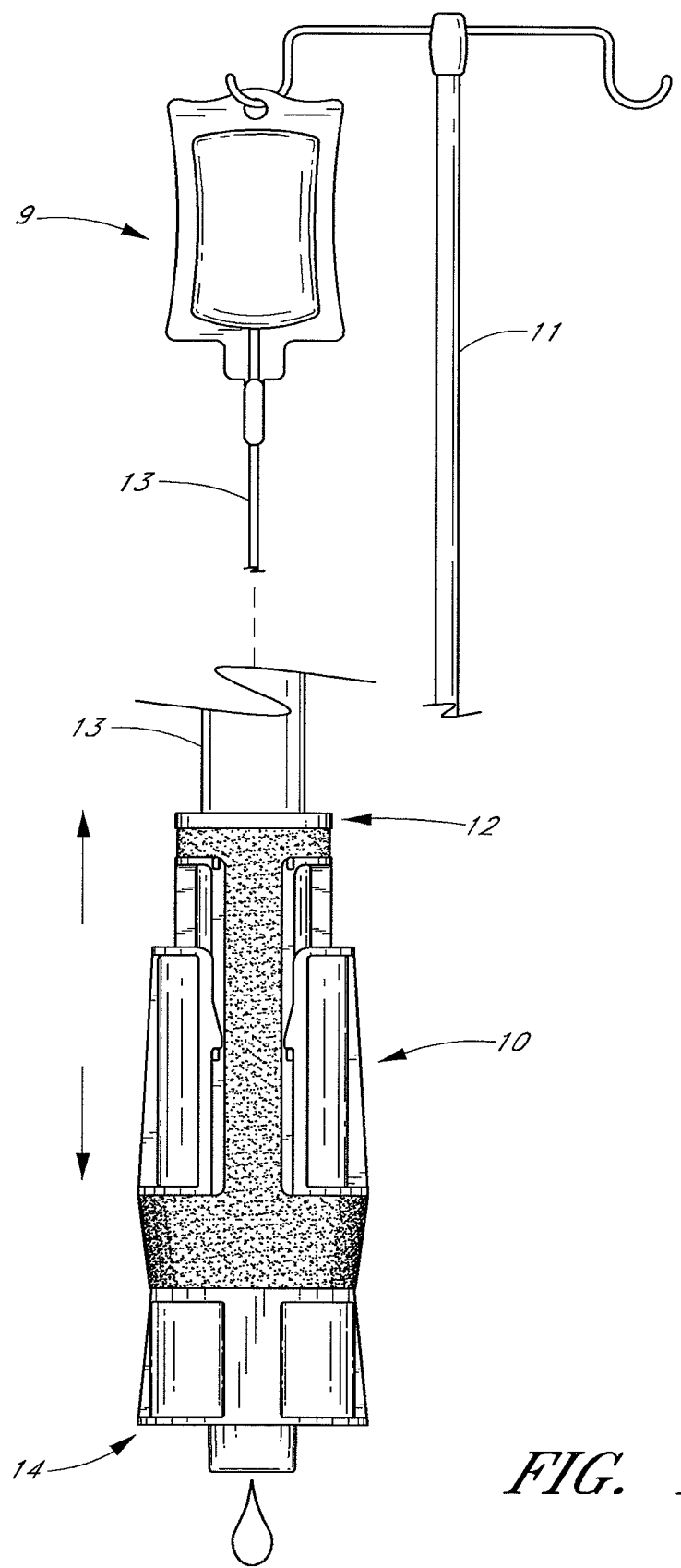
FIG. 1B shows a perspective view of the connector of FIG. 1A in a stretched, substantially opened configuration.

In FIG. 1B, the connector 10 is illustrated in an open position. Fluid can flow out into the first end 12 of the connector 10 and out of the second end 14 of the connector 10. A health care provider can move the male luer connector 10 into this configuration by grasping the second end of the closeable male luer 10 with two fingers, grasping the tubing 13 with two other fingers, and gently moving the fingers in opposite directions.

The IV delivery system illustrated in FIGS. 1A and 1B can be easily readied for fluid communication with a patient. In most circumstances, the tubing 13 is filled with air when it is initially connected to the IV bag 9. If the other end of the tubing 13 is connected to a closed connector, as illustrated in FIG. 1A, the air cannot escape and fluid cannot enter the tubing 13 from the IV bag 9. The luer connector 10 is therefore manually moved into the opened position until all of the air has been purged through the luer 10 and the fluid in the IV bag 9 fills the tubing 13 and connector 10. This procedure is known as "priming." As soon as the fluid line and connector are properly primed, the health care provider can quickly release the opposing forces applied to the second end 14 of the luer connector 10 and the tubing 13, and the closing mechanism of the luer connector 10 can rapidly stop the flow of fluid through the luer connector 10.

Figure 1C:
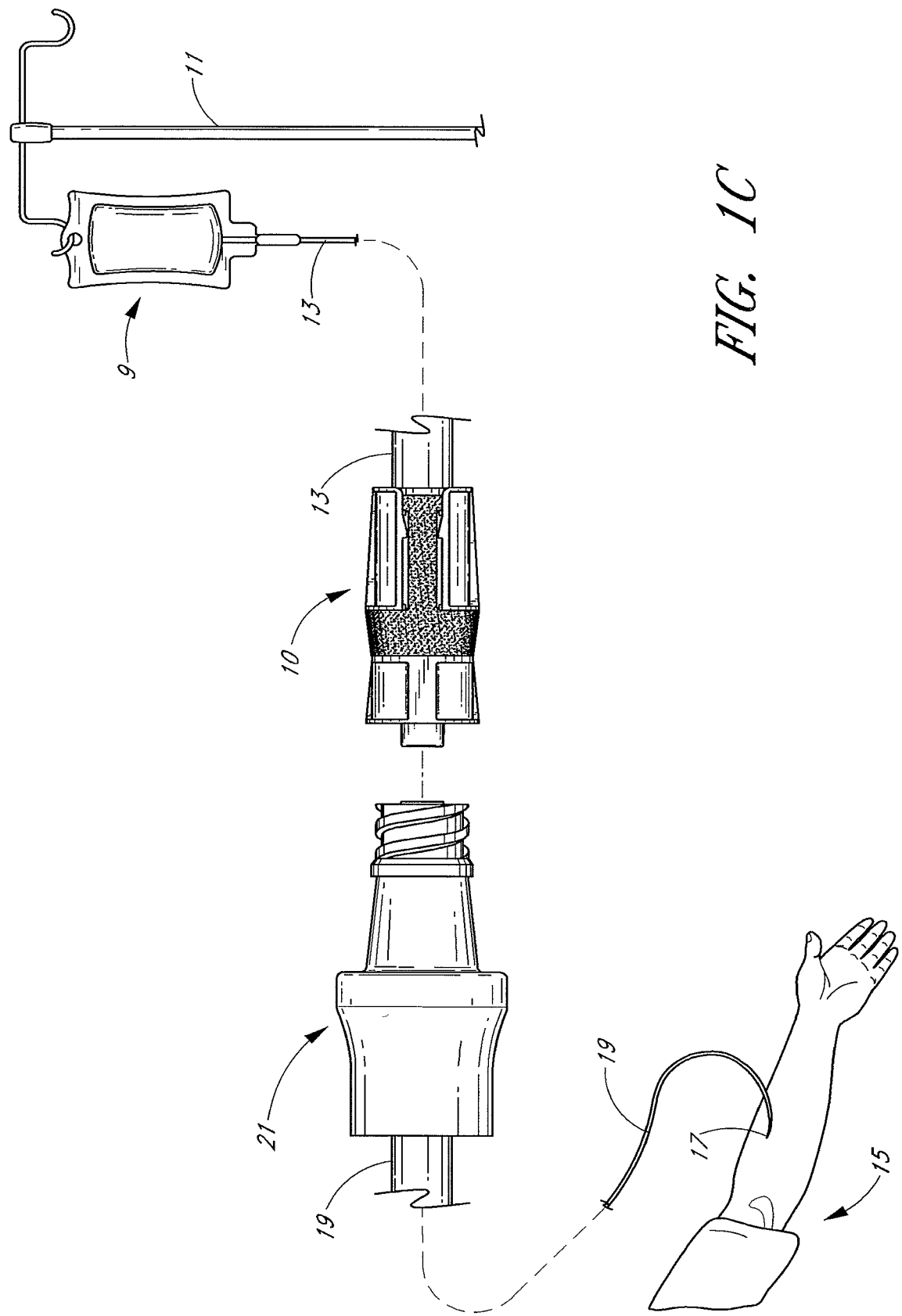
FIG. 1C shows a perspective view of an embodiment of the connector of FIG. 1A being connected to an exemplary female connector attached to tubing inserted into a patient.

Referring now to FIG. 1C, a catheter 17 has been inserted into a patient's arm 15. The catheter 17 penetrates the skin of the arm 15 and is preferably fluidly connected with the patient's bloodstream. The catheter 17 is also connected to a length of medical tubing 19 attached to a female medical connector 21. The example of a female medical connector 21 illustrated in FIG. 1C is a version of the Clave® connector manufactured by ICU Medical, Inc., San Clemente, Calif. Various embodiments of a connector of this type are illustrated and described in U.S. Pat. No. 5,685,866, which is incorporated herein by reference in its entirety. It is contemplated that many of the male luer embodiments disclosed herein can be used with other types of female connectors. The tubing 19, catheter 17, and female connector 21 were previously primed with fluid using standard procedures. The luer connector 10 is primed as described previously and brought into engagement with the female connector 21. As described in further detail below, when the male connector 10 and female connector 21 are engaged, fluid is permitted to flow from the IV bag 9 into the patient. When the male connector 10 and female connector 21 are disengaged, fluid is once again prevented from flowing out of the second end 14 of the male connector 10. In general, fluid is also prevented from flowing out of the opening in the female connector 21.

The embodiment illustrated in FIGS. 1A-1C is described in further detail below. Each of the other embodiments disclosed herein can be used in the illustrated fluid system, and in various modifications and alternatives thereof. Further, it is contemplated that the various embodiments of connectors in accordance with the inventions can be used in a wide variety of additional medical fluid systems. For example, the disclosed connectors can also be used to transfer bodily fluids such as blood, urine, or insulin, nourishing fluids, and/or therapeutic fluids such as fluids used in chemotherapy treatments. The disclosed connectors can also be used to interconnect various other components of fluid transfer systems.

Figure 2:
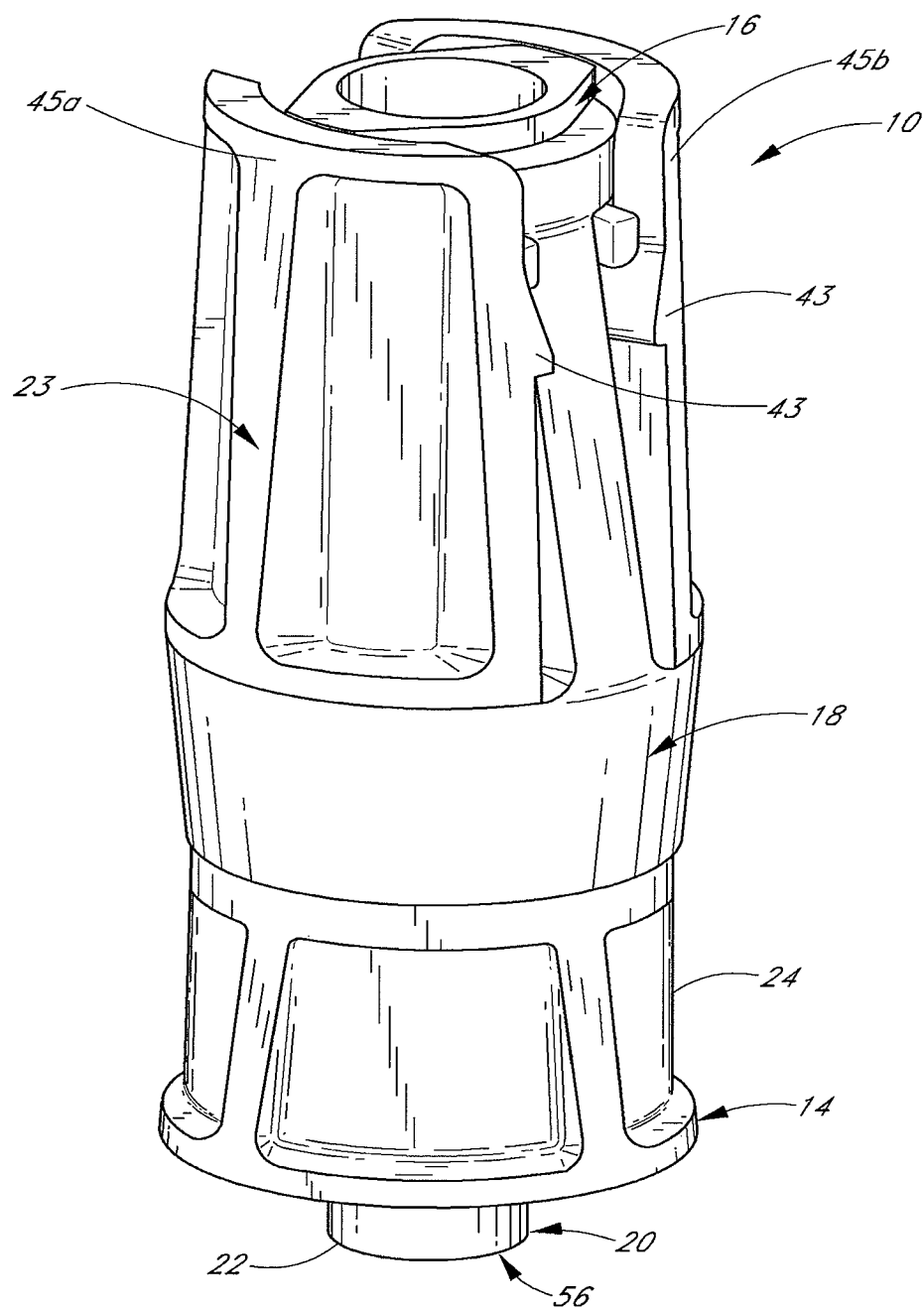
FIG. 2 shows a perspective view of an embodiment of a closeable male luer connector.

Referring now to FIGS. 2-9, the closeable male luer of FIGS. 1A-1C is illustrated in greater detail. As illustrated in FIG. 2, the assembled luer connector 10 comprises four portions: a housing 23, a valve member 16, a resilient member 18, and a sealing ring 20 (not visible in FIG. 2). These portions are individually illustrated in FIGS. 3 through 6, and will be discussed in further detail with reference to these Figures. The luer connector 10 can be constructed of more or fewer portions, and such portions can be combined into different configurations.

Figure 3:
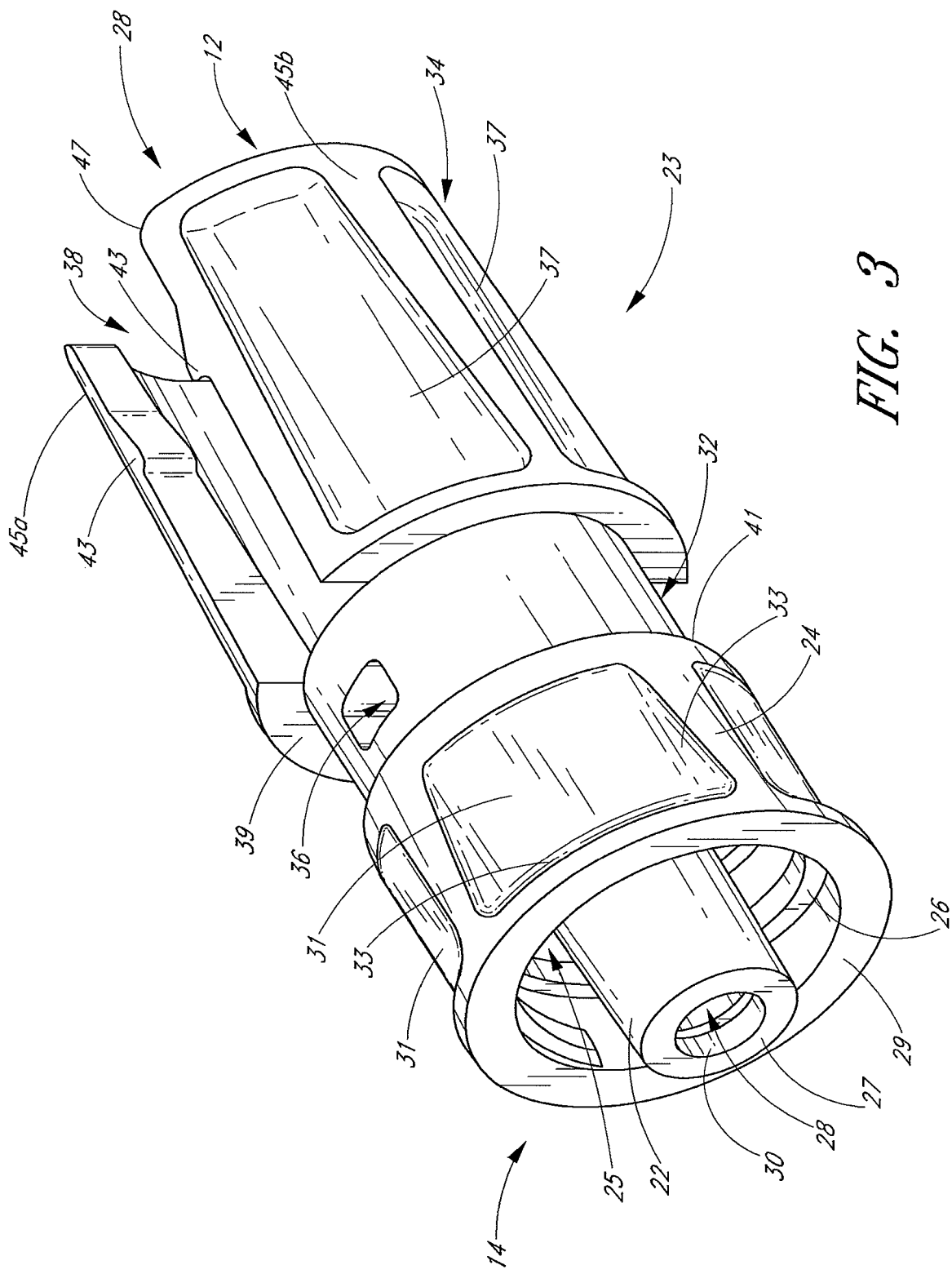
FIG. 3 shows a perspective view of a housing portion of the connector of FIG. 2.

FIG. 3 illustrates the housing 23 of the connector 10, apart from the other portions of the luer connector 10. The housing 23 is generally a tube-like structure with an axial passageway 28 that extends from the first end 12 of the connector 10 through the upper housing 34, and the middle portion 32, and the luer tip 22, to the second end 14 of the housing 23. In some embodiments, the length of the housing 23 from the first end 12 to the luer tip 22 is approximately 1⅛ inches. The housing 23 is preferably, but not necessarily, less than or equal to about 1½ inches from the first end 12 to the second end 14 so that the weight and bulk of the connector are minimized. The housing 23 can have any suitable length for a particular application. The luer tip 22 connects to the remainder of the housing 23 at a base 25 that is surrounded by a shroud 24. The end 27 of the luer tip 22 towards the second end of the luer connector 10 extends some distance beyond the edge 29 of the shroud.

The shroud 24 preferably has inner threads 26 on an interior wall that help securely attached the connector 10 in a removable fashion to another medical implement. In other embodiments, the shroud 24 can include other structures or materials for providing a releasable connection, including quick-release mechanisms and other means. The shroud 24 includes a plurality of depressions 31 on an outer surface to assist the user in firmly grasping and twisting the shroud 24 of the housing 23 with the fingers. The depressions 31 have upwardly tapering sidewalls 33 that prevent the fingers from sliding off the connector 10. On an end towards the first end of the connector 10 of each depression 31, the surface of the housing 23 is approximately co-planar with the surface of the depression 31, while on an end towards the second end 14 of the connector 10 of each depression 31, the surface of the housing 23 is offset from, and preferably lies above, the surface of the depression 31. This configuration allows the fingers to comfortably slide in a direction towards the second end 14 of the connector 10 along the housing 23 into a position for gripping or twisting the connector 10. Once the fingers are in the desired position, a tapered wall 33 on an end towards the second end 14 of the connector 10 of the depression 31 resists further movement by the fingers in the direction of the second end 14. A series of depressions 31 extend around substantially the entire outer surface of the shroud so that the user's fingers, when positioned on opposite sides of the connector 10, will likely encounter a depression 31 regardless of the orientation of the connector 10 during use.

In the illustrated embodiment, the tip 22 has a tapered external wall. The diameter of the tip 22 becomes gradually smaller from the base 25 towards the second end 27. The tip 22 includes a hole at its second end 27. At the base 25 of the luer tip 22, an interior hole 35 (see FIG. 8) leads into a region of the fluid passageway 28 in the middle portion 32 of the luer connector 10. The dimensions of the luer tip can be made to comply with applicable standards and/or regulations, such as the ANSI standards.

The interior wall of the luer tip 22 preferably includes a shelf 30 that extends radially inwardly toward the axis of the fluid passageway 28 surrounded by the luer tip 22, making the fluid passageway 28 narrower at its second end 27 than in the region adjacent to the second end 27. In the illustrated embodiment, the surface of the shelf 30 that faces radially inwardly toward the central axis of the connector 10 is tapered in a manner similar to the taper of the outer surface of the tip 22 (see FIGS. 8 and 9). In this configuration, the inner diameter of the shelf 30 narrows in a direction from the side towards the first end to the side of the shelf 30 towards the second end. As described in further detail below, the shelf 30 in the luer tip 22 helps to block and/or impede fluid flow through the connector 10 when the second end of the valve member 16 abuts against it.

The middle portion 32 of the housing 23 lies between the shroud 24 and the upper housing 34. As illustrated, the middle portion 32 has a smaller outer diameter than either the shroud 24 or upper housing 34. The middle portion 32 also has two generally rectangular openings 36 disposed on opposite sides of the housing 23 from each other. When the connector 10 is assembled, the middle portion 32 is generally covered by a portion of the resilient member 18 (see, e.g., FIG. 2). As a result, the middle portion 32 does not generally come into contact with the fingers during use. Thus, in some embodiments, a grippable surface need not be used for the middle portion 32. The middle portion 32 can therefore have a smaller diameter and smoother surface than either of the other sections of the housing 23.

The upper housing 34 is generally split into two wall sections 45a, 45b by two gaps 38 (only one shown in FIG. 3). The upper housing 34 includes a series of depressions 37 similar in shape and function to the depressions 31 on the shroud 24. The upper housing 34 may also comprise one or more protrusions 43 that extend into the gaps 38. In the assembled configuration, the protrusions 43 help to retain a portion of the resilient member 18 between the gaps 38 in the wall sections 45a, 45b (see FIG. 2). In some embodiments, the protrusions 43 are tapered from a smaller thickness on their ends towards the first end of the connector to a larger thickness on their ends towards the second end of the connector. The tapering of the protrusions 43 helps in the insertion and retention of the portion of the resilient member 18 in a desired position and orientation, while allowing for bending and contortion of the resilient member 18 during use. The protrusions 43 also help prevent the valve member 16 from advancing too far in the direction of the first end as the connector 12 is moved into the opened position by contacting the set of protrusions 44 toward the second end of the valve member 16. The tapering of the protrusions 43 allows the protrusions 44 of the valve member 16 to be advanced towards the second end during assembly into the housing 23 past the protrusions 43 of the housing 23. The corners 47 towards the first end of the connector on each of the wall sections are preferably rounded to prevent snagging, scratching, or other damage or irritation to the fingers or resilient member 18 during use.

As shown in FIG. 3, the exterior surface of the upper housing 34 includes a lower shelf 39 and the exterior surface of the shroud 24 includes a shelf 41 configured to help retain a central portion of the resilient member 18 around the housing 23 in the assembled configuration (see FIG. 2). The shelf 39 of the upper housing 34 is preferably substantially horizontal to discourage any sliding of the resilient member 18 in the direction of the first end of the connector. The shelf 41 of the shroud 41 is preferably tapered (see FIG. 8) to assist in the proper positioning of the resilient member 18 on the housing 23 during manufacturing of the connector 10.

The housing 23 can be constructed from any of a number of different materials. In some embodiments, the housing 23 can be constructed from a relatively rigid material, such as polycarbonate or other polymeric material. The housing 23 and/or valve member 16 of this embodiment, or components of other embodiments, can also be constructed of a hydrophobic material, such as Bayer Makrolon, or any other suitable material.

Figure 4A:
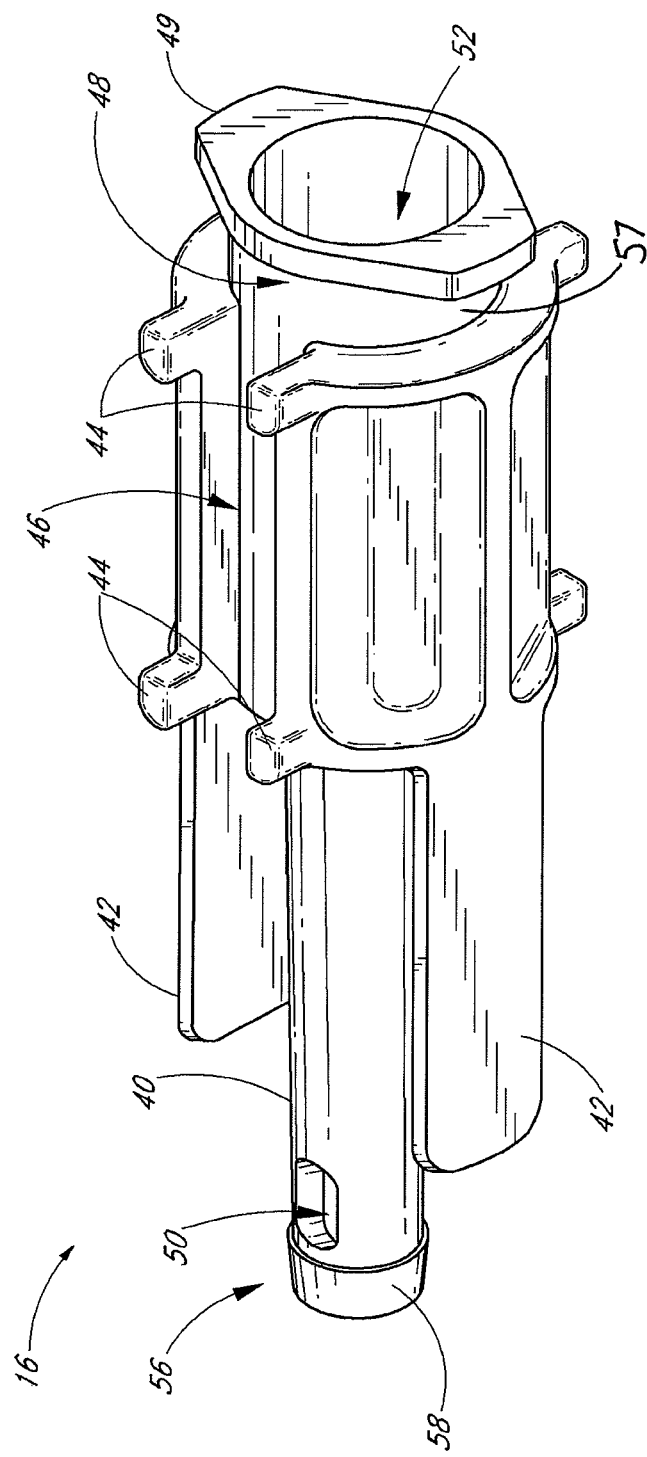
FIG. 4A shows a perspective view of a valve member portion of the connector of FIG. 2.

Referring now to FIG. 4A, the valve member 16 of the male luer 10 is illustrated apart from the other components of the connector 10. In some embodiments, the valve member 16 comprises a fluid passageway 52 of varying diameter extending from the first end 48 of the valve member 16 to the second end 56 thereof, surrounded by additional structures. Near the first end 48, the valve member 16 and corresponding section of the fluid passageway 52 are relatively wide to accommodate a section of standard-diameter medical tubing inserted therein. Near the middle of the valve member 16, a tube 40 surrounding a portion of the fluid passageway 52 is attached to the portion near the first end of the valve member 16. The tube is adjacent to two approximately parallel struts 42 along at least a portion of the tube 40. The tube 40 can have a circular cross-section or other appropriate cross-section. The struts 42 are preferably relatively thin and approximately planar. A first end of each strut 42 connects to the valve member 16 at approximately the middle section of the valve member 16, and a second end of each strut extends toward the second end 56 of the valve member 16. The second end 56 of the valve member 16 preferably extends further than the ends of the struts. There is preferably an open space between the inner wall of each strut 42 and the outer wall of the tube 40.

From near the middle of the valve member 16 to the first end 48 thereof, the fluid passageway 52 comprises a wider region with protrusions 44 along its external surface. Protrusions 44 form two channels 46 (only one is shown in FIG. 4A) lengthwise along opposing sides of the body of the valve member 16. In some embodiments, the struts 42 are spaced circumferentially from the channels 46, as illustrated.

Near the first end of the valve member 16 and tube 40, a circumferential channel 57 may be formed around the perimeter of the body of the valve member 16. Raised tabs 49 can be formed along the edge of the channel 57 toward the first end of the connector, while the raised middle portion of the valve member 16 can form the edge of the channel 57 toward the second end of the connector. In some embodiments, the raised tabs 49 do not extend evenly about the perimeter of the first end of the valve member 16, but instead have two larger sections that are spaced diametrically from each other.

The amount of material necessary to construct the valve member 16 can be reduced by indentations made in the outer layers of this portion. The tube 40 can have a passage 52 disposed therethrough. This passage 52 preferably extends from a hole at the first end of the valve member 16 to a pair of holes 50 (only one shown in FIG. 4A) positioned substantially adjacent to the second end of the valve member 16. In the illustrated embodiment, these holes 50 are generally rectangular in shape. The region of the tube 40 near the second end of the connector can also be formed with only one hole or more than two holes, and other shapes for one or more of the holes can also be employed. For example, the holes 50 can be formed with a tear-drop shape (e.g., narrow on one end and wider on an opposite end), which facilitates an injection molding process of manufacture. Further, in some embodiments, the valve member 16 can be constructed without a fluid path and function as a blocking plunger for fluid flowing around the valve member 16 rather than a means for conveying fluid between the first and second ends of the connector 10.

The tube 40 of the valve member 16 comprises, at its second end, a flange section 58. The flange section 58 preferably extends further in the radial direction than the adjacent portion of the tube 40. In some embodiments, the flange section 58 can be formed of the same or substantially the same material as the rest of the tube 40. The flange section 58 preferably tapers from the first end of the valve member 16 towards the second end of the tube 40. In some embodiments, the taper is formed at a 5-degree angle, and has a substantially identical taper to that of the radially inwardly facing surface of the shelf 30 of the housing 23. Other amounts of taper, or no taper, can also be used.

The valve member 16, like the housing 23 of FIG. 3, may be constructed from a number of different materials. Examples of such materials include polycarbonate or other polymeric materials. The valve member 16 can be approximately the same length or somewhat shorter than the housing 23. For example, the length of the valve member 16 can be approximately 1 inch. In some embodiments, the valve member 16 can be substantially shorter than the length of the housing 23. The valve member 16 can be formed from the same rigid materials as the housing 23. In certain applications, for example, semi-rigid or even more flexible materials may be desirable for use in the valve member 16, and more particularly for the flange section 58 toward the second end of the tube 40.

The valve member 16 can be manufactured through injection molding. In some embodiments, at least two gates are used to facilitate distribution of molten plastic throughout the mold. Preferably, one gate can be located along one of the sides of the valve member 16 between the end of the struts 42 towards the first end of the connector and the raised tabs 49 and another can preferably be located near the holes 50 in the valve member 16. The locations of the gates are not fixed, however, and other locations on the valve member 16 can be used for gates when injection molding the valve member 16. Constructing both the housing 23 and the valve member 16 of this or other embodiments out of the same material lessens the chance of deteriorated performance of the connector 10 due to thermal expansion/contraction or chemical interaction between the connector 10 and its environment.

Although the valve member 16 of the illustrated embodiment is configured as shown in FIG. 4A, many other configurations are possible. In some embodiments, the valve member 16 can be relatively smooth on its external surface, and can principally comprise the tube 40 defining the passage 52. In still other embodiments, different numbers of struts 42 can be disposed along the sides of the valve member 16.

Figure 4B:
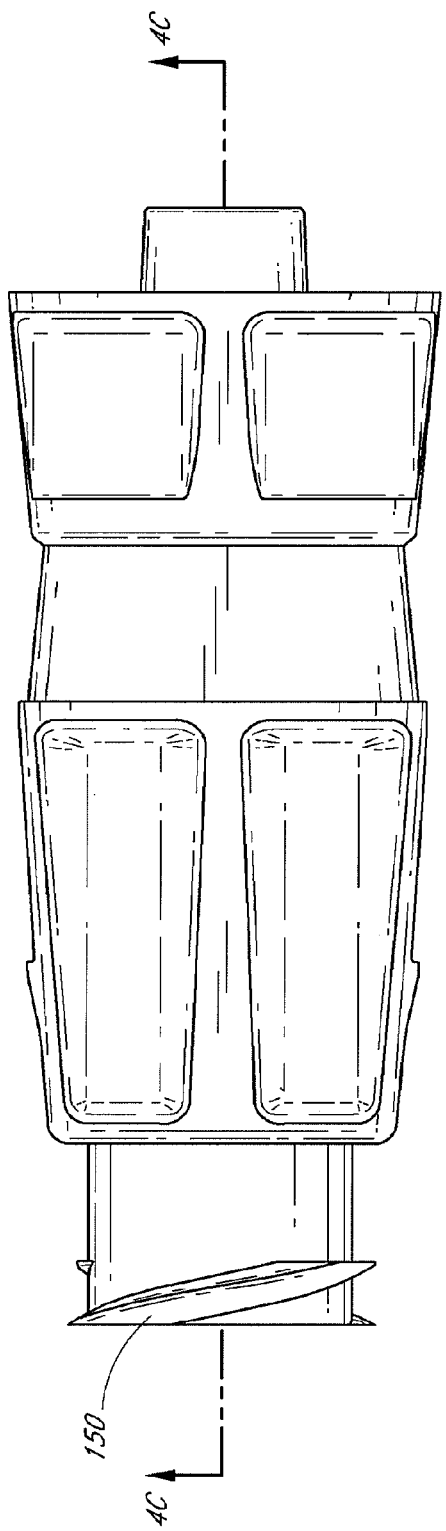
FIG. 4B shows a perspective view of another embodiment of a valve member portion of the connector of FIG. 2.

As can be seen in the embodiment illustrated in FIG. 4B, the raised tabs 150 near the first end of the valve member 16 can also comprise an external engaging surface 150, such as a screw thread, for removably attaching a medical implement (not shown), such as a syringe, with the first end of the valve member 16.

Figure 4C:
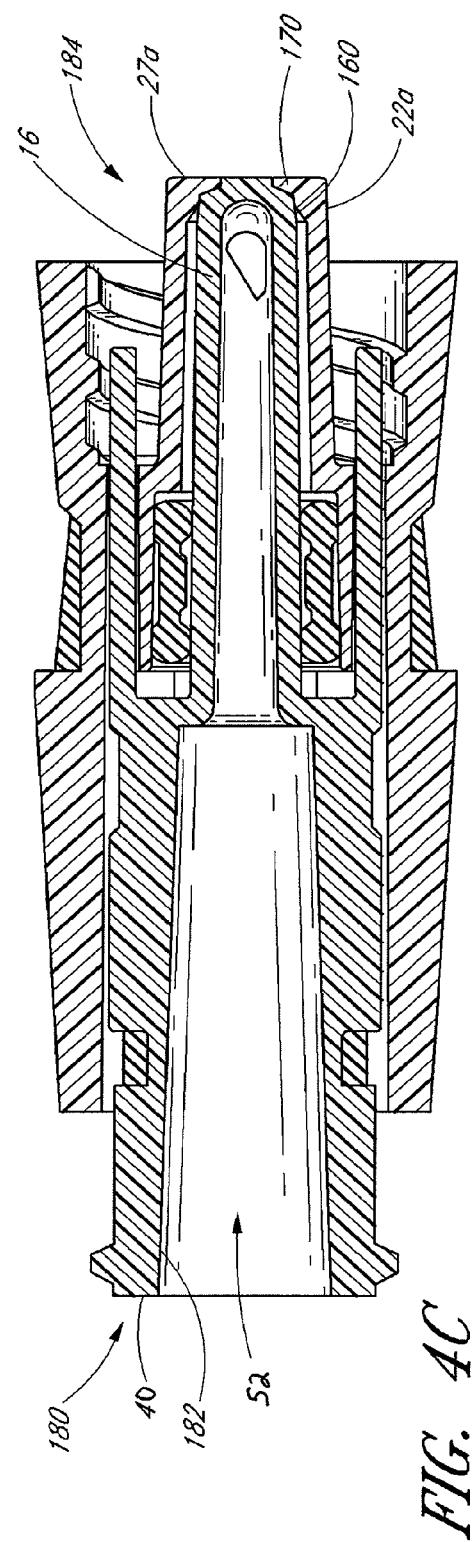
FIG. 4C shows a cross-sectional view of the embodiment of the valve member portion of the connector of FIG. 4B.

In the embodiment illustrated in FIG. 4C, the channel 52 additionally can be tapered along the internal surface 182. The taper of the channel 52 can result in a decrease in width of the channel with a larger size at the first end 180 of the valve member 16 and a smaller size towards the second end 184 of the valve member. The internal taper of the channel 52 can compliment and closely fit with the taper of a male luer. Such an internal taper can conform to ANSI standards and/or regulations, such as the standard for medical syringes. In the illustrated embodiment, the tube 40 of the valve member 16 does not have a flange section 58 that extends radially outwardly beyond the wall of the tube 40, as in the embodiment of FIG. 4A. Instead, the wall of the tube 40 tapers radially inwardly in the region of the second end. The second end 27a of the luer tip 22a can have a smaller cross-sectional second portion 170 which decreases the likelihood of fluid escaping along the internal surface of the second end 27a of the luer tip 22a. Near the second end 27a of the luer tip 22a, a larger cross-sectional region 160 can transition to the smaller cross-sectional portion 170 towards the second end of the connector in many different ways, such as with an abrupt stair-step transition as illustrated in FIG. 4C or with a gradual tapering transition, or other transitions. Some sample cross-sectional diameters of the opening at the second end 27a of the luer 22a include those of about 2 mm or less, including about 0.5 mm, 0.75 mm, 1.0 mm, 1.25 mm, 1.5 mm, and 1.75 mm. The diameters of the opening in the second end 27a can also be in the ranges of 0.4 mm-1.8 mm, 0.5 mm-1.5 mm, and 0.5-1.0 mm. Other diameters, either inside or outside the listed ranges can also be used. Additionally, the second end of the valve member 16 can be sized appropriately to occupy the space in the opening of the second end 27*a* of the luer 22*a*.

As shown in FIGS. 4B and 4C, the closeable male luer connector 10 has both a female end 180 and a male luer end 184. The closeable female connector 21 of FIG. 1C (referenced above) and 210 of FIGS. 10 and 11 (described in more detail below), as well as other standard female connectors with similar external structure, also have both female and male ends. In many embodiments, such female connectors utilize seals or other fluid barriers to impede the flow of fluid on the female end but not on the male end. In many of the embodiments of the closeable male luer connectors illustrated herein, there is no seal or other fluid barrier shown on the female end. However, the female end of any of the closeable male luer connectors disclosed herein can be configured to include a closeable female end. For example, the structure for selective fluid-impedence with the female connector 21 or 210, or any of the other standard female connectors, could be included within the female end of any of the closeable male luer connectors disclosed herein to provide a connector that selectively seals or impedes fluid flow on both ends. In some embodiments of this type with closeable female and male ends, it can be advantageous for a resilient seal element to be positioned at or near the female opening, as shown in U.S. Pat. No. 5,685,866. By positioning the seal element in this manner, it is possible to cleanse the female opening prior to use with antiseptic with a wiping motion to avoid a harmful accumulation of debris, bacteria, antiseptic, or other unwanted substances on the seal element and/or in the region between the seal element and the housing of the connector adjacent to the seal element.

Figure 5:
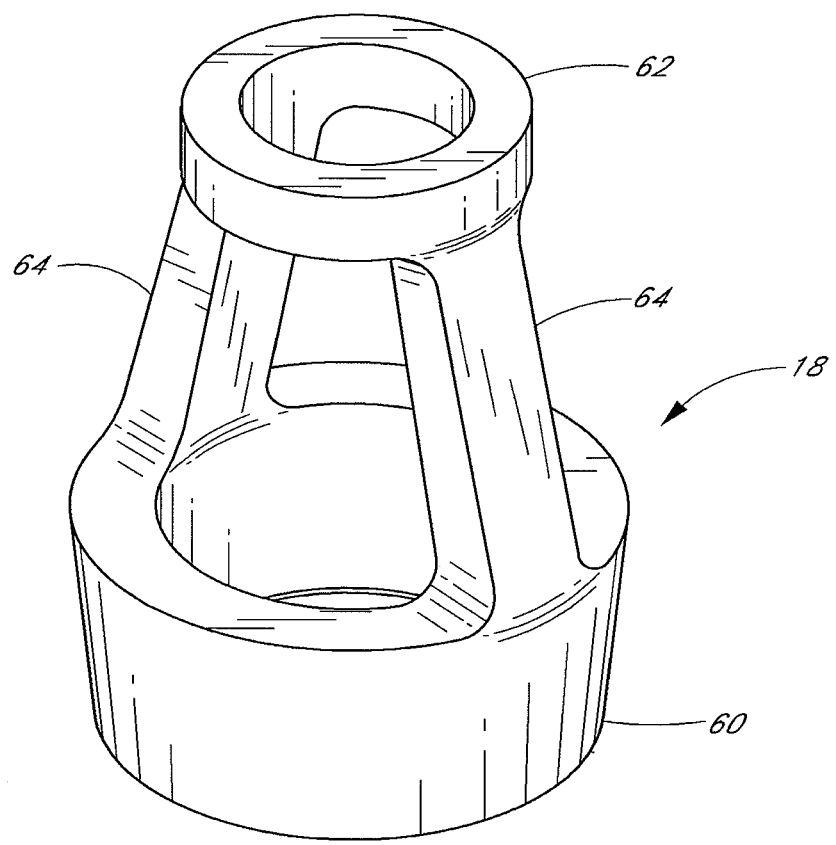
FIG. 5 shows a perspective view of a resilient member of the connector of FIG. 2.

Turning now to FIG. 5, the resilient member 18 is discussed in greater detail. In the illustrated embodiment, the resilient member 18 is formed from two rings 60, 62 separated by two elastic members 64. The rings 60, 62 and/or the elastic members 64 can be made of a deformable material configured to exert a restoring force when stretched. Thus, if the rings 60, 62 are pulled in opposing directions, the elastic members 64 function to restore the rings 60, 62 to their unextended configuration.

The elastic members 64 can be constructed from a number of elastic materials. In some embodiments, the elastic members 64 are made from a silicon rubber elastic material. In other embodiments, the elastic members 64 can be made from a shape-memory material. In still other embodiments, the elastic members 64 and/or the resilient member 18 can comprise springs or other structures capable of exerting a restoring force.

The rings 60, 62 can also be constructed from a number of materials. In some embodiments, the rings 60, 62 are constructed from the same deformable elastic material that comprises the elastic members 64. Thus, the rings 60, 62 can be stretched into a diameter to extend around the appropriate portion of the housing 23 to which each respective ring 60, 62 is attached. The resilience of the rings 60, 62 can function to effectively hold each ring 60, 62 in place on the housing 23. In other embodiments, the rings 60, 62 can be constructed from rigid or semi-rigid materials, and can, for example, comprise half-circles that can be snapped into and out of position. In some embodiments, the resilient member 18 can be integrated into the valve member 16 or housing 23. In some embodiments, other structures and/or configurations can be used to selectively urge the valve member 16 and the housing 23 together in a different manner than a resilient member 18.

Figure 6:
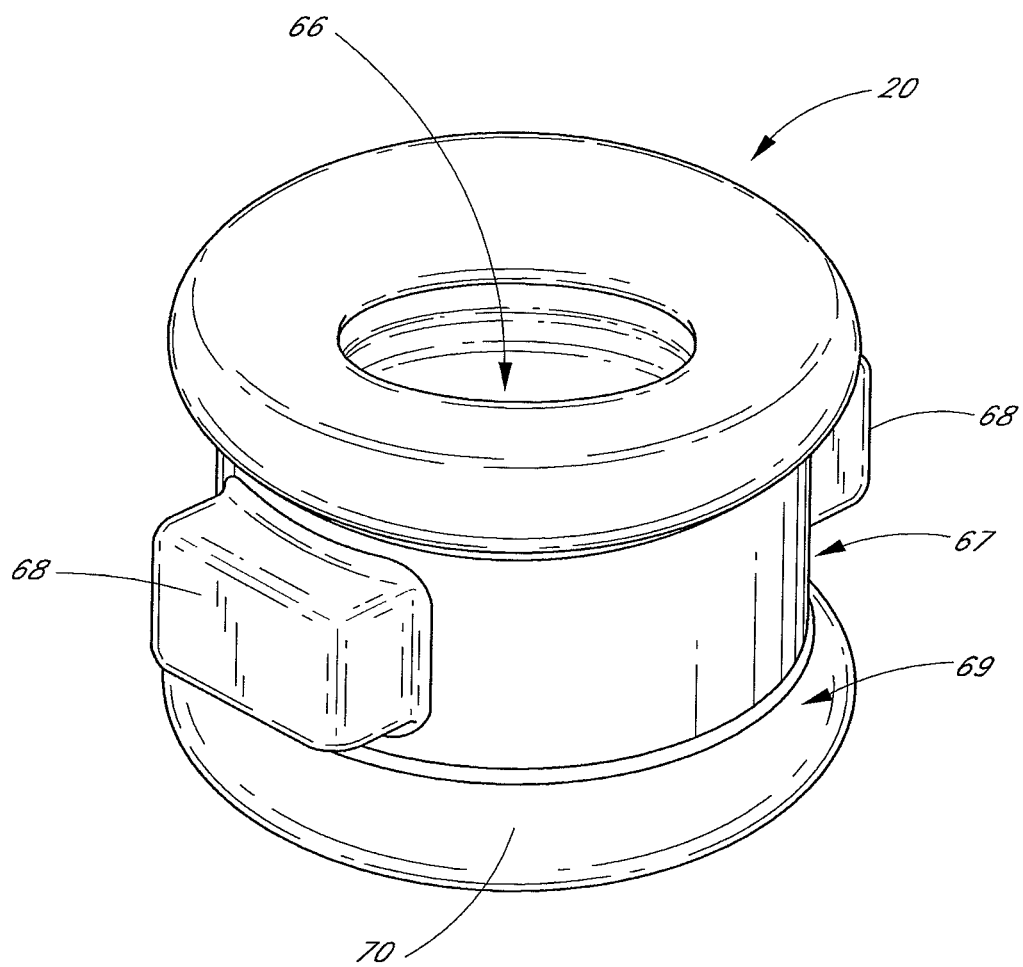
FIG. 6 shows a perspective view of a sealing portion of the connector of FIG. 2. The relative size of the sealing portion is increased in comparison with the components of the connector shown in other figures to facilitate viewing.

Turing now to FIG. 6, the sealing portion 20 is described in greater detail. In some embodiments, the sealing portion 20 is substantially cylindrical and has a bore 66 extending therethrough. In some embodiments, the sealing portion 20 further comprises a pair of generally rectangular protrusions 68 extending from the sidewalls of the cylindrical portion at diametrically opposed positions. The protrusions 68 can have different shapes and/or positions. The sealing portion 20 can also have a generally smaller-diameter middle portion 67 surrounded by two rings 69 at either end with larger diameters.

The sealing portion 20 can be constructed from a number of different materials. In some embodiments, the sealing portion 20 is made from a silicon-based deformable material 70. Silicon-based deformable materials are among those that form fluid-tight closures with plastics and other rigid polymeric materials. The sealing portion 20 can be made from the same material as the resilient member 18.

Figure 7:
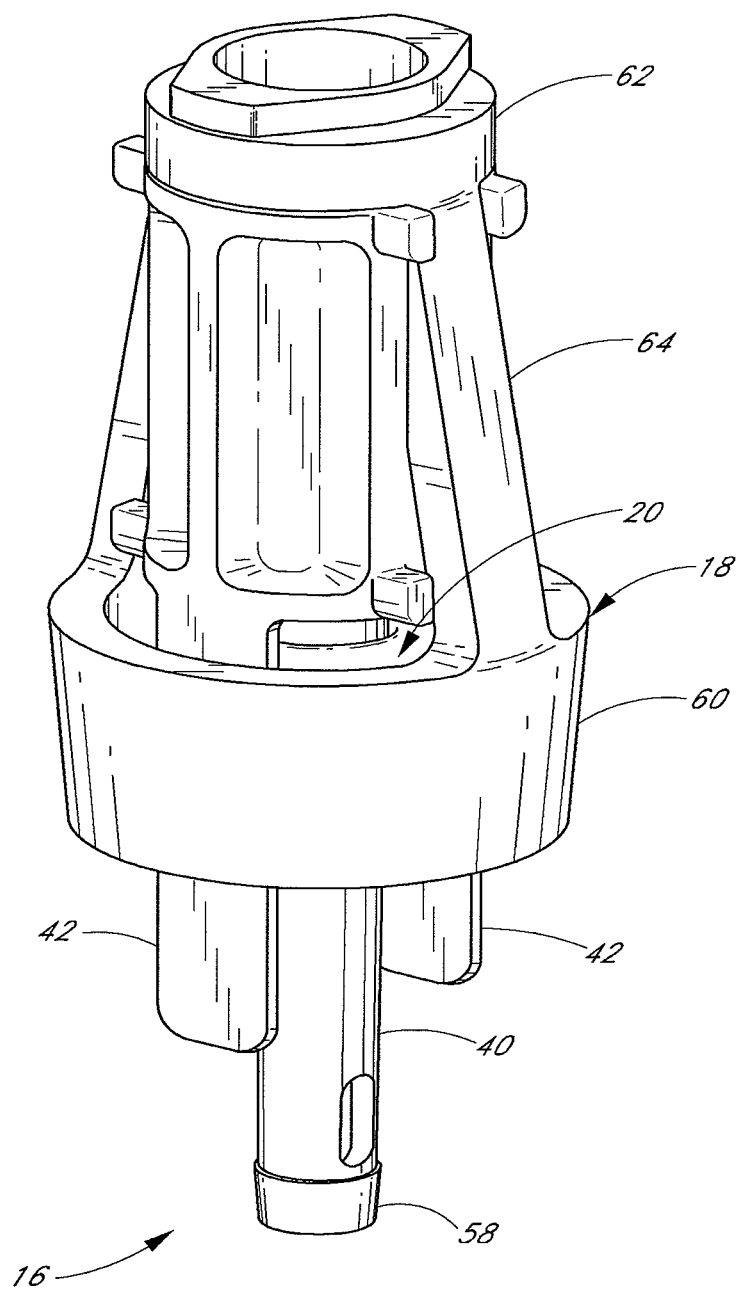
FIG. 7 shows a perspective view of certain components of the connector of FIG. 2 in a partially assembled configuration. The housing portion of FIG. 5 is not shown in FIG. 7.

In FIG. 7, certain components of the male luer 10 of an embodiment are shown. As illustrated, the housing 23 is omitted. The valve member 16, the resilient member 18, and the sealing portion 20 are shown in their respective assembled locations.

Certain interconnections between the various portions of the male luer 10 will now be discussed in further detail. As shown, the smaller ring 62 of the resilient member 18 fits within the circumferential channel 57 of the valve member 16. In some embodiments, the smaller ring 62 can be stretched until it has a larger inner diameter than the raised tabs 49 at the first end of the valve member 16. Once the small ring 62 has been advanced into position about the circular channel 57, it can be released, so that it wraps tightly about the circular channel 57, as shown.

The larger ring 60 of the resilient member 18 extends around the middle portion 32 of the housing 23 (as shown in FIG. 2), and can be stretched and positioned in a manner similar to that described above with respect to the small ring 62. The elastic members 64 of the resilient member 18 can then extend between the small ring 62 and the larger ring 60 of the resilient member 18 and preferably extend along and within the channels 46 in the valve member 16. Once located within these channels, the elastic members 64 are, in effect, trapped by the protrusions 44 along the channel outer walls. As seen in FIG. 2, the elastic members 64 can also extend along the gaps 38 in the upper housing 34 of the housing 23. The gaps 38 are generally located above the channels 46 in the illustrated embodiment. The resilient member 18 thereby provides an elastic connection between the housing 23 and valve member 16, pulling the valve member 16 into engagement with the housing 23.

The sealing portion 20, which is partially hidden by the resilient member 18 in FIG. 7, preferably fits snugly around the tube 40 and lies in between the struts 42 of the valve member 16.

Figure 8:
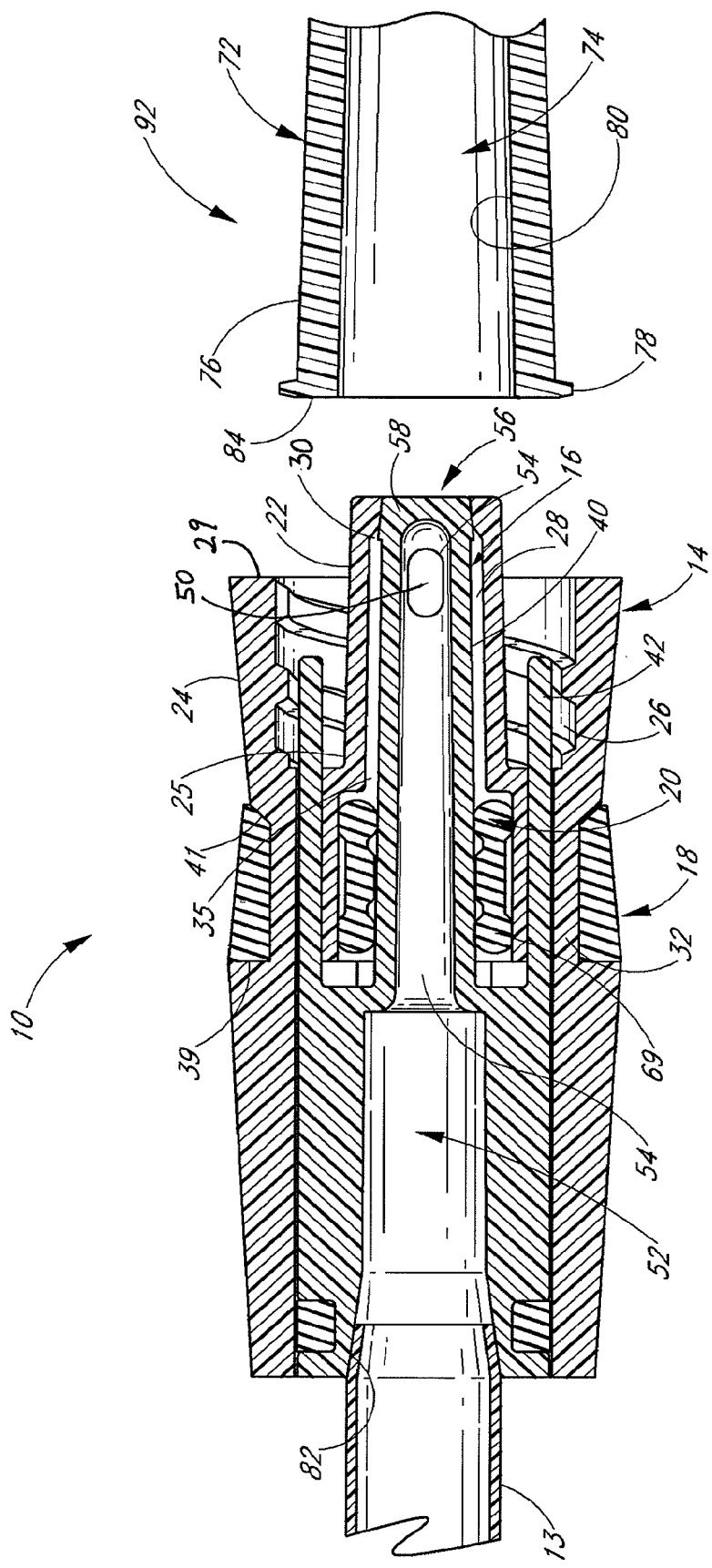
FIG. 8 shows a cross-sectional view of the connector of FIG. 2 adjacent a female portion of another medical implement. At this stage, fluid is impeded through the connector of FIG. 2.

FIG. 8 illustrates a cross-section of the male luer of the present embodiment adjacent an exemplary female connector 92. In this cross-sectional view, the interconnections and interactions between the housing 23, valve member 16 and sealing portion 20 can be seen in greater detail. The valve member 16 is configured to be positioned within the housing 23. As illustrated, the tube 40 of the valve member 16 can be inserted into and through the lumen 28. Meanwhile, the struts 42 are configured to pass through corresponding slots that extend lengthwise through the middle portion 32 of the housing 23. In an assembled configuration, the struts 42 are adjacent to the tip 22 along two sides, and the tube 40 is at least partially contained within the tip 22. The protrusions 44 are captured within the gaps 38 formed in the upper housing 34 of the housing 23.

A closing mechanism 56 is adapted to close the fluid passage 54 extending through the closable male luer 10 from fluid communication with the external environment, preferably whenever the male luer 10 is not engaged with the female connector 92. In the illustrated embodiment, the fluid passageway 54 comprises the lumen 28 as well as the passage 52 of the valve member 16. The closing mechanism 56 of the illustrated embodiment comprises both the flange section 58 of the tube 40 and the internal taper of the raised portion 30 of the lumen 28. As these two surfaces contact, they can form a closure at or near the second end 20 of the male luer 10.

The substantially matched internal tapering surfaces of the raised portion 58 of the tube 40 and the raised portion 30 of the lumen 28 assist in providing closure of the female connector 92. Preferably a relatively fluid-tight closure is formed. The engagement between the raised portions 30 and 58 can also be created in a number of other ways. In some embodiments, the material of the flange section 58 and the material of the raised portion 30 of the lumen 28 are configured to fit closely together, and are made of sufficiently compatible materials, to form a fluid-tight closure. In other embodiments, the flange section 58, and/or additional portions of the valve member 16, can be constructed from a deformable material that more closely follows the contours of the internal surface of the lumen 28, and the lumen 28 need not have a taper. The sealing portion 20 is configured, in some embodiments, to prevent fluid from escaping from within the male luer connector 10. When the valve member 16 engages the housing 23, the sealing portion 20 sits between the middle portion 32 of the housing 23 and the tube 40. When fluid flows within the lumen 28 of the housing 23 and along the outer surface of the tube 40, the fluid is prevented from flowing past the middle portion 32 by the sealing portion 20, and more particularly by the rings 69 at either end of the sealing portion 20.

The sealing portion 20 is preferably held in position between the housing 23 and valve member 16 by the protrusions 68 (see FIG. 6) configured to fit within the holes 36 in the middle portion 32 of the housing 23. The protrusions 68 help to maintain the sealing portion 20 in proper alignment.

With reference to the embodiment illustrated in FIG. 8, the structure of an exemplary female connector 92 will now be discussed in further detail. The female connector 92 can comprise an elongate body 72 having a fluid passageway 74 therethrough, and the female connector 92 can have a tip 76 near its distal end. In some embodiments, the tip 76 of the female connector 92 has a radially extending surface 78 disposed on its external surface. The female connector 92 can have a fluid conduit positioned within the female connector 92. The fluid conduit is not included or required in all female connectors compatible with the connectors 10 disclosed herein. Along a proximal inner surface 80 of the female connector 92, the fluid passageway 74 is preferably tapered such that the diameter of the fluid passageway 74 decreases in the distal direction.

As shown in FIG. 8, the housing 23, the valve member 16, the resilient member 18, and the sealing portion 20 are in an assembled configuration, in which the closing mechanism 56 forms a closing engagement between the flange section 58 and the interior of the lumen 28. In addition, the sealing portion 20 is in closing engagement between the valve member 16 and the housing 23. Fluid from the passage 52 can flow through the windows or holes 50 of the tube 40 of the valve member 16. In this position, the windows 50 communicate with the interior of the tip 22, but not yet with the external environment. The lumen 28 is closed at its second end by the closing mechanism 56 and at its first end by the sealing portion 20.

As shown in FIG. 8, the struts 42 of the valve member 16 extend through slots in the housing 23 such that their ends extend to positions near the end of the shroud 24 toward the second end of the connector. These struts 42 are configured to engage the proximal ends 84 of the female connector 92 as the female connector 92 advances into engagement with the closeable male luer 10.

In FIG. 8, the male and female luers are shown in an unengaged configuration. To engage the male luer 10 and female connector 92, the radially extending surface 78 of the female connector 92 are screwed into the inner threads 26 of the male luer 10.

Figure 9:
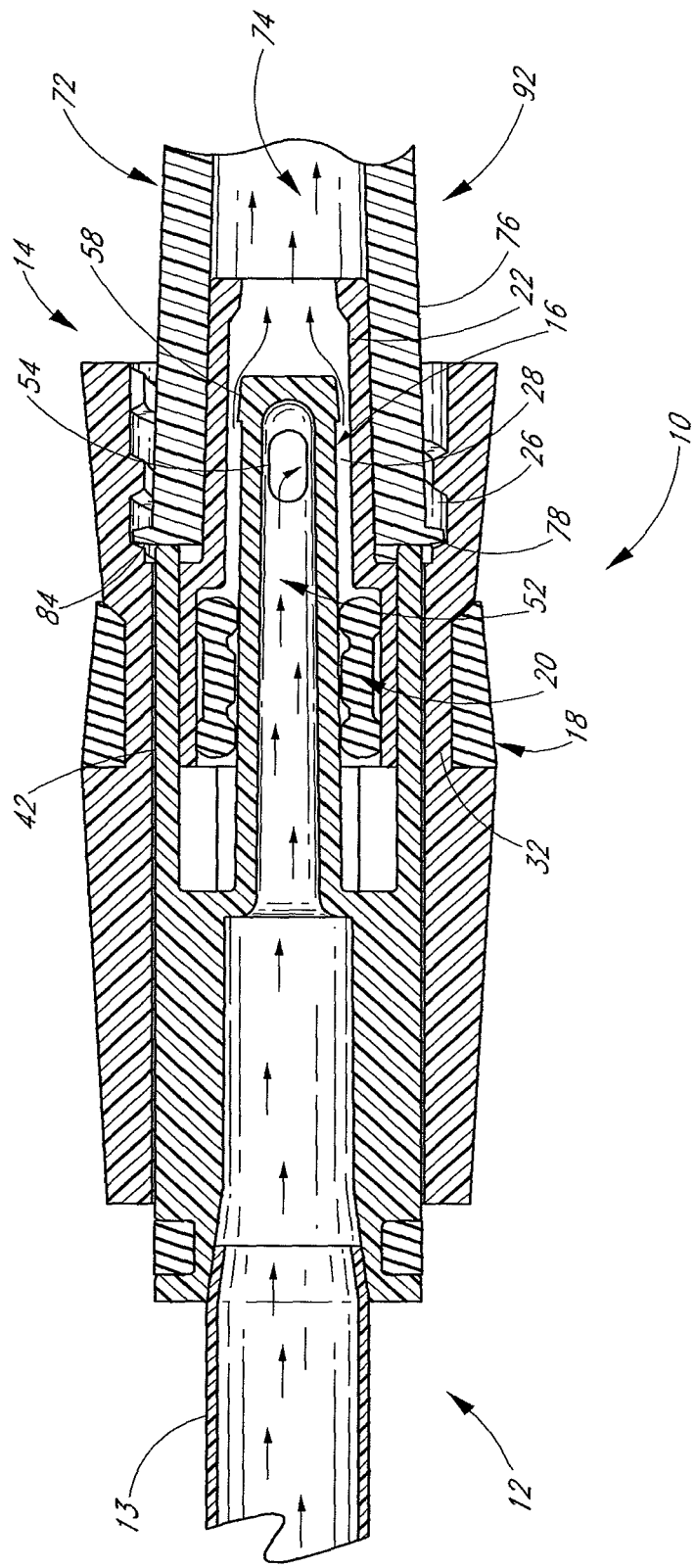
FIG. 9 shows a cross-sectional view of the connector of FIG. 2 in engagement with the medical implement of FIG. 8. Fluid is flowing through the engaged connectors.

As shown in FIG. 9, the two luers can be threadedly engaged towards one another until the taper of the inner surface 80 of the female connector 92 lies adjacent the correspondingly tapered external surface of the tip 22. In other embodiments, the two luers can be threadedly engaged until the second end of the tip 22 forms a closure with a corresponding surface (not shown) of the female connector 92.

As the male luer connector 10 and female connector 92 move towards each other into threaded engagement, the proximal end 84 of the tip of the female connector 92 contacts the struts 42 of the valve member 16. As the male luer connector 10 and female connector 92 move further into threaded engagement, the struts 42, and thereby the valve member 16, are moved in the direction of the first end of the male connector by the female connector 92, displacing the valve member 16 relative to the housing 23. Thus, the flange section 58 moves from the second end of the tip 22 of the housing 23 towards the first end of the male connector. As these two tapered surfaces separate, a space forms between the valve member 16 and the housing 23 and fluid is allowed to pass through the hole 30' into the fluid passageway 74 of the female connector 92, or vice versa. When used with some embodiments of the female connector 92, an internal fluid conduit contacts the second end of the valve member 16 before the housing of the female connector 92 contacts the struts 42 to open the male connector 10. In some embodiments, the closure remains intact until the inner surface 80 of the tip of the female connector 92 has formed a closing engagement with the outer surface of the tip 22 of the male luer 10. Thus, the passage 54 of the male luer 10 need not be in fluid communication with the external environment.

As the valve member 16 moves relative to the housing 23, the elastic members 64 (not shown in FIG. 9) of the resilient member 18 distend and exert a restoring force. As long as the female connector 92 engages the male luer 10, this restoring force can be resisted by the radially extending surface 78 of the female connector 92 contacting the inner threads 26 of the housing 23. However, when the female connector 92 is withdrawn from the male luer 10, the resilient member 18 returns the valve element of the valve member 16 to closing engagement with the lumen 28.

Despite the relative movement between the housing 23 and the valve member 16, the sealing portion 20 preferably maintains a fluid barrier between the outer surface of the tube 40 and the inner surface of the lumen 28. In some embodiments, the position of the sealing portion 20 is maintained by the protrusions 68. In other embodiments, the sealing portion 20 can be positioned by gluing the outer surface of the deformable material 70 to the inner surface of the lumen 28 of the housing 23. Other means of fixing the sealing portion 20 can also be used.

As shown in FIG. 9, in the opened configuration, the fluid passageway 74 of the female connector 92 can fluidly communicate with the passage 52 of the valve member 16. Fluid can thereby flow from tubing 13 attached to the male luer 10, into the passage 52 of the valve member 16, through the windows 50 into the lumen 28, out from the lumen 28 through the hole 30' at the second end of the tip 22 into the fluid passageway 74 of the female connector 92, and vice versa. Fluid is prevented from escaping the male luer 10 through the gap between the housing 23 and valve member 16 by the sealing portion 20. A fluid-tight closure can also be formed between corresponding tapers of the tip 22 of the housing 23 and the inner surface 80 of the female connector 92.

Figure 10:
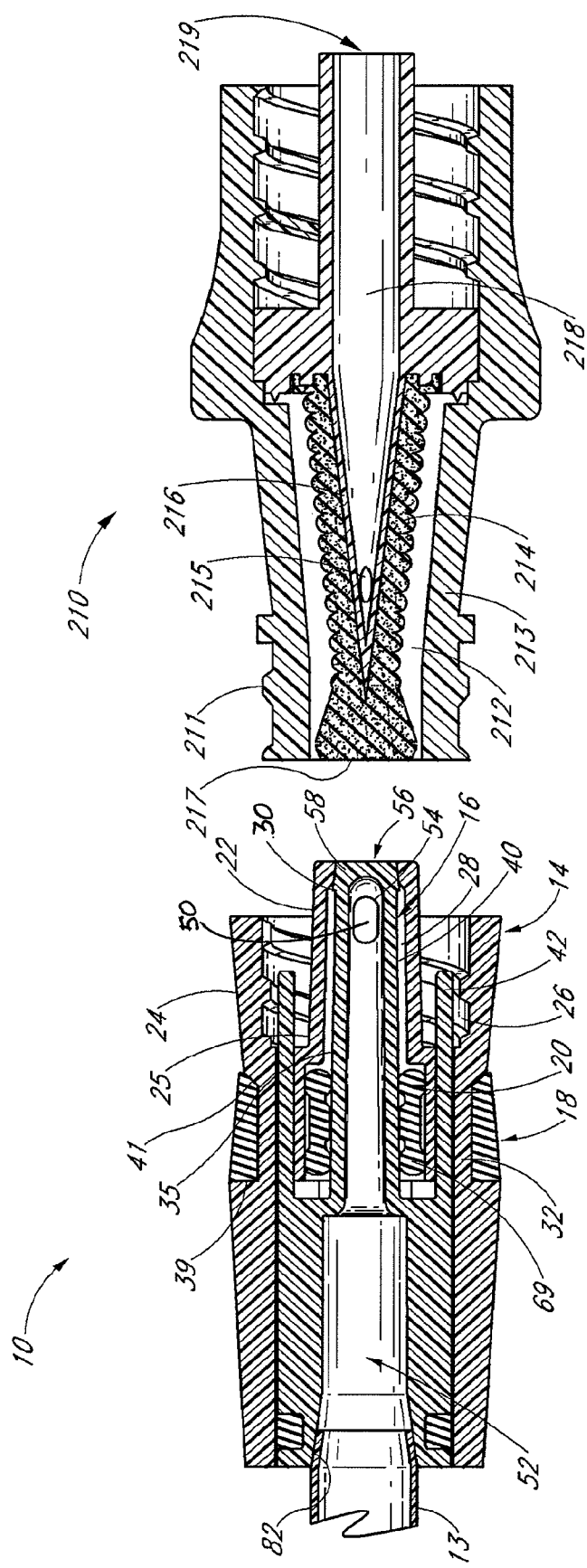
FIG. 10 shows a cross-sectional view of the connector of FIG. 2 adjacent another medical implement with a closeable female luer connector. At this stage, fluid is impeded through the connector of FIG. 2 and the female luer connector.

Turning to FIG. 10, the connector 10 is displayed adjacent to a closeable female luer connector 210. In the sample embodiment illustrated here, the closeable female luer connector 210 comprises an outer housing 213, a void space 212, a fluid passageway 218, a fluid conduit 216 with one or more holes 215, a compressible seal element 214 with a proximal surface 217, and a threaded engagement region 211. The closeable female connector 210 is positioned with its proximal end adjacent the second end 56 of the male connector 10. The threaded engagement region 211 of the closeable female connector 210 can conform to standard sizing for luer connectors, such as those that meet ANSI standards. The compressible seal element 214 can be composed of water-impermeable, resilient material which can reduce in size when a force is exerted upon it. The fluid conduit 216 can be composed of a rigid material, such as polycarbonate plastic, which is capable of resisting deformation when a force sufficient to compress the seal element 214 is exerted upon the closeable female connector 210.

The fluid passageway 218 can place the fluid conduit 216 in fluid communication with the second end 219 of the closeable female connector 210. At least one hole 215 in the fluid conduit 216 can be sealed by the compressible seal element 214 to prevent the fluid passageway 218 from being in fluid communication with the void space 212 between the compressible seal element 214 and the inner wall of the housing 213 and/or with the exterior of the housing 213. The hole or holes 215 can be sized appropriately small enough to permit fluid to pass between the fluid passageway 218 and the void space 212 at an appropriate flow rate. One such size for the hole or holes 215 is approximately 1 mm in diameter, although irregular shapes and other sizes can be used. Holes of at least about 1 mm or approximately 1 mm-3 mm, or less than about 1 mm can also be used. The connector 10 can be engaged with a tubing 13 containing a fluid.

Figure 11:
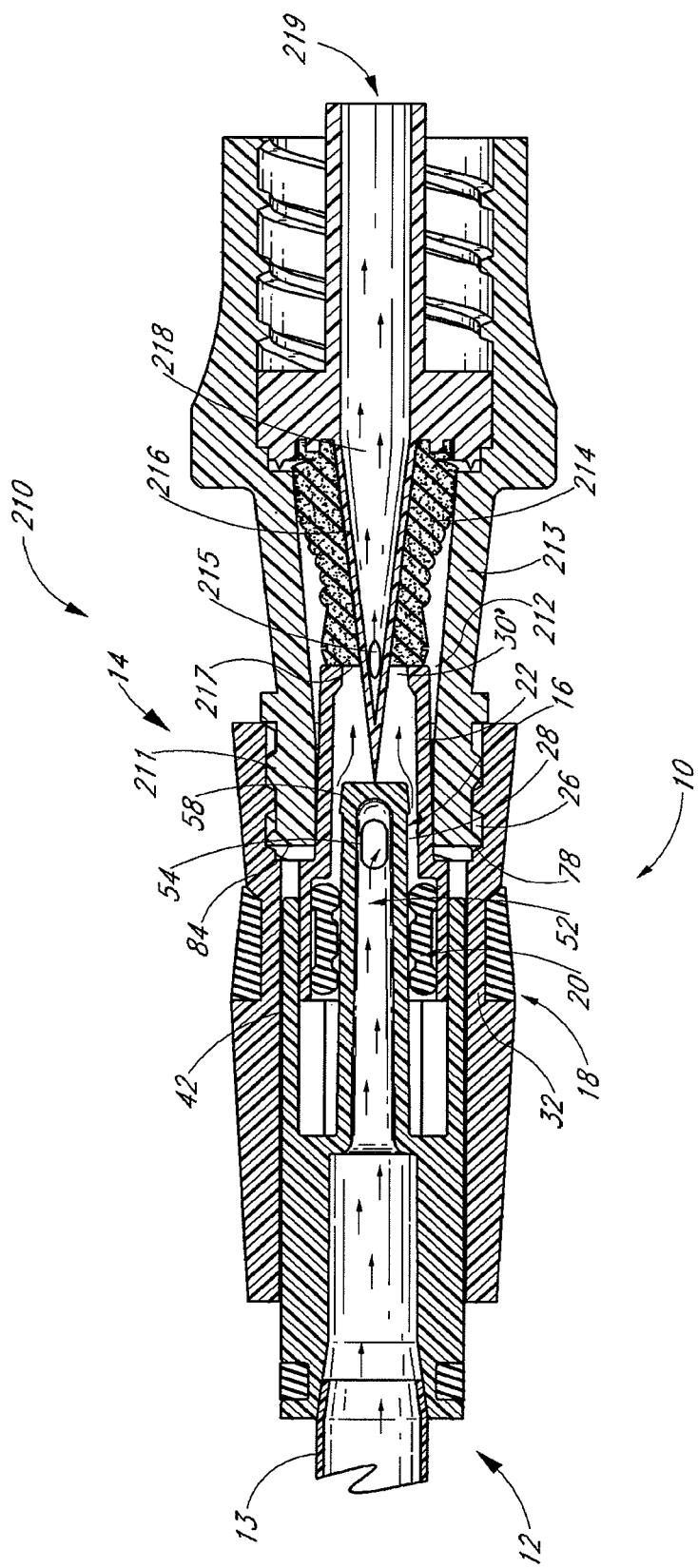
FIG. 11 shows a cross-sectional view of the connectors of FIG. 10 after engagement. Fluid is flowing through the engaged connectors.

With reference to FIG. 11, the connector 10 can be threadedly engaged with the closeable female connector 210. The threaded region 211 of the closeable female connector 210 can engage with the inner threads 26 of the male connector 10 to engage the connectors 10, 210, as illustrated. In the illustrated engagement, the luer tip 22 advances into the closeable female connector 210 by compressing the compressible seal element 214. As can be seen, the luer tip 22 contacts the compressible seal element 214 on the proximal surface 217 of the compressible seal element 214. The force exerted to engage the connectors 10, 210 and to engage the threaded regions 26, 211 is sufficient to compress the seal element 214 to expose the holes 215 in the fluid conduit 216. With the seal element 214 compressed, the fluid passageway 218 is in fluid communication with the interior space of the luer tip 22.

As the luer tip 22 advances further into the closeable female connector 210, the fluid conduit 216 contacts the end of the valve member 16 towards the second end of the male connector. The valve member 16 is displaced towards the first end of the male connector by the contact and continued advancement of the luer tip 22. The resilient member 18 exerts a closing force in a direction towards the second end of the male connector on the valve member 16. As a result, the tip of the valve member 16 towards the second end of the male connector generally maintains contact with the fluid conduit 216 throughout the engagement. As the valve member is moved in a direction towards the first end of the male connector, the flange section 58 of the valve member 16 separates from the interior surface of the housing 23 through which the hole 30' passes. As a result, the windows 50 are opened to fluid communication with the closeable female connector 210. The compressed seal element 214 inhibits fluid flow into the interior of the closeable female connector 210 beyond the luer tip 22. In this configuration, fluid can flow from the tubing 13 at the end of the valve member 16 toward the second end of the male connector and into the tube 40 through the windows 50 into the interior of the lumen 28, out the hole 30' in the luer tip 22, into the interior of the outer housing 213 of the closeable female connector 210, in the holes 215 of the fluid conduit 216 and into the fluid channel 217 in the interior of the fluid conduit 216. Thus, the second end of the connector 210 is placed in fluid communication with the proximal end 219 of the closeable female connector 210. Additionally, the sealing portion 20 preferably maintains a fluid barrier between the outer surface of the tube 40 and the inner surface of the lumen 28, confining the flow of fluid towards the closeable female connector 210. When the surface of the valve member towards the second end of the connector is directly contacted by a female connector member such as the fluid conduit 216, the struts 42 may not be engaged by the female connector.

The connectors 10, 210 can be threadedly disengaged. During disengagement, the force exerted by the resilient member 18 can return the connector 10 to its pre-engaged state by directing the valve member 16 to engage the flange section 58 of the end of the valve member 16 toward the second end of the male connector with the internal surface of the luer tip 22. Likewise, the resilient material of which the compressible seal is composed can return to its shape in the closed position, and the proximal surface 217 can seal the proximal tip of the closeable female connector 210.

Figure 12:
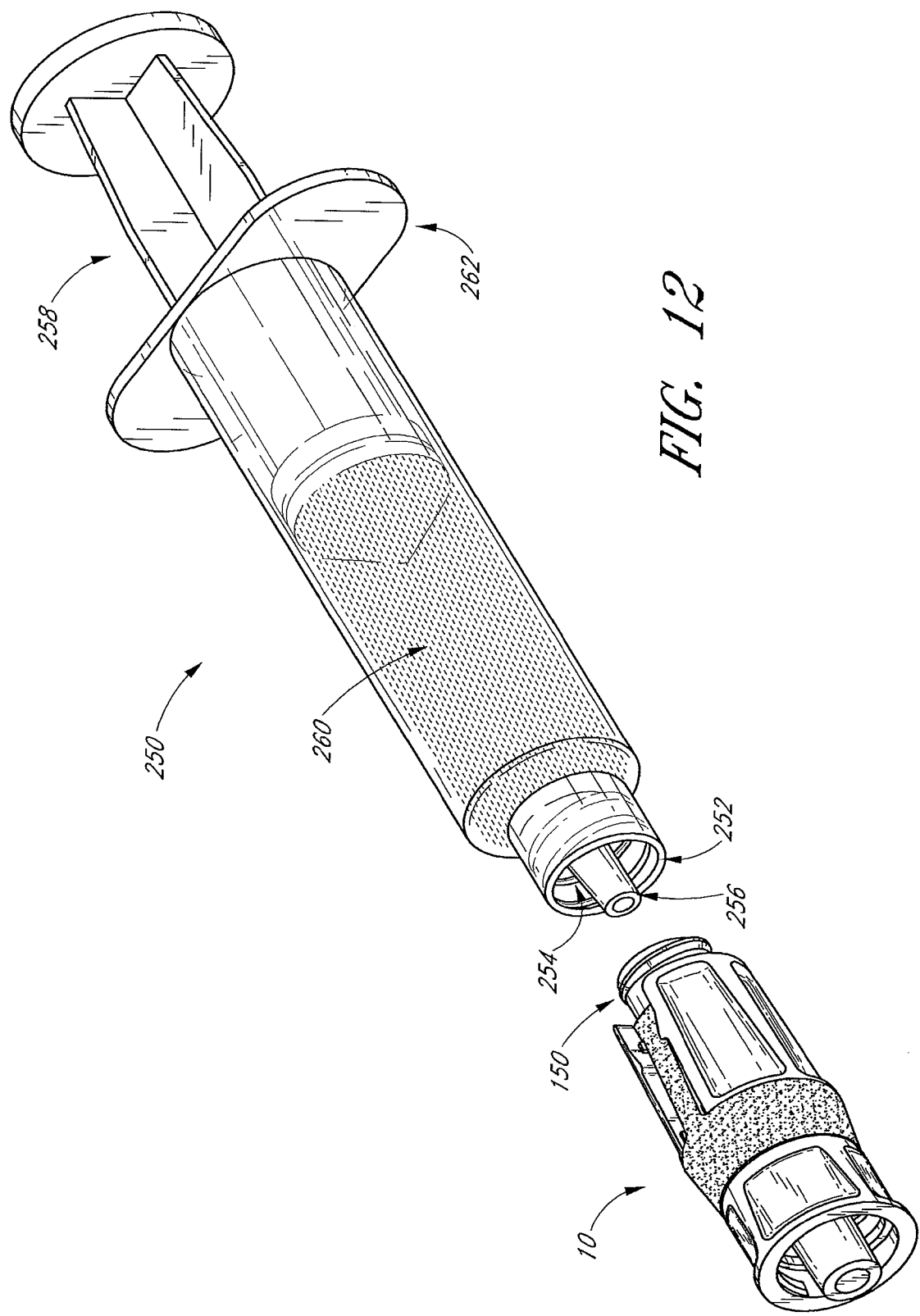
FIG. 12 shows a perspective of the connector of FIG. 2 adjacent a syringe with a male luer tip. At this stage, fluid is impeded through the connector.

Referring now to FIG. 12, the connector 10 can be engaged with a syringe 250. In FIG. 12, the syringe 250 and connector 10 are displayed adjacent to each other. The syringe can comprise a male luer connector 252, a plunger 258, a reservoir 260, and convenient finger anchors 262. The luer connector 252 can further comprise an internally threaded shroud 254 and a syringe luer tip 256. In the illustrated embodiment of the connector 10, a threaded surface 150 is disposed on the outside surface of the first end of the valve member 16.

Figure 13:
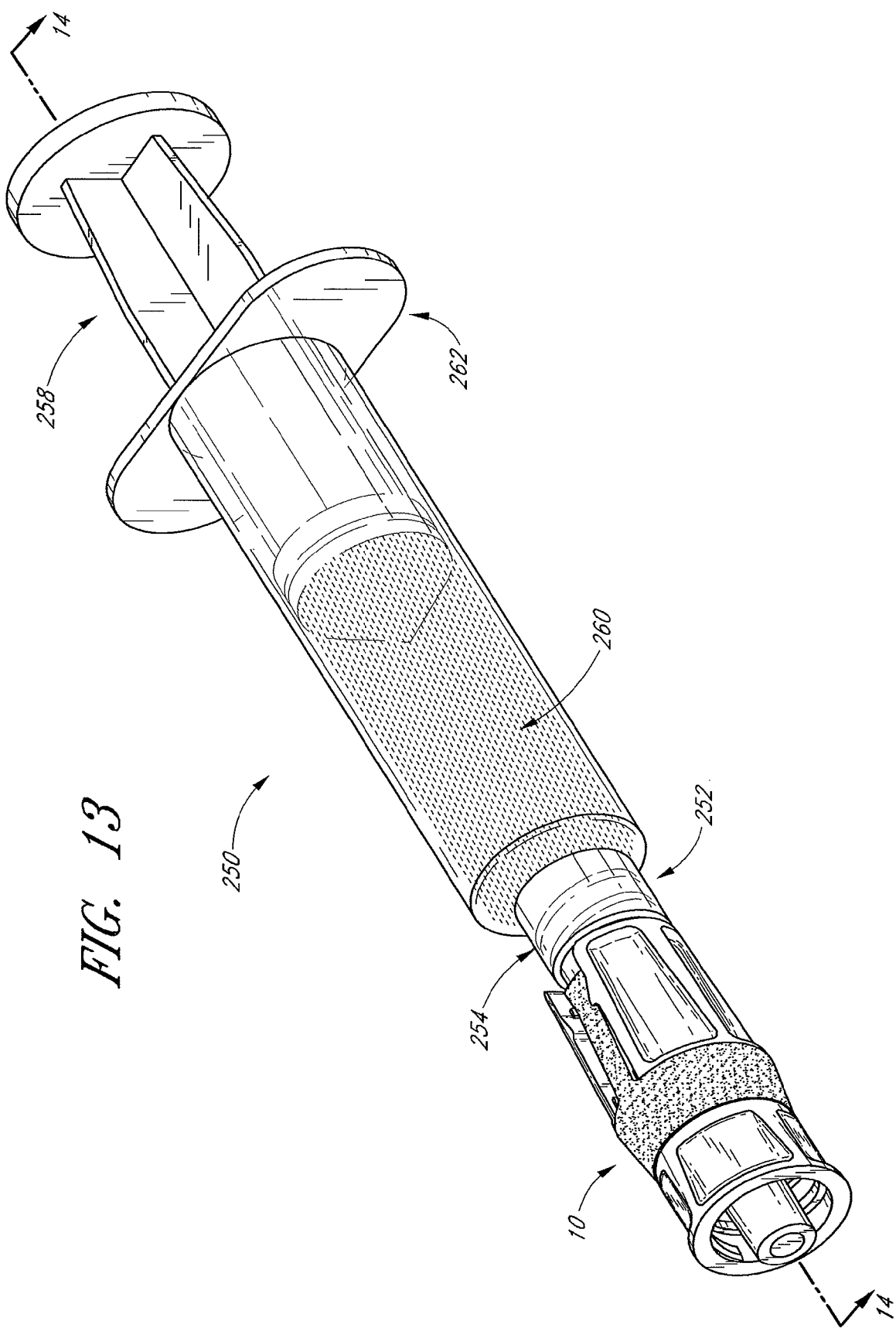
FIG. 13 shows a perspective view of the components of FIG. 12 after engagement. At this stage, fluid is still impeded through the connector.

With reference now to FIG. 13, the connector 10 can be threadedly engaged with the syringe 250. The shroud 254 can engage with the end 16 of the valve member toward the first end of the connector to connect the connector 10 to the syringe 250. The reservoir 260 of the syringe 250 can be placed in fluid communication with the tube 40 interior to the valve member 16.

Figure 14:
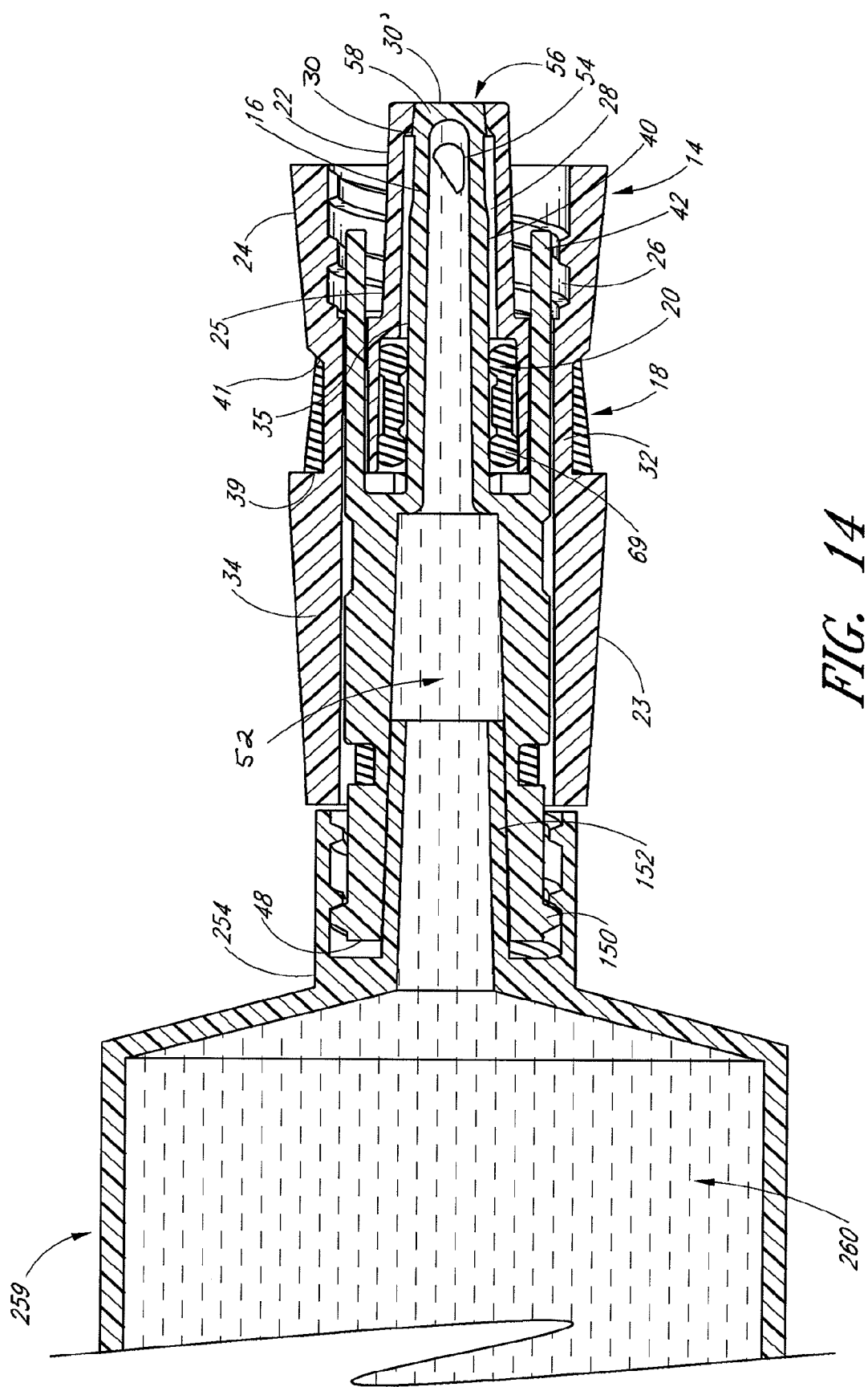
FIG. 14 shows a cross-sectional view of the connector and the male luer tip of the syringe of FIG. 13.

Turning to FIG. 14, the engagement illustrated in FIG. 13 is shown in a cross-sectional view. The syringe 250 is threadedly engaged with the connector 10 by the engagement between the shroud 254 and the threaded surface 150 of the valve member 16. The luer tip 252 of the syringe 250 is extended into the tube 40 of the valve member 16. The reservoir 260 of the syringe, shown here with a fluid in the reservoir 260, is in fluid communication with the interior of the valve member 16. The fluid can pass through the tube 40 and towards the luer tip 22 of the connector 10. In the illustrated embodiment, the fluid cannot exit the connector 10 out its male luer tip 22 because the flange section 58 is in contact with the interior surface of the lumen 28. Accordingly, the hole 30' in the tip of the housing 23 towards the second end of the connector is blocked by the valve member 16. In order for the syringe 250 and connector 10 to transition from the stage shown in FIG. 12 to the stage shown in FIG. 14, the valve member 16 may need to be temporarily opened to release air (as described in more detail below).

Figure 15:
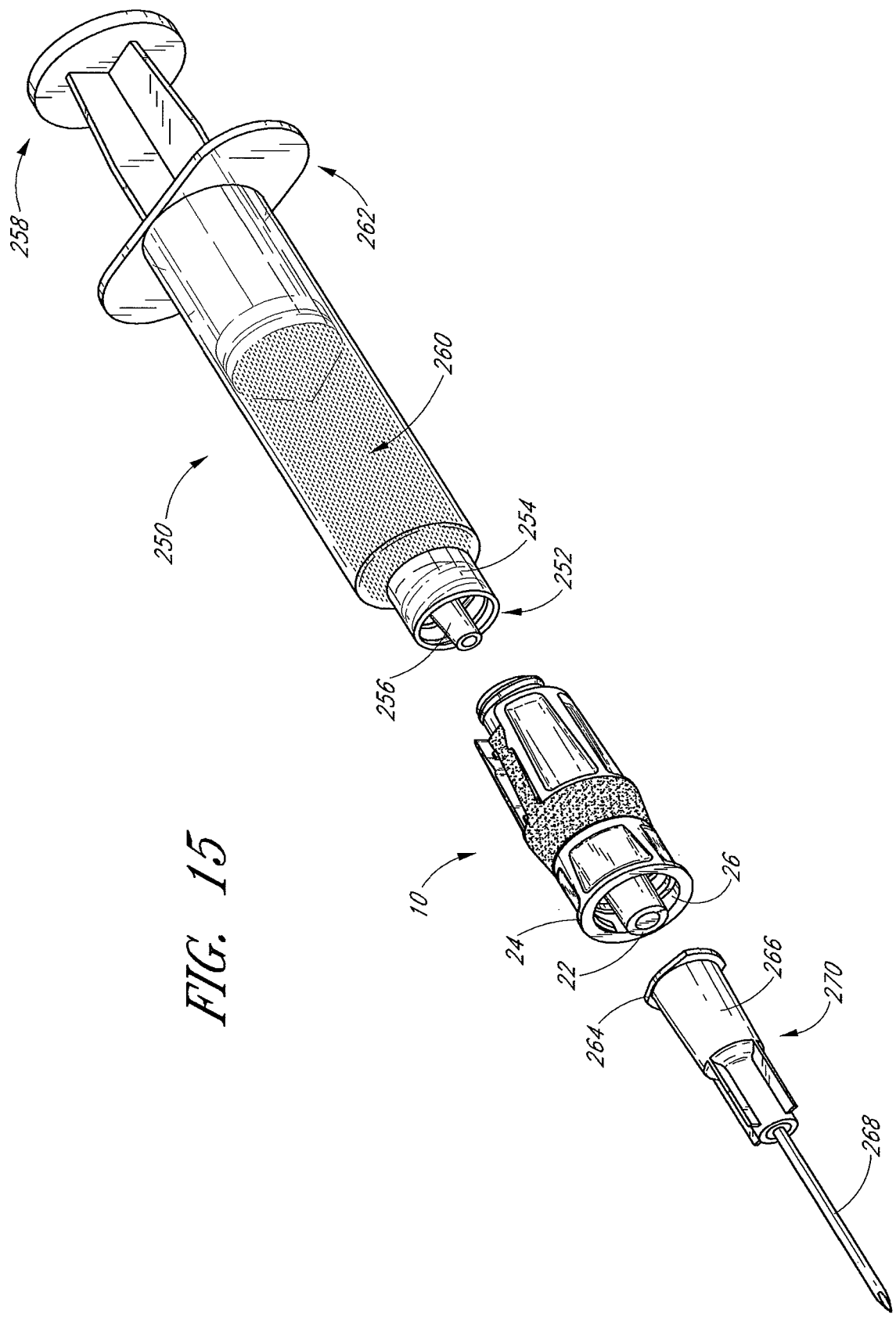
FIG. 15 shows a perspective view of the a closeable male luer connector located with its first end adjacent a syringe with a male luer tip and with its second end located adjacent a hypodermic needle with a female luer attachment portion.

Referring to FIG. 15, the connector 10 is shown adjacent to and between a syringe 250 and a hypodermic needle with sheath 270. The syringe 250, like that of FIG. 12, can comprise a male luer connector 252, a plunger 258, a reservoir 260, and convenient finger anchors 262. The luer connector 252 can further comprise an internally threaded shroud 254 and a syringe luer tip 256. The needle with sheath 270 can comprise a housing 266 with raised tabs 264 on the engagement end and a needle 268.

Figure 16:
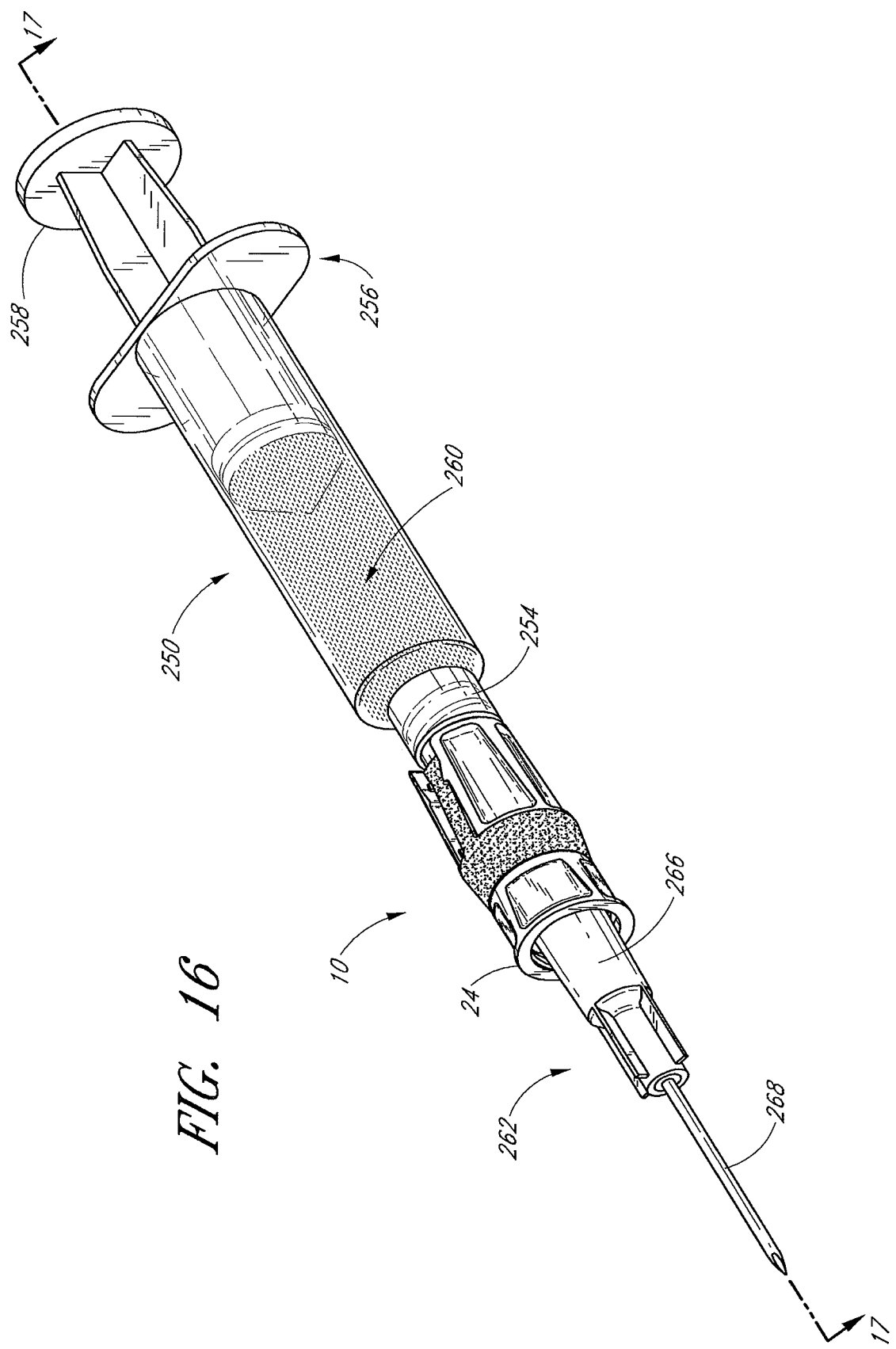
FIG. 16 shows a perspective view of the components of FIG. 15 in engagement. At this stage, fluid can flow through the connector.

With reference to FIG. 16, the connector 10 is shown threadedly engaged with both the syringe 250 and needle with sheath 270. The threaded surface 150 of the valve member 16 of the connector 10 can engage with the threaded shroud 154 of the syringe 250. Accordingly, the luer tip 256 can protrude into the tube 40 of the valve member 16. Similarly, the raised tabs 264 can engage with the inner threads 26 of the shroud 24 of the connector 10. The luer tip 22 of the connector 10 can protrude into the housing 266 of the needle sheath.

Figure 17:
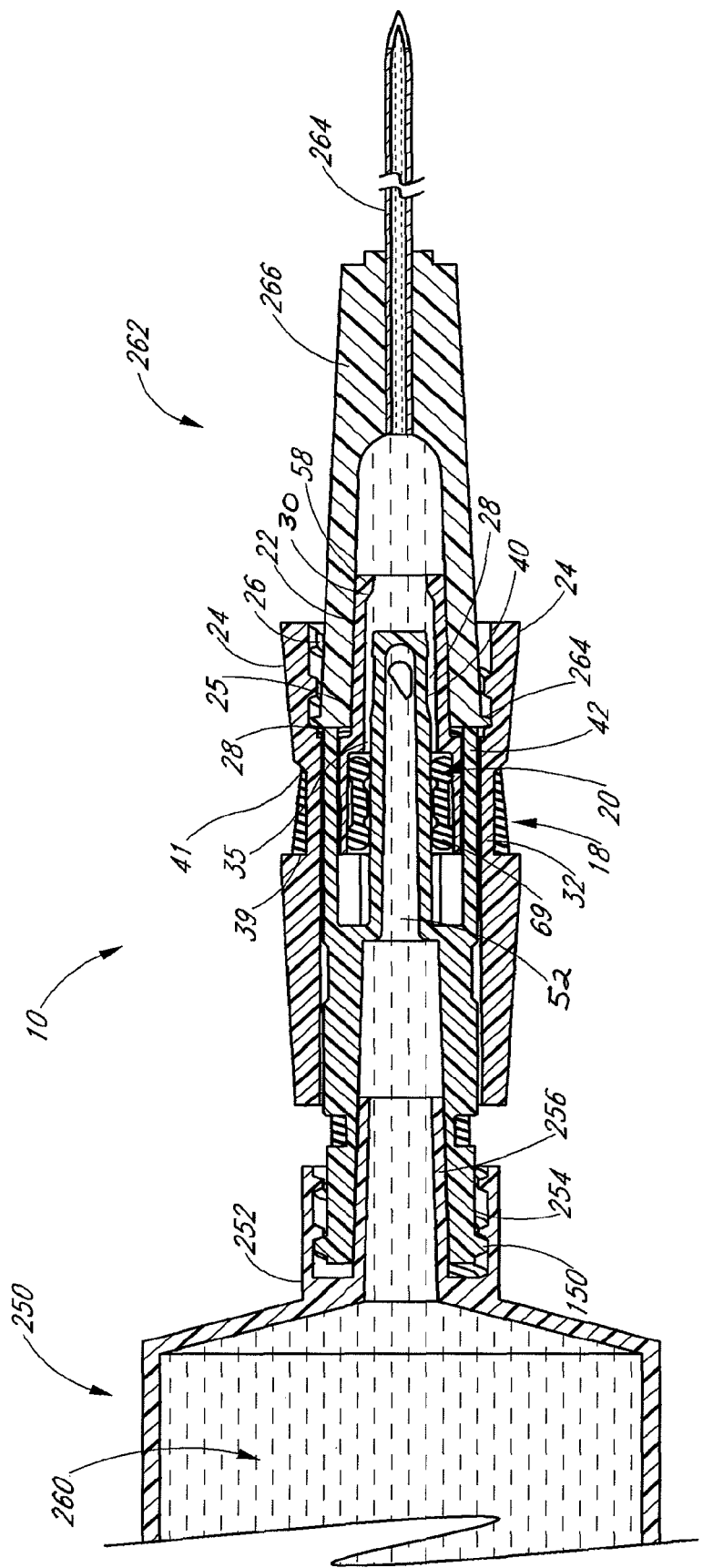
FIG. 17 is a cross-sectional view of the connector, male luer tip of the syringe, and hypodermic needle of FIG. 16. At this stage, fluid can flow through the connector.

In FIG. 17, the engagement shown in FIG. 16 is illustrated in a cross-sectional view. The connector 10 is engaged by a syringe 250 and a needle with a sheath 270. The syringe 250 is threadedly engaged with the threaded surface 150 of the valve member 16 of the connector 10. The needle with sheath 270 is threadedly engaged with the inner threads 26 of the shroud 24.

The luer tip 256 of the syringe 250 protrudes into the tube 40 of the valve member 16. The reservoir 260 of the syringe 250 is in fluid communication with the tube 40 of the valve member 16 through the luer tip 256.

The connector 10 is engaged with the needle with a sheath 270. The housing 266 of the needle with sheath 270 has raised tabs 264 near its proximal end. The raised tabs 264 threadedly engage the inner threads 26 of the shroud 24 of the connector 10. As the luer tip 22 advances into the housing 266 of the needle 268, the proximal end of the housing 266 can contact the struts 42 of the valve member 16. When the needle with sheath 270 is fully engaged with the connector 10, the valve member 16 has been displaced a distance which separates the flange section 58 from the tapered interior wall of the lumen 28 sufficiently to permit fluid to flow out the windows 54 of the valve portion 16. The fluid can then flow out the hole 30: in the end of the luer tip 22 and into the housing 266 of the needle with sheath 270. The hollow needle 268 permits the fluid to flow from within the housing 266 out the distal tip of the needle 268. The sealing portion 20 preferably maintains a fluid barrier between the outer surface of the tube 40 and the inner surface of the lumen 28, confining the fluid in the lumen and the direction of flow toward the hole 30' in the luer tip 22. Thus, at this stage, the syringe 250 is in fluid communication with the distal tip of the needle 268. As was previously illustrated in FIGS. 13 and 14, in some embodiments, the connector 10 will generally not permit fluid to flow out of the syringe 250 without a component engaged with the second end 14 of the connector 10. The component illustrated in FIGS. 15-17 is a needle with a sheath 270; however, other components, such as those which permit fluid flow and possess a female luer engagement portion, can also be used.

Figure 18A:
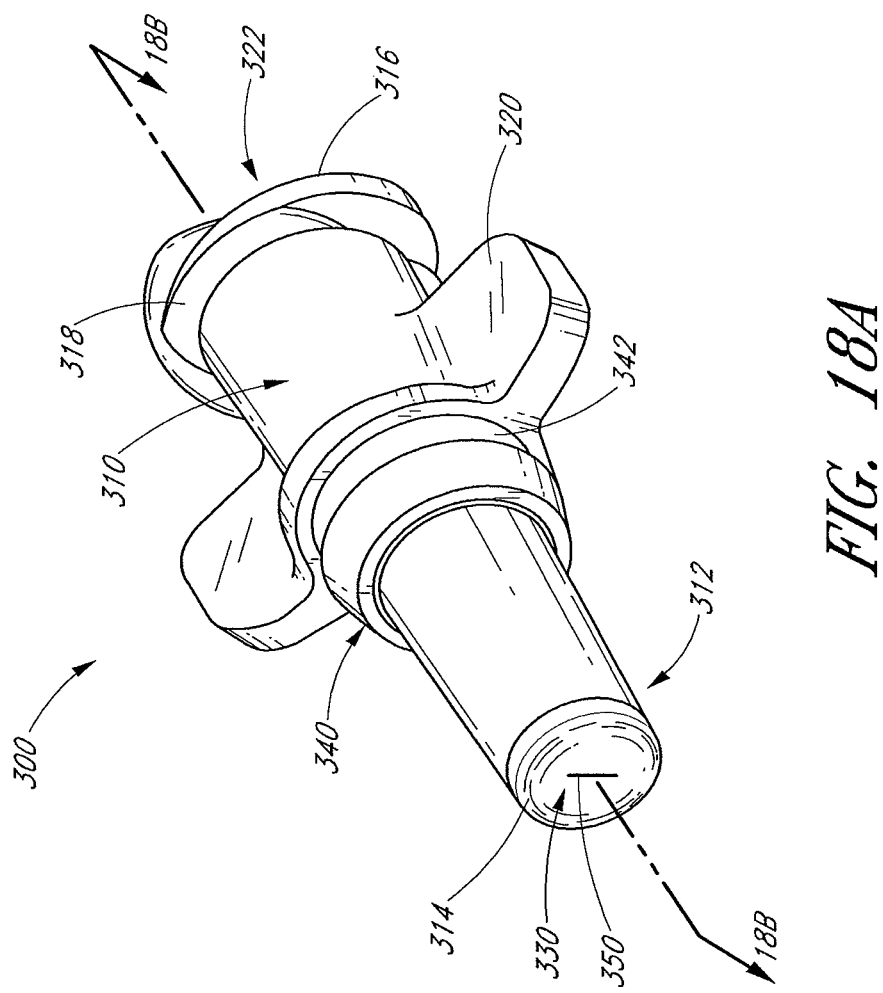
FIG. 18A is a perspective view of another embodiment of a closeable male luer connector.

FIG. 18A displays a perspective view of another embodiment of a closeable male luer. The rotatable connector 300 is comprised of a housing 310, an internal passageway 322 and a seal element 330. The housing is further comprised of a luer tip 312, a luer receiver 316 at the first end of the connector 300, an engagement portion 318, a manipulation portion 320, and a raised portion 340. The seal element 330 can have an opening 350 along its face 314 in a transverse direction. The internal passageway 322 can extend from the luer receiver 316 to the luer tip 312. The housing 310 can be composed of a water-impermeable material, such as a polycarbonate plastic. The housing 310 can also be composed of a hydrophobic plastic. Other examples of materials suitable for construction of the housing 310 are glassed-filled GE Valox 420 or polypropylene. Depending on the application, many other materials can also be used.

The housing 310 illustrated is configured to receive a male luer tip at the luer receiver 316 by threadedly engaging the male luer at its engagement portion 318. The receiver 316 can conform to ANSI standards for a luer receiver. The illustrated manipulation portion 320 has two tabs extending radially from the central axis of the housing 310. The manipulation portion 320 is configured to aid the user in grasping and rotating the connector 300.

The housing 310 illustrated is also constructed to provide a closeable male luer at its second end. The luer tip 312 at the second end can be constructed to ANSI standards for a male luer tip. The luer tip joins the main body of the housing 310 at the raised portion 340. The raised portion 340 is constructed to inhibit the luer tip 312 from advancing too far into a luer receiver. The housing 310 can also have a recessed portion 342 behind the raised portion 340. The luer tip 312 can also have a seal element 330 which has a face 314 towards the second end of the connector. The seal element 330 can be any water-impermeable, resilient material, including without limitation, silicone. The selection of the material for construction of the seal can be accomplished by one skilled in the art. The luer tip 312 can taper smaller in a direction from the raised portion 340 as it approaches its second end.

The seal element 330 can also have an opening 350 in the face 314 toward the second end of the connector prior to engagement with any other component. The opening 350 can be a slit in a transverse direction to the longitudinal axis of the housing 310. The opening 350 can be centered across the face 314, or located in another position on the face 314. The seal element 330 can cover the entire second end of the luer tip 312, or only a portion thereof. The seal element 330 can be attached to the housing by an overmolding process, among other attachment methods. In such an overmolding process, the housing 310 can be formed by injection molding in a first step, and then in a second step, the housing 310 can be re-inserted into a mold (or remain in a mold) and an appropriately sized molding pin (not shown) can be inserted through a wider end of the housing 310, such as the second end. Silicone material can then be injected into the mold to form the seal element 330. In other embodiments, the seal element 330 can be glued or otherwise adhered into the housing 310.

As can be seen from the illustrated embodiment in FIG. 18A, the seal element 330 can inhibit fluid from flowing through the housing 310 when the luer tip 312 is not engaged with another component. Thus, when a fluid-containing component (not shown) with a male luer connector is connected to the luer receiver 316, the connector 300 can be used to control flow of fluid through its luer tip 312. For example, when a fluid-containing component such as a syringe is engaged with the connector 300, fluid is permitted to fill the housing 310 of the connector 300 by flowing through the internal passageway 322, but the seal element 330 can substantially inhibit flow of fluid out the luer tip 312. If the interior space of the housing is filled with air or another gas before the fluid enters, the connector 300 may need to be opened to allow the air or other gas to escape before the fluid can enter. In some embodiments, as described in detail below, the internal surface of the seal element 330 can be adapted to increase the resistance against the widening of the opening 350, which could allow fluid to escape when the fluid (not shown) exerts a pressure against the seal element 330 from the internal passageway 322. Thus, the connector 300 inhibits flow of fluid from a fluid-bearing component when the connector 300 is attached to the male luer of the fluid-bearing component without another component connected to the luer tip 312 of the connector 300.

In some modes of use, the opening 350 on the face 314 of the seal element 330, normally closed in the position shown, can be opened when the luer tip 312 comes in contact with a suitable female connector, such as a Clave® connector sold by ICU Medical, San Clemente, Calif. An illustrated engagement of this configuration is discussed in detail below. The engagement can be achieved in many other ways, and with many other structures, including connectors other than the Clave® connector.

Figure 18B:
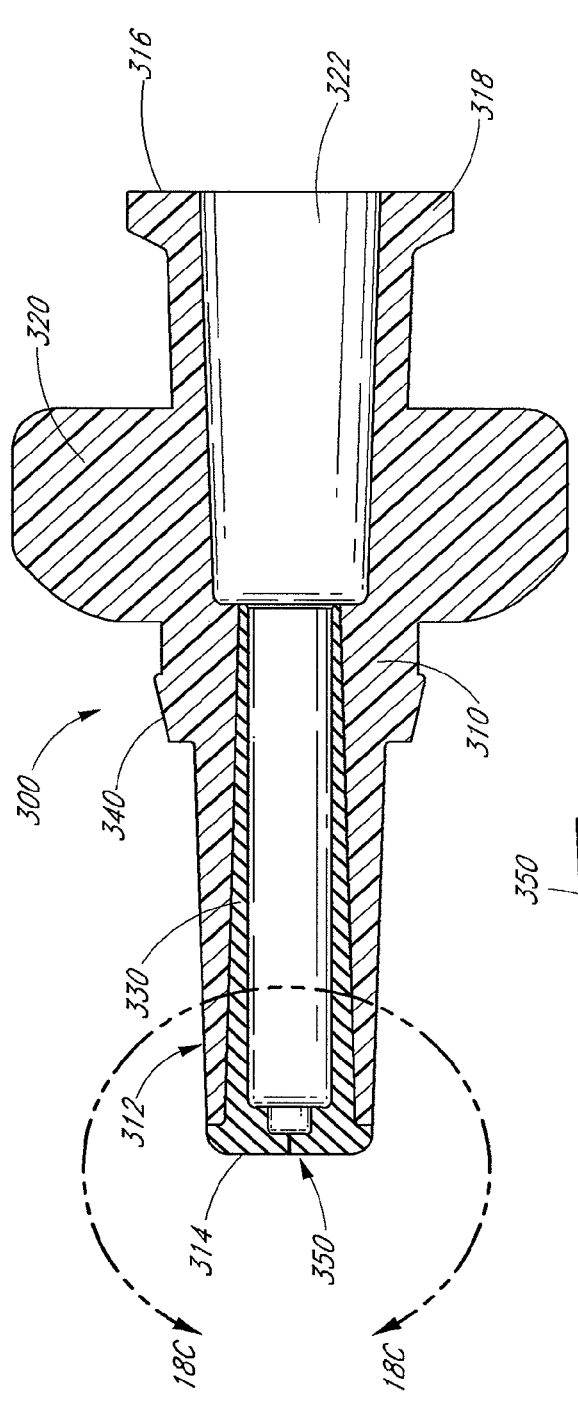
FIG. 18B is a cross-sectional view of the connector of FIG. 18A.

FIG. 18B is a cross-sectional view of the connector 300 illustrated in FIG. 18A. The connector 300 can have an internal passageway 322 which connects the luer receiver 316 to the luer tip 312. The engagement portion 318 can be configured to receive an internally threaded shroud of a male luer connector (see FIG. 19). The manipulating portion 320 can extend radially away from the internal passageway 322, as shown. The seal element 330 can extend along at least part of the internal passageway 322, and can be disposed across at least part of the second end of the connector 300. The seal element 330 can extend beyond the end of the luer tip 312. The seal element 330 can have a cross-sectional area approximately equal to the housing 310 at the end of the luer tip 312. In those embodiments where the luer tip 312 and seal element 330 are generally circular, the outside diameter of the seal element 330 can be equal to the outside diameter of the luer tip 312. The seal element 330 is not confined to a circular shape (nor are any other structures disclosed herein), and other shapes can be used. In other embodiments, the seal element 330 does not extend beyond the end of the housing 310 towards the second end of the connector 300, but can have a maximum outer dimension equal to that of the inner dimension of the luer tip 312. The seal element 330 can have a closing portion 324. The closing portion 324 can permit fluid flow through the seal element 330 of the connector 300, but is biased to generally close the opening 350 in the seal element 330. The structure of the closing portion 324 can be adapted to resist permitting fluid (not shown) from exiting the opening 350 when the luer tip 312 is not engaged with another component, as described in further detail below.

Figure 18C:
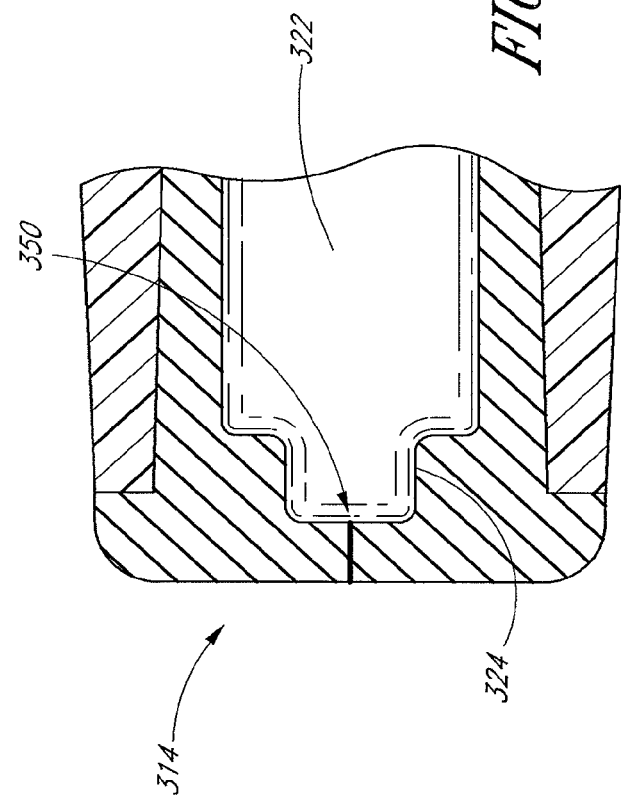
FIG. 18C is a detail of the cross-sectional view of the connector of FIG. 18A.

As can be seen in FIG. 18C, which is a detail of the cross-sectional view presented in FIG. 18B, the seal element 330 can comprise the entire face of the second end of the connector 300. In other embodiments, the seal element 330 may not extend beyond the housing 300. The internal passageway 322 can extend to the seal at the second end of the connector 300.

Figure 19:
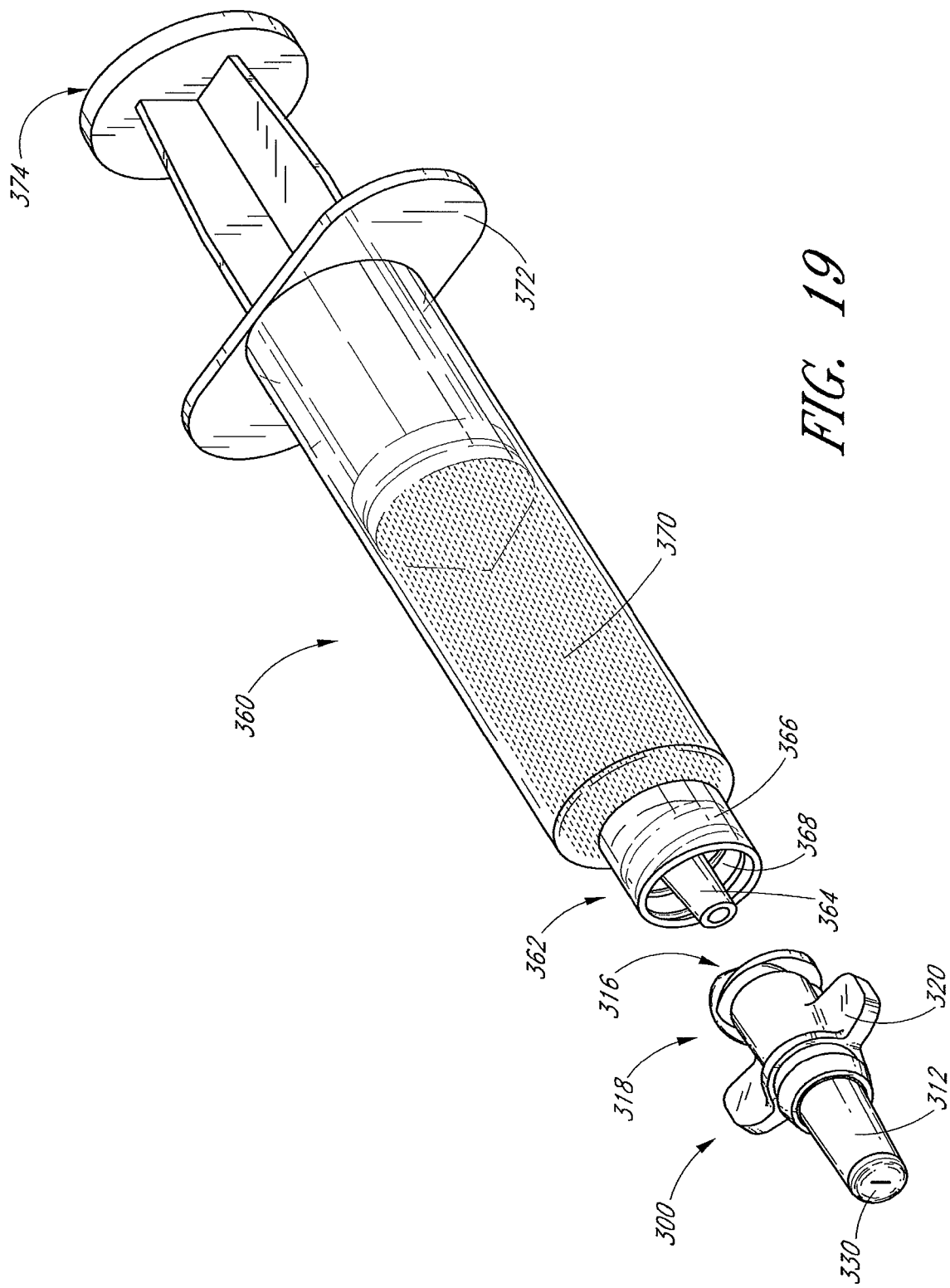
FIG. 19 is a perspective view of the connector of FIG. 18A located adjacent a syringe with a male luer tip.

FIG. 19 illustrates a perspective view of the connector 300 adjacent a syringe 360. As in previous descriptions, the syringe can comprise a male luer connector 362, a fluid reservoir 370, a plunger 374, and finger anchors 372. The luer receiver 316 of the connector 300, which can be of appropriate size and shape to engage with standard luer connectors, is positioned to receive the luer tip 364 of the syringe 360. The internal threads 368 of the shroud 364 of the syringe 360 are properly aligned to threadedly connect with the engagement portion 318. In this way, the receiver 316 can engage the luer connector 362 and connect the connector 300 to the syringe 360. Before engagement of the syringe 360 with the connector 300, the fluid within the reservoir 370 is not inhibited from exiting the luer tip 364 by any physical component.

Figure 20:
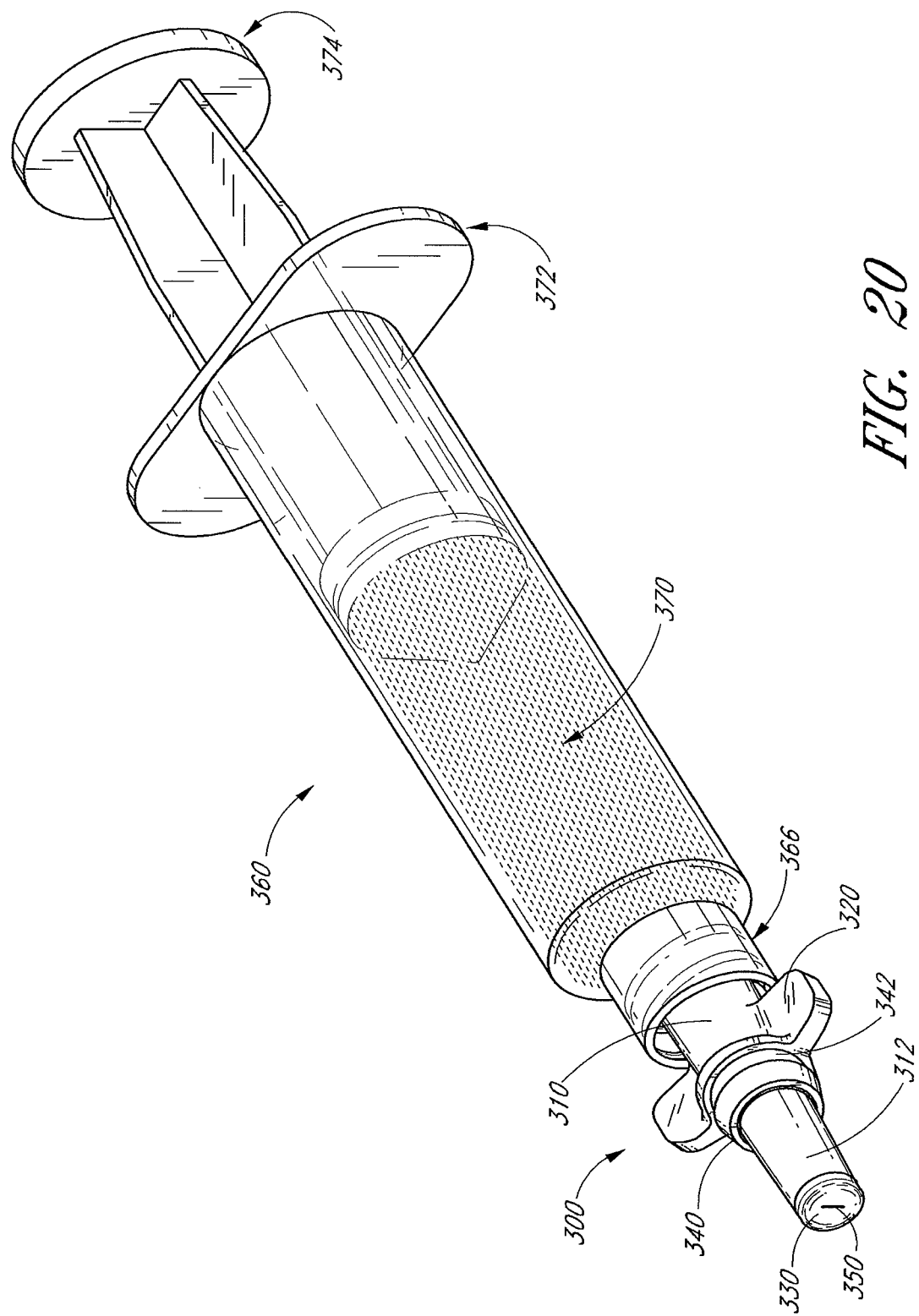
FIG. 20 is a perspective view of the components of FIG. 19 in engagement.

Referring now to FIG. 20, a perspective view of the connector 300 threadedly connected to a syringe 360 is shown. The connector 300 can be connected to the syringe 360, or other medical implement, by many other means, such as glue, adhesive, solvent, ultrasonic welding, epoxy, interference fits, mechanical connections, and/or unitary constructions. The receiver 316 (not shown) contains at least part of the luer tip 364 of the syringe 360. The luer tip 364 extends at least partially into the internal passageway 322. The threaded engagement portion 318 is engaged with the internal threads 368 of the shroud 364 of the syringe 360. Fluid from the reservoir 370 can then flow freely within the housing 310 of the connector 300, by way of the internal passageway 322. If the interior space of the housing is filled with air or another gas before the fluid enters, the connector 300 can be opened to allow the air or other gas to escape before the fluid can enter. In some cases, the housing 310 of the connector 300 may be filled with a gas, such as air. Before the fluid enters the housing 310, the connector may need to be opened to allow the gas to escape before the fluid can flow. The seal element 330 inhibits fluid from leaving the connector 300. The luer tip 312 of the connector 300 can be used to connect the connector-syringe 300, 360 combination to other components for controlled fluid transfer. The connector 300 can also be formed integrally with the syringe 360 (not shown), such that the housing 310 of the connector is formed by the fluid-delivery end of the syringe. During use of this combination connector-syringe, the male luer tip 312 of the connector 300 can, in effect, replace the luer tip 364 of the syringe for connection purposes.

Certain medications, such as chemotherapy medications, are contact toxins, and avoiding exposure to the skin is desirable. Such medications are often stored in a syringe with a hypodermic needle, such as depicted in FIGS. 15 and 16. Under certain conditions, without the use of a closeable male luer connector, it can be possible for the toxic fluid to flow out of the syringe. Even if steps are taken to avoid accidental fluid flow, such as orienting the syringe with attached needle such that gravity aids the retention of the medication within the syringe, the medication can also vaporize and seep out of the hypodermic needle in a gaseous state. The use of a closeable male luer between the syringe and hypodermic needle inhibits the uncontrolled flow of medication, in both liquid and gaseous states. Accordingly, risk of accidental exposure to such toxic medications is minimized.

Figure 21:
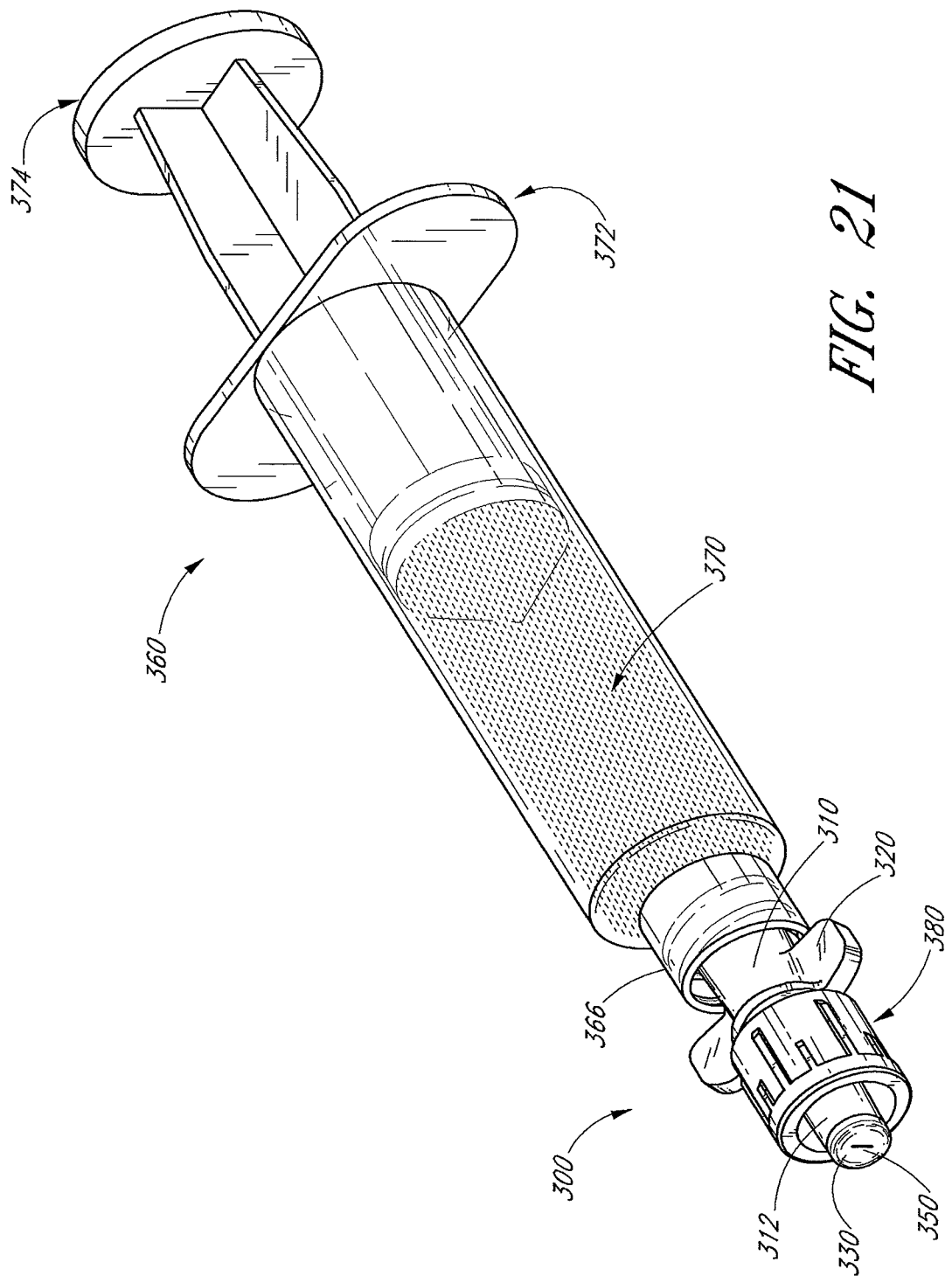
FIG. 21 is a perspective view of another embodiment of a closeable male luer connector engaged with a syringe with a male tip.

Referring now to FIG. 21, the closeable male luer connector 300 is illustrated in another embodiment, wherein an internally threaded shroud 380 is disposed on the housing 310. The shroud 380 at least partially or entirely encircles the housing 310 at approximately the recessed portion 342 (visible in FIG. 18A). In some embodiments, the shroud 380 is not attached to the connector 300, and instead can rotate freely about the longitudinal axis of the connector 300. The raised portion 340 (visible in FIG. 18A) can inhibit the movement of the shroud 380 towards the luer tip 312 of the connector 300. Additionally, the manipulation portion 320 of the connector 300 can inhibit the movement of the shroud 380 towards the luer receiver 316. The shroud 380 can be threaded consistent with ANSI specifications for luer connectors. The shroud 380 can assist the luer tip 312 in forming a connection between the connector 300 and other components (not shown).

Figure 22A:
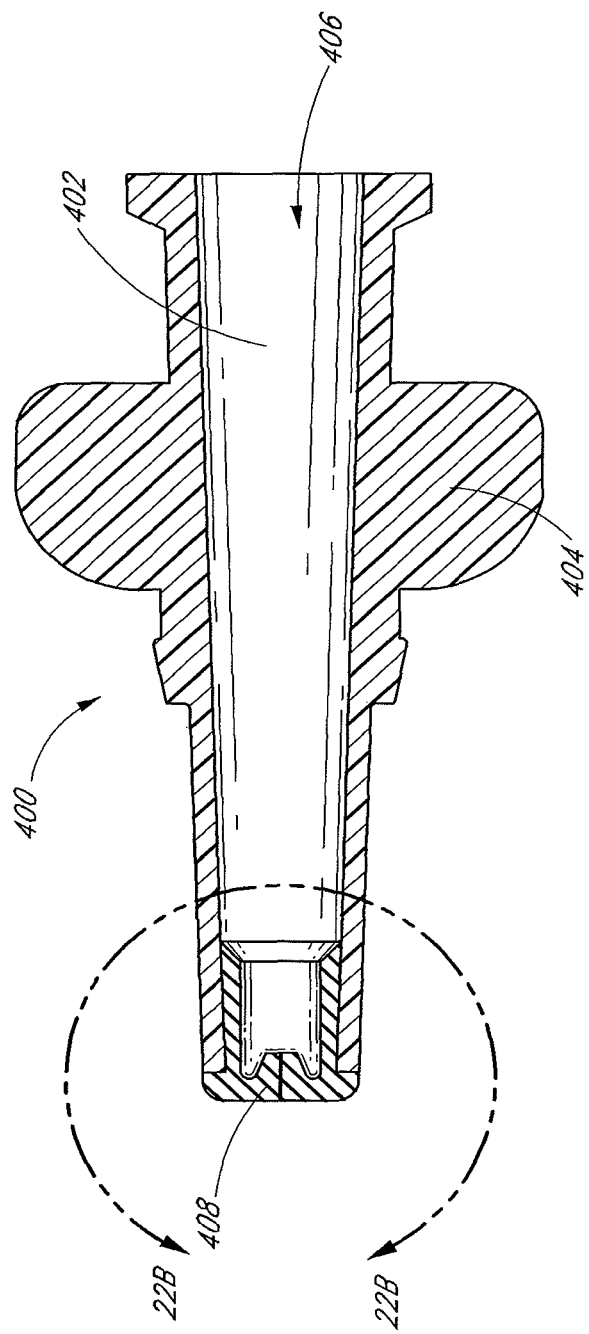
FIG. 22A is a cross-sectional view of another embodiment of a closeable male luer connector.

With reference now to FIG. 22A, the cross-section of a closeable male luer connector 400 with a continuously tapering internal passageway 402 is illustrated. The housing's 404 tapering internal passageway 402 permits for varied injection molding techniques of manufacture. For example, if the taper is wider at an end with a luer receiver 406, a molding pin can be tapered in a corresponding manner to closely fit against the wall of the internal passageway 402, producing a seal 408 that is shorter than the seal illustrated in FIG. 18B.

Figure 22B:
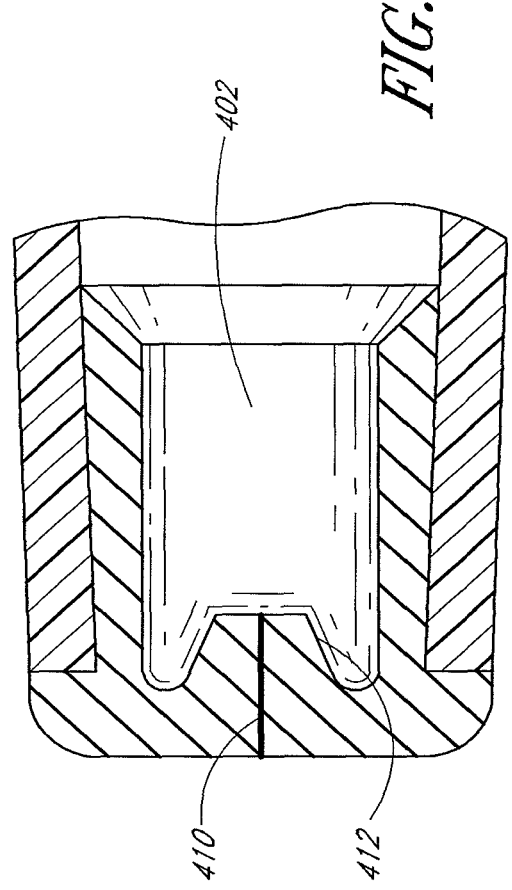
FIG. 22B is a detail of the cross-sectional view of the connector of FIG. 22A.

With reference to FIG. 22B, the seal 408 in the illustrated embodiment has a closing portion 412 similar to that of the closing portion 324 in FIG. 18B. In addition, the internal surface of the seal 408 can be adapted to increase resistance against permitting fluid from exiting the opening 410 when a fluid (not shown) in the internal passageway 402 exerts a pressure against the seal 408. The internal surface of the closing portion 412 can include slanted surfaces against which such fluid presses to urge the opening 410 more tightly closed.

Turning to FIG. 23A, a side view of another embodiment of the connector 400 of FIG. 22A is displayed. An internally threaded shroud 420 is disposed about the outer surface of the housing 404.

As can be seen in FIG. 23B, the housing 404 can have a raised portion 424 which inhibits axial movement of the shroud 420 toward the luer tip 416. The housing 404 can also have a manipulation portion 418 which extends radially outwardly from the longitudinal axis of the connector 400. The housing 404 also has an internal passageway 428 extending from the luer receiver 414 to the seal element 430. The manipulation portion 418 can inhibit movement of the shroud towards the luer receiver 414 of the connector 400. The manipulation portion can also be a convenient place for the user to place his or her fingers while turning the connector 400. Additionally, there can be a recessed portion 426 of the connector 400. The recessed portion 426 can be a portion of the connector 400 with a smaller outer diameter than the outer diameter of the raised portion 424 or the manipulation portion 418. The shroud 420 can be disposed on the connector 400 such that a narrow portion of the shroud 420 encircles the connector 400 about the recessed portion 426. The shroud 420 can be unaffixed to the housing 404 and thus free to rotate. The internal threads 422 of the shroud can conform to ANSI standards for luer connectors, allowing the shroud to assist the luer tip 416 in engaging the female connector of another component (not shown).

Figure 23C:
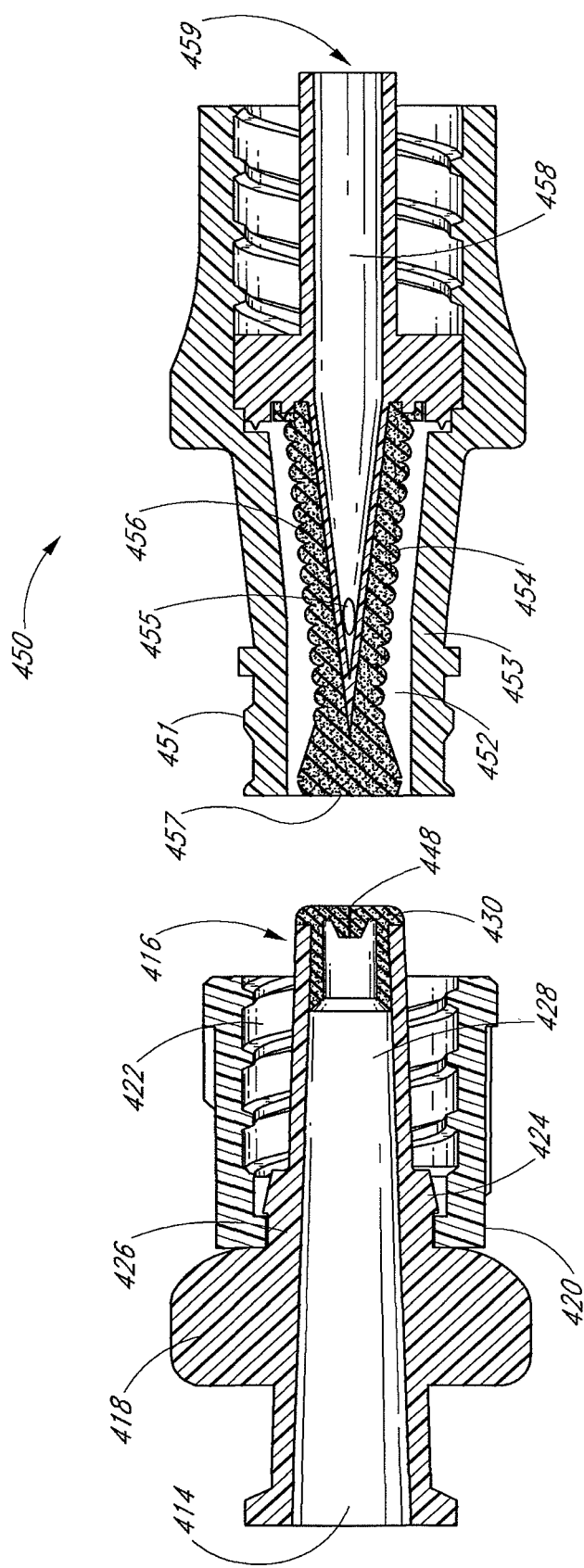
FIG. 23C is a perspective view an embodiment of a closeable male luer connector adjacent a closeable female connector. At this stage, fluid flow is impeded through the female luer connector.

FIG. 23C depicts the closeable male luer connector 400 of FIG. 23B in the proximity to a suitable female connector 450, such as a Clave® connector sold by ICU Medical, San Clemente, Calif. The female connector 450 is similar to that illustrated in FIG. 10.

Figure 23D:
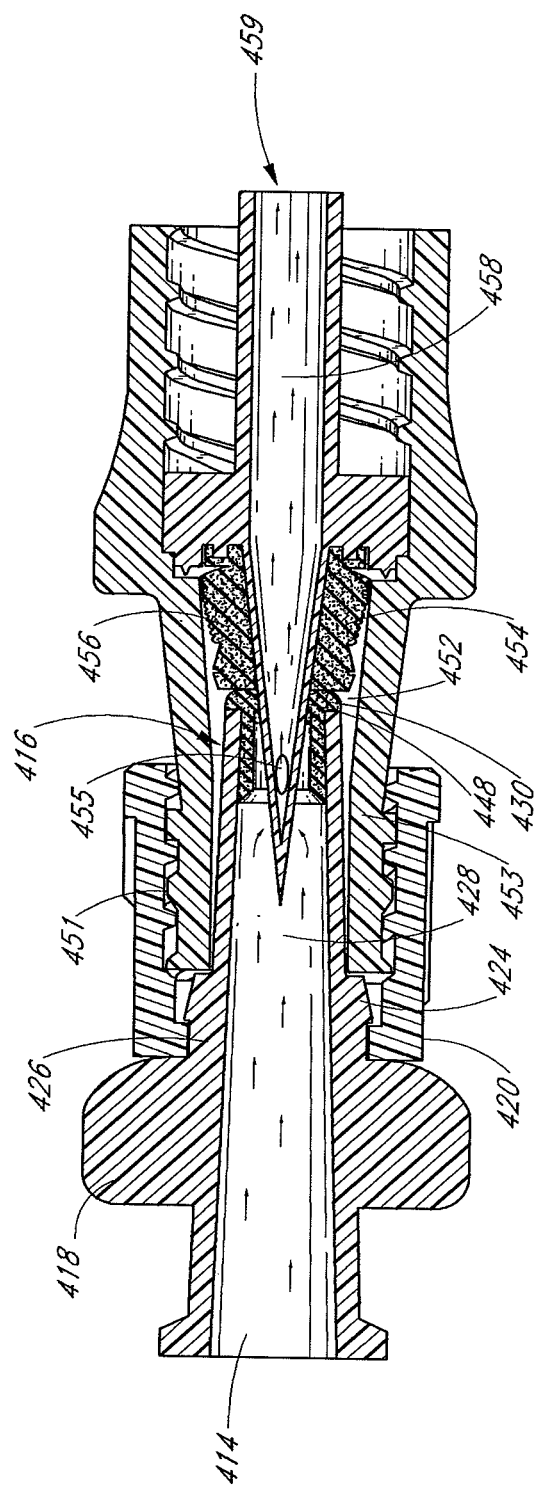
FIG. 23D is a perspective view of the components of FIG. 23C in engagement.

FIG. 23D illustrates an engagement between the male luer connector 400 and female connector 450. The internal threads of the shroud 420 can engage with a threaded region 451 of the female connector 450. The luer tip 416 of the male luer connector 400 can advance into the female connector 450 by compressing a compressible seal 454. As the male connector 400 advances, a stationary fluid conduit 456 of the female connector 450 can penetrate the opening 448 in the seal element 430 of male connector 400. The fluid conduit 456 can advance far enough into the male connector 400 that the holes 455 advance into the internal passageway 428 of the male connector 400. Once the holes 455 of the female connector 450 are disposed within the internal passageway 428 of the male connector, fluid can flow from the luer receiver 414 of the male connector 400 through the internal passageway 428 of the male connector 400 to the holes 455 of the fluid conduit 456 of the female connector 450. The fluid can then flow through the holes 455 and into a fluid conduit 458 of the female connector 450. Thus, fluid can flow from the first end of the male connector 400 to the distal end of the female connector 450 when the two are engaged. When the connectors 400, 450 are disengaged, the fluid conduit 456 withdraws from the internal passageway 428 and the seal element 430 closes, thereby inhibiting fluid flow through the male connector 400. Additionally, the compressible seal 411 of the female connector 450 returns to its original position, and inhibits flow through the holes 455 in the fluid conduit 456.

With reference now to FIG. 24A, a closeable male luer connector 500 is displayed in a perspective view. The connector 500 has a housing 510 and a seal 514. The housing is comprised of a manipulation portion 512. In this exemplary illustration, the manipulation portion 512 includes wings 516. The wings 516 are adapted to provide a place for the user to grasp and rotate the housing 510 of the connector 500.

Referring now to FIG. 24B, the connector 500 of FIG. 23A is shown in cross-section. The wings 516 are shown as extending outward from the longitudinal axis of the connector 500 and towards the luer receiver 518 of the connector. The internal passageway 520 of the housing 510 has a continual taper, as described in the embodiment of the connector 400 in FIG. 22A.

Turning to FIG. 25A, a side view of a closeable male luer connector 600 is illustrated. The connector 600 has a housing 610, a seal element 614, and a shroud 620. The housing comprises an internal passageway 640, a luer tip 612, and a manipulation portion 616. The manipulation portion can be constructed to comprise two wings 630, as described in FIG. 24A. The shroud can have internal threading 622, and such threading can be constructed to comply with ANSI specifications for luer connectors. The seal element 614 can be biased closed when not engaged.

With reference now to FIG. 25B, a cross-sectional view of the connector 600 from FIG. 25A is displayed. The shroud 620 can encircle the housing 610 at a recessed portion 652 of the housing 610. A raised portion 650 can inhibit motion of the shroud 620 in the direction of the second end of the connector 600 while the manipulation portion 616 can inhibit motion of the shroud in the direction of the first end of the connector 600. The internal threading 622 of the shroud 620 can be used to engage other components (not shown) when used in conjunction with the luer tip 612. The continuously tapering internal passageway 640 has characteristics that assist in injection molding as discussed with regard to FIG. 22A.

Figure 26A:
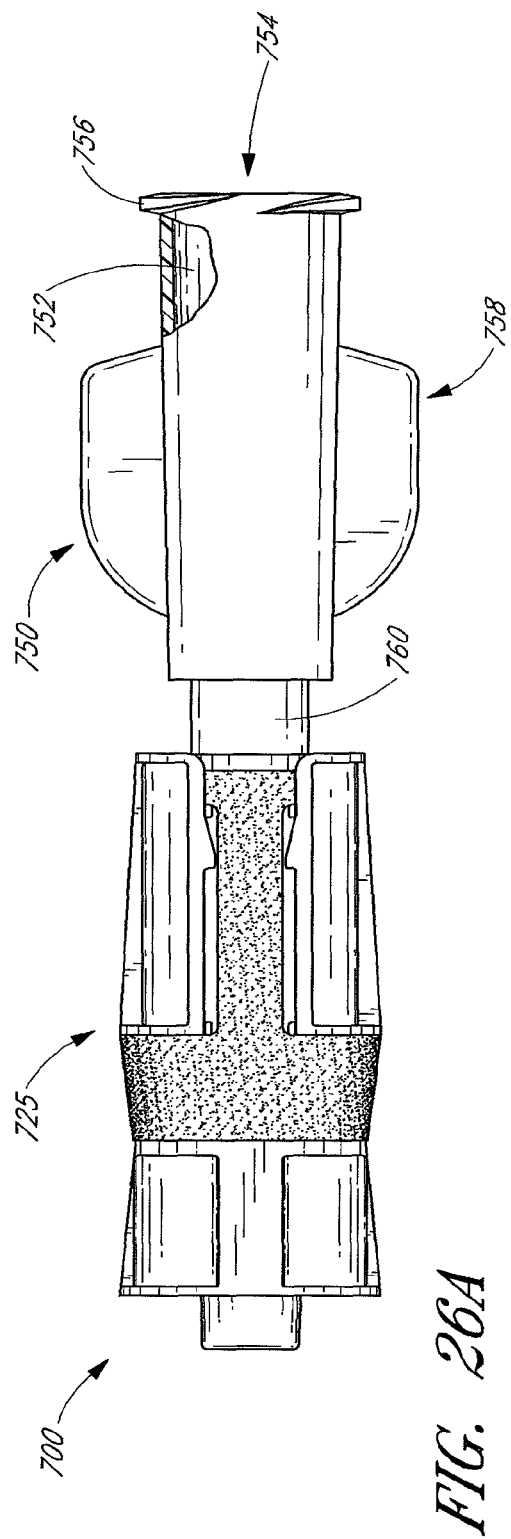
FIG. 26A is a perspective view of another embodiment of a closeable male luer with a flexibly connected female luer connector.

Referring to FIG. 26A, a perspective view of a closeable male luer assembly 725 comprising a closeable male luer 700 and a flexibly connected female luer connector 750 is displayed. The closeable male luer 700 can embody any number of the aspects and features described in this application. The female luer connector 750 is adapted to receive a standard male luer connector (not shown). The female luer connector 750 is located adjacent the male luer connector 700 and flexibly connected to it. The female luer connector 750 comprises an internal passageway 752, a luer receiver 754, and an engagement portion 756. The internal passageway 752 places the luer receiver 754 in fluid communication with an internal passageway of the closeable male luer connector 700. The closeable male luer connector 700 can be attached to the female luer connector 750 through a flexible segment 760. In some embodiments, such a segment 760 can include an accordion-like flexible portion of resilient material. In other embodiments, a straight, flexible material can be used. In other embodiments, both a flexible outer segment and a flexible tube can be used to connect the closeable male luer 700 with the female luer 750.

The flexible segment 752 permits the user to orient the female connector 750 of the assembly 725 in a different attitude than that of the closeable male luer connector 700. As an example, the closeable male luer 700 can remain stationary against a patient's arm while the female connector 750 is angled away from the arm to assist in easy connection with a syringe or other component (not shown). By flexibly connecting the closeable male luer 700 to the female luer connector 750, the moment generated by moving the female luer connector 750 is accepted at a point between the two components of the assembly 725 and is less likely to be transmitted to another component (not shown) attached to the closeable male luer connector 700. Such a component could include an I.V. site, where angling of the connection could result in harm to the patient. Moreover, the moment will be less likely to bend and/or dislodge the tip of the tube 40 from the interior of the lumen 28 (see, e.g., FIG. 28).

Figure 26B:
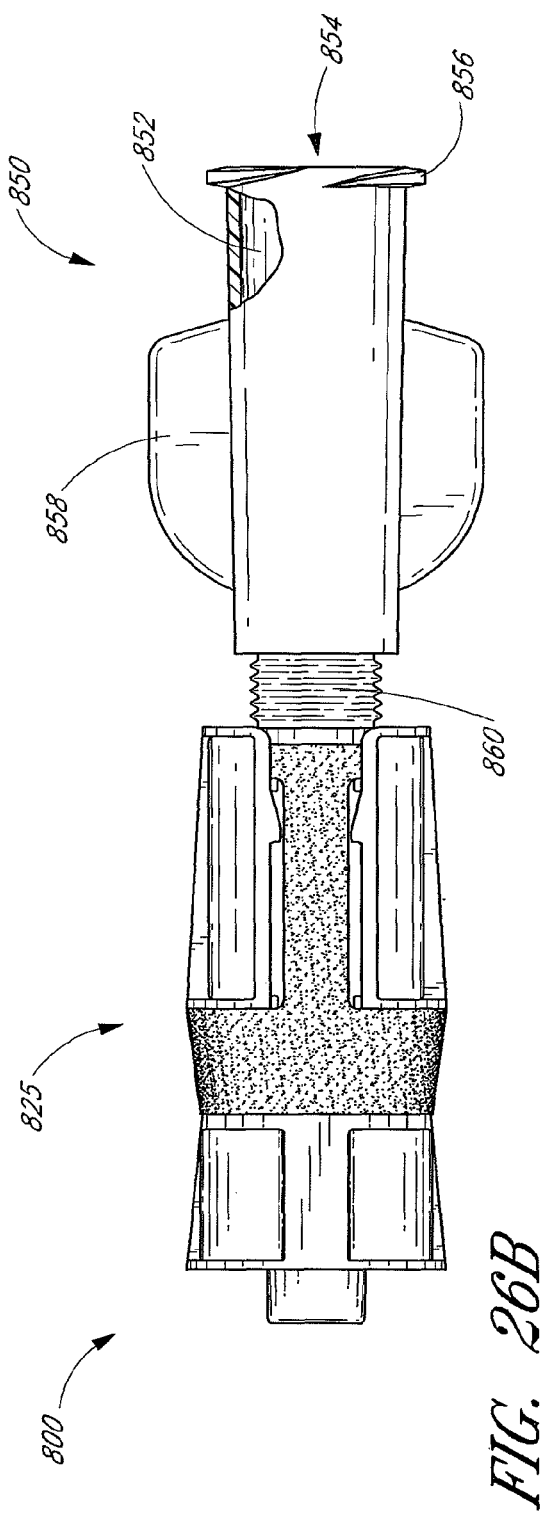
FIG. 26B is a perspective view of another embodiment of a closeable male luer with a flexibly connected female luer connector.
Figure 27:
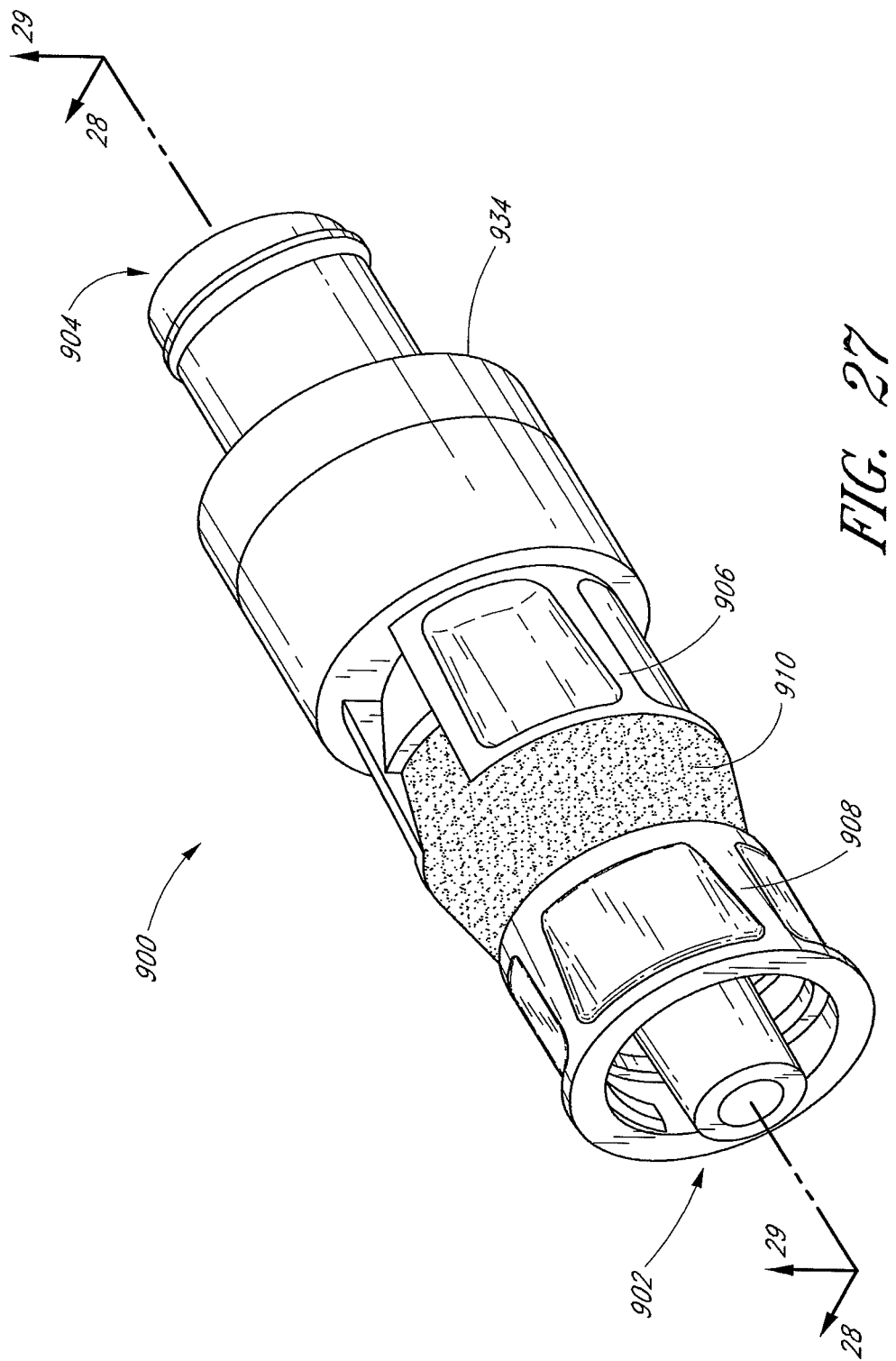
FIG. 27 is a perspective view of another embodiment of a closeable male luer connector.

FIG. 26B illustrates another embodiment of a closeable male luer assembly 800 comprising a closeable male luer connector 825 and a flexibly connected female luer connector 850. The connectors 825, 850 and their components are similar in many respects to the embodiment depicted in FIG. 26 and can embody any number of the aspects and features described above. The closeable male luer connector 825 and the female luer connector 850 are flexibly connected by a connecting member 860. The connecting member 860 places the connectors 825, 850 in fluid communication. The connecting member 860 illustrated here comprises an accordion-shaped plastic conduit. The connecting member 860 is configured to permit the closeable male connector 825 and the female luer connector 850 to be positioned at different angular orientations. By way of example, the closeable male luer connector 825 can remain stationary while the female luer connector 850 can be positioned at an angle to the closeable male luer connector 825. In another example, the female luer connector 850 can remain stationary while the closeable male luer connector can be positioned at an angle to the female luer connector 850. In yet another example, the closeable male luer connector 825 and the female luer connector 850 can both be placed at an angle.

FIGS. 27-32 illustrate another embodiment of a closeable male luer connector 900 with a male end 902 and a female end 904. In some respects, the connector 900 is similar in structure and assembly to other embodiments disclosed and illustrated herein. For example, the connector 900 can include an outer housing 906, a shroud 908, a resilient member 910, an internal valve member 912, and an internal sealing portion 914. All of the descriptions, illustrations, and features of each embodiment disclosed herein can be applied to other embodiments disclosed herein. As described below, the connector 900 can be effective in preventing or minimizing the potential dripping of fluid out of the male end 902 when the male end 902 is in the process of closing.

As illustrated in FIGS. 28 and 29, the valve member 912 can have an internal fluid passageway 916 with a varying cross-sectional area. In some embodiments, the valve member 912 does not have an internal passageway and fluid instead flows around the valve member 912. As shown, the cross-sectional area of a region 918 of the passageway 916 positioned generally within the male end 902 of the housing 906 can be relatively narrow; the cross-sectional area of a region 920 of the passageway 916 positioned generally in the middle of the connector 900 can be wider and have a tapering wall as shown; a region 922 of the passageway 916 positioned closer to the female end 904 can have a larger internal volume than the second region 920; a region 924 of the passageway 916 can be connected to region 922 by way of a narrow opening 926; and a region 928 can be connected to region 924. In some embodiments, region 928 can be connected to region 924 by way of a narrow opening (not shown). In some embodiments, the connector 900 can also include one or more struts 921 to facilitate opening the connector 900.

As discussed above, the region 928 and the female end 904 of the housing 906 can be structured to include one or more of the components of the closing female end of connectors 21, 210 (and/or any components from other types of closing female connectors) to permit the female end 904 of the connector 900 to be selectively opened or closed to fluid flow.

An internal conduit 932 can partially or completely surround the region 924 of the internal fluid passageway 916. The conduit 932 can be secured to a base 934, and the base 934 can be secured to the female end 904 on one side and to an intermediate portion 936 on the other side. In the illustrated embodiment, the outer perimeter of the base 934 extends to the outer perimeter of the housing 906, but it can be configured in many other ways. The intermediate portion 936 can be secured to the remainder of the housing 906. On the end of the valve member distal from the male end 902, an internal conduit 938 can surround region 922 of the fluid passageway 916. In the illustrated embodiment, the internal conduit 938 of the valve member is larger in cross-sectional area and in internal volume than is the internal conduit 932 surrounding region 924. A seal element 940 can be positioned in a region of interface between internal conduits 932, 938 to prevent or minimize leakage of fluid out of the passageway 916 at such interface, while permitting relative axial movement between internal conduits 932, 938. In some embodiments, internal conduits 932, 938 are rigid and do not flex or bend under normal operating conditions. In some embodiments, outer housing portions 906, 908, 934, and 936 are molded into a single, contiguous housing. In other embodiments, they may be molded separately and later joined together to form the housing.

Figure 30:
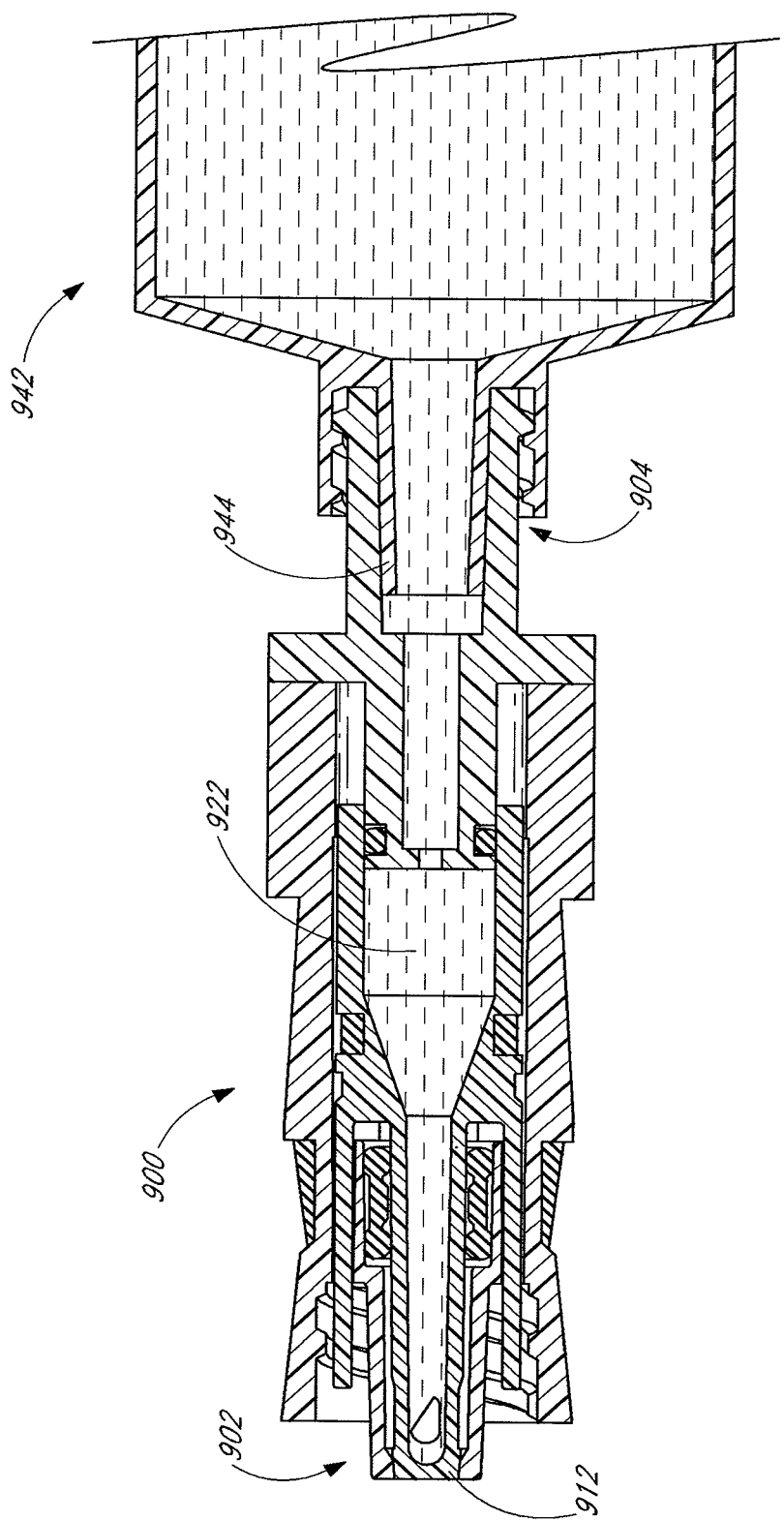
FIG. 30 is a cross-sectional view of the connector of FIG. 27 engaged with a syringe with a male luer tip. At this stage, fluid flow is impeded through the male luer connector.

As shown in FIG. 30, the female end 904 of the connector 900 can be connected to a male portion 944 of another medical implement such as a syringe 942. In this and in all other embodiments disclosed herein, any of a wide variety of other types of medical implements can be attached to the disclosed connectors. In the configuration illustrated in FIG. 30, the connector 900 and syringe 942 are filled with a fluid, such as chemotherapy medication. The fluid cannot escape from the connector 900 under normal conditions because it is impeded on one side by the interface between the valve member 912 and the male end 902 and on the other side by the fluid pressure or structure within the medical implement 942.

Figure 31:
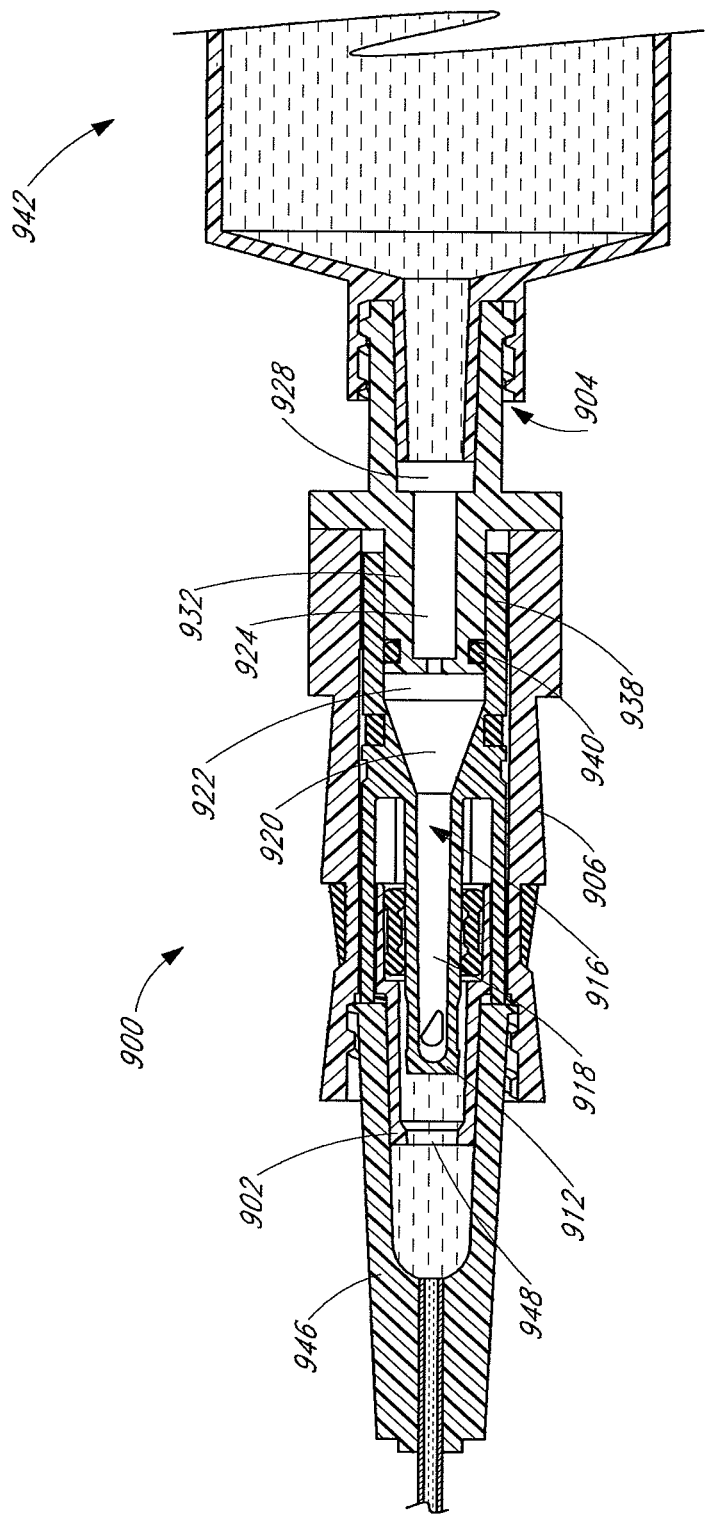
FIG. 31 is a cross-sectional view of the connector and syringe of FIG. 30 engaged with a tube having a female luer attachment portion. At this stage, fluid flow is permitted through this assembly.

As illustrated in FIG. 31, when the valve member 912 is urged away from the male end 902 upon attachment of connector 900 to another medical implement (such as the female connector housing 946 of a plastic IV tube), internal conduit 938 moves in the direction of the female end 904, overlapping at least a portion of internal conduit 932. Fluid is then permitted to flow between medical implements 942, 946 by way of the connector 900. In this second, opened configuration or position, region 922 is smaller than it was in the first, closed configuration or position (see FIG. 30). On the other hand, regions 918, 920, and 928 generally remain about the same size. In some embodiments, including some in which the valve member 912 does not have an internal flow path, a region of changing volume within the connector 900 can be provided by overlapping structures in sliding engagement without directing the fluid flow through the valve member 912. For example, if the valve member is solid, it can be advanced into and withdrawn from conduit 932, and a suitable opening (e.g. in conduit 932 or base 934) can permit fluid to flow through the housing 906 to the male end 902. In some embodiments, including some in which the valve member 912 does not have an internal flow path, the valve member could include a sleeve that can be overlapped over conduit 932 and a suitable opening (e.g. in conduit 932 or base 934) can permit fluid to flow through the housing 906 to the male end 902.

In some embodiments, upon disconnection of the medical implement 946 from the connector 900, the male end 902 can automatically close when the valve member 912 moves within the housing 906 toward the male end under the biasing force of the resilient member 910. In certain circumstances, the movement of a valve member within a fluid passageway could push a small volume of fluid within the male end through the male opening and outside of the connector, resulting in a drip induced by the closing of the valve. However, in the illustrated embodiment, such a drip is generally prevented or minimized.

Figure 32:
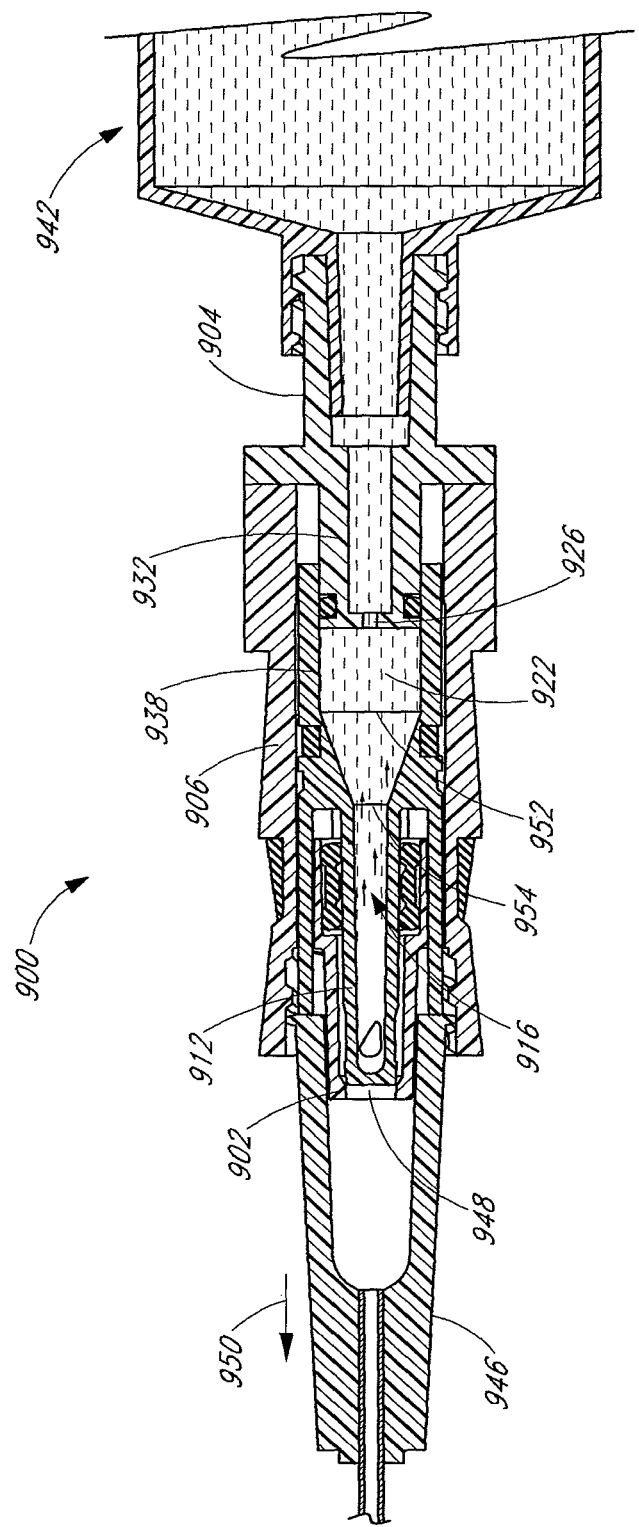
FIG. 32 is another cross-sectional view of the connector, syringe, and tube of FIG. 31. At this stage, the connector is in the process of closing.

As shown in FIG. 32, as the medical implement 946 and the valve member 912 advance in the direction of arrow 950, the region of overlap between internal conduits 932, 938 can decrease and the volume of region 922 of the fluid passageway 916 can increase. The volume of region 922 can eventually return to its approximate original volume in the closed configuration (see FIG. 30). The expanding volume of region 922 during closure of the male luer urges fluid from elsewhere in the passageway 916 to move into region 922.

In some embodiments, the growing void in region 922 cannot be filled by fluid between region 922 and the syringe or other medical implement 942 because the movement of such fluid is prevented by structures in the medical implement 942 (such as the stem seal within the syringe, not shown). Moreover, in some embodiments, such as that shown in FIG. 32, the opening 926 between region 922 and the end of the female connector 904 is substantially smaller than the openings 952, 954 between regions 922, 920, and the remainder of the fluid passageway 916 within the male luer. In this configuration, there can be less fluid resistance within the male end 902 than within the female end 904. In some embodiments, the cross-sectional area of opening 926 is less than one-half the cross-sectional area of opening 954. In some embodiments, the cross-sectional area of opening 926 is less than one-quarter the cross-sectional area of opening 954. In some embodiments, the cross-sectional area of opening 926 is less than one-fifth the cross-sectional area of opening 954. This configuration makes it more likely that fluid will be drawn from the male end 902 into the connector rather than from the female end 904.

As a result of the void in region 922, fluid between the valve member 912 and the internal wall of the male end 902 is pulled back within the body of the connector 900 toward region 922 rather than being pushed out of the male opening. As the connector 900 closes, the increasing volume in the interior of the connector 900 tends to draw fluid in from the opening 948 rather than permit the fluid to be expelled. In the illustrated embodiment, this is achieved in part by providing a cross-sectional area of the region 922 that is substantially larger than the cross-sectional area of opening 948. The volume in region 922 increases faster than the volume in 948 decreases as the valve member 912 moves into the closed position. In some embodiments, the rigid walls of the overlapping internal conduits 938, 932 can sustain extended repeat movement and usage with minimal wear. The walls of the overlapping internal conduits 938, 932 generally do not deform or weaken, which could otherwise affect the size of the void created inside of the connector during closure. Moreover, the walls of the overlapping internal conduits 938, 932 generally do not bulge or buckle under relatively high fluid pressures within the connector, nor do they generally permit the valve member 912 to become misaligned within the internal cavity of the housing 906 under most conditions.

In some embodiments of a closeable male luer connector disclosed herein, it may be difficult to "prime" the connector (i.e., replace air inside of the connector with fluid) without forcing air into one or more medical implements to which the connector is attached. In such embodiments, a separate priming cap can be attached to the male end of the connector. The priming cap can be structured in many different ways.

Figure 33:
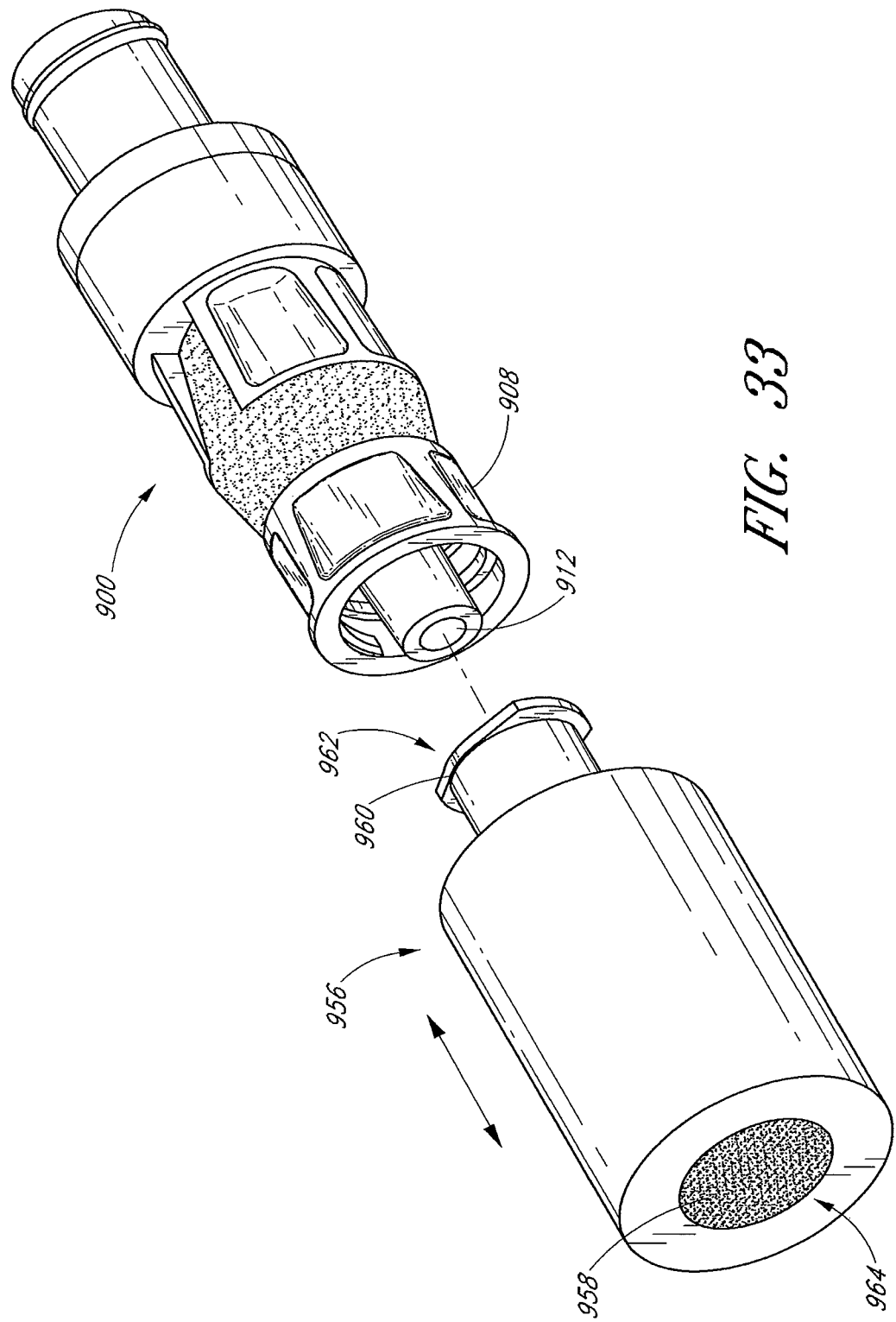
FIG. 33 is a perspective view of the connector of FIG. 27 prior to engagement with an embodiment of a priming cap.

FIG. 33 provides an example of a priming cap 956 that can be used with a closeable male luer connector 900. A suitably configured priming cap can be used with any of the embodiments of the male luer connectors disclosed herein. In some embodiments, the priming cap 956 can include a structure to open the closeable male luer connector 900 (such as a rigid internal conduit, not shown, for pushing against the valve member 912 or a female end 962 with a housing wall 960 configured to abut the struts inside of the shroud 908), permitting fluid to escape from inside of the closeable male luer connector 900. The priming cap 956 can also include an internal fluid passageway (not shown) through which fluid from the opened male luer connector 900 can pass. The fluid passageway can lead to an exit bore 964. The priming cap 956 can also include a filter 958 through which the escaping air can pass but not the advancing liquid. In the illustrated embodiment, the filter 958 is positioned in the exit bore 964. Thus, the air can be evacuated from the male luer connector 900, through the priming cap 956, and out of the exit bore 964, while the liquid generally remains inside the male luer connector 900 and priming cap 956. When priming is completed, the priming cap 956 can be removed and discarded, which automatically closes the closeable male luer connector 900, and another medical implement can be attached to the closeable male luer connector 900. Many other structures and configurations of priming caps also can be used.

Figure 34:
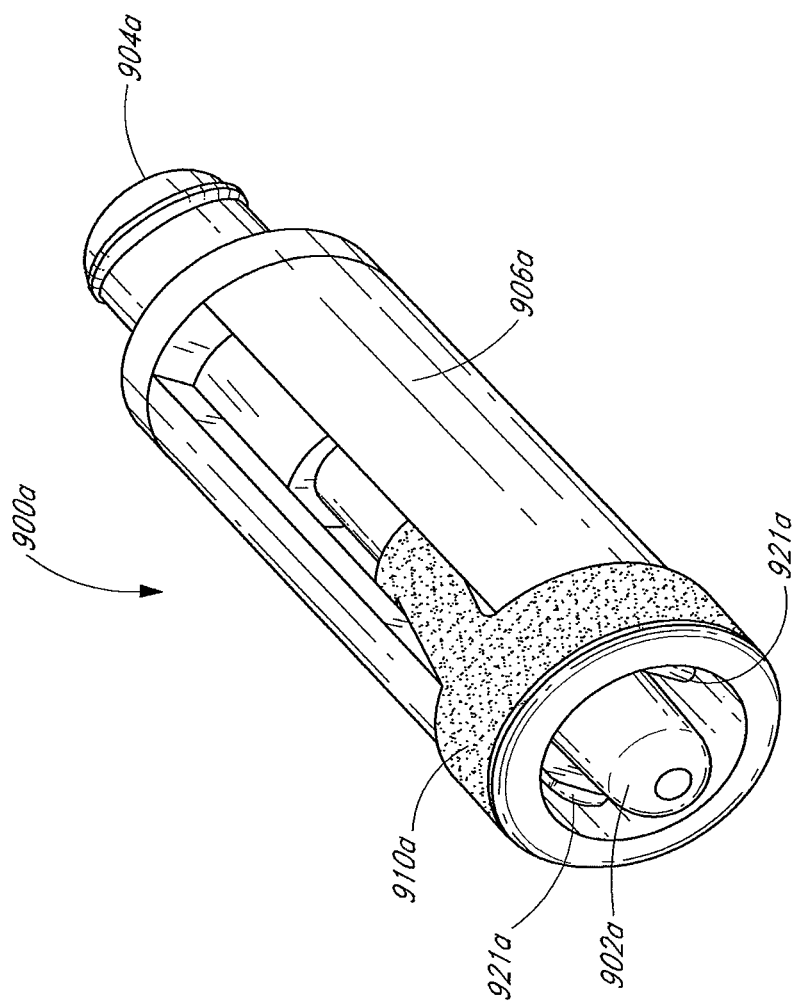
FIG. 34 is a perspective view of another embodiment of a closeable male luer connector.
Figure 35:
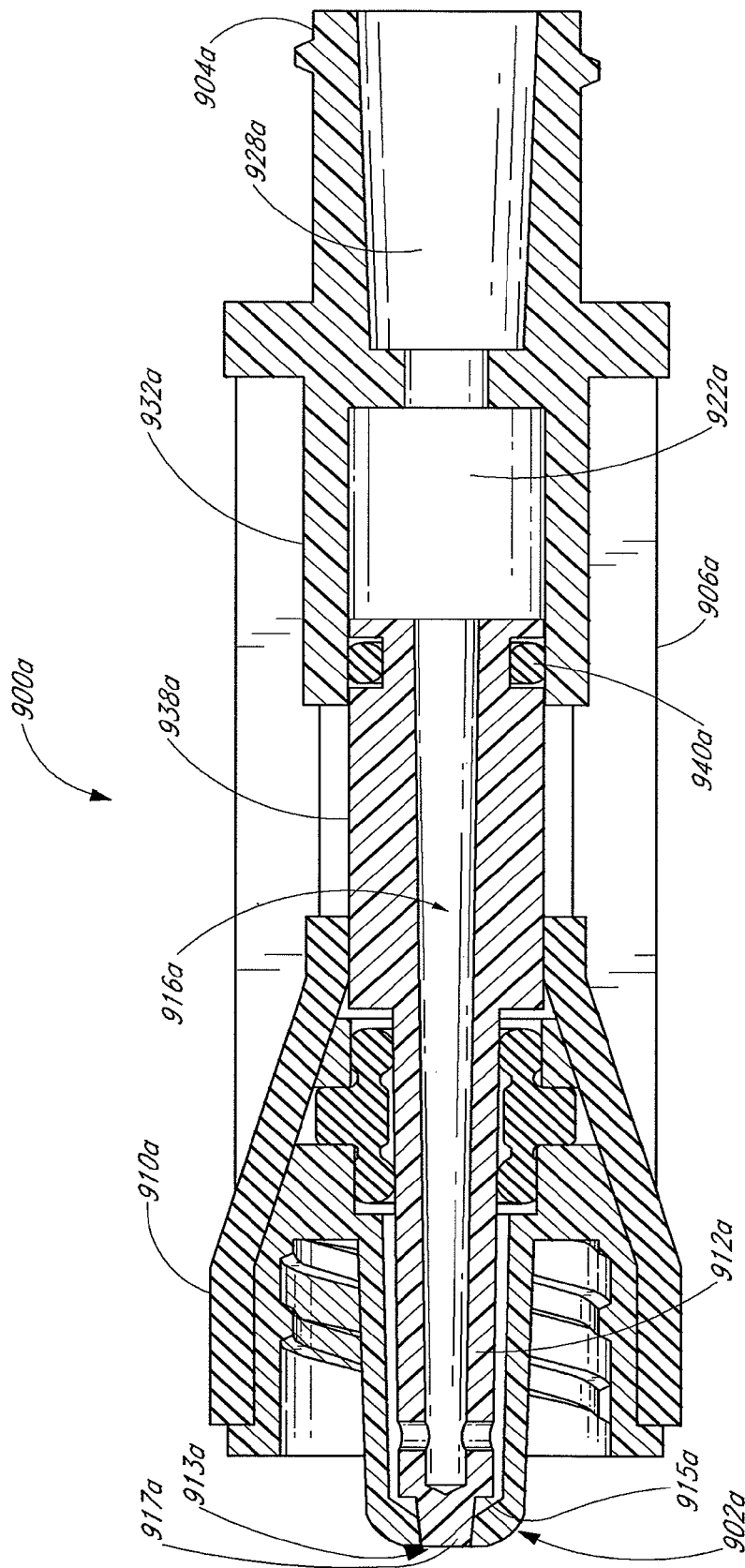
FIG. 35 is a cross-sectional view of the connector of FIG. 34.

FIGS. 34-35 illustrate another embodiment of a closeable male luer connector 900a with a male end 902a, a housing 906a, a female end 904a, and a resilient member 910a, and struts 921a. As shown in FIG. 35, an end 913a of the valve member 912a near the tip of the male end 902a can have a first surface 915a with a larger cross-sectional surface area than a second surface 917a configured to abut an internal side of the tip of the male end 902a. This configuration can assist in creating an interface that is further resistant to leakage from the male luer connector 900a through the male end 902a. In the embodiment of FIG. 35, the internal conduit 938a is smaller in cross section than is the internal conduit 932a. The relative moment between conduits 932a, 938a produces a change in the volume of region 922a, as in the embodiment illustrated in FIGS. 27-32. A resilient seal 940a prevents or minimizes fluid leakage at the interface between the conduits 932a, 938a. When the closeable male luer connector 900a is in the first, closed position, as shown, the volume of region 922a is larger than when the closeable male luer connector 900a is in the second, opened position. Internal passageway 916a may have straight walls such that the passageway 916a maintains a relatively constant cross-sectional area. In some embodiments, the walls of passageway 916a may include a taper. In many respects, the closeable male luer connector 900a functions in a similar manner to the closeable male luer connector 900 of FIGS. 27-32.

Figure 36:
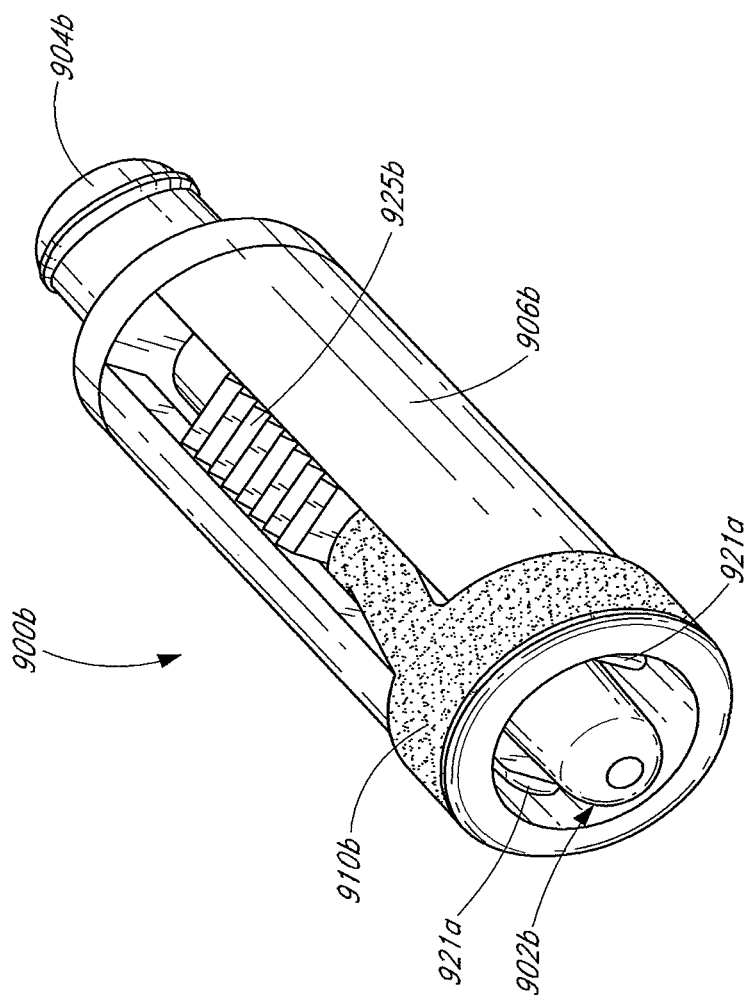
FIG. 36 is a perspective view of another embodiment of a closeable male luer connector.
Figure 37:
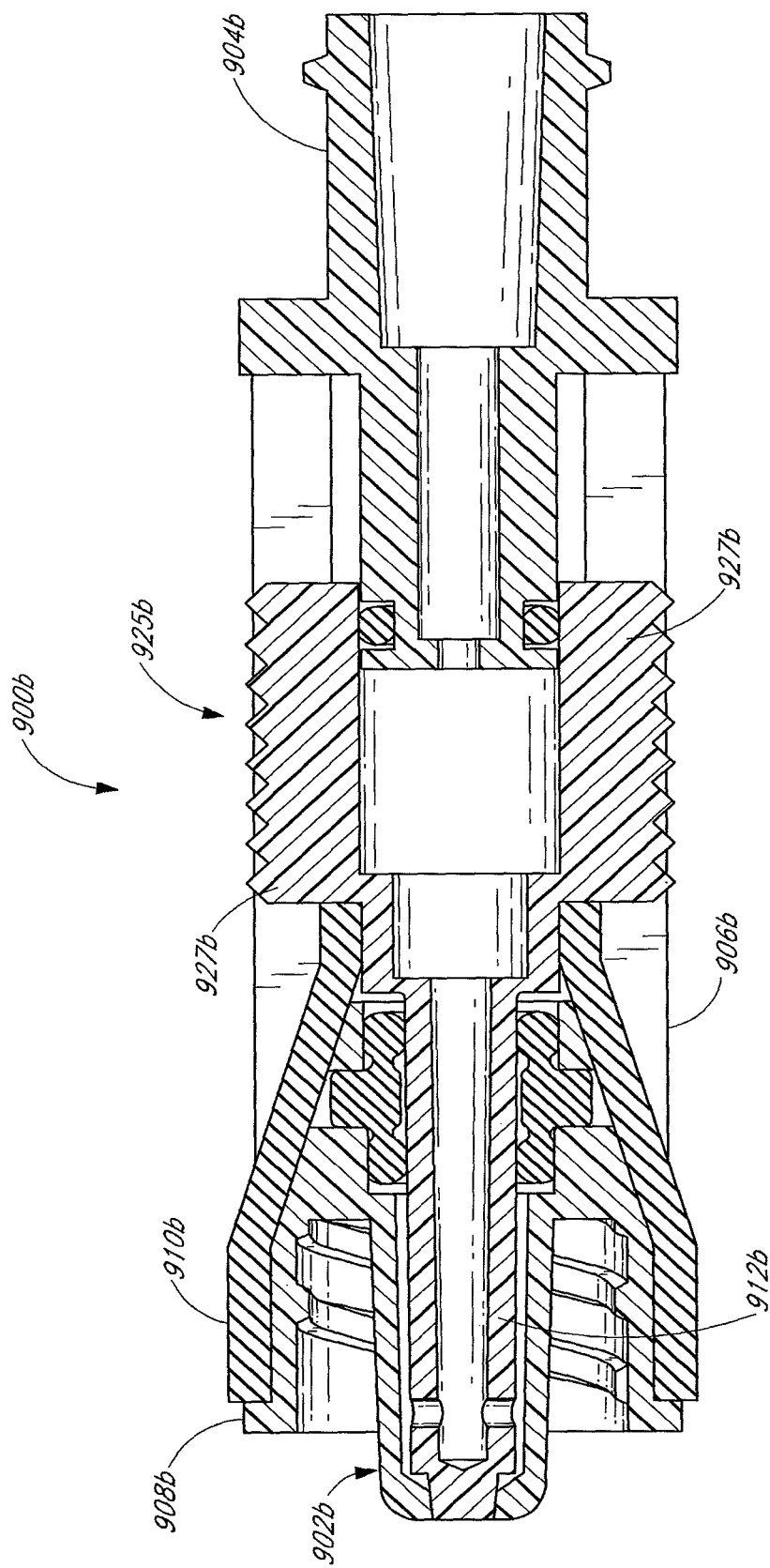
FIG. 37 is a cross-sectional view of the connector of FIG. 36.

FIGS. 36-37 illustrate another embodiment of a closeable male luer connector 900b with a male end 902b, a housing 906b, a female end 904b, and a resilient member 910b. This embodiment also includes an actuator 925b for manually opening and closing the male luer connector 900b. Many different types of manual actuators can be used, including those employing springs, buttons, levers, and other structures. In the illustrated embodiment, the valve member 912b includes at least one lateral side 927b that can be contacted by the fingers and advanced toward either the male end 902b or toward the female end 904b. In the illustrated embodiment, the valve member 912b includes struts 921b within the shroud 908b. As such, when the lateral side 927b is moved toward the male end 902b, the male luer connector 900b can be closed unless the male luer connector 900b is attached at its male end 902b to another medical implement. When the lateral side 927b is moved toward the female end 904b, the male luer connector 900b can be opened, even when another medical implement has not yet been attached at the male end 902b of the connector 900b. As shown in FIG. 36, the exterior surface of the actuator 925b can be serrated or otherwise textured to avoid slipping of the fingers, and the exterior surface of the actuator 925b can be positioned slightly below the outer perimeter of the housing 906b to avoid unintentional opening or closing of the connector 900b, especially during installation or other movement of the connector 900b. In some embodiments, the valve member 912b may not include struts within the shroud 908b.

The actuator 925b, or some other structure for manual opening and closing of the connector 900b, can be particularly advantageous in some applications during priming of the closeable male luer connector 900b. It allows for the connector 900b to be opened while air within the connector 900b is evacuated into the environment before the connector 900b is attached to another implement (which would otherwise cause the evacuated air to be forced into such other implement). A priming cap may not be necessary when manual means are provided for opening and closing the connector 900b.

Figure 38:
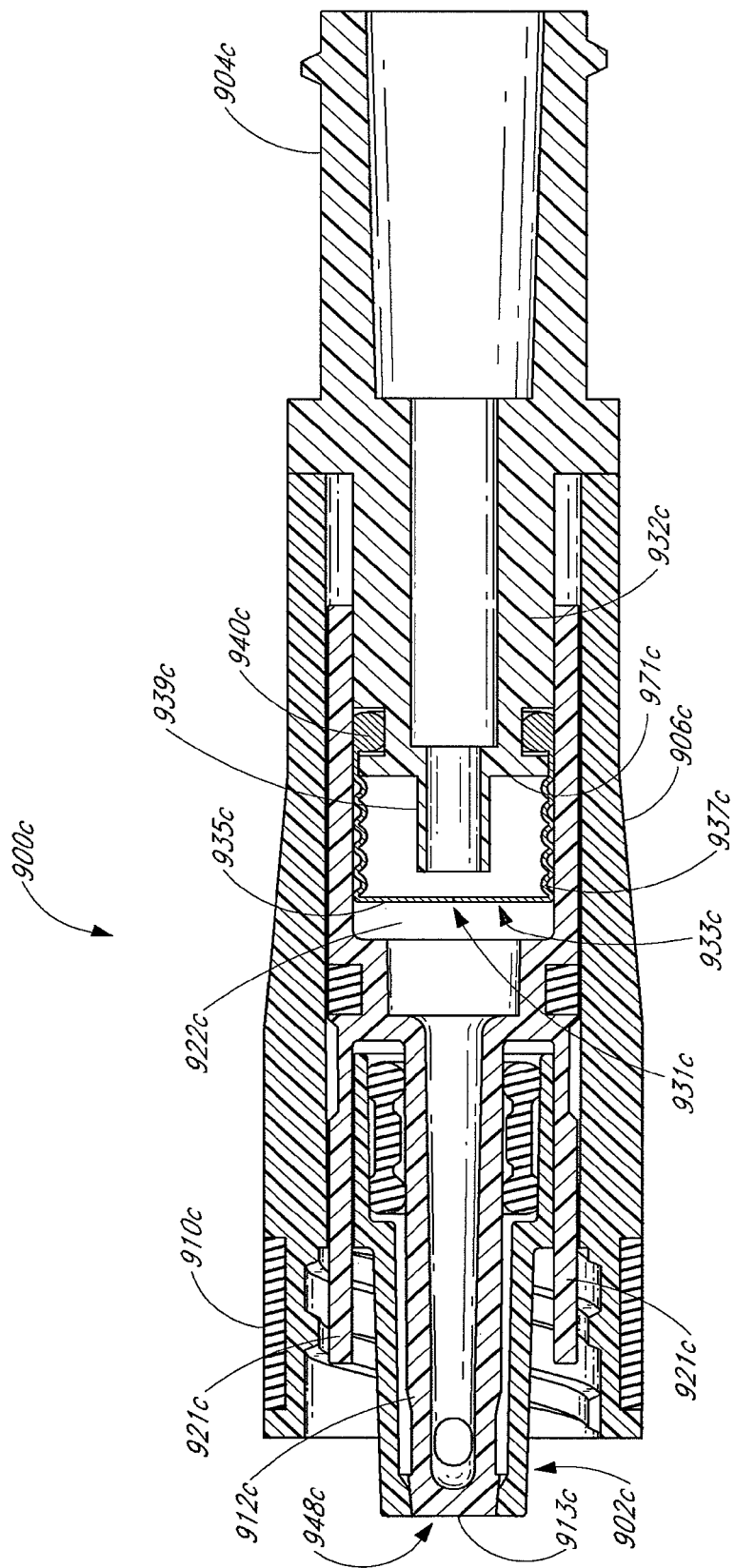
FIG. 38 is a cross-sectional view of another embodiment of a closeable male luer connector.
Figure 39:
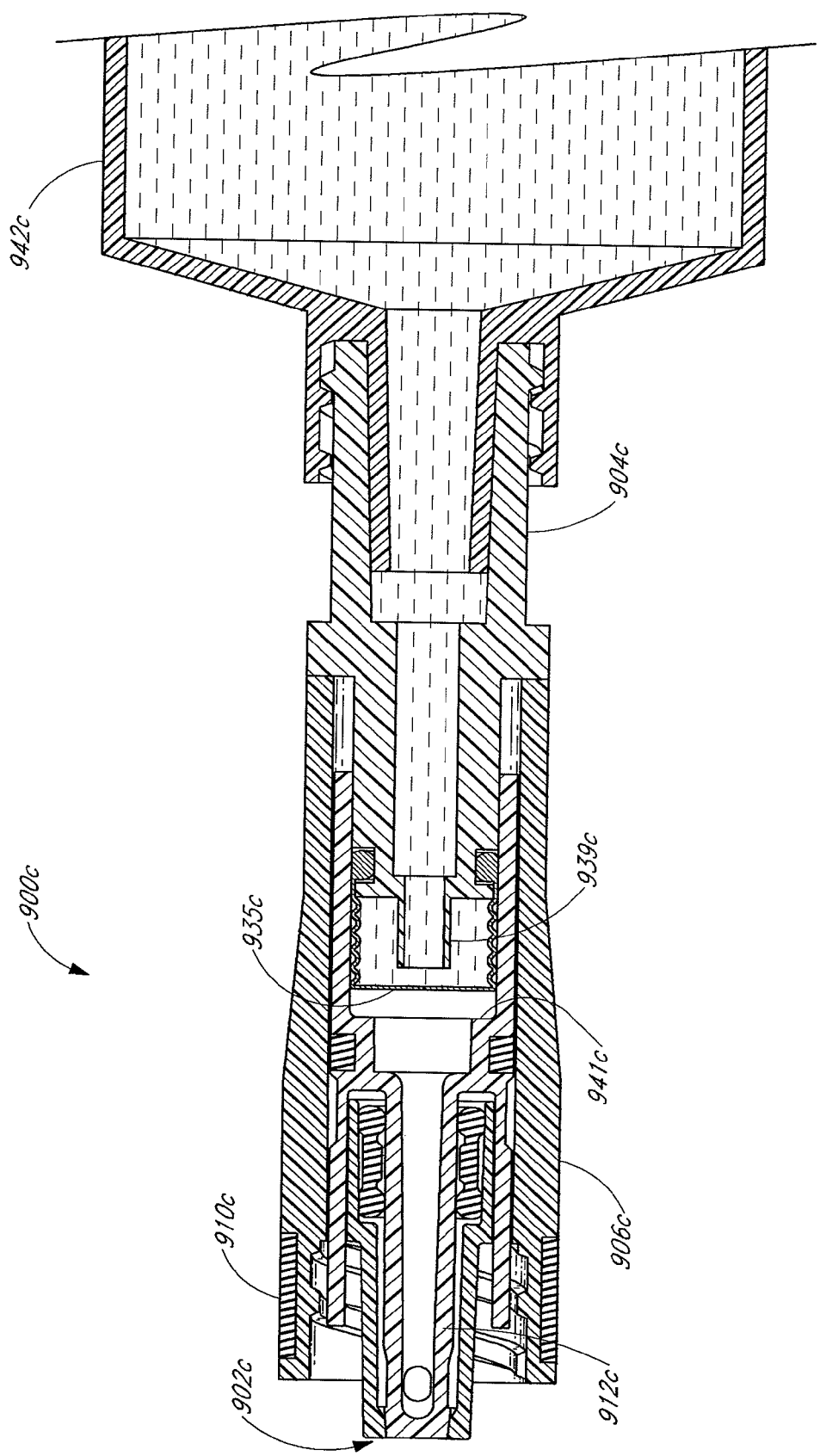
FIG. 39 is a cross-sectional view of the connector of FIG. 38 engaged with a syringe with a male luer tip. At this stage, fluid flow is impeded through the male luer connector.
Figure 39A:
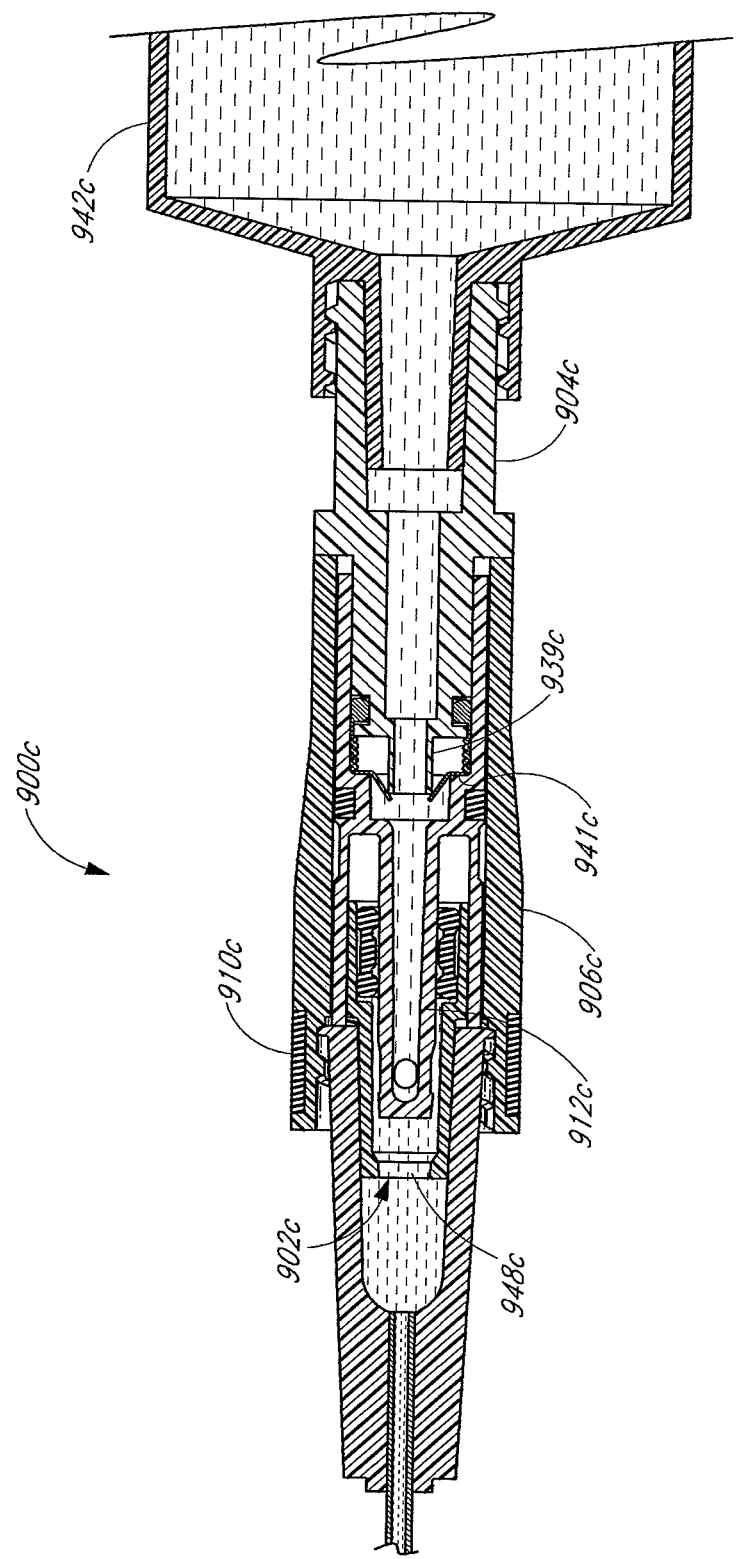
FIG. 39A is a cross-sectional view of the connector and syringe of FIG. 39 engaged with a tube having a female luer attachment portion. At this stage, fluid flow is permitted through this assembly.

FIGS. 38-39A illustrate another embodiment of a closeable male luer connector 900c with a male end 902c, a housing 906c, a female end 904c, and a resilient member 910c. This embodiment also includes an internal structure for impeding or halting the flow of fluid. A resilient covering 933c is positioned generally within region 922c. The covering 933c can include a forward surface 935c, which is generally flat in the illustrated embodiment, a slit 931c, and a sidewall 937c. The sidewall 937c can be corrugated to facilitate axial compression of the covering 933c. The sidewall 937c can be connected to a seal element 940c as shown, or the sidewall 937c can be attached to a forward end 971c of the conduit 932c. The conduit 932c can be in fluid communication with a secondary conduit 939c.

As shown in FIG. 39A, when the valve member 912c is moved toward the female end 904c, an internal shoulder 941c on the valve member 912c comes into contact with the forward surface 935c of the covering 933c, causing the covering 933c to compress or otherwise move in the direction of the female end 904c. On the other hand, the secondary conduit 939c generally remains stationary and abuts against the other side of the forward surface 935c of the covering 933c. The opposing forces exerted against the covering 933c by the shoulder 941c and the conduit 939c cause the covering to bend and the slit 931c opens up to permit fluid flow through the connector 900c. The selective opening of the covering 933c (or another type of internal fluid impedance structure) can be accomplished in many other ways and in many other configurations. The selective opening within the connector 900c allows the female end of the region 922c to close or substantially close before the end 913c of the valve member 912c engages the opening 948c of the male end 902c of the connector 900c. With one end closed and the region 922c expanding as the valve member 912c continues to move toward the male end 902c, the increasing volume urges fluid from the male end 902c and into the region 922c.

Figure 40:
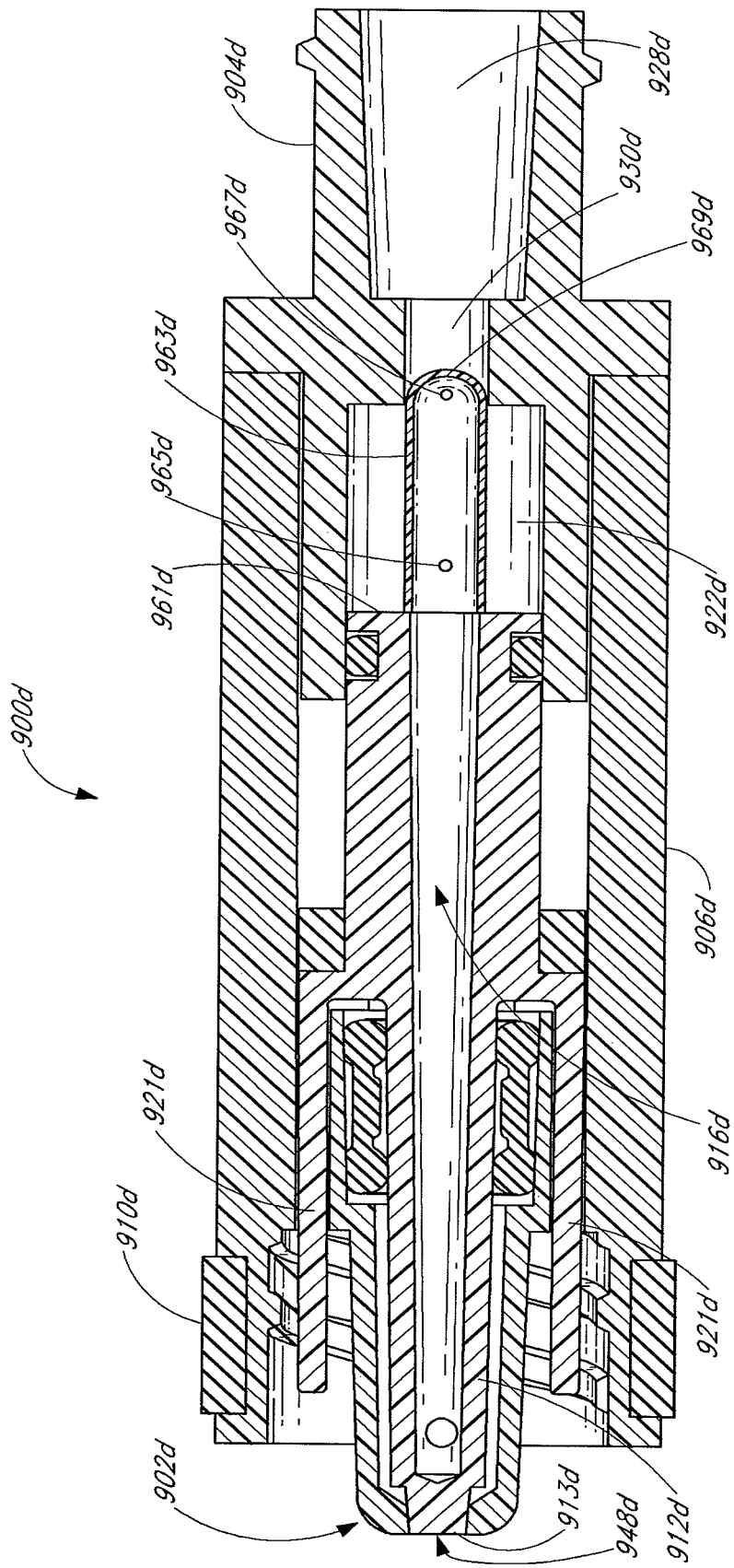
FIG. 40 is a cross-sectional view of another embodiment of a closeable male luer connector.

FIG. 40 illustrates another embodiment of a closeable male luer connector 900d with a male end 902d, a housing 906d, a female end 904d, and a resilient member 910d. As with the embodiment of FIGS. 38-39, this embodiment also includes an internal structure for impeding or halting the flow of fluid between the female end 904d and the internal cavity of the connector 900d. On an end of the valve member 912d, a fluid chamber 963d is positioned in fluid communication within the passageway 916d of the valve member 912d. In the closed position of the illustrated embodiment, the fluid chamber 963d has a hole 965d positioned in the region 922d and a hole 967d positioned in the passage 930d between region 922d and the region 928d of the female end 904d. In many circumstances, the flow of fluid is blocked or diminished between the female end 904d into the interior of the connector 900d due to the close peripheral fit between the conduit 963d and the passage 930d. However, when the valve member 912d is advanced toward the female end 904d, and the tip 969d of the fluid chamber 963d moves out of the passage 930d and in the direction of the female end 904d, the hole 967d becomes exposed to the region 928d of the female end 904d. This enables fluid communication between the female end 904d and the interior of the connector 900d. When the valve member 912d is returned to its original closed position, the fluid chamber 963d returns to its position within the region 922d and the tip 969d is positioned within the passage 930d, once again preventing or impeding fluid flow between the female end 904d and the interior of the connector 900d. As the valve member 912d returns to its original closed position, fluid flow between the female end 904d and the interior of the connector 900d is generally impeded as soon as the hole 967d moves into passage 930d, preferably before the end 913d of the valve member 912d engages the opening 948d of the male end 902d of the connector 900d. With fluid flow in the region 922d in the direction of the female end 904d of the connector 900d impeded, fluid is preferably drawn from the male end 902d and into the expanding region 922d. Many other structures and configurations can be used to accomplish the selective communication of fluid between the female end 904d and the interior of the connector 900d.

Figure 41:
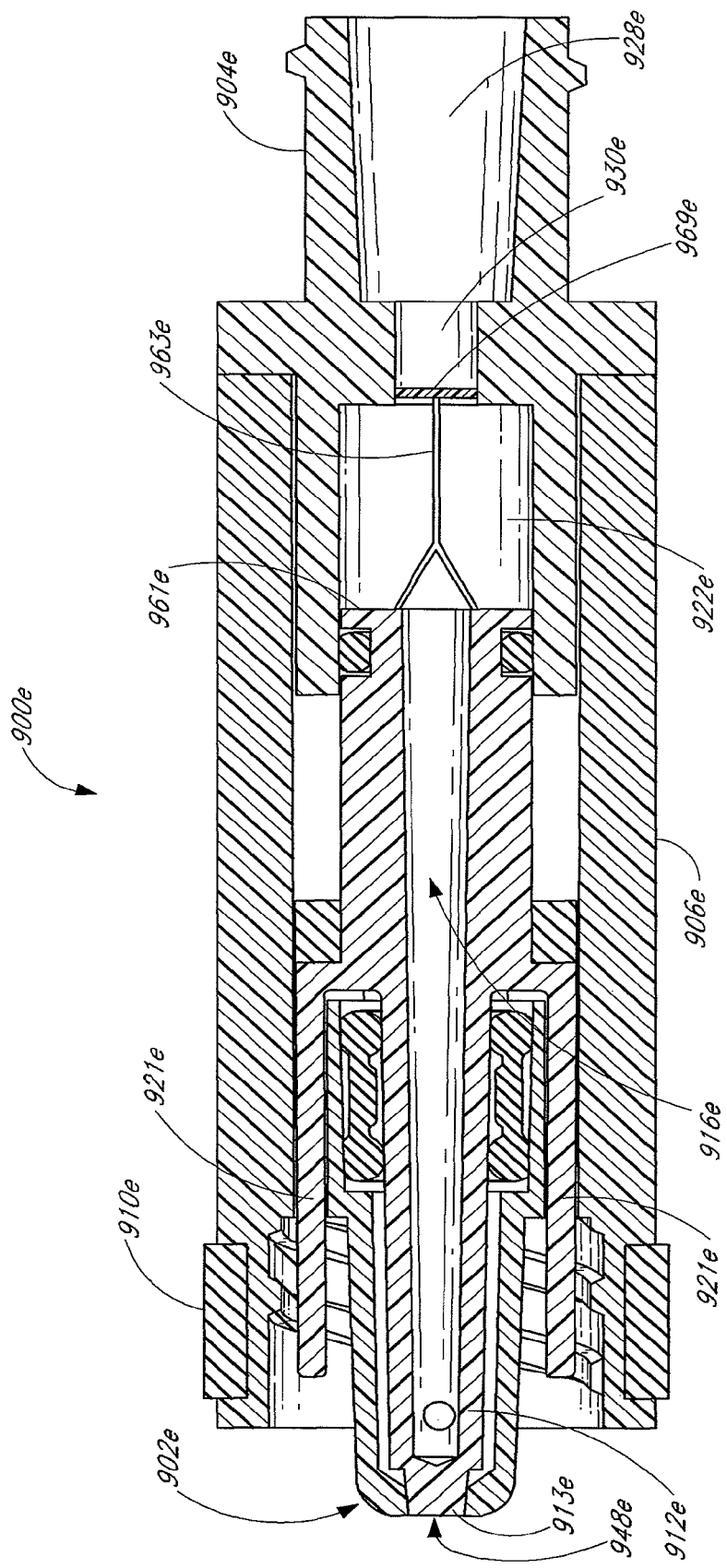
FIG. 41 is a cross-sectional view of another embodiment of a closeable male luer connector.

FIG. 41 illustrates another embodiment of a closeable male luer connector 900e with a male end 902e, a housing 906e, a female end 904e, and a resilient member 910e. As with the embodiments of FIGS. 38-40, this embodiment also includes an internal structure for impeding or halting the flow of fluid between the female end 904e and the internal cavity of the connector 900e. On an end of the valve member 912e, a poppet 963e is positioned in fluid communication within the passageway 916e of the valve member 912e. Poppet 963e may include a first end engaging an outer surface 961e of the valve member 912e and a second end 969e. Alternatively, poppet 963e may be formed integrally with the valve member 912e. The walls of the poppet 963e generally rigid and generally do not deform or weaken. Moreover, the walls of the poppet 963e generally do not bulge or buckle under relatively high fluid pressures within the connector, nor do they generally permit the second end 969e to become misaligned within the internal cavity of the connector 900e under most conditions. Many configurations of the poppet 963e are possible. For example, the walls of the poppet 963e near the surface 961e may include holes or slits to facilitate fluid flow therethrough. The walls may be formed from legs extending from surface 961e with separation between the legs to facilitate fluid flow therethrough. In some embodiments, the poppet 963e includes 3 legs. In some embodiments, the poppet 963e includes 4 or more legs.

In the closed position of the illustrated embodiment, the second end 969e of poppet 963e is positioned in the passage 930e between region 922e and the region 928e of the female end 904e. In many circumstances, the flow of fluid is blocked or diminished between the female end 904e into the interior of the connector 900e due to the close peripheral fit between the second end 969e of the poppet 963e and the passage 930e. However, when the valve member 912e is advanced toward the female end 904e, at least a portion of the second end 969e of the poppet 963e moves out of the passage 930e and in the direction of the female end 904e, enabling fluid communication between the female end 904e and the interior of the connector 900e. When the valve member 912e is returned to its original closed position, the poppet 963e returns approximately to its original position within the region 922e and the second end 969e is positioned within the passage 930e, once again preventing or impeding fluid flow between the female end 904e and the interior of the connector 900e. The second end 969e may include one or more flanges (not shown) extending in the direction of the male end 902e of the connector 900e. These flanges would at least partially remain within the passage 930e when the connector 900e is in the opened position to assist maintaining the axial alignment of the poppet 963e. As the valve member 912e returns to its original position, fluid flow between the female end 904e and the interior of the connector 900e is generally impeded as soon as the second end 969e moves into passage 930e, preferably before the end 913e of the valve member 912e engages the opening 948e of the male end 902e of the connector 900e. With fluid flow in the region 922d in the direction of the female end 904d of the connector 900d impeded, fluid is preferably drawn from the male end 902d and into the expanding region 922d. Many other structures and configurations can be used to accomplish the selective communication of fluid between the female end 904e and the interior of the connector 900e.

Figure 42:
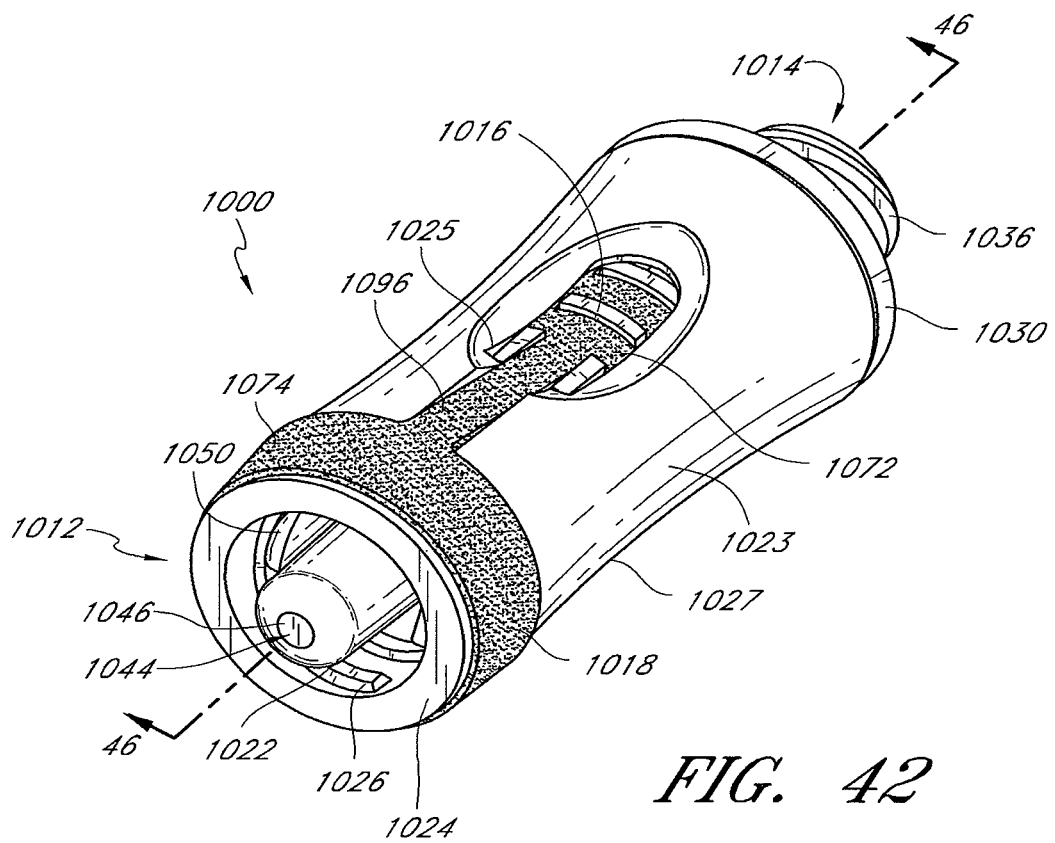
FIG. 42 is a perspective view of an embodiment of a closeable male luer connector in a closed position.

FIG. 42 illustrates another embodiment of a closeable male luer connector 1000. As shown in the embodiment illustrated, the closeable male luer connector 1000 can have a first end 1012 and a second end 1014. The first end 1012 can comprise a male luer tip 1022 and a valve member 1016 (shown in more detail in FIG. 47). The luer tip 1022 and valve member 1016 can be supported by a housing 1023. The valve member 1016 can be coupled to the housing 1023 by a resilient member 1018. An end cap 1030 can be coupled to the housing 1023 near the second end 1014 of the closeable male luer connector 1000. The end cap 1030 can have external threads 1036. The embodiment of a closeable male luer connector 1000 shown in FIG. 42 is in a closed position. In the closed position, valve member 1016 cooperates with male luer tip 1022 to impede the flow of fluid through the connector 1000.

As illustrated in FIG. 42, the housing 1023 can have a shroud 1024 surrounding the luer tip 1022. The shroud 1024 can have internal threads 1026. The internal threads 1026 and luer tip 1022 can form a male luer engagement that conforms to ANSI specifications for male luer connectors. The end cap 1030 can have a receptacle shape that conforms to ANSI standards for female luer connectors and can receive a male luer connector. The external threads 1036 can be disposed to threadedly engage corresponding internal threads of a male luer connector.

The valve member 1016 can be at least partially enclosed by the housing 1023. As shown, the housing 1023 can have at least one side opening 1025, exposing at least a portion of the valve member 1016 and/or allowing at least a portion of the resilient member 1018 to pass into the inside of the housing 1023. In some embodiments, housing 1023 can define two side openings 1025 which can be disposed opposite each other on the sides of the connector 1000. In some embodiments, side opening 1025 can extend only part way along the housing 1023 (such as in a central region of the housing 1023 as shown) to provide increased strength in the housing near the second end 1014. In the illustrated embodiment, the resilient member 1018 is coupled with the valve member 1016 near the side openings of the housing 1023. The external side walls 1027 of the housing can be contoured. For example, the external surface of the housing can include a narrower portion near the central region of the housing 1023, or a generally hour-glass-shaped outer surface, or larger cross-section portion(s) near the ends. These shapes can provide tactile confirmation of the proper placement of a user's fingers on the connector 1000 during use and/or provide a more comfortable gripping surface. In some embodiments, an outward projection or projections (not shown) can be incorporated on the resilient member 1018 to provide additional or more effective gripping surfaces on the connector 1000.

The housing 1023 can include a luer tip 1022 near the first end 1012 of the connector 1000. The luer tip 1022 can have a hole 1021 at the end which can permit fluid to flow from within the housing 1023 out the luer tip 1022. The valve member 1016 can include a valve closure end 1044. The closure end 1044 can engage the interior of the luer tip 1022 to inhibit the flow of fluid through the luer tip 1022. In some embodiments, an interference fit between the valve member 1016 and the housing 1023 inhibits fluid from flowing out the luer tip 1022. In some embodiments, this interference fit is between the closure end 1044 and the hole 1021. In some embodiments, the valve member 1016 can include a resilient section disposed near the first end 1012 of the housing 1023 to engage the housing 1023 near the luer tip 1022 to inhibit fluid flow therethrough.

As shown in the embodiment of the connector 1000 illustrated in FIG. 42, a valve closure face 1046 can be disposed across the luer tip 1022 when the connector 1000 is in the closed position. In some embodiments, valve closure face 1046 can extend further beyond the hole 1021 outside of the luer tip 1022 when the connector 1000 is in the closed position. In some embodiments, the valve closure face 1046 is recessed within the luer tip 1022. In some embodiments, the valve closure face 1046 is substantially flush with the end of the luer tip 1022. In some embodiments, the valve closure face 1046 is configured to be swabbable when the connector 1000 is in the first or closed position.

Figure 43:
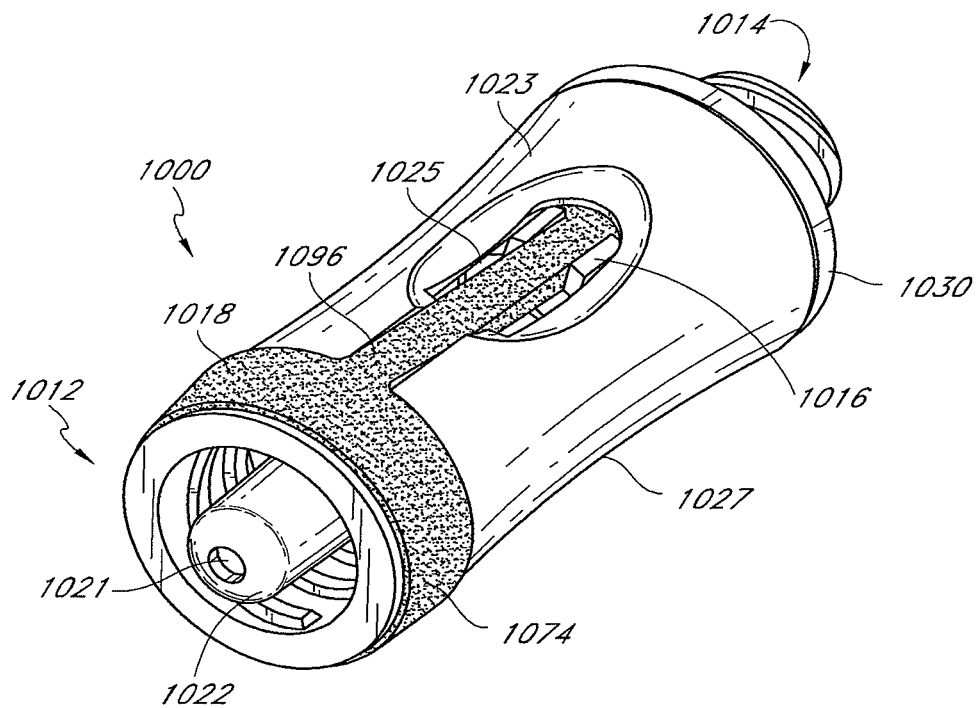
FIG. 43 is a perspective view of the closeable male luer connector of FIG. 42 in an open position.

As shown in FIG. 43, the luer connector 1000 can be manipulated to a second or open position. In the open position of the illustrated embodiment, the valve member 1016 is retracted from the luer tip 1022, thereby opening the hole 1021 in the tip 1022. As will be described in greater detail below, fluid can pass from the luer receptacle at the second end 1014 through the interior of the connector 1000 and exit the luer tip 1022 at the first end 1012 when the connector 1000 is opened. When closed, fluid is impeded or blocked from passing through the luer connector 1000 under normal operating conditions.

The resilient member 1018 can be constructed of a material that elastically deforms. Accordingly, in some embodiments, the housing 1023 can remain coupled to the valve member 1016 by the resilient member 1018 when the luer connector 1000 is moved to the open position.

In the example shown, the change in relative positions of the housing 1023 and valve member 1016 can cause at least a portion of the resilient member 1018 to expand. Consequently, the resilient member 1018 exerts a closing force on the housing 1023 and valve member 1016, biased toward returning the luer connector 1000 to a closed state. The amount of tension carried by the resilient member 1018 can be adjusted by varying in the distance the housing 1023 and valve member 1016 are separated and/or by construction of the resilient member 1018 from a variety of materials having different elastic properties. In some embodiments, the connector 1000 is configured to be difficult enough to open to prevent accidental or unintentional opening. In some embodiments, the difficulty of opening the connector is controlled at least in part by the tension carried by the resilient member 1018.

Figure 44:
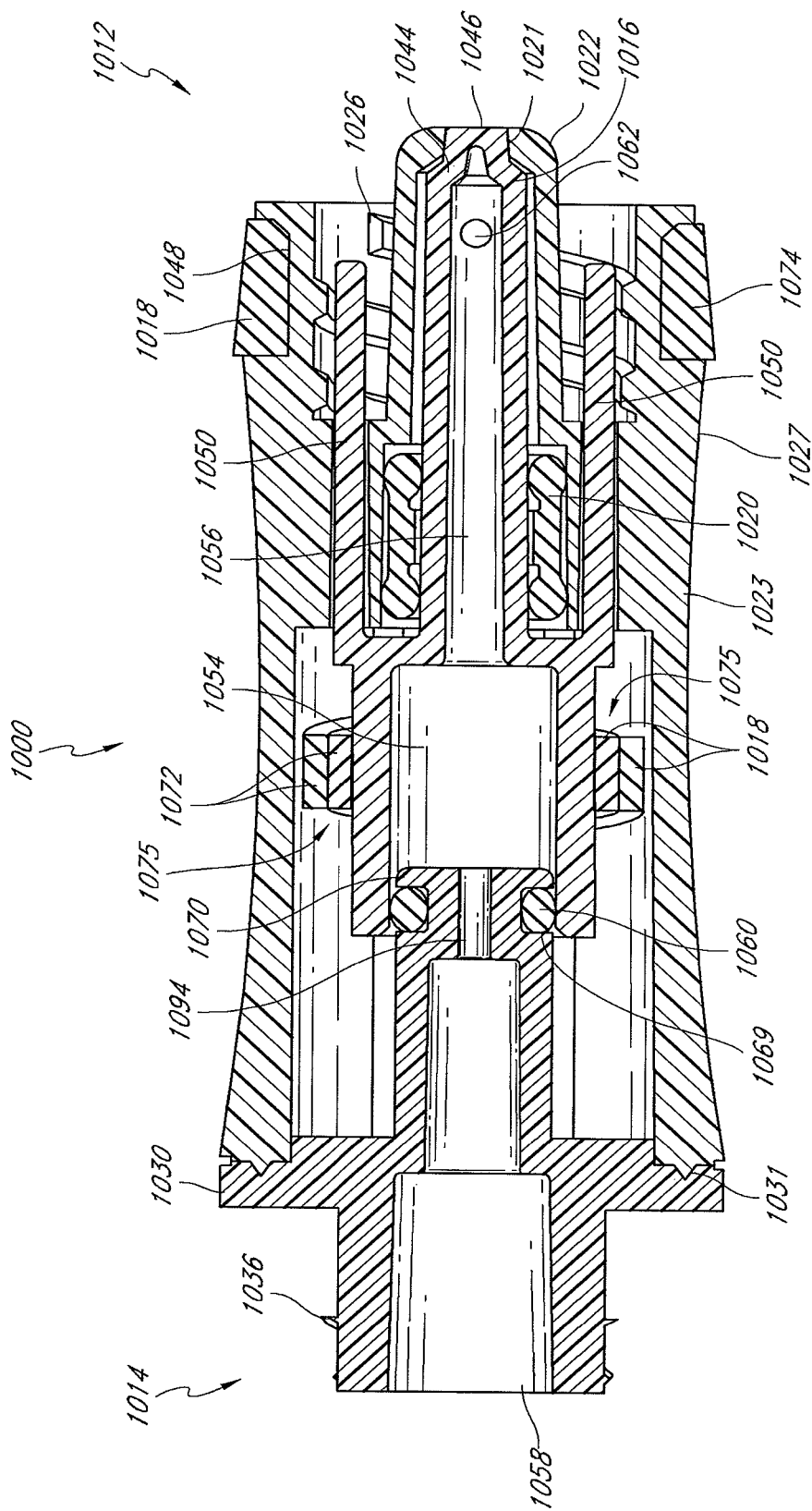
FIG. 44 is a cross-sectional view of the closeable male luer connector of FIG. 42.

FIG. 44 illustrates a cross-sectional view of a closeable male luer in the closed position. As can be seen, the valve closure end 1044 can press against the interior of the luer tip 1022 to inhibit fluid from passing out the luer tip 1022. The valve member 1016 can include at least one strut 1050. In some embodiments, strut 1050 can extend from approximately the middle of the valve member 1016 toward the first end 1012. The connector 1000 can have two struts 1050, as illustrated, or the luer connector 1000 can have more or fewer as desired. The struts 1050 can be located around the luer tip 1022, but within the housing 1023, as shown. The struts 1050 can be located within the inner diameter of the inner threads 1026, and are therefore positioned to couple with at least a portion of a female luer receptacle as it engages with the luer tip 1022.

Figure 46:
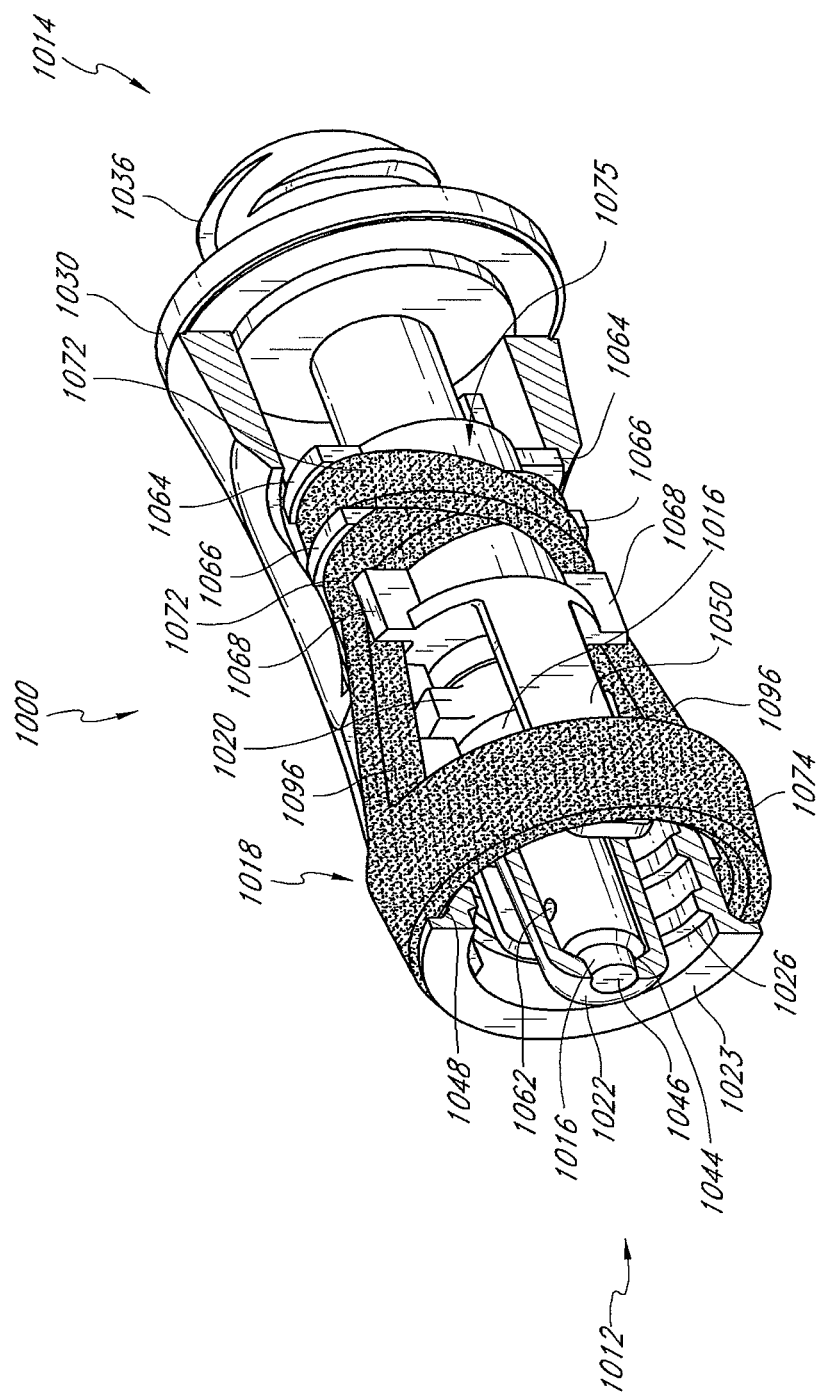
FIG. 46 is a cutaway perspective view of the closeable male luer connector of FIG. 42 taken along the line 46-46.

As shown in FIG. 46, the resilient member 1018 can have a first ring 1074 and at least one securing ring 1072. Although two securing rings 1072 are shown, one or more can be used in different embodiments of the connector 1000. The first ring 1074 can be disposed in an indented groove 1048 in the outer surface of the housing 1023 toward the first end 1012. The elastic member 1018 can be tight enough around the housing 1023 to keep the first ring 1074 in place when a force is exerted on the resilient member 1018 by a change in relative positions of the housing 1023 and the valve member 1016. As will be described in more detail below, the securing ring or rings 1072 can be disposed around the valve member 1016 in different patterns.

A passageway 1056 can extend through a portion of the valve member 1016 near the first end 1012. The passageway 1056 can be circular in cross-section, as shown in the illustrated embodiment, or the passageway 1056 can have other geometric shapes. The passageway 1056 can have at least one port 1062 near the first end 1012. In the illustrated embodiment, two ports 1062 are located on opposite side of the valve member 1016 and are circular, though other locations and shapes can be used.

In the embodiment illustrated in FIG. 44, the connector 1000 is in a closed position, and the relative positions of the valve member 1016 and housing 1023 can create a chamber disposed between the passageway 1056 and the luer receiver 1058. The chamber 1054 can be in fluid communication with the passageway 1056. The chamber 1054 can be wider than the passageway 1056, as illustrated. In some embodiments, the chamber 1054 can have the same diameter as the passageway 1056 and, in some embodiments, the chamber 1054 can have a smaller diameter than the passageway 1056. The chamber 1024 can also be configured with a non-circular cross-section in any other appropriate shape. The chamber 1054 can be bounded on the end toward the second end 1014 of the housing 1023 by the plunger 1070.

The plunger 1070 can be a portion of the end cap 1030 extending towards valve member 1016. The plunger 1070 can have a conduit 1094 through it. The conduit 1094 can place the chamber 1054 in fluid communication with the luer receiver 1058. The plunger 1070 can have an outer dimension sufficient to substantially close one end of the chamber 1054, as shown. In the illustrated embodiment, the plunger 1070 is circular to match the geometry of the chamber 1054, but other geometric shapes can be used as appropriate.

The plunger 1070, though substantially sealing one end of the chamber 1054, can have an outer dimension that does not contact the wall of the valve member 1016 creating the chamber 1054. Accordingly, to inhibit fluid from escaping past the plunger 1070, an O-ring 1060 can be disposed in a groove 1069 behind the plunger 1070. The O-ring 1060 can contact the wall of the valve member 1016, as shown, inhibiting fluid from flowing out of the chamber 1054. In some embodiments, the plunger 1070 is a portion of the end cap 1030. The end cap 1030 can be coupled with the housing 1023 through sonic welding, an adhesive, or any other suitable method for coupling. In the illustrated embodiment, end cap 1030 is coupled to housing 1023 with sonic welds 1031. One such weld 1031 has a substantially triangular shape as shown, though other shapes are also possible. Accordingly, the plunger 1070 can be considered to be in a static position relative to the housing 1023. In some embodiments, the plunger 1070 is formed integrally with the housing 1023 and the end cap 1030 is a separate piece appropriately attached to the housing 1023 such as by sonic welding. In some embodiments, end cap 1030 is integrally formed with housing 1023.

As shown in the illustrated embodiment in FIG. 44, fluid can flow in the luer receiver 1058 and pass to the conduit 1094. From the conduit 1094, fluid can pass to the chamber 1054 and from the chamber 1054 into the passageway 1056. As shown in the illustrated embodiment, when the connector 1000 is in the closed position, the valve closure end 1044 of the valve member 1016 can seal the hole in the luer tip 1022, preventing fluid from passing out the end of the luer tip 1022. Fluid generally can, however, exit the passageway 1056 through the ports 1062 in the valve member 1016. The fluid can reside in the interior of the luer tip 1022, but can be prevented from flowing back towards the second end 1014 on the outside of valve member 1016 by the sealing ring 1020. Accordingly, when the connector 1000 is in the closed position, as illustrated, there generally can be fluid communication between the luer receiver 1058 and the interior of the luer tip 1022, without permitting fluid to exit the first end 1012 of the connector 1000.

Figure 45:
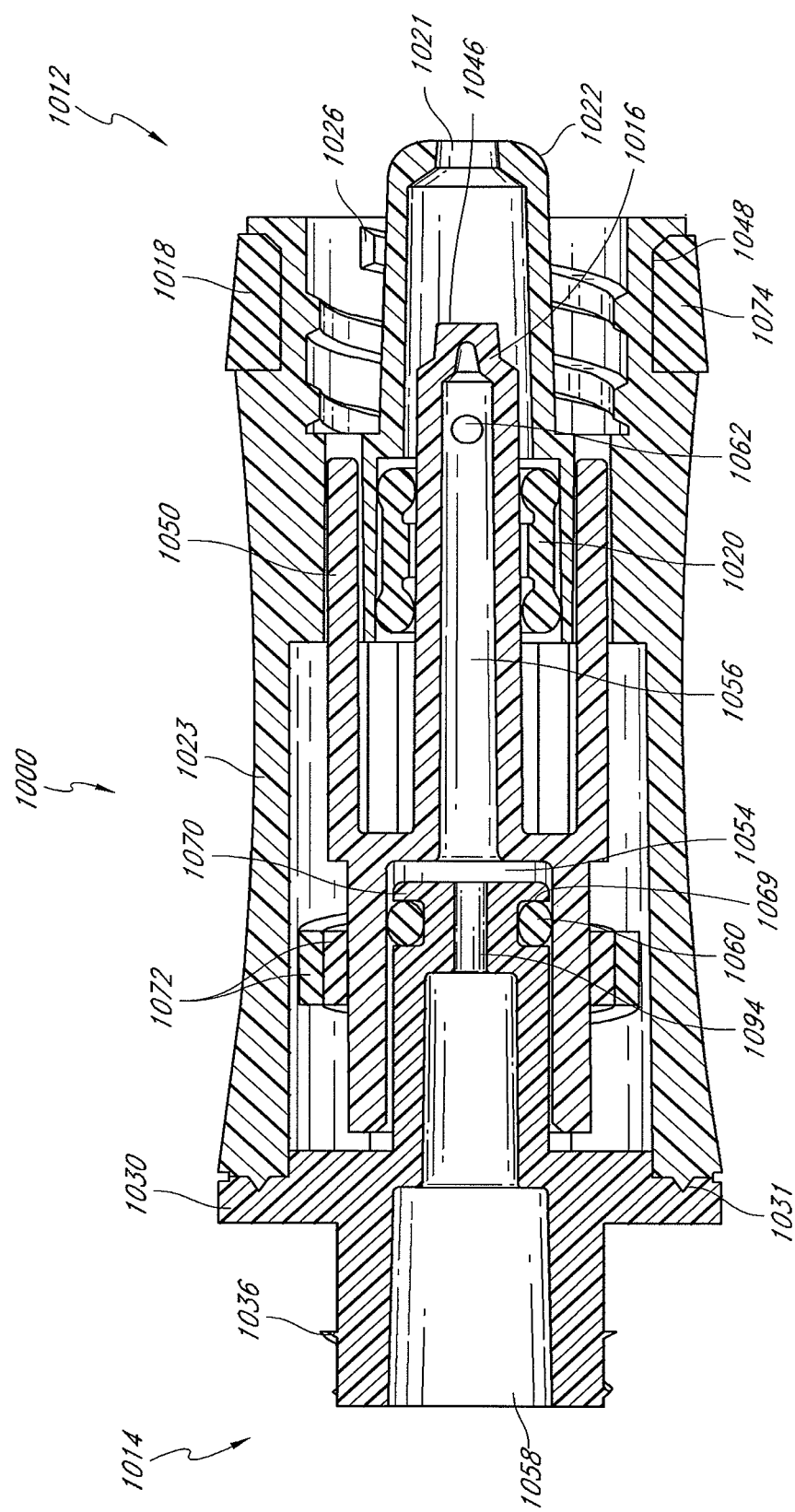
FIG. 45 is a cross-sectional view of the closeable male luer connector of FIG. 43 taken along plane orthogonal to the cross-sectional plane of FIG. 41.

In FIG. 45, an illustration of an embodiment of the connector 1000 in an open position is shown. The connector 1000 can be changed to the open position when a female luer connector (not shown) is mated with the luer tip 1022 of the first end 1012 of the connector. When the female luer connector is engaged with the first end 1012 of the connector 1000, a portion of the female luer connector can engage the inner threads 1026 and can be advanced to at least partially enclose the luer tip 1022. Accordingly, when the female luer connector is engaged with the inner threads 1026, a portion of the female connector can engage with the struts 1050 and push the valve member 1016 towards the second end 1014 of the housing. In the embodiment illustrated in FIG. 45, the valve member 1016 is disposed towards the second end 1014, resulting in the connector 1000 being in an open state.

In some embodiments, when the valve member 1016 is displaced toward the second end 1014, the valve closure end 1044 (see FIG. 44) separates from the luer tip 1022 including removal of the valve closure face 1046 from the hole 1021 in the luer tip 1022. Accordingly, fluid can pass out the hole in the luer tip 1022 from within the housing. The sealing ring 1020 can still inhibit fluid from exiting the interior of the luer tip 1022 towards the second end 1014 of the connector 1000. Accordingly, in the open position, fluid can pass from the luer receiver 1058 through the conduit 1094, chamber 1054, passageway 1056, port or ports 1062 in the valve member 1016, into the interior of the luer tip 1022, and out the hole 1021 in the end of the luer tip 1022.

As can be seen in the illustrated embodiment, when the struts are displaced toward the second end 1014 of the connector 1000, the valve member 1016 is positioned closer to the end cap 1030. Accordingly, the wall portion of the valve member 1016 containing the terminus of the passageway 1056 is positioned closer to the plunger 1070 portion of the end cap 1030. Thus, the volume of the chamber 1054 can be reduced when the connector 1000 is in the open position.

Correspondingly, when the connector 1000 is changing from an open position to a closed position, the volume of the chamber 1054 increases as the valve member 1016 shifts toward the first end 1012 of the connector 1000. As the volume of the chamber 1054 increases, the valve closure end 1044 of the valve member 1016 advances towards the first end 1012 to seal the hole in the luer tip 1022. If no additional fluid is introduced into the connector 1000 through the luer receiver 1058, the existing fluid in the luer tip 1022 can be drawn back through the ports 1062, through the passageway 1056 towards the chamber 1054 by the vacuum effect created when the volume of the chamber 1054 increases. In this case, fluid can be inhibited from exiting the hole in the luer tip 1022 as the valve closure end 1044 moves into place in the hole because the fluid can instead be drawn back to the chamber 1054. In some embodiments, fluid at or near the valve closure face 1046 is encouraged to move into the interior of the connector 1000 rather than remain on the surface of the closure face 1046 as the valve member 1016 moves toward the first end 1012 of the housing 1023.

If, however, additional fluid is still being introduced into the connector 1000 through the luer receiver 1058, the additional fluid can advance to the chamber 1054 and collect there as the valve member 1016 moves toward the first end 1012 to close the luer tip 1022. In this case, pressure from the newly-introduced fluid can be inhibited from forcing fluid to flow out the luer tip 1022 as the valve member 1016 seals the tip 1022. Accordingly, fluid flow is permitted through the connector 1000 while a female connector is coupled with the first end 1012 of the connector 1000, but inhibited while the female connector is being disengaged and after the female connector has been decoupled.

As described in greater detail below, it is desirable to inhibit certain medicines from contacting the skin. Thus, the connector 1000 advantageously assists in retaining fluid within the connector 1000 when it is being decoupled from a female luer connector or other connection. Accordingly, reducing the likelihood of fluid exiting through the luer tip 1022 when decoupling occurs results in a corresponding reduction in the chance of exposure of toxic medicine to the skin of a user or a patient.

In FIG. 46, a cutaway of a connector 1000 is shown with a portion of the housing removed. As can be seen, the resilient member 1018 can have a first ring 1074 disposed in a groove 1048 of the housing 1023. The resilient member can extend towards the second end 1014. The valve member 1016 can have a plurality of outwardly-extending protrusions, embodied in the illustrated connector as upper flanges 1064, lower flanges 1066, and notch flanges 1068. The resilient member can have two securing rings 1072 disposed around the valve member 1016 and held in place by one or more of the flanges 1064, 1066, and 1068.

As shown in the illustrated embodiment, the securing rings 1072 can be connected to the first ring 1074 by straps 1096. The straps 1096 can generally extend between the first end 1012 and the second end 1214, passing between the notch flanges 1068 of the valve member 1016. In some embodiments, the securing rings 1072 can be held in place by one edge of the notch flange 1068, and the lower flange 1066. The securing rings 1072 can extend further toward the second end 1014 from the strap 1096, crossing each other as shown in the illustrated embodiment. In some embodiments, a separate strap 1096 can be used to connect the first ring 1074 to each of the securing rings 1072. Separation of the securing rings 1072 by connecting them through the first ring 1074 and separate straps 1096 may facilitate manufacture of the connector 1000, particularly when the side slots 1025 do not extend all the way to the end of the housing 1023 near the second end 1014 of the connector 1000. The portion of the securing ring 1072 farthest from the strap 1096 can be enclosed by the lower and upper flanges 1064, 1066, securing it in place around the valve member 1016 as shown. Accordingly, when the valve member 1016 is moved toward the second end 1014 through engagement with a female connector as described above, the resilient member 1018 can exert a force on the valve member 1016 drawing it toward the first end 1012. In the illustrated embodiment, the securing rings 1072 are shown overlapping, though many other arrangements or structures are possible, including other arrangements of rings or configurations of the resilient member having greater or fewer securing rings 1072 or a first ring 1074 differently constructed or disposed can be used. As mentioned above, in some embodiments the securing rings 1072 are crossed over each other. When there are two rings 1072, crossing them over each other creates two cross-over points 1075. In some embodiments, the thickness of one or both of the securing rings 1072 is reduced at the cross-over points 1075 to create a substantially uniform securing ring 1072 around the valve member 1016.

FIG. 47 illustrates an embodiment of the valve member 1016 comprising the valve closure face 1046 at the end of the valve closure end 1044. The ports 1062 can be located near the closure face 1046, or as far back as is practical from the face 1046, before the sealing ring 1020 (see FIG. 46). The ports 1062 can be circular, as illustrated, or can have other shapes. The struts 1050 are shown extending toward the first end 1012 of the valve member 1016. There can be one, two, or more struts 1050. In some embodiments, the connector 1000 does not include struts 1050. Rather, the connector 1000 is adapted to be otherwise opened when placed in mating engagement with a female connector. For example, the female connector can include an engagement member (not shown) which could engage the valve closure face 1044 to open the connector 1000, or a manually actuated slider or button can be appropriately configured to open the connector 1000.

The notch flanges 1068 can be comprised of two parallel protrusions from the main body of the valve member 1016, or otherwise appropriately sized to couple with the resilient member 1018. The lower flange 1066 can be perpendicular to the notch flanges 1066, as illustrated. The lower flange 1066 can also comprise more than one protrusion, extending a lesser or greater distance from the main body of the valve member 1016 as appropriate to couple with the resilient member 1018. The upper flange 1064 can be parallel to the lower flange 1066 and spaced apart at least the height of a securing ring 1072 to engage the ring 1072 and inhibit the ring 1072 from moving under pressure to encircle a different portion of the valve member 1016.

FIG. 48 illustrates an embodiment of the end cap 1030. The end cap 1030 can have a sealing portion 1098 shaped and configured to substantially seal the second end 1014 of the housing 1023. The luer receiver 1058 can extend in one direction from the sealing portion 1098. The luer receiver 1058 can be appropriately sized to couple with a male luer portion (not shown) conforming to ANSI standards for luer devices. The luer receiver 1058 can have external threads 1036 to engage the male luer portion, as shown. In some embodiments, raised tabs or other protrusions can be used to engage the male luer portion.

In some embodiments, the plunger 1070 is at the end of a portion extending the other direction from the sealing portion 1098. The plunger 1070 can be sized and configured to substantially seal the chamber 1054 within the valve member 1016. An indentation or slot 1069 between the sealing portion 1098 and the plunger 1070 can be sized and shaped to accommodate an O-ring 1060, as illustrated and described above.

Figure 49:
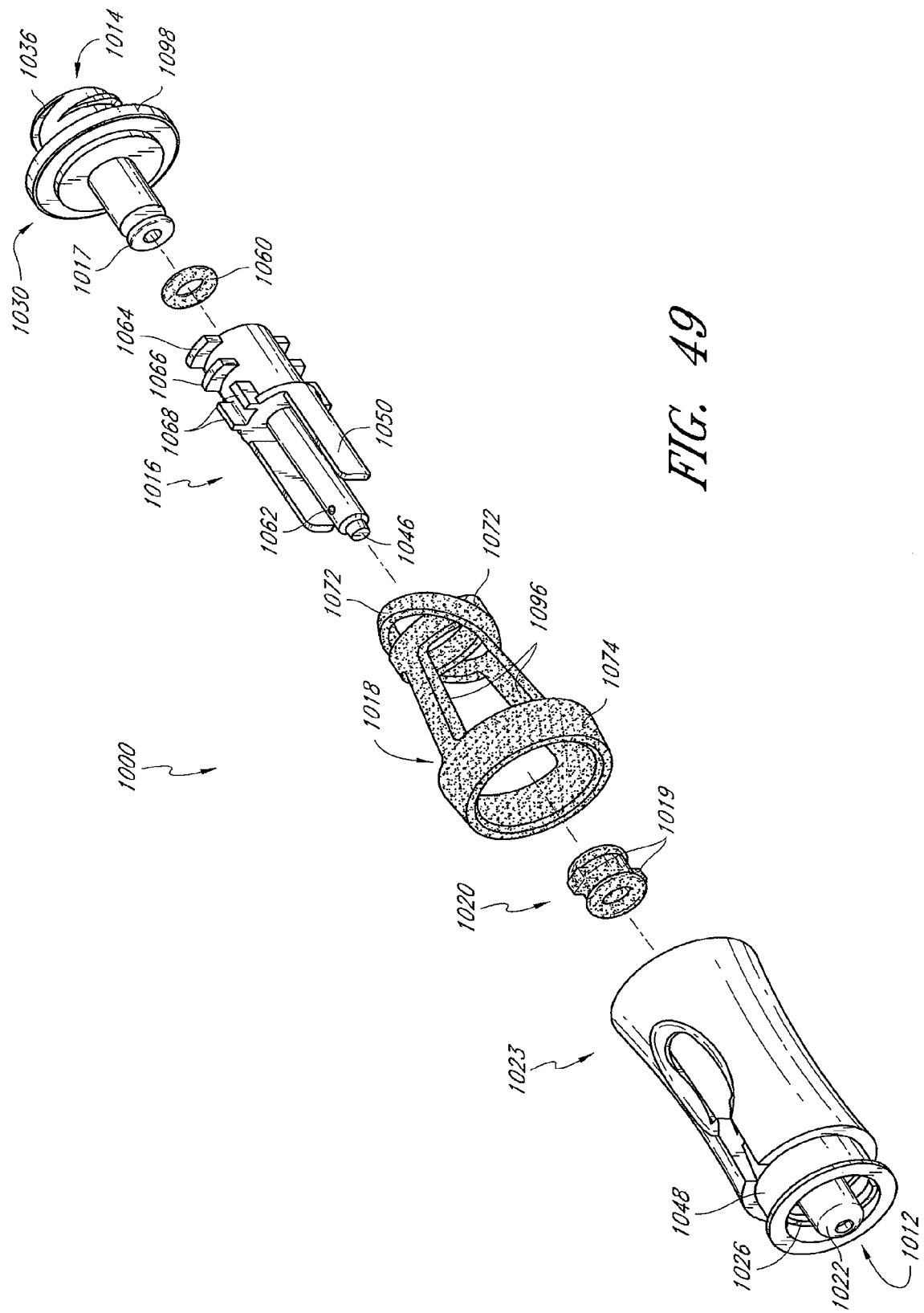
FIG. 49 is an exploded view of the components of an embodiment of a closeable male luer connector.

FIG. 49 illustrates an exploded view of the components of an example of an embodiment of a connector 1000. In the illustrated embodiment, the resilient member 1018 is shown with overlapping securing rings 1072. The end cap 1030 can be positioned toward the second end 1014 of the connector 1000. The O-ring 1060 can be disposed around a portion of the end cap 1030, and the plunger 1070 can be positioned within the valve member 1016, entering it from the second side 1014.

The resilient member 1018 is disposed around both the housing 1023 and the valve member 1016, elastically coupling them together. The sealing ring 1020 is disposed around the valve closure end 1044 of the valve member 1016 and inside the housing 1023. The sealing ring 1020 can have one or more protrusions 1019 corresponding to indentations in either the valve member 1016 or the housing 1023 to substantially secure the sealing ring 1020 in place. In the illustrated embodiment, two protrusions 1019 extend out from the sealing ring 1020 to couple with the housing 1023. More or fewer protrusions 1019 can be used or the sealing ring 1020 can be configured to secure to the valve member 1016.

Figure 50:
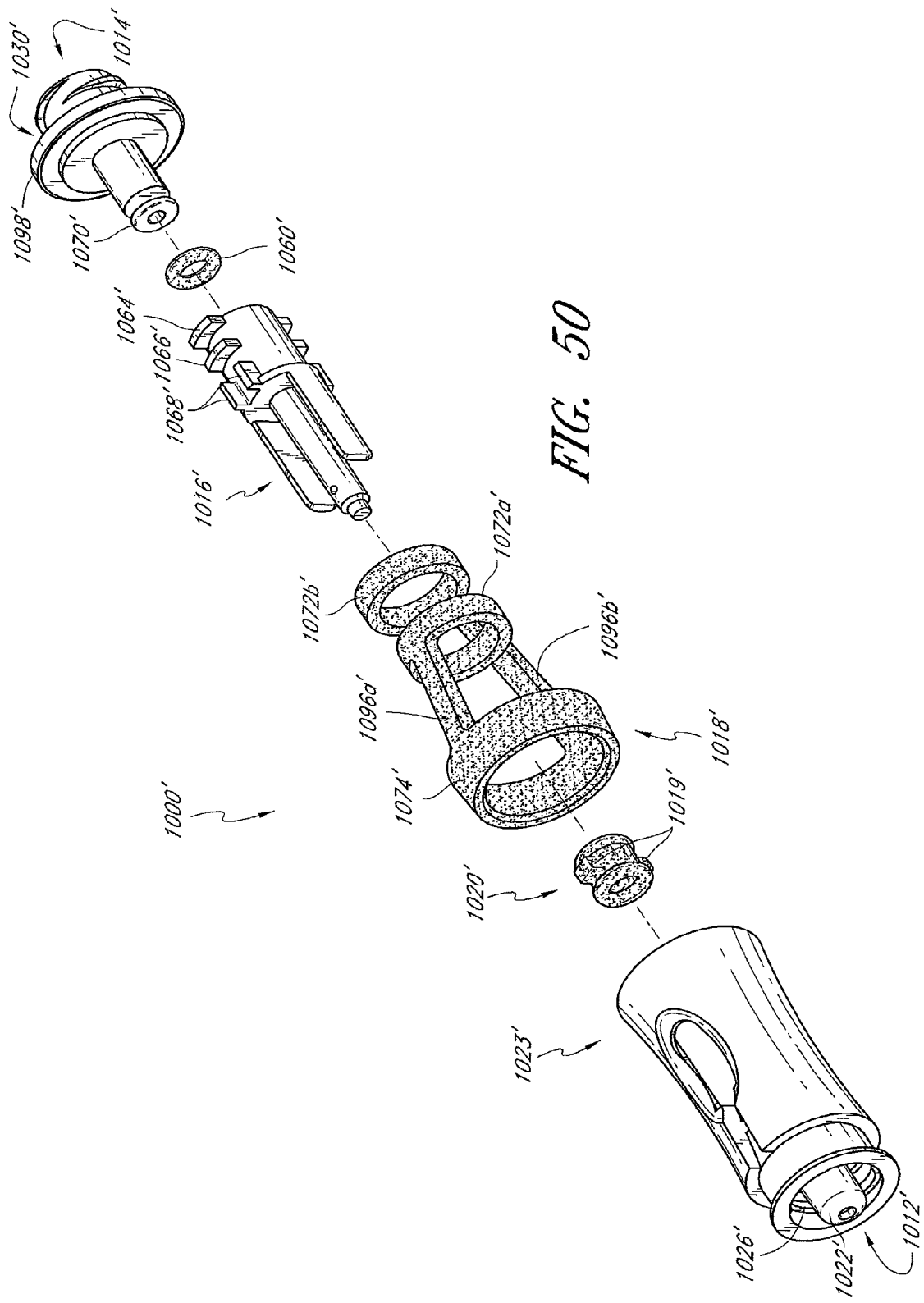
FIG. 50 is an exploded view of the components of an embodiment of a closeable male luer connector.

In another embodiment illustrated in FIG. 50, components are generally numbered similar to those in previous embodiments; however, a prime (') has been added to corresponding numerals. As can be seen, the illustrated connector 1000' has a resilient member 1018' wherein the securing rings 1072' are not overlapping, but set at a spaced interval. The straps 1096' extend from the first ring 1074' to the securing ring 1072', 1072' at different distances. Accordingly, first strap 1096a' is shorter than second strap 1096b'. The shorter strap 1096a' is connected to the first securing ring 1072a', positioned closer to the first end 1014' of the connector 1000', and the first ring 1074'. Likewise, the longer strap 1096b' can extend from the first ring 1074' to the second securing ring 1072b'.

The first securing ring 1072a' can be disposed between the notch flanges 1068' and the lower flange 1066'. The second securing ring 1072b', extending further toward the second end 1014', can be disposed between the lower flange 1066' and the upper flange 1068'. The configuration of the resilient member 1018' in the illustrated embodiment performs in a similar way as previous embodiments. Other configurations are also possible.

As described above, some medications, including those used during chemotherapy, can be harmful in certain forms of exposure to a patient. For example, exposure to the skin can sometimes result in a chemical burn. Inhalation of aerosolized forms of some medications can be harmful. Thus, control over the containment of the medication is highly desirable.

At present, some potentially harmful medications are distributed in sealed vials. The medication is removed from the vial by inserting a needle, and drawing the medication into a syringe. The needle is then withdrawn from the vial and the medication can be dispensed. However, by inserting the needle into the medication for drawing into the syringe, medication is disposed on the outside of the needle, which can inadvertently come in contact with the skin and cause harm. Alternatively, an injector which penetrates the vial with a withdrawal mechanism can be used. In such an injector, the medication is drawn through the mechanism and passed directly to a needle for injection without the additional step of withdrawing the mechanism from the vial. Even if such an injector is used, there is still the possibility of latent medication remaining on the needle used to inject the medication, or on the mechanism after the vial is decoupled.

Additionally, some medications can be distributed by attaching a needle to a syringe with the medication located therein. The engaged syringe with medication and needle is sterilized and placed into a vacuum-sealable container. The container is then evacuated and sealed. This type of arrangement can result in the draw of medication out through the syringe when the container is evacuated. While in the sealed container, the medication may aerosolize or coat the outer surface of the components.

Additionally, when the ambient atmospheric pressure of the treatment location is different, particularly lower, than that of the internal pressure of the medication within a container, it is possible that an uncontrolled spray of medication can occur. For example, medication may escape when a vial with a greater internal pressure than the ambient atmosphere is penetrated by a needle for drawing the medication into a syringe. Alternatively, medication may escape when the needle is withdrawn from the vial before the vial seal completely closes.

A syringe mated with a closeable male luer can generally inhibit the flow of medication except during desired applications. For example, in some embodiments, a syringe with a closeable male luer connected will not leak medication when packaged for shipment, even if the package is vacuum-sealed. Once the package is opened, the male luer connector can be engaged with a female luer connector of an IV tube, for example, and the medication dispensed only when the connection is engaged. Following flow of the medication from the syringe through the engaged connectors and into the IV tube, the male luer connector can be disengaged from the female luer connector. As described above, the male luer connector can close on disengagement, preventing excess flow through the connector. When a closeable female luer connector, such as a Clave® connector sold by ICU Medical, San Clemente, Calif., is used, flow is inhibited from exiting the female connector as well.

Additionally, a syringe with a closeable male luer can be engaged with a needle as described above. Flow through the needle can thus be controlled by proper use of the closeable male luer connector. Medication can also be disposed within a syringe with an integrally formed, and/or permanently attached, closeable male luer. Thus, direct exposure of the dangerous medications described can be essentially limited to the highly controlled environments where the medications are produced and contained. Such medications can be placed in a syringe with a closeable male luer connector prior to distribution for use, minimizing the risk of inadvertent exposure of the medication during use of the medication.

Figure 51:
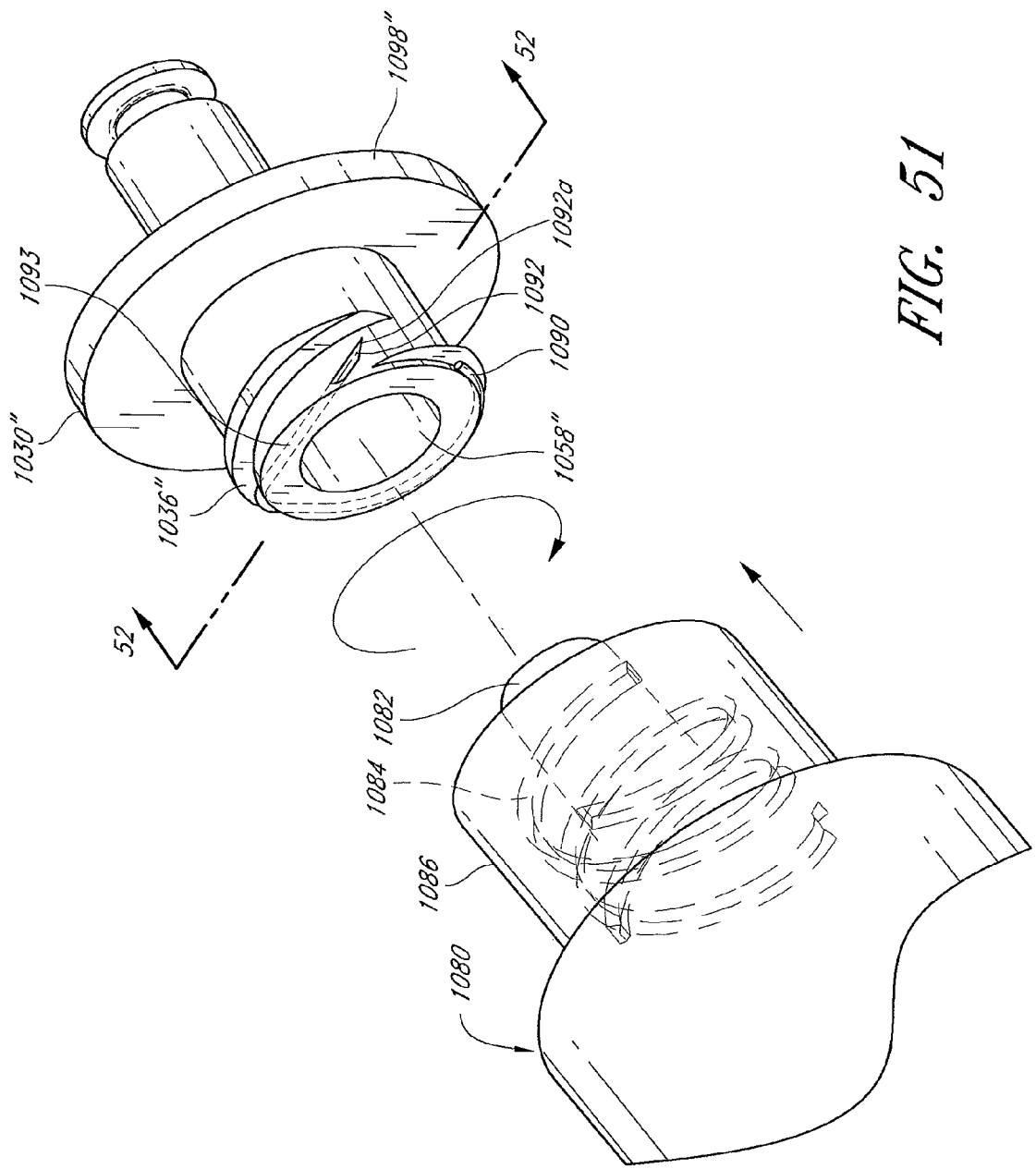
FIG. 51 is a perspective view of an engagement arrangement of an embodiment of a component of a non-reversible closeable male luer connector.

FIG. 51 illustrates an embodiment of the end or end cap 1030" with an example of a structure for preventing the female end of the connector from easily disengaging from a male luer inserted therein. This type of structure can have many different embodiments and configurations, such as the illustrated retaining barb 1090. Many of the components illustrated in FIG. 51 are generally similar to those described above, except that a double prime (") has been added to distinguish them.

The illustrated embodiment shows a retaining barb 1090 partially encircling the luer receiver 1058" and partially extending through the receiver 1058". The retaining barb 1090 can comprise a wire having a partially circular shape through a portion of the wire, an angled section 1091, a straight section 1093, and a barb point 1092. The circular portion of the barb 1090 can correspond to the outer diameter of the luer receiver 1058", which can be along at least a portion of the external threads 1036". The angled section 1091 can comprise a transition in the barb 1090 from a circular shape to the straight section 1093, as shown in the illustrated embodiment. In the illustrated embodiment, the straight section 1093 passes through a portion of the solid wall of the luer receiver 1058", ending in the barb point 1092. In some embodiments, luer receiver 1058" includes an elongate structure extending from the wall of the receiver 1058" and does not necessarily include the other components of the illustrated barb 1090.

As illustrated in FIGS. 51-53, 55, in some embodiments, the barb point 1092, 1092''' can comprise an inclined barb surface 1092a, 1092a'''. As illustrated most clearly in FIG. 51, in some embodiments, the inclined barb surface 1092a can be configured to face toward the outer surface of the luer receiver 1058". Conversely, as illustrated most clearly in FIG. 52, in some embodiments, the inclined barb surface 1092a can be configured to face away from the outer surface of the luer receiver 1058". Similarly, as illustrated most clearly in FIG. 55, in some embodiments, the inclined barb surface 1092a''' can be configured to face outward (i.e., away from the partially circular portion of the retaining barb 1090'''). Conversely, in some embodiments (not illustrated), the inclined barb surface 1092a" can be configured to face inward (i.e., toward the partially circular portion of the retaining barb 1090'''). In some embodiments, the barb 1090 is substantially symmetrical about its axis (e.g., it does not have a flat inclined surface), or the barb 1090 has a flat or rounded end with no point.

In some embodiments, the barb 1090 can continue to extend around the luer receiver 1058" without penetrating it. In some embodiments, the barb 1090 can extend through the inner wall of the luer receiver 1058", and can potentially contact a male luer connector introduced into the luer receiver 1058". Although circular metal wire is shown in the illustrated embodiment, wire having other cross-sections or other materials besides metal wire, such as plastic or a metal sheet, can also be used.

As described below, the barb point 1092 can have several shapes, each adequate to perform the necessary retention. The barb point 1092 can extend from the outer wall of the luer receiver 1058", or, as illustrated, the straight section 1093 can continue for a distance before the wire forms the barb point 1092.

A syringe 1080 is illustrated adjacent the luer receiver 1058". The syringe can comprise a syringe shroud 1086 having inner syringe threads 1084. The syringe shroud 1086 and threads 1084 can partially surround a syringe tip 1082, with all components generally conforming to ANSI standards for luer connectors. The external threads 1036" can be configured to engage corresponding threads 1084 on the inner surface of the syringe shroud 1086. The luer receiver 1058" can be configured to accept the syringe tip 1082, thereby creating a luer connection.

Figure 52:
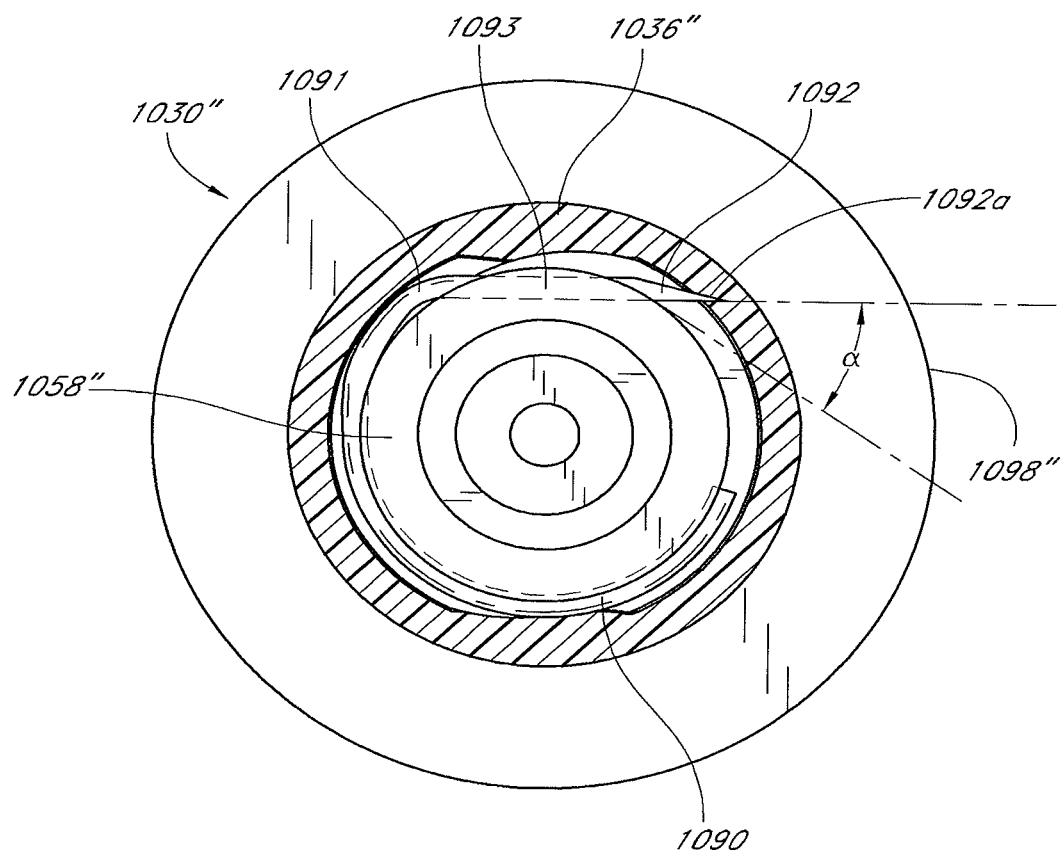
FIG. 52 is a cross-sectional view of the embodiment of FIG. 51 taken along the line 52-52.

FIG. 52 illustrates a cross-sectional view of the end cap 1030" of FIG. 51 taken along the line 52-52. As shown, the barb 1090 can extend at least partially around the luer receiver 1058". In the illustrated embodiment, the barb 1090 is disposed adjacent the external thread 1036". The barb 1090 can partially encircle the luer receiver 1058" before extending through the receiver 1058" with a straight section 1093. The barb point 1092 can extend outwardly away from the luer receiver 1058" and external thread 1036". In some embodiments, the barb point 1092 can extend beyond the circular plane defined by the external threads 1036". In some embodiments, barb 1090 forms an angle α with a line tangent to the external wall of the luer receiver 1058". In some embodiments, angle α is in the range of approximately 5 to approximately 75 degrees. In some embodiments, angle α is in the range of approximately 10 to approximately 35 degrees. Generally, angle α is less than approximately 90 degrees. In some embodiments, angle α is in the range of approximately 15 to approximately 30 degrees.

When a male luer connector, such as the syringe 1080, is coupled with the illustrated end cap 1030", the coupling can be initiated by twisting the syringe 1080 and luer receiver 1058" to engage the threaded surfaces 1036". As the engagement occurs, the barb point 1092 can be angled as shown to slide along the inside of the syringe shroud 1086, guided by the syringe threads 1084. The barb point 1092 can be placed in a tangential position, relative to the luer receiver 1058", as shown to emphasize the accommodation of engagement. In addition, the angle of the point 1092 can be aligned to simulate an extension of the curvature of the luer receiver 1058".

Once engagement is finished and the coupling is complete, a reverse twisting motion is generally used to decouple syringes from luer receivers. However, when disengagement is attempted with the illustrated receiver 1058", the reverse twisting motion causes the barb point 1092 to encounter at least a portion of the syringe shroud 1086, and become at least partially embedded therein. The barb point 1092 can be angled to intersect the syringe shroud 1086 when decoupling is attempted.

As the barb point 1092 pierces the syringe shroud 1086, it can substantially inhibit the continued disengagement, resulting in increased difficulty in decoupling the syringe 1080 and the connector 1000. For this reason, once a connector 1000 with the retaining barb 1090 is coupled to a syringe or other medical device, it can be difficult or impossible to decouple the connector without applying increased torque and/or structural damage to at least one of the devices.

FIGS. 53 and 54 illustrate an embodiment of the retaining barb 1090 having a sharp barb point 1092. As shown, the circular shape transitions through the angled section 1091 to a straight section 1093 before ending in the barb point 1092. Although the straight section 1093 can be at least partially embedded in the end cap 1030", other configurations can be used.

In the illustrated embodiment, the barb point 1092 can be elliptically shaped, and/or lack a true point. For example, the barb 1090 can have a sharpened rounded edge or some other appropriate structure. The illustrated embodiment can be formed by cutting the barb 1090 at an angle, resulting in the point 1092 shown.

Figures 55, 56:
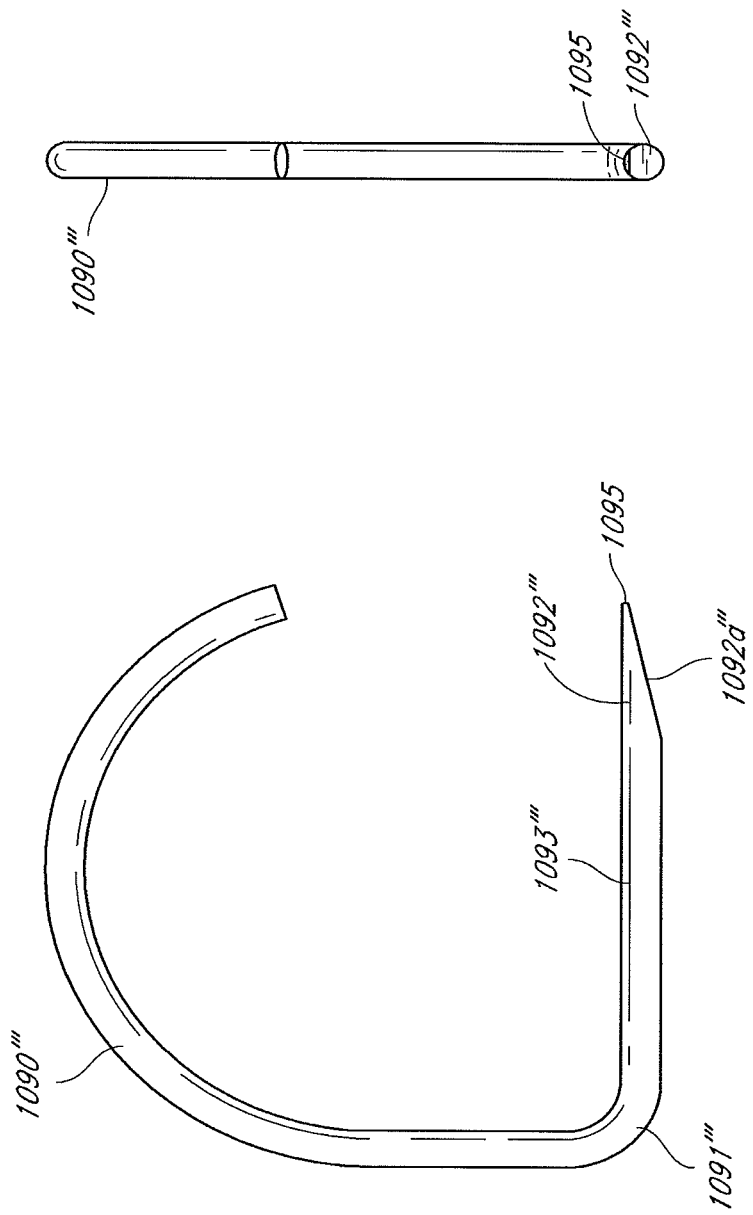
FIG. 55 is a side view of an embodiment of a component of a non-reversible closeable male luer.
FIG. 56 is a side view of the component of FIG. 55.

FIGS. 55 and 56 illustrate another embodiment of the retaining barb 1090''', wherein the component sections are substantially similar, except that a triple prime (''') has been added. In the illustrated embodiment, a barb point face 1095 is present at the tip of the barb point 1092'''. The point face 1095 can be formed by cutting the tip of the barb point 1092''' to enhance the ability of the barb 1090 to puncture a medical device during decoupling. Alternatively, the point face 1095 can be formed by making a cut similar to the one that forms the barb point 1092 in FIGS. 53 and 54, except that the cut need not completely cross the diameter of the barb 1090''' prior to intersecting the end of the wire from which the barb 1090''' is formed. In some embodiments, this can produce a flat barb point face 1095

Although the barb 1090 has been described to lock the luer connector 1000 to another medical device, many other methods of making a coupling between medical devices difficult or impossible to reverse can also be used. For example, one or more barb point(s), bumps, clips, and/or protrusions appropriately formed on the luer receiver 1058 or other structure can also be used.

Additionally, the retaining barb or other removal-impeding structure can be used with other medical devices besides the closeable male luer connector 1000 described above. The barb can be attached to any suitable medical device having a portion adapted to connect to another luer connector. Any other suitable device can be configured to include removal-impeding structure. For example, any of the devices disclosed in the following U.S. patent applications and patents, or other devices in the same or similar categories, can be configured to include removal-impeding structures: U.S. Pat. No. 6,428,520, issued Aug. 6, 2002; U.S. Pat. No. 6,245,048, issued Jun. 12, 2001; U.S. Pat. No. 6,695,817, issued Feb. 24, 2004; U.S. Pat. No. 6,758,833, issued Jul. 6, 2004; and U.S. Pat. No. 6,599,273, issued Jul. 29, 2003; U.S. Patent Publication Nos. 2006/0161115, published Jul. 20, 2006 and 2006/0173420, published Aug. 3, 2006; and U.S. Provisional Patent Applicant No. 60/854,524, filed Oct. 25, 2006. A removal-impeding structure can be especially advantageous when the contents of a fluid container to which a connector is attached can be unsanitary, harmful, and/or toxic.

Figure 57:
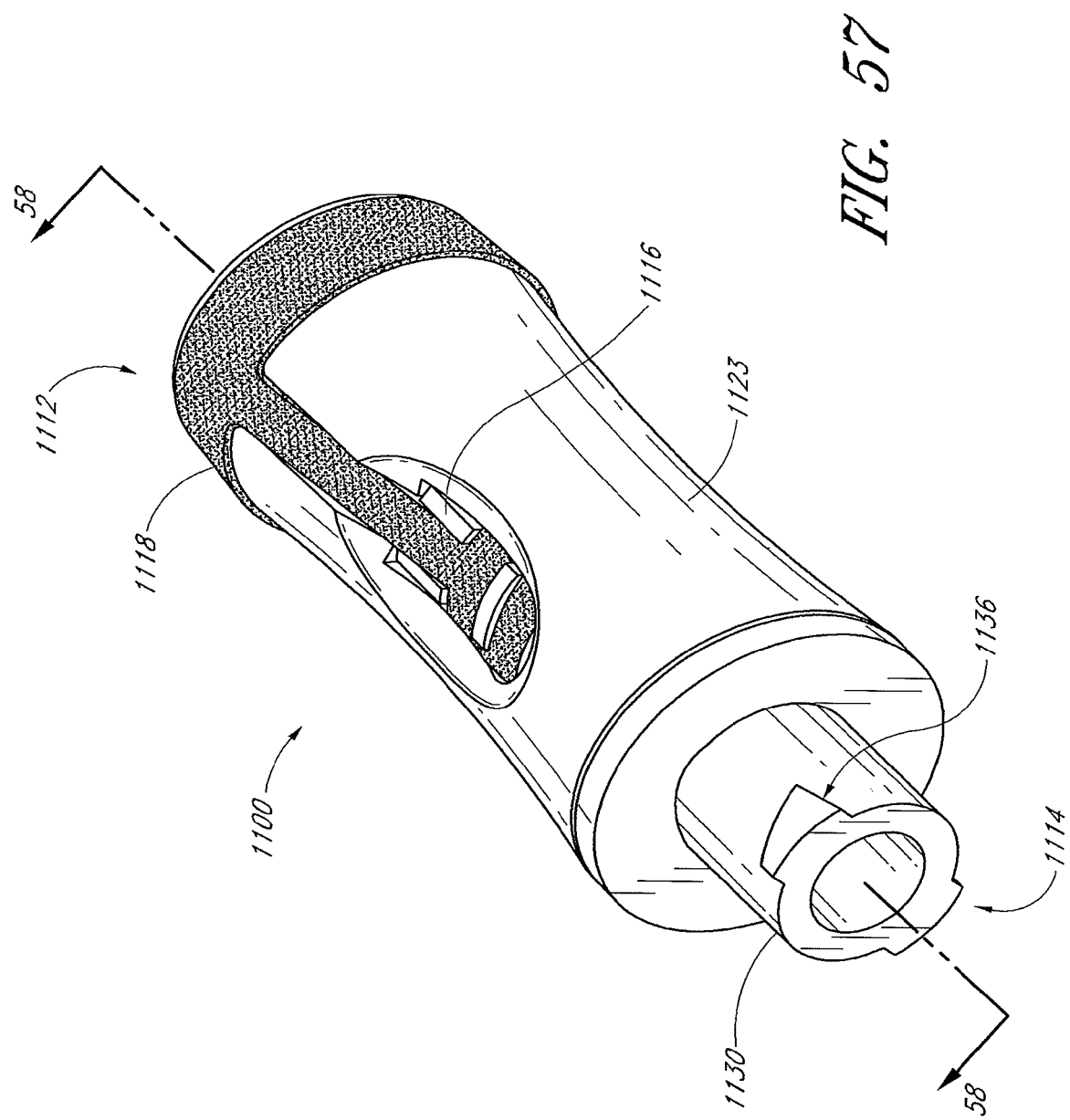
FIG. 57 is a perspective view of an embodiment of a closeable male luer connector in a closed position.
Figure 58:
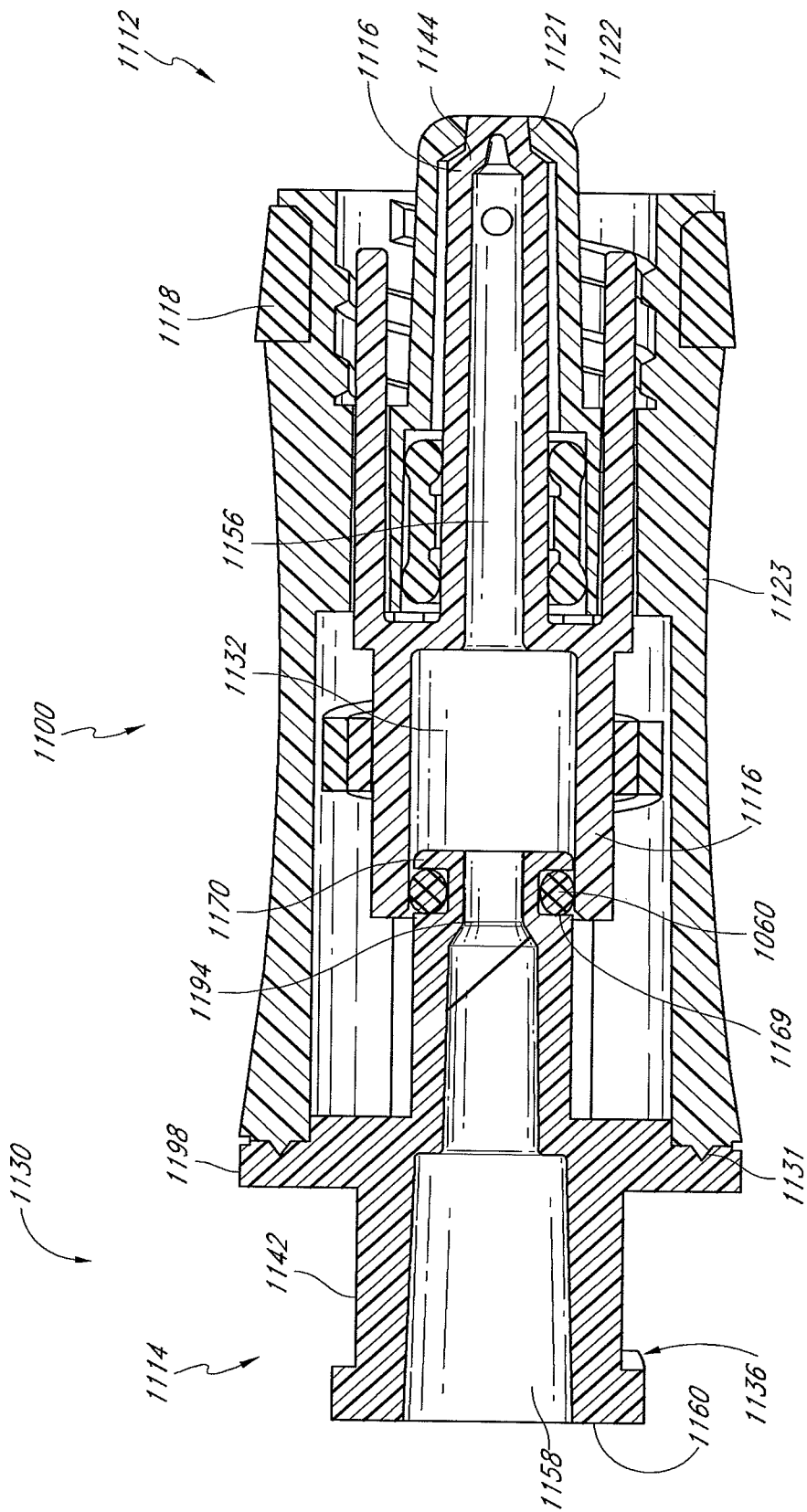
FIG. 58 is a cross-sectional view of the closeable male luer connector of FIG. 57 taken along the line 58-58.

FIGS. 57 and 58 illustrate another embodiment of a closeable male luer connector 1100 wherein the end cap 1130 can comprise a structure for preventing the female end of the connector from easily disengaging from a male luer inserted therein. The closeable male luer connector 1100 illustrated in FIGS. 57 and 58 is similar to the closeable male luer connector 1000 described above, except as described below. The end cap 1130 of the closeable male luer connector 1100 defines another example of a locking arrangement 1136 thereon that, as will be described in greater detail below, is configured not only to threadably engage the corresponding internal threads of a male luer connector or other component such as a syringe, but also to prevent or impede the disengagement or unthreading of the male luer connector from the corresponding male luer connector or other component to which the closeable male luer connector 1100 is attached. Because the locking arrangement 1136 can generally be used with any end cap or closeable male luer, the following description will focus mainly on the locking arrangement 1136 and not on the features of the closeable male luer 1100 that are similar to those same features described above for closeable male luer 1000.

The end cap 1130 can be formed by plastic injection molding or any other suitable manufacturing process. The end cap 1130 can be formed from a 20% glass-filled polycarbonate material, but can be formed from any one or more other materials, such as polycarbonate, glass-filled polycarbonate, other suitable rigid plastics, metals, alloys, etc., or combination thereof. As with the end cap 1030 of the closeable male luer connector 1000 described above, the end cap 1130 can be coupled with the housing 1123 through sonic welding, an adhesive, or any other suitable method for coupling. In the embodiment illustrated in FIG. 58, the end cap 1130 can be coupled to the housing 1123 with sonic welds 1131. One such weld 1131 has a substantially triangular shape as shown, though other shapes are also possible.

Figure 59:
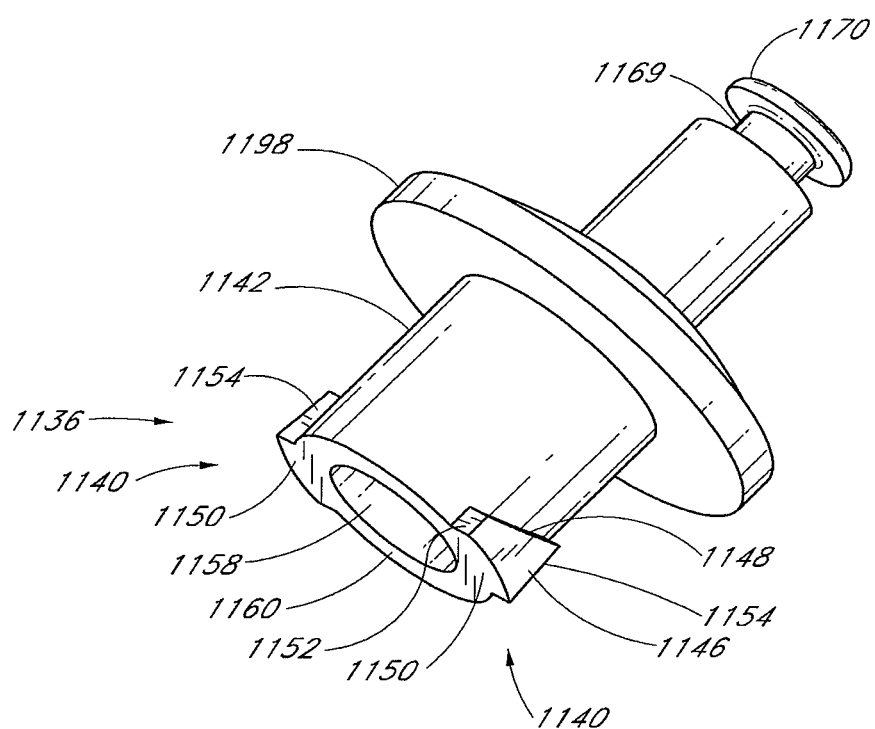
FIG. 59 is a perspective view of the female connector component of the closeable male luer connector of FIG. 57.

As shown in FIG. 59, in some embodiments, the end cap 1130 can be formed to define a plunger 1170. The plunger 1170 can be sized and configured to substantially seal the chamber 1132 within the valve member 1116. An indentation or slot 1169 between the sealing portion 1198 and the plunger 1170 can be sized and shaped to accommodate an O-ring or other annular seating member, as illustrated in FIG. 58. Alternatively, plunger 1170 can be shaped to substantially mate with sealing portion 1198 without the use of an additional annular sealing member. The plunger 1170 can be considered to be in a static position relative to the housing 1123. In some embodiments, the plunger 1170 can be formed integrally with the housing 1123 and the end cap 1130 is a separate piece appropriately attached to the housing 1123, such as by sonic welding. In some embodiments, the end cap 1130 can be integrally formed with the housing 1123.

Similar to the closeable male luer connector 1000 described above, the closeable male luer connector 1100 can have a first end 1112 and a second end 1114. The first end 1112 can comprise a male luer tip 1122 and a valve member 1116. The luer tip 1122 and valve member 1116 can be supported by a housing 1123. The valve member 1116 can be coupled to the housing 1123 by a resilient member 1118. As with the end cap 1030 of the closeable male luer connector 1000, the end cap 1130 of the closeable male luer connector 1100 can be coupled to the housing 1123 near the second end 1114 of the closeable male luer connector 1100. The embodiment of the closeable male luer connector 1100 shown in FIG. 58 is in a closed position, whereby a valve closure end 1144 is positioned within the hole 1121 in the luer tip 1122, thereby sealing the hole 1121 in the tip 1122. Thus, similar to the closeable male luer connector 1000 described above, valve member 1116 cooperates with male luer tip 1122 to impede the flow of fluid through the connector 1100 in the closed position.

Further, the closeable male luer connector 1100 can be manipulated to a second or open position in a manner similar to that of the closeable male luer connector 1000 described above. In the open position of some embodiments, the valve member 1116 and valve closure end 1144 are retracted from the luer tip 1122, thereby opening the hole 1121 in the tip 1122. In the open position, fluid can pass from the luer receptacle at the second end 1114 through the interior of the connector 1100 and exit the luer tip 1122 at the first end 1112. As illustrated most clearly in the cross-sectional view of FIG. 58, a passageway 1156 can be in fluid communication with a chamber 1132 that can extend through a portion of the valve member 1116. The chamber 1132 can also be in fluid communication with the internal space of the luer receiver 1158 via conduit 1194. Thus, as shown in the illustrated embodiment in FIG. 58, fluid can flow in the luer receiver 1158 and pass to the conduit 1194. From the conduit 1194, fluid can pass to the chamber 1132 and from the chamber 1132 into the passageway 1156. Under normal operating conditions, fluid is impeded or blocked from passing through the luer connector 1100 when the luer connector 1100 is closed, as shown in FIG. 58.

The end cap 1130 can have a sealing portion 1198 shaped and configured to substantially seal the second end 1114 of the housing 1123. The luer receiver 1158 can extend in an outward direction from the sealing portion 1198. The luer receiver 1158 can be appropriately sized to couple with a male luer portion (not shown) conforming to ANSI standards for luer devices or to a syringe. The luer receiver 1158 illustrated herein can have a locking arrangement 1136 that in some embodiments serves at least the following functions. The locking arrangement 1136 can threadably engage with the corresponding internal threads of a male luer connector or other component such as a syringe when the end cap 1130 is rotated or threaded in a first direction (which can be clockwise) into the male luer connector of such a component. Additionally, the locking arrangement 1136 can substantially prevent or impede the rotation or unthreading of the end cap 1130 or female portion of the male luer connector 1100 in a second direction relative to the corresponding male luer portion of the mating component when a torque is applied to the end cap 1130 (which can be in a counter-clockwise direction) relative to the component to which the end cap 1130 and the male luer connector 1100 are attached.

In the illustrated embodiment, the locking arrangement 1136 can comprise a pair of oppositely disposed protrusions 1140 located on an outside surface 1142 of the end cap 1130. In some embodiments, the locking arrangement 1136 can comprise only one protrusion 1140 located on the outside surface 1142 of the end cap 1130. In some embodiments, the locking arrangement 1136 can comprise three protrusions 1140 located on the outside surface 1142 of the end cap 1130, which can be spaced apart at radial equidistant positions. The protrusions 1140 each preferable comprise an outside surface 1146, a top surface 1148, a bottom surface 1150, a minor side surface 1152, and a major side surface 1154. In some embodiments, the locking arrangement 1136 can comprise more than three locking portions.

The protrusions 1140 can be positioned on the end cap 1130 such that the planar bottom surface 1150 is coplanar with the planar end surface 1160 of the end cap 1130. Each protrusion 1140 can be configured such that the outer surface 1146 defines a diameter that is approximately slightly less than the inside surface diameter of the shroud 1183 of the male luer connector or other component that the end cap 1130 mates with, as illustrated most clearly in FIG. 62. In the illustrated embodiment, the outer surface 1146 defines a diameter that is approximately 0.312 inch. This configuration is preferred though not required so that the outer surface 1146 does not interfere with, or impart a significant force against, the inside surface of the shroud of the male luer portion of the component that the end cap 1130 is mating with. In some embodiments, the outer surface 1146 can be configured to provide an interference fit with the inside surface of the shroud to, in whole or in part, substantially impede the decoupling of the end cap 1130 from the male luer portion of the component to which it is connected.

In the illustrated configuration, for each protrusion 1140, the intersection of the bottom surface 1150 and the major side surface 1154 can define a sharp first corner 1162. Similarly, the intersection of the top surface 1148 and the major side surface 1154 can define a sharp second corner 1164. The projected length of the major side surface 1154 can be slightly greater than the distance between adjacent, facing side walls of the internal thread of the mating component. In the illustrated embodiment, the projected length of the major side surface 1154 is approximately 0.08 inch (i.e., the shortest distance between the second corner 1164 and the planar end surface 1160 is approximately 0.08 inch). To prevent a portion of the minor side surface 1152 from interfering with the internal threads of the mating component, the length of the minor side surface 1152 can be less than the projected length of the major side surface 1154 and also less than the distance between adjacent, facing side walls of the internal thread of the mating component.

Figure 62:
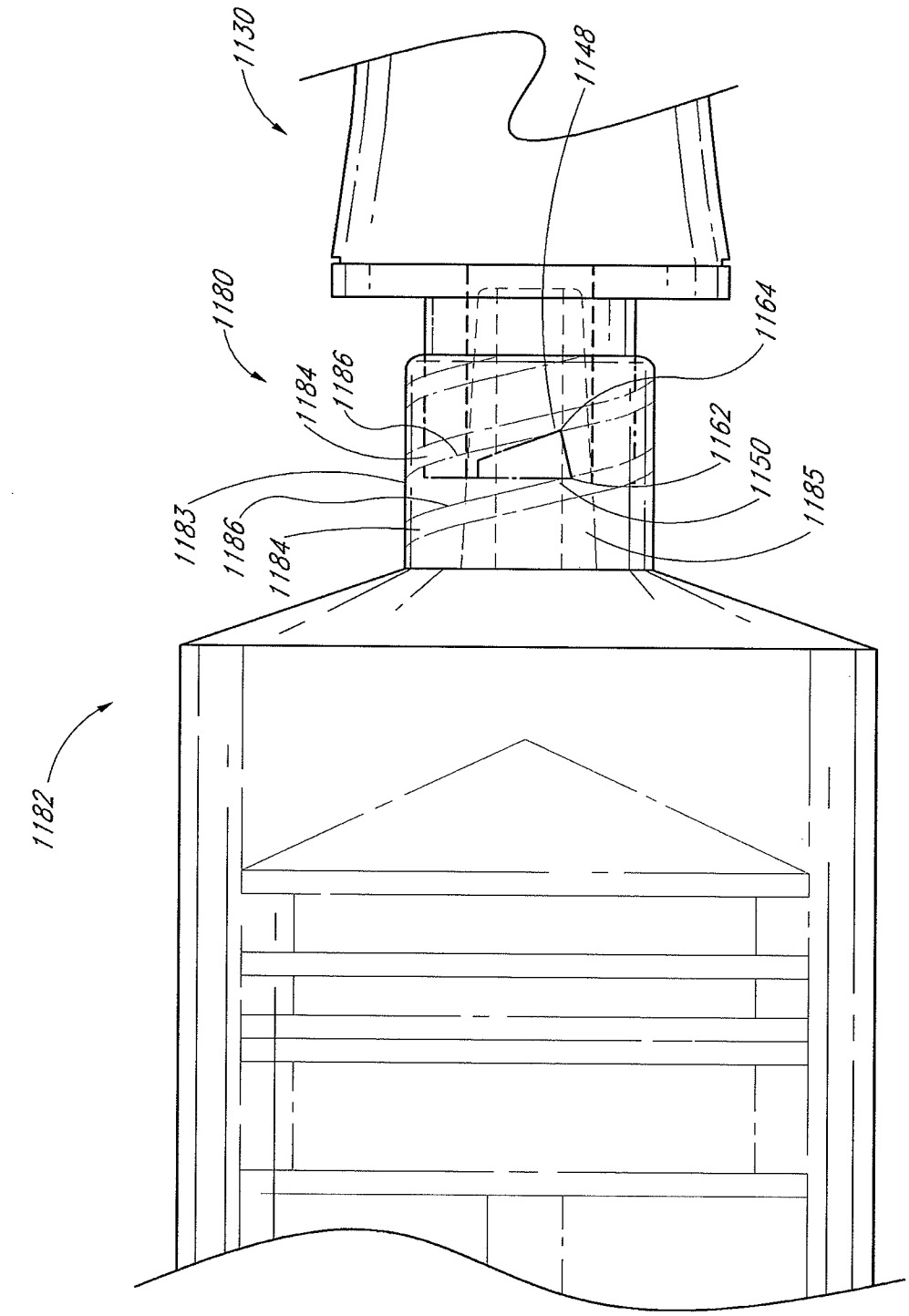
FIG. 62 is an enlarged side view of an end cap portion of the female connector component shown in FIG. 59 threadably inserted into a male connecting portion of a mating component.

FIG. 62 is an enlarged side view of a portion of the end cap 1130 of the female connector component shown in FIG. 59, threadably inserted into a male connecting portion 1180 of a mating component 1182. As stated above, the mating component 1182 can be a male luer connector or other component such as a syringe. In FIG. 62, the mating component 1182 that is illustrated is a syringe. The illustrated mating component 1182, or syringe, has a syringe shroud 1183 having inner syringe threads 1184. As illustrated in FIG. 62, the syringe shroud 1183 and threads 1184 can partially surround a syringe tip 1185, with all components generally conforming to ANSI standards for luer connectors. The luer receiver 1158 can be configured to accept the syringe tip 1185, thereby creating a luer connection.

As is illustrated therein, the protrusion 1140 can be configured such that, when the end cap 1130 is threadably inserted into the male luer portion 1180 of the mating component 1182, the protrusion 1140 creates an interference fit with respect to the internal threads 1184 of the male luer portion 1180 of the mating component 1182 that impedes, substantially impedes, or prevents unthreading or decoupling of the end cap 1130 from the mating component 1182. However, the protrusion 1140 preferably does not significantly inhibit the ability of the user to thread or tighten the end cap 1130 into the mating component 1182. In the illustrated embodiment, the first and second corners 1162, 1164 can exert a force on the side walls 1186 of the internal threads 1184 of the male luer portion 1180 of the mating component 1182 such that either or both of the preferably sharp corners 1162, 1164 elastically or plastically deforms and embeds into the sides walls 1186 of the internal threads 1184.

Figure 60:
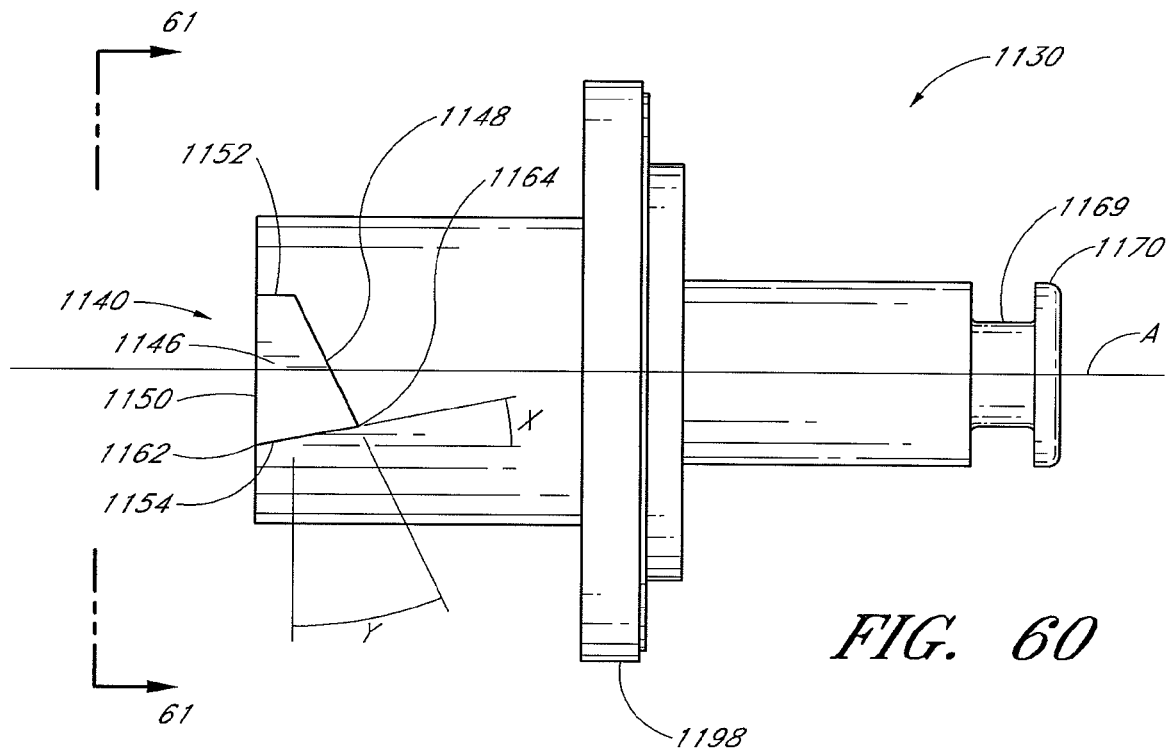
FIG. 60 is a side view of the female connector component shown in FIG. 59.
Figure 61:
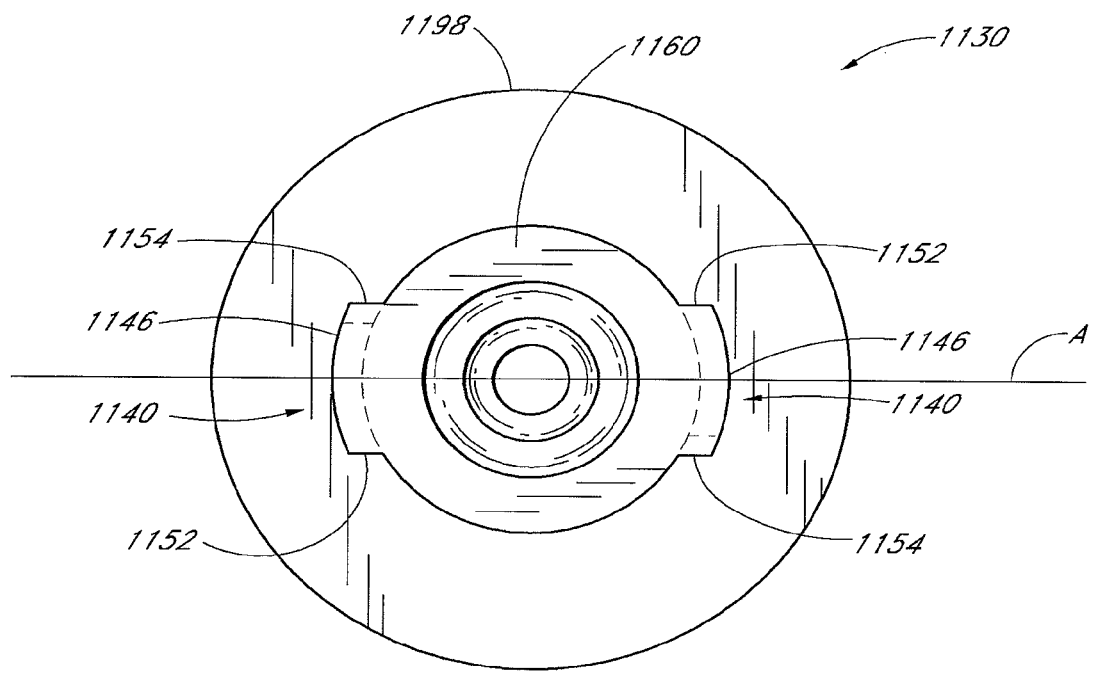
FIG. 61 is a front view of the female connector component shown in FIG. 59.

In some embodiments, as illustrated in FIGS. 60 and 61, the minor side surface 1152 of each protrusion 1140 can define a plane that is parallel to, but offset from, a horizontal plane (e.g., plane A) intersecting the centerline axis of the end cap 1130 and the line 62-62. The major side surface 1154 of each protrusion 1140 can define a plane that can be inclined at an angle X relative to plane A when the end cap 1130 is oriented as shown in FIG. 60. In the illustrated embodiment, the major side surface 1154 of each protrusion 1140 can be inclined at an angle, such as an angle that is approximately 12°, relative to a horizontal plane when the end cap 1130 is oriented as shown in FIG. 60. In some embodiments, the major side surface 1154 of each protrusion 1140 can be inclined at an angle that is between approximately 0° and approximately 12°, or between approximately 12° and approximately 20°, or between approximately 20° and approximately 30°, or between approximately 30° and approximately 40°, relative to a horizontal plane when the end cap 1130 is oriented as shown in FIG. 60. In some embodiments (not illustrated), each of the two side surfaces 1152, 1154 can define a plane that intersects a longitudinal centerline axis of the end cap 1130.

As illustrated most clearly in FIG. 60, the top surface 1148 of each protrusion 1140 can be inclined at an angle Y relative to a vertical plane when the end cap 1130 is oriented as shown in FIG. 60. In the illustrated embodiment, the top surface 1148 of each protrusion 1140 can be inclined at an angle, such as an angle of approximately 24°, relative to a vertical plane when the end cap 1130 is oriented as shown in FIG. 60. In some embodiments, the top surface 1148 of each protrusion 1140 can be inclined at an angle that is between approximately 10° and approximately 24°, or between approximately 24° and approximately 40°, or between approximately 40° and approximately 60°, relative to a vertical plane when the end cap 1130 is oriented as shown in FIG. 60.

While the locking arrangement 1136 was described above in particular detail and was illustrated and described to be applied to the end cap 1130 illustrated in FIGS. 57-62, the configuration of the locking arrangement 1136 is not limited to this configuration. The locking arrangement 1136 can be configured from any of a wide range of similar materials to those described herein or other materials that are known in those skilled in the art that are suitable for such applications. Further, the geometrical configuration of the locking arrangement 1136 is not confined to the specific arrangements illustrated and described herein. For example, the protrusions 1140 can be configured to comprise only one protrusion 1140, or can comprise a plurality of protrusions 1140. Moreover, the protrusion 1140 can be formed such that the top surface 1148 intersects directly with the bottom surface 1150 (i.e., so that the protrusion 1140 has three sides and does not include the minor side surface 1152).

The protrusion 1140 can be of any suitable geometric configuration that provides an interference fit with the internal threads of the mating component so as to impede, substantially impede, or prevent unthreading or decoupling the end cap 1130 from a mating component, while not significantly inhibiting the ability of the user to thread or tighten the end cap 1130 into the mating component. Or, more generally, the protrusion 1140 can be of any suitable geometric configuration that generally impedes, substantially impedes, or prevents unthreading or disconnecting the end cap 1130 from a mating component, but does not significantly inhibit the ability of the user to thread or tighten the end cap 1130 into the mating component. For example, the outer surface 1146 can be configured such that it provides an interference with the inside surface of the shroud of the mating component and/or such that it elastically or plastically deforms the inside surface of the shroud of the mating component to inhibit the decoupling of the end cap 1130 from the mating component. Also, the applicability of the locking arrangement 1136 is not confined to the end cap 1130. Any end cap or other component having external threads can be configured to comprise the locking arrangement 1136 described herein. For example, an end of a catheter can include the locking arrangements described herein so as to impede, substantially impede, or prevent unthreading or decoupling of the catheter from a luer lock component.

Figure 63:
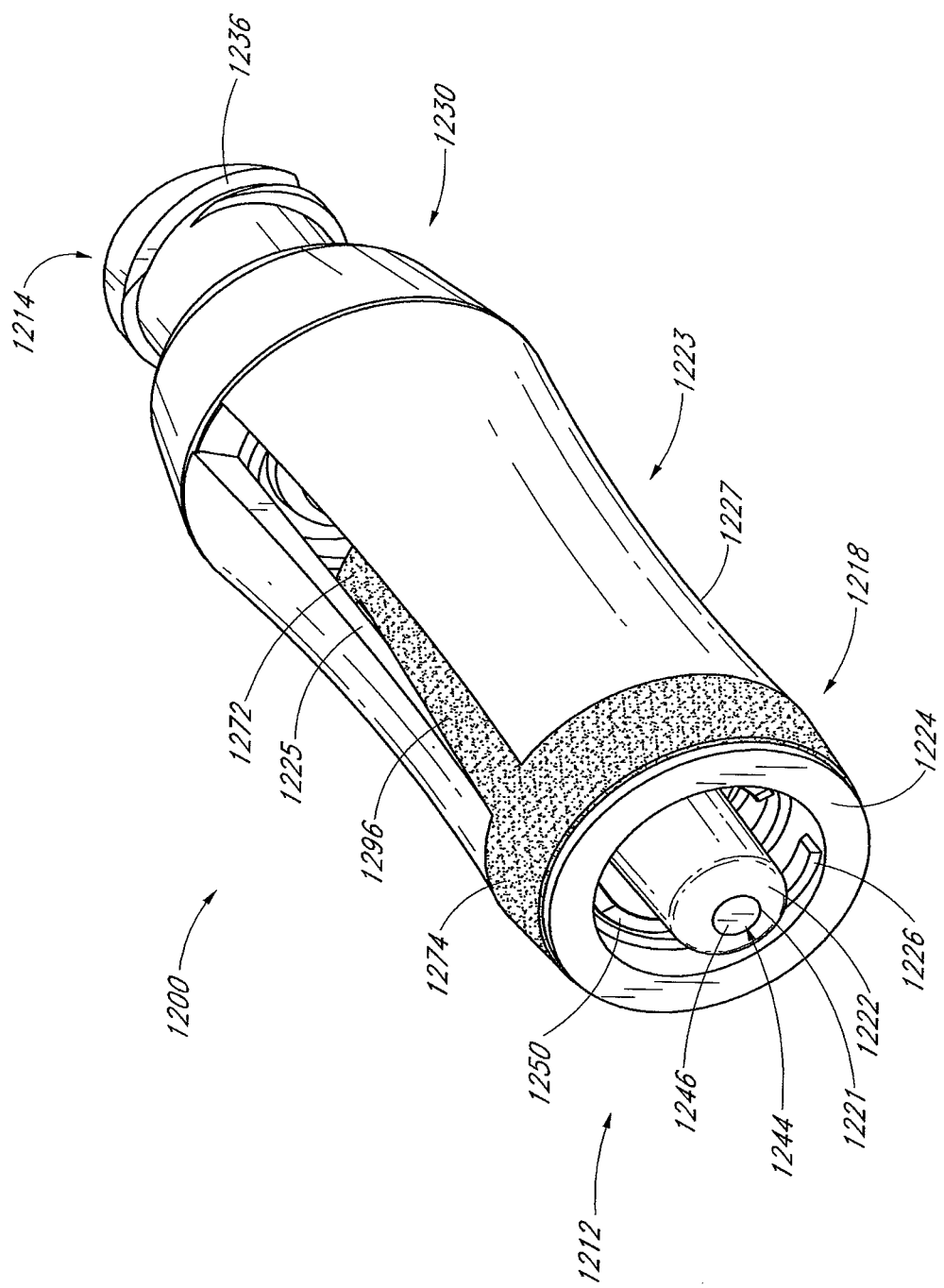
FIG. 63 is a perspective view of another embodiment of a closeable male luer connector in a closed position.

FIG. 63 illustrates another embodiment of a closeable male luer connector 1200 configured to prevent or inhibit the male portion of the coupled component from unthreading or decoupling from a closable male luer connector 1200. Any of the components comprising the luer connector 1200 can comprise any of the configurations, features, components, and/or materials of any of the other luer connectors described herein or that are known to one of ordinary skill in the art. Additionally, any of the other luer connectors described above can comprise any of the configurations, features, and components of the luer connector 1200. For example, the features relating to preventing or inhibiting disconnection can be used with any suitable medical or other fluid connector.

Figure 64:
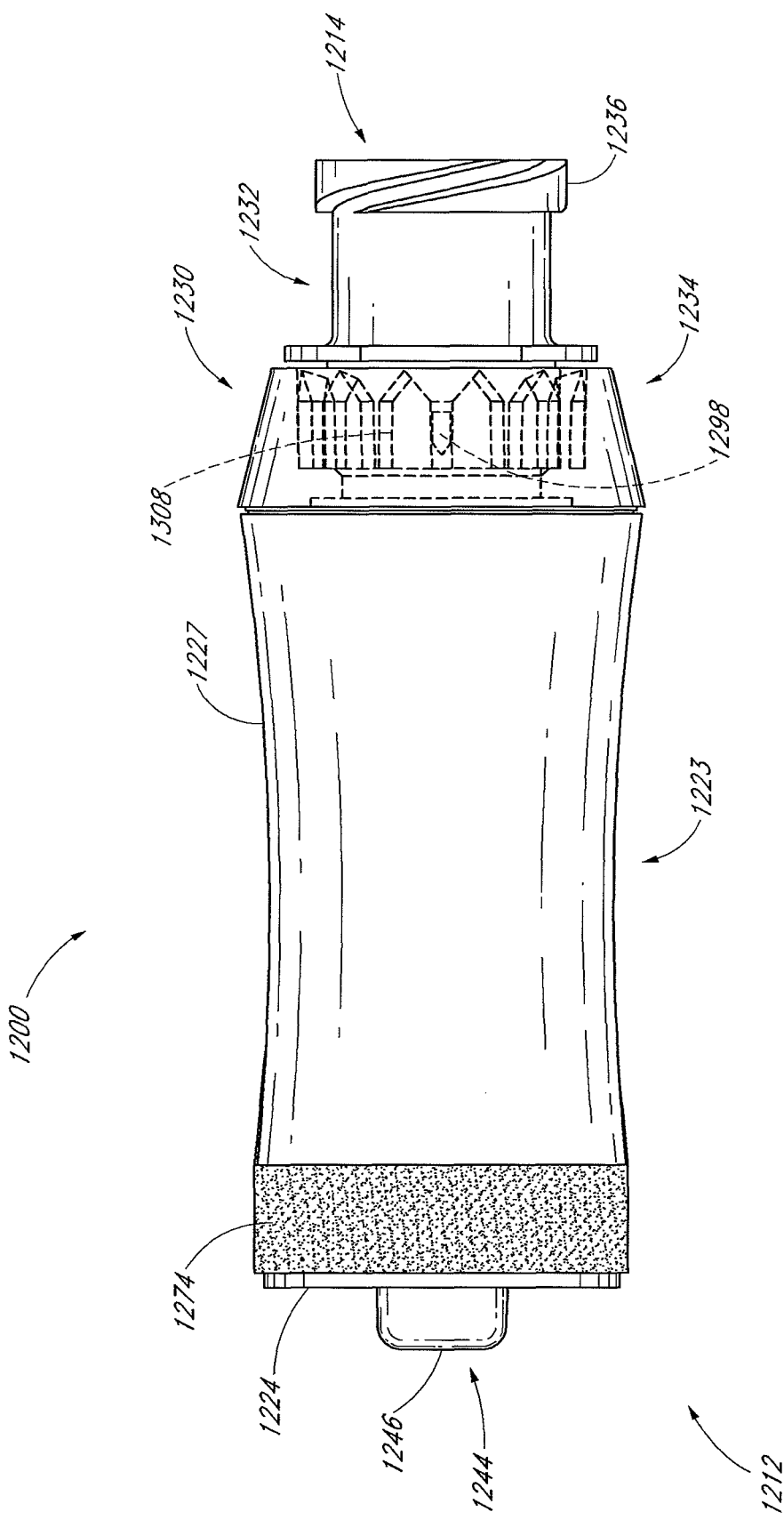
FIG. 64 is a side view of the embodiment of the closeable male luer connector shown in FIG. 63 again in a closed position, showing certain internal features of the closable male luer connector in dashed lines.
Figure 65:
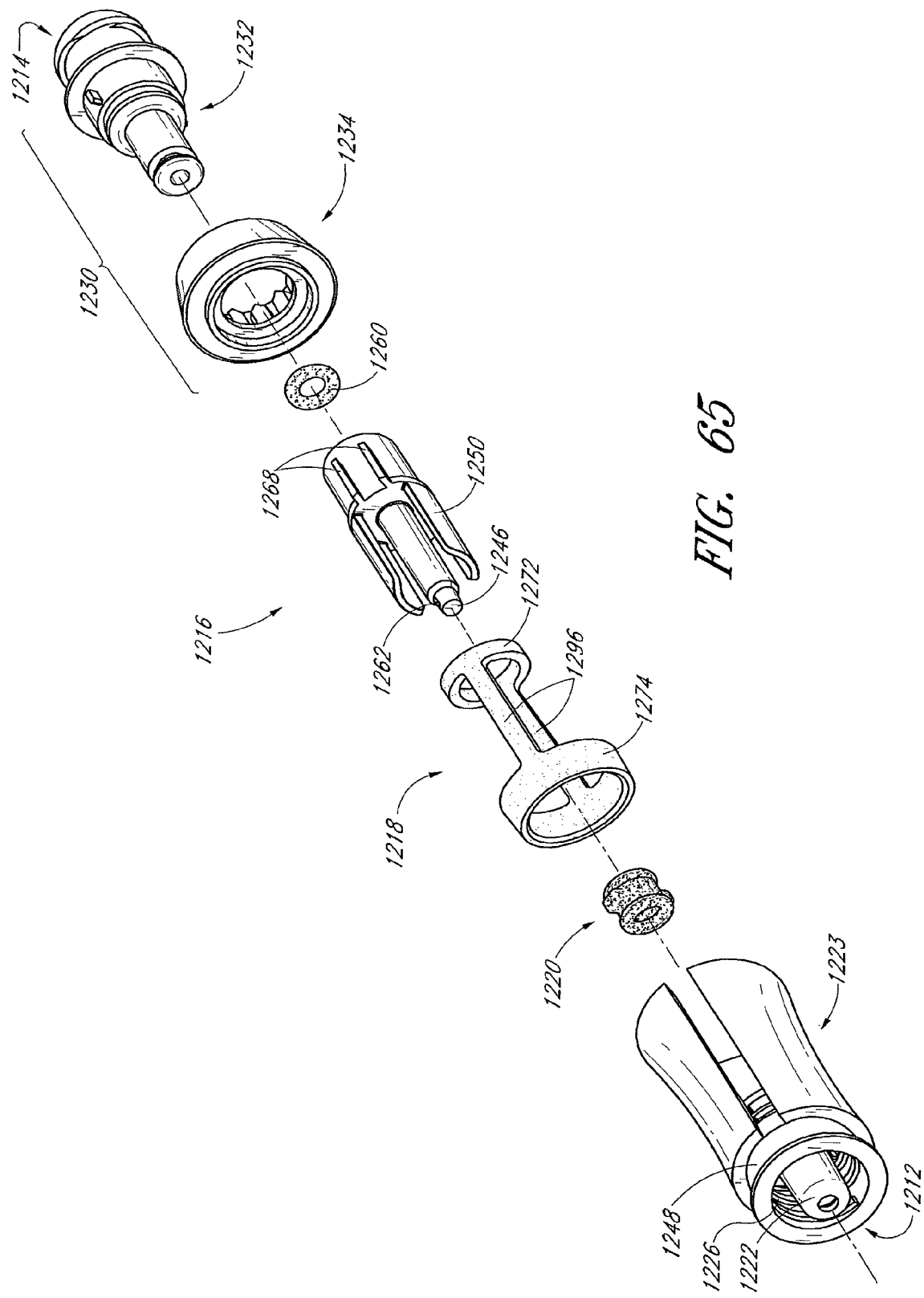
FIG. 65 is an exploded perspective view of the components of the embodiment of the closeable male luer connector shown in FIG. 63.
Figure 66:
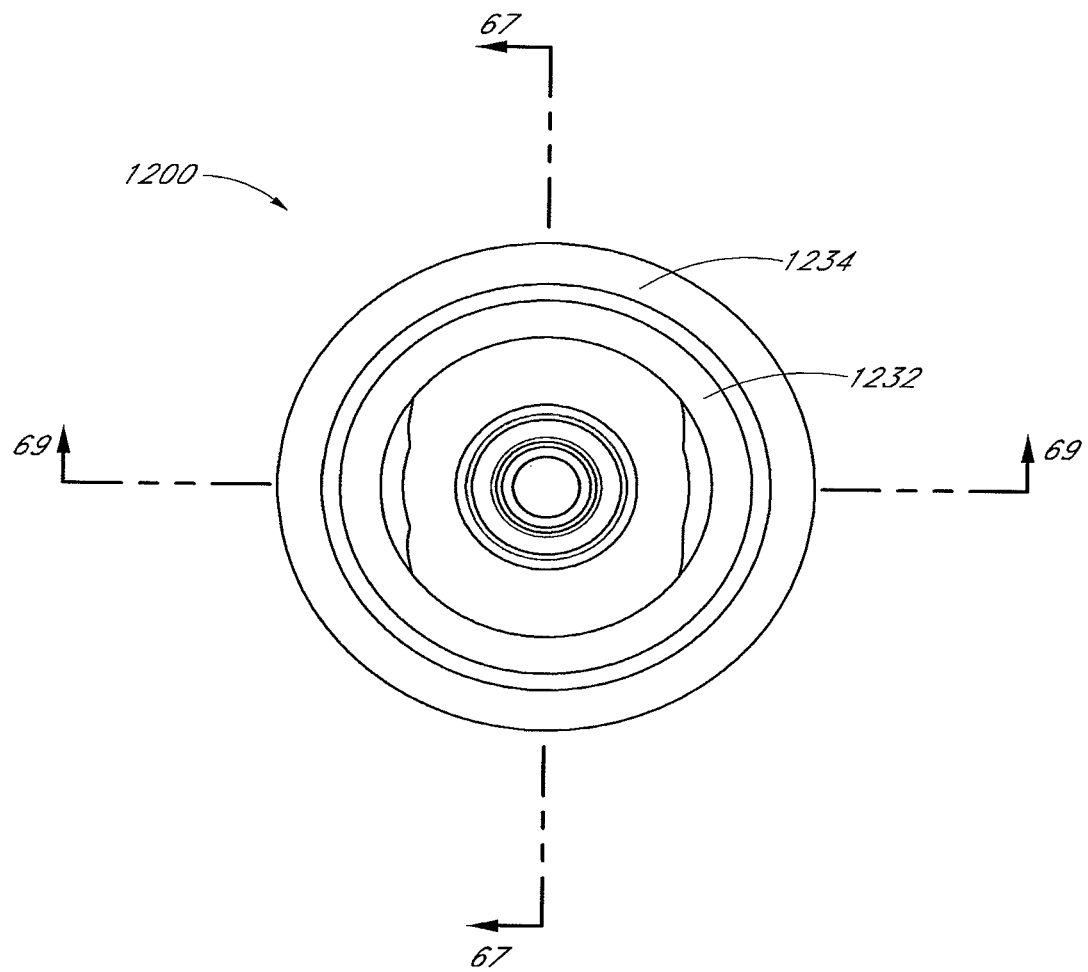
FIG. 66 is an end view of the female end of the embodiment of the closable male luer connector shown in FIG. 63.

FIGS. 63 and 64 are a perspective view and a side view, respectively, of the closeable male luer connector 1200 in a first or closed position. In FIG. 64, some of the internal features of the closable male luer connector 1200 are shown in dashed lines. FIG. 65 is an exploded perspective view of the components of the embodiment of the closeable male luer connector 1200 shown in FIG. 63. With reference to FIG. 63 and/or FIG. 64, the closeable male luer connector 1200 can have a first end 1212 and a second end 1214. The first end 1212 can comprise a male luer tip 1222 and a valve member 1216 (shown in more detail in FIGS. 65 and 71). The luer tip 1222 and valve member 1216 can be supported by a housing 1223. The valve member 1216 can be coupled to the housing 1223 by a resilient member 1218.

An end cap portion 1230 (sometimes referred to herein as an end cap or a female member) can be coupled to the housing 1223 near the second end 1214 of the closeable male luer connector 1200. One or more of the components of the end cap portion 1230 can be integral or unitary with the housing. With reference to FIG. 65, as will be described in greater detail below, in some embodiments, the end cap 1230 can comprise a first end cap component 1232 (sometimes referred to herein as a first member) and a second end cap component 1234 (sometimes referred to herein as a second member) that can be coupled together as described below. With reference to FIG. 76, the second end cap component 1234 can define an outer surface 1234a that is tapered, conical, or substantially conical in shape. However, in some embodiments, the outside surface 1234a can be substantially cylindrical, ovular, a combination of conical and ovular, or any other desired shape. The end cap 1230 can have external threads 1236. As mentioned, the embodiment of a closeable male luer connector 1200 shown in FIGS. 63 and 64 is in a closed position. In the closed position, valve member 1216 can cooperate with male luer tip 1222 to substantially impede the flow of fluid through the connector 1200.

As illustrated in FIG. 63, the housing 1223 can have a shroud 1224 surrounding the luer tip 1222. The shroud 1224 can have internal threads 1226. The internal threads 1226 and luer tip 1222 can form a male luer engagement that conforms to ANSI specifications for male luer connectors. The end cap 1230 can have a receptacle shape that conforms to ANSI standards for female luer connectors and can receive a male connecting component of another connector or syringe. The external threads 1236 can be disposed to threadedly engage corresponding internal threads of a male connecting portion of the coupling component.

The valve member 1216 can be at least partially enclosed by the housing 1223. As shown, the housing 1223 can have at least one side opening 1225, exposing at least a portion of the valve member 1216 and/or allowing at least a portion of the resilient member 1218 to pass into the inside of the housing 1223. In some embodiments, housing 1223 can define two side openings 1225 which can be disposed opposite each other on the sides of the connector 1200. In some embodiments, side opening 1225 can extend only part way along the housing 1223 (such as in a central region of the housing 1223 as shown) to provide increased strength in the housing near the second end 1214. In the illustrated embodiment, the resilient member 1218 can be coupled with the valve member 1216 near the side openings of the housing 1223. The external outer surface 1227 of the housing can be contoured. For example, the external surface of the housing can include a narrower portion near the central region of the housing 1223, or a generally hour-glass-shaped outer surface, or a larger cross-section portion(s) near the ends. These shapes can provide tactile confirmation of the proper placement of a user's fingers on the connector 1200 during use and/or provide a more comfortable gripping surface. In some embodiments, an outward projection or projections (not shown) can be incorporated on the resilient member 1218 to provide additional or more effective gripping surfaces on the luer connector 1200.

As in other embodiments described herein, the luer tip 1222 near the first end 1212 of the connector 1200 can have a hole 1221 at the end which can permit fluid to flow from within the housing 1223 out the luer tip 1222 when the valve member 1216 is in the open position (not illustrated). The valve member 1216 can include a valve closure end 1244. The closure end 1244 can engage the interior of the luer tip 1222 to inhibit the flow of fluid through the luer tip 1222. In some embodiments, an interference fit between the valve member 1216 and the housing 1223 inhibits fluid from flowing out of the luer tip 1222. In some embodiments, this interference fit is between the closure end 1244 and the hole 1221. In some embodiments, the valve member 1216 can include a resilient section disposed near the first end 1212 of the housing 1223 to engage the housing 1223 near the luer tip 1222 to inhibit fluid flow therethrough.

As shown in the embodiment of the connector 1200 illustrated in FIG. 63, a valve closure face 1246 can be disposed across the luer tip 1222 when the connector 1200 is in the closed position. In some embodiments, valve closure face 1246 can be configured to extend further beyond the hole 1221 outside of the luer tip 1222 when the connector 1200 is in the closed position. In some embodiments, the valve closure face 1246 can be recessed within the luer tip 1222. In some embodiments, the valve closure face 1246 can be substantially flush with the end of the luer tip 1222. In some embodiments, the valve closure face 1246 is configured to be swabbable when the connector 1200 is in the first or closed position.

The luer connector 1200 can be manipulated to a second or open position. In the open position, the valve member 1216 can be retracted from the luer tip 1222, thereby opening the hole 1221 in the tip 1222. As will be described in greater detail below, fluid can pass from the luer receptacle at the second end 1214 through the interior of the connector 1200 and exit the luer tip 1222 at the first end 1212 when the connector 1200 is opened. When closed, fluid is impeded or blocked from passing through the luer connector 1200 under normal operating conditions.

The resilient member 1218 can be constructed of a material that elastically deforms. Accordingly, in some embodiments, the housing 1223 can remain coupled to the valve member 1216 by the resilient member 1218 when the luer connector 1200 is moved to the open position. In the illustrated embodiment, the change in relative positions of the housing 1223 and valve member 1216 can cause at least a portion of the resilient member 1218 to extend. Consequently, the resilient member 1218 exerts a closing force on the housing 1223 and valve member 1216, biased toward returning the luer connector 1200 to a closed state. The amount of tension carried by the resilient member 1218 can be adjusted by varying the distance by which the housing 1223 and valve member 1216 are separated, by increasing the thickness of the resilient member 1218, and/or by construction of the resilient member 1218 from a variety of materials having different elastic properties. In some embodiments, the connector 1200 is configured to be difficult enough to open to prevent accidental or unintentional opening. In some embodiments, the difficulty of opening the connector is controlled at least in part by the tension carried by the resilient member 1218. In some embodiments, the resilient member 1218 can be configured as a spring positioned inside the housing 1223 for biasing the valve member 1216 to the closed position. Movement of the connector 1200 to the open position can compress the spring and movement of the connector 1200 to the closed position can allow the spring to expand to release some or all of the compression.

FIGS. 66-70 show the luer connector 1200 in the first or closed position. As can be seen in these Figures, valve member 1216 can comprise at least one strut 1250. In the illustrated embodiment, the valve member 1216 can comprise two struts 1250. In some embodiments, the valve member 1216 can comprise more than two struts 1250. In some embodiments, each strut 1250 can extend from approximately the middle of the valve member 1216 toward the first end 1212 of the luer connector 1200. The struts 1250 can be located around the luer tip 1222, but within the housing 1223, as shown. The struts 1250 can be located within the inner diameter of the inner threads 1226, and can be positioned to couple with at least a portion of a female luer receptacle as it engages with the luer tip 1222.

With reference to FIG. 63, the resilient member 1218 can comprise at least one ring 1274 and at least one securing ring 1272. However, in other embodiments, the resilient member 1218 can comprise more than one ring 1274 or more than one securing ring 1272. The first ring 1274 can be disposed in an indented groove 1248 in the outer surface of the housing 1223 toward the first end 1212. The resilient member 1218 can be tight enough around the housing 1223 to keep the first ring 1274 in place when a force is exerted on the resilient member 1218 by a change in relative positions of the housing 1223 and the valve member 1216. As with the other embodiments of the luer connector described above, the securing ring or rings 1272 can be disposed around the valve member 1216 in different patterns.

Figure 67:
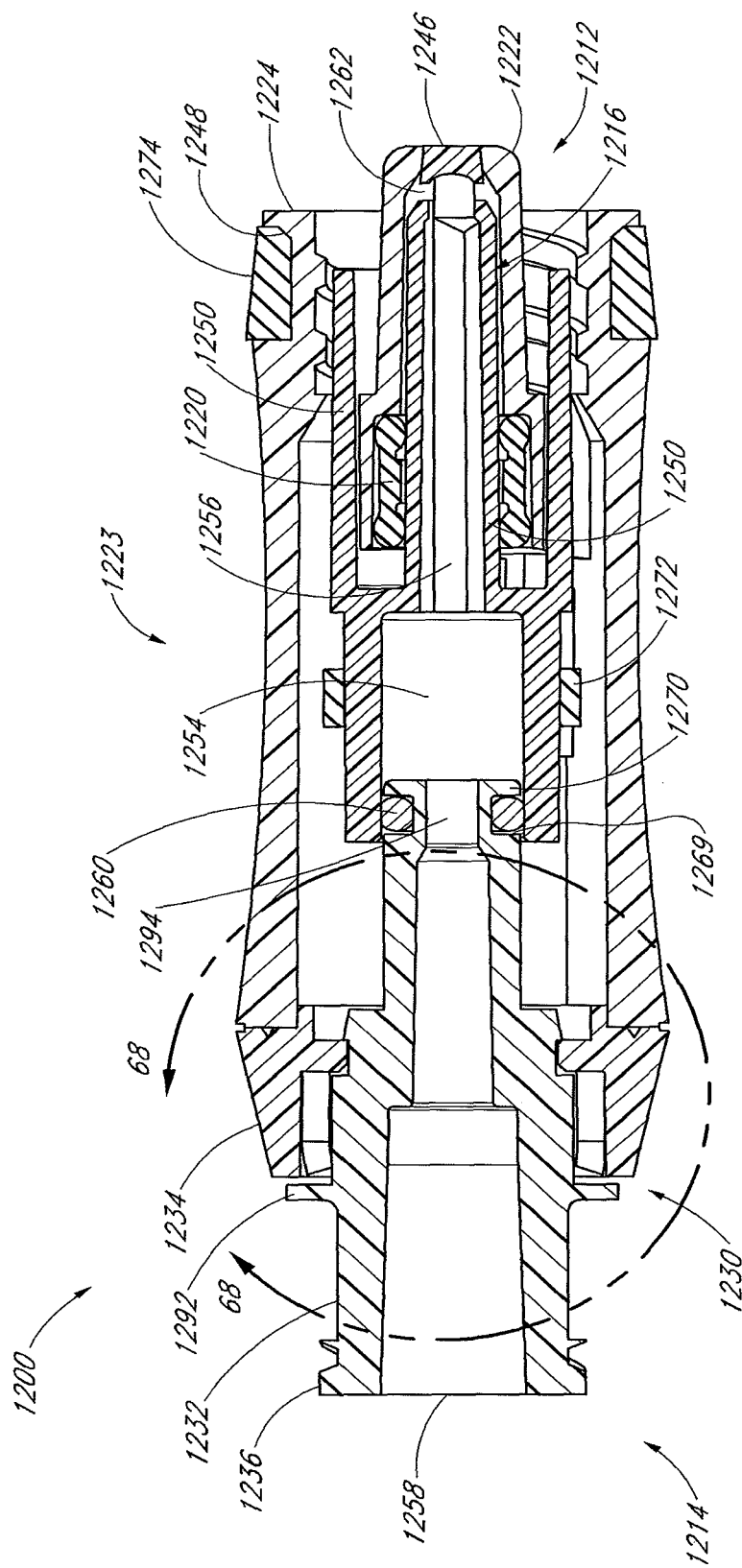
FIG. 67 is a cross-sectional view of the embodiment of the closeable male luer connector shown in FIG. 63, taken along the line 67-67 in FIG. 66.

As most clearly illustrated in FIG. 67, a passageway 1256 can extend through a portion of the valve member 1216 near the first end 1212. The passageway 1256 can be circular in cross-section, as shown in the illustrated embodiment, or the passageway 1256 can have other geometric shapes. The passageway 1256 can have at least one port 1262 near the first end 1212. In the illustrated embodiment, two ports 1262 are located on opposite sides of the valve member 1216 and are circular, though other locations and shapes can be used.

In the embodiment illustrated in FIG. 67, the luer connector 1200 is in a closed position, and the relative positions of the valve member 1216 and housing 1223 can create a chamber disposed between the passageway 1256 and the luer receiver 1258. The chamber 1254 can be in fluid communication with the passageway 1256. The chamber 1254 can be wider than the passageway 1256, as illustrated. In some embodiments, chamber 1254 can have the same diameter as the passageway 1256. In some embodiments, chamber 1254 can have a smaller diameter as compared to the passageway 1256. The chamber 1224 can also be configured with a non-circular cross-section in any other appropriate shape. The chamber 1254 can be bounded on the end toward the second end 1214 of the housing 1223 by the plunger 1270.

The plunger 1270 can be a portion of the end cap 1230 extending towards valve member 1216. The plunger 1270 can have a conduit 1294 through it. The conduit 1294 can place the chamber 1254 in fluid communication with the luer receiver 1258. The plunger 1270 can have an outer dimension sufficient to substantially close one end of the chamber 1254, as shown. In the illustrated embodiment, the plunger 1270 can be circular so as to match the geometry of the chamber 1254, but other geometric shapes can be used, as appropriate.

The plunger 1270 can have an outer dimension that is comparable to the inner dimension of the wall of the valve member 1216 creating the chamber 1254, but that does not contact such wall to permit relative movement between the components. To inhibit fluid from escaping past the plunger 1270, an O-ring 1260 can be disposed in a groove 1269 behind the plunger 1270. The O-ring 1260 can contact the wall of the valve member 1216, as shown, inhibiting fluid from flowing out of the chamber 1254. In some embodiments, the plunger 1270 is a portion of the end cap 1230. The end cap 1230 can be coupled with the housing 1223 through sonic welding, an adhesive, or any other suitable method for coupling. In the illustrated embodiment, end cap 1230 is coupled to housing 1223 with sonic welds 1231. One such weld 1231 has a substantially triangular shape as shown, though other shapes are also possible. Accordingly, the plunger 1270 can be considered to be in a static position relative to the housing 1223. In some embodiments, the plunger 1270 is formed integrally with the housing 1223 and the end cap 1230 is a separate piece appropriately attached to the housing 1223 such as by sonic welding. In some embodiments, the second end cap component 1234 can be integrally formed with the housing 1223. However, as will be described in greater detail below, the first end cap component 1232 can also be formed separately as compared to the second end cap component 1234 or the housing 1223.

As shown most clearly in FIG. 67, fluid can flow into the luer receiver 1258 and pass to the conduit 1294. From the conduit 1294, fluid can pass to the chamber 1254 and from the chamber 1254 into the passageway 1256. As shown in the illustrated embodiment, when the connector 1200 is in the closed position, the valve closure end 1244 of the valve member 1216 can seal the hole in the luer tip 1222, preventing fluid from passing out the end of the luer tip 1222. Fluid generally can, however, exit the passageway 1256 through the ports 1262 in the valve member 1216. The fluid can reside in the interior of the luer tip 1222, but can be prevented from flowing back towards the second end 1214 on the outside of valve member 1216 by the sealing ring 1220. Accordingly, when the connector 1200 is in the closed position, as illustrated, there generally can be fluid communication between the luer receiver 1258 and the interior of the luer tip 1222, without permitting fluid to exit the first end 1212 of the connector 1200.

The connector 1200 can be changed to the open position when a female luer connector (not shown) is mated with the luer tip 1222 of the first end 1212 of the connector. When the female luer connector is engaged with the first end 1212 of the connector 1200, a portion of the female luer connector can engage the inner threads 1226 and can be advanced to at least partially enclose the luer tip 1222. Accordingly, when the female luer connector is engaged with the inner threads 1226, a portion of the female connector can engage with the struts 1250 and push the valve member 1216 towards the second end 1214 of the housing. With reference to FIG. 63, the connector 1200 will be in an open position when the valve member 1216 is disposed towards the second end 1214.

In some embodiments, when the valve member 1216 is displaced toward the second end 1214, the valve closure end 1244 (see FIG. 63) can separate from the luer tip 1222, withdrawing the valve closure face 1246 from the hole 1221 in the luer tip 1222. Accordingly, fluid can pass out the hole in the luer tip 1222 from within the housing. The sealing ring 1220 can inhibits fluid from exiting the interior of the luer tip 1222 towards the second end 1214 of the connector 1200. Accordingly, in the open position, fluid can pass from the luer receiver 1258 through the conduit 1294, chamber 1254, passageway 1256, port or ports 1262 in the valve member 1216, into the interior of the luer tip 1222, and out the hole 1221 in the end of the luer tip 1222.

As can be seen in the illustrated embodiment, when the struts 1250 are displaced toward the second end 1214 of the connector 1200, the valve member 1216 is can be moved or positioned closer to the end cap 1230. Accordingly, the wall portion of the valve member 1216 containing the terminus of the passageway 1256 is positioned closer to the plunger 1270 portion of the end cap 1230. Thus, the volume of the chamber 1254 can be reduced when the connector 1200 is in the open position.

Correspondingly, when the connector 1200 is changing from an open position to a closed position, the volume of the chamber 1254 increases as the valve member 1216 shifts toward the first end 1212 of the connector 1200. As the volume of the chamber 1254 increases, the valve closure end 1244 of the valve member 1216 advances towards the first end 1212 to seal the hole in the luer tip 1222. If no additional fluid is introduced into the connector 1200 through the luer receiver 1258, the existing fluid in the luer tip 1222 can be drawn back through the ports 1262, through the passageway 1256 towards the chamber 1254 by the vacuum effect created when the volume of the chamber 1254 increases. In this case, fluid can be inhibited from exiting the hole in the luer tip 1222 as the valve closure end 1244 moves into place in the hole because the fluid can instead be drawn back to the chamber 1254. In some embodiments, fluid at or near the valve closure face 1246 is encouraged to move into the interior of the connector 1200 rather than remain on the surface of the closure face 1246 as the valve member 1216 moves toward the first end 1212 of the housing 1223.

If, however, additional fluid is still being introduced into the connector 1200 through the luer receiver 1258, the additional fluid can advance to the chamber 1254 and collect there as the valve member 1216 moves toward the first end 1212 to close the luer tip 1222. In this case, pressure from the newly-introduced fluid can be inhibited from forcing fluid to flow out the luer tip 1222 as the valve member 1216 seals the tip 1222. Accordingly, fluid flow is permitted through the connector 1200 while a female connector is coupled with the first end 1212 of the connector 1200, but inhibited while the female connector is being disengaged and after the female connector has been decoupled.

As described in greater detail below, it is desirable to inhibit certain medicines from contacting the skin. Thus, the connector 1200 advantageously assists in retaining fluid within the connector 1200 when it is being decoupled from a female luer connector or other connection. Accordingly, reducing the likelihood of fluid exiting through the luer tip 1222 when decoupling occurs results in a corresponding reduction in the chance of exposure of toxic medicine to the skin of a user or a patient.

Figure 71:
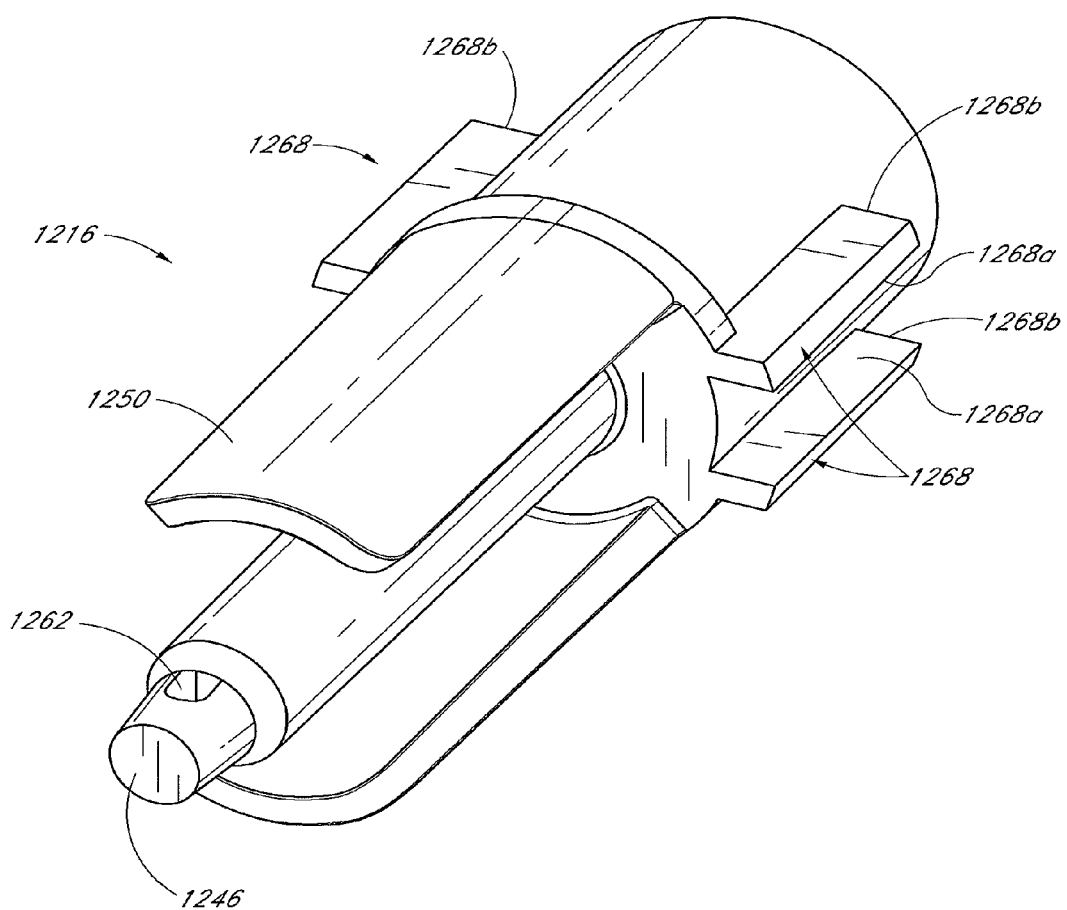
FIG. 71 is a perspective view of a portion of the embodiment of the closeable male luer connector shown in FIG. 63.
Figure 72:
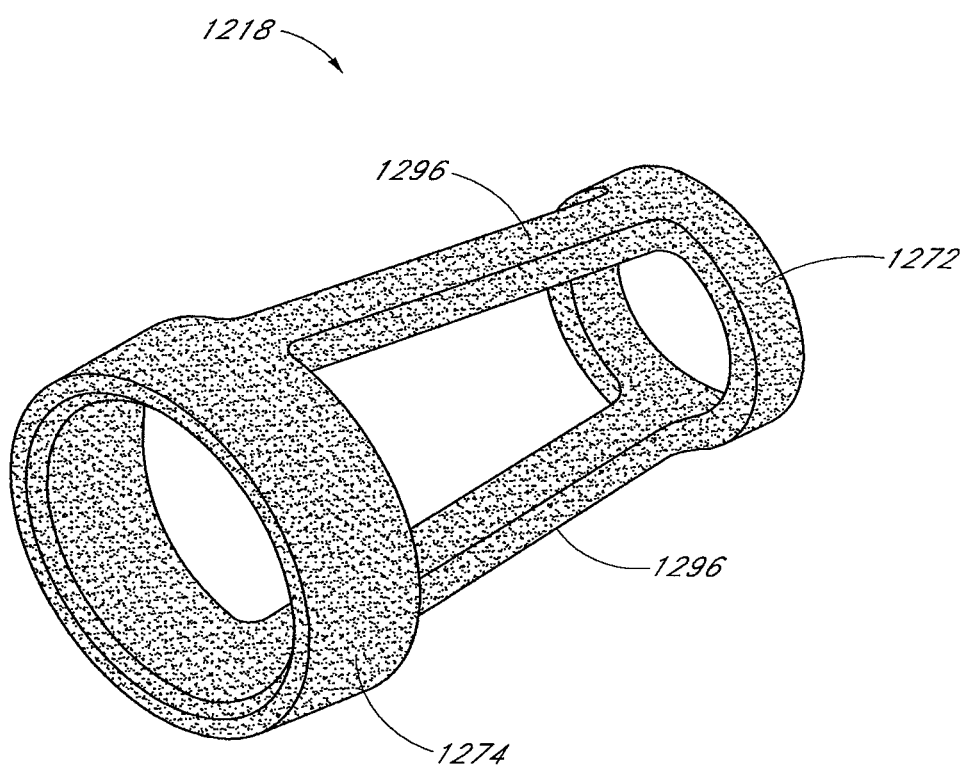
FIG. 72 is a perspective view of a portion of the embodiment of the closeable male luer connector shown in FIG. 63.
Figure 73:
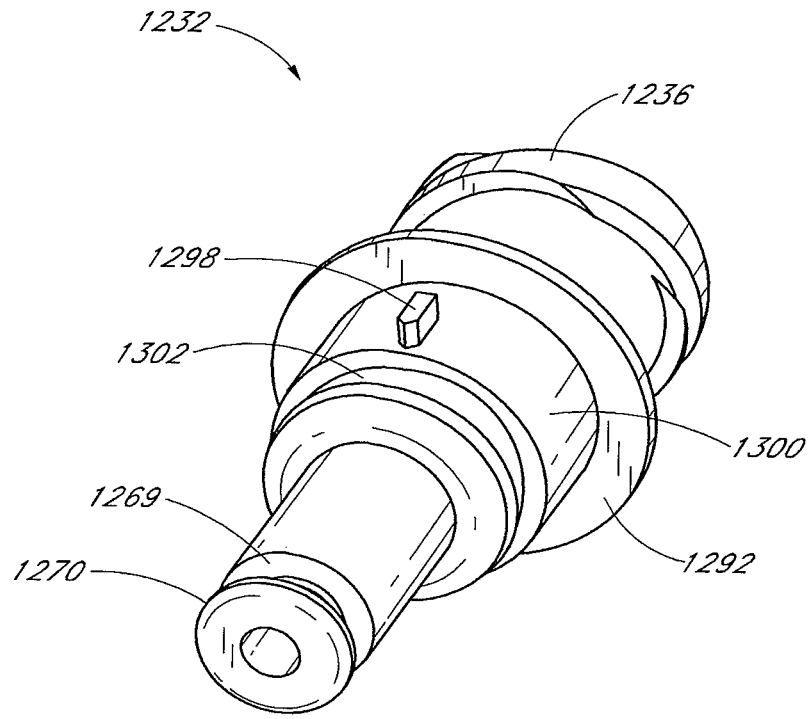
FIG. 73 is a perspective view of a portion of the closeable male luer connector shown in FIG. 63.

FIGS. 71, 72, and 73 are a perspective view of the valve member 1216, the resilient member 1218, and the housing 1223, respectively, of the embodiment of the closeable male luer connector 1200 shown in FIG. 63. As previously discussed, the resilient member 1218 can have a first ring 1274 that is disposed in the groove 1248 of the housing 1223. The resilient member can extend towards the second end 1214. The valve member 1216 can have a plurality of outwardly-extending protrusions to support the resilient member 1218. In particular, with reference to FIG. 71, the valve member 1216 can comprise four notch flanges 1268. The securing ring 1272 (shown in FIG. 72) can be secured around the valve member 1216 and held in place by the notch flanges 1268. However, the configuration of the valve member 1216 is not so limited. The valve member 1216 can comprise any number of flanges in addition to or alternatively to the notch flanges 1268 to secure the resilient member 1218 or the securing ring 1272 of the resilient member 1218 to the valve member 1216. In the illustrated embodiment, the inside surfaces 1268*a* of the notch flanges 1268 can provide lateral support to the bands 1296 of the resilient member 1218 so as to prevent the bands 1296 from sliding laterally relative to the valve member 1216. Additionally, the aft surfaces 1268*b* of the notch flanges 1268 can prevent the securing ring 1272 of the resilient member 1218 from sliding axially in the direction of the valve closure face 1246 of the valve member 1216. In other embodiments, the resilient member 1218 can comprise two or more, or, essentially, any number of rings or bands.

Additionally, with reference to FIG. 71, one or more of the ports 1262 can be located at or near the closure face 1246, or as far back as is practical from the face 1246, before the sealing ring 1220. When one or more ports 1262 are located at the closure face 1246, another port opening mechanism can be employed such as a resilient seal. The ports 1262 can be circular, as illustrated, or can have other shapes. The struts 1250 are shown extending toward the first end 1212 of the valve member 1216. There can be one, two, or more struts 1250. In some embodiments, the connector 1200 does not include struts 1250. Rather, the connector 1200 can be adapted to be otherwise opened when placed in mating engagement with a female connector. For example, the female connector can include an engagement member such as, but not limited to, a valve spike or other protrusion (not shown) which could engage the valve closure face 1244 to open the connector 1200, or a manually actuated slider or button can be appropriately configured to open the connector 1200.

Figure 74:
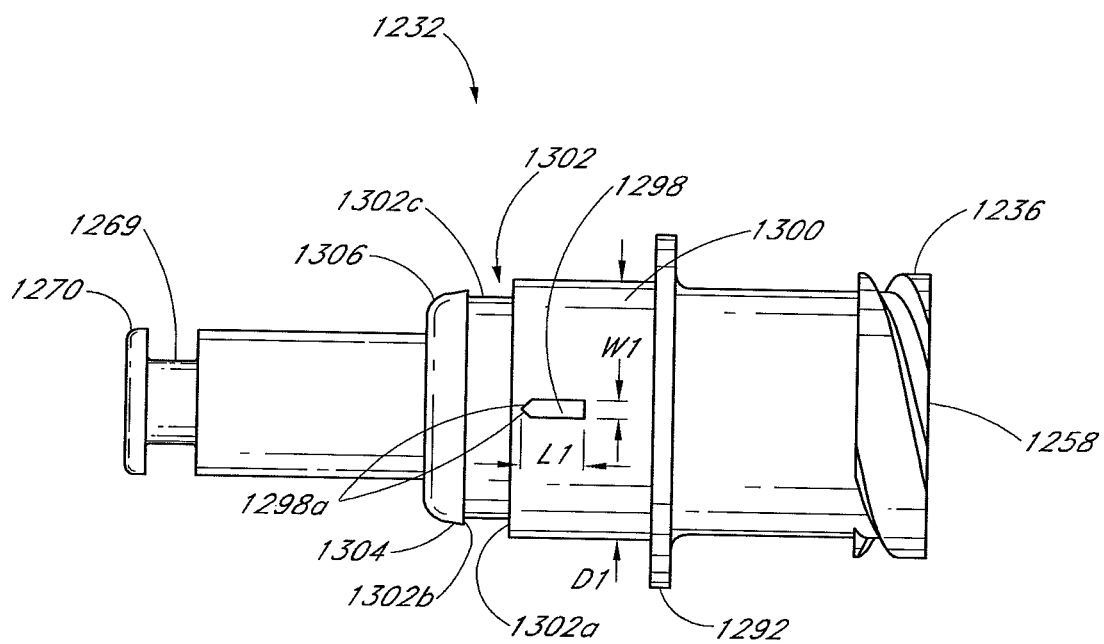
FIG. 74 is a side view of the component shown in FIG. 73.

With reference to FIGS. 73 and 74, the first end cap component 1232 can have a covering portion 1292 shaped and configured to substantially cover and, in some embodiments, generally seal a portion of the second end 1214 of the housing 1223. The luer receiver 1258 can extend away from the covering portion 1292. The luer receiver 1258 can be appropriately sized to couple with a male luer portion (see, e.g. FIG. 12) conforming to ANSI standards for luer devices. The luer receiver 1258 can have external threads 1236 to engage the male luer portion, as shown. In some embodiments, raised tabs or other protrusions can be used to engage the male luer portion.

In some embodiments, the plunger 1270 is at the opposite end of a portion of the first end cap component 1232 from the covering portion 1292. The plunger 1270 can be sized and configured to substantially seal the chamber 1254 within the valve member 1216. An indentation or slot 1269 between the covering portion 1292 and the plunger 1270 can be sized and shaped to accommodate an O-ring 1260, as described above. Additionally, with reference to FIGS. 73 and 74, the first end cap component 1232 illustrated therein can comprise a pair of protrusions or tabs 1298 (also referred to herein as locking elements or engaging surfaces) protruding radially outward from the outer surface 1300. In some embodiments, the first end cap component 1232 can comprise a pair of tabs 1298 arranged so as to be diametrically opposing one another. In some embodiments, the first end cap component 1232 can comprise only one tab 1298 protruding from the surface 1300. In some embodiments, the first end cap component 1232 can comprise more than two tabs 1298 protruding from the surface 1300. As will be described in greater detail below, the tabs 1298 can engage or interlock with complementary tabs or protrusions on the second end cap component 1234 to prevent the first end cap component 1232 from rotating relative to the second end cap component 1234 when the two components are assembled together, as shown most clearly in FIG. 64 or 69.

Additionally the first end cap component 1232 can define an annular groove 1302 which, as will be described in greater detail below, can interact with complementary features on the second end cap component 1234 to axially restrain the movement of the first end cap component 1232 with respect to the second end cap component 1234. Further, as illustrated most clearly in FIG. 74, the first end cap component 1232 can also define an angled or tapered surface 1304 and a rounded surface 1306 both positioned between the annular groove 1302 and the plunger 1270. As will be described in greater detailed below, the angled or tapered surface 1304 and rounded surface 1306 can facilitate the coupling or assembly of the first end cap component 1232 to the second end cap component 1234. In some embodiments, the first end cap component 1232 can comprise only an angled or tapered surface 1304 or a rounded surface 1306. In other embodiments, the first end cap component 1232 can be configured so as to not comprise either of those two features. In some embodiments, the first end cap component 1232 and/or the second end cap component 1234 can comprise any suitable features, lubricants, or materials to facilitate the coupling of the first end cap component 1232 and the second end cap component 1234, or, as will be discussed, to facilitate the rotation of the first end cap component 1232 relative to the second end cap component 1234.

In the illustrated embodiment, the tabs 1298 are substantially rectangular in cross-section. However, the geometry of the tabs 1298 is not so limited. The tabs 1298 can define any suitable or desired cross-sectional geometry, such as but not limited to a square, circular, or ovular geometry. In some embodiments, for example, a plurality of tabs 1298 each defining a circular cross-section can be arranged in a linear fashion along a side of the second end cap component 1234.

Figure 75:
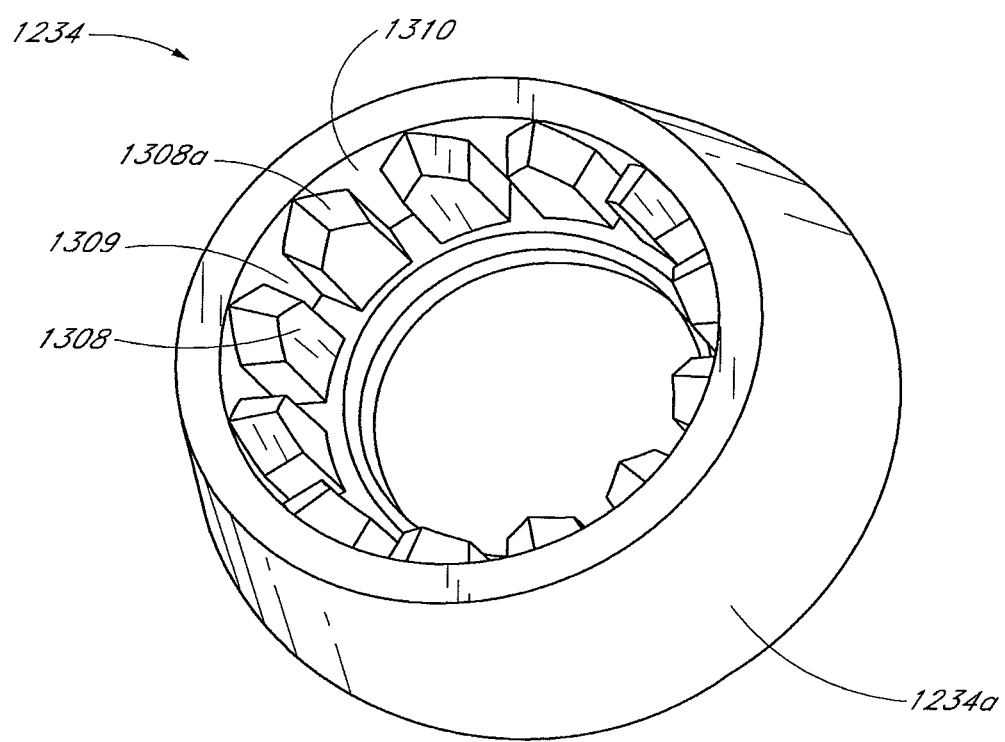
FIG. 75 is a perspective view of a portion of the embodiment of the closeable male luer connector shown in FIG. 63.

With reference to FIGS. 74-76, the second end cap component 1234 can comprise an array of protrusions or tabs 1308 (also referred to herein as locking elements or engaging surfaces) which protrude, in some embodiments, in a radially inward direction from the inside surface 1310 of the second end cap component 1234, so as to create a radial array of depressions or channels 1309. With reference to FIG. 64, the first end cap component 1232 can be assembled with the second end cap component 1234 such that each of the one or more tabs 1298 formed on the first end cap component 1232 is positioned in one or more of the depressions or channels 1309 between each of the plurality of tabs 1308 formed on the second end cap component 1234. Accordingly, each of the one or more tabs 1298 can be sized and configured such that the approximate width (represented by "W1" in FIG. 74) of each of the one or more tabs 1298 formed on the surface 1300 of the first end cap component 1232 is less than the approximate width (represented by "W2" in FIG. 76) of the depressions or channels 1309 between each of the tabs 1308 formed on the second end cap component 1234.

In the illustrated embodiment, the tabs 1308 are substantially rectangular in cross-section. However, the geometry of the tabs 1308 is not so limited. The tabs 1308 can define any suitable or desired cross-sectional geometry, such as but not limited to a square, circular, or ovular geometry.

Additionally, as mentioned, each of the one or more tabs 1298 on the first end cap component 1232 can be configured to shear or break off before any of the plurality of tabs 1308 on the second end cap component 1234 shear or break off. Accordingly, in some embodiments, each of the one or more tabs 1298 on the first end cap component 1232 can be configured so that the minimum approximate amount of force or torque required to shear or break each tab 1298 away from the surface 1300 on the first end cap component 1232 is less than the minimum approximate amount of force required to shear or break any of the tabs 1308 away from the inside surface 1310 of the second end cap component 1234. In some embodiments, the minimum amount of force required to shear or break each tab 1298 away from the surface 1300 on the first end cap component 1232 can be significantly less than the minimum amount of force required to shear or break any of the tabs 1308 away from the inside surface 1310 of the second end cap component 1234.

In some embodiments, the tabs or protrusions that are configured to shear or break off can be formed on the second end cap component 1234 instead of being formed on the first end cap component 1232, as described above. In other words, in some embodiments, one or more tabs formed on the second end cap component 1234 can be sized and/or configured the same as any of the tabs 1298 described above, and one or more tabs formed on the first end cap component 1232 can be sized and/or configured the same as any of the tabs 1308 described above such that the tabs formed on the second end cap component 1234 shear or break off before any of the tabs formed on the first end cap component 1232. In short, the configurations of the tabs 1298 and in tabs 1308 described above can be reversed. In general, other complementary engaging surfaces may be employed. In the illustrated embodiments, each of the components includes radially projecting tabs. In some embodiments, one or the other of the components may include appropriately sized slots for accommodating a radially projecting tab.

In some embodiments, the approximate minimum amount of force required to shear or break each tab 1298 away from the surface 1300 on the first end cap component 1232 can be less than approximately one-third of the approximate minimum amount of force required to shear or break each of the tabs 1308 away from the inside surface 1310 of the second end cap component 1234. In some embodiments, the approximate minimum amount of force required to shear or break each tab 1298 away from the surface 1300 on the first end cap component 1232 can be between approximately one-third and one-half of the minimum approximate amount of force required to shear or break any of the tabs 1308 away from the inside surface 1310 of the second end cap component 1234.

In the illustrated embodiment, where two tabs 1298 are formed on the surface 1300, the amount of torque required to shear or break both of the two tabs 1298 away from the surface 1300 on the first end cap component 1232 can be approximately 4 in-lb or more. In some embodiments, the amount of torque required to shear or break both of the two tabs 1298 away from the surface 1300 on the first end cap component 1232 can be approximately 3 in-lb or more. In some embodiments, the amount of torque required to shear or break both of the two tabs 1298 away from the surface 1300 on the first end cap component 1232 can be approximately 5 in-lb or more.

With reference to FIG. 74, the cross-sectional area of each of the tabs 1298 can be based on the approximate length (represented by "L1" in FIG. 74) and approximate width (represented by "W1" in FIG. 74) of each of the one or more tabs 1298 at the surface 1300 of the first end cap component 1232. The tab 1298 can be used to define a band around the surface 1300 calculated by multiplying the length L1 of the tab 1298 by the circumference of the surface 1300. In some embodiments, as in the illustrated embodiment, where each of the one or more tabs 1298 is configured to shear away from the surface 1300 of the first end cap component 1232 when the desired level of torque is reached, the aggregate cross-sectional area of the tab(s) 1298 can be substantially smaller than the band around the surface 1300.

In some embodiments, the ratio of the aggregate cross-sectional area of all of the one or more tabs 1298 to the value of the outside diameter (represented by "D1" in FIG. 74) of the surface 1300 of the first end cap component 1232 upon which each of the one or more tabs 1298 can be formed or attached can be approximately 1 to 46 or higher. The cross-sectional area of each of the tabs 1298 can be any suitable value that results in each of the one or more tabs 1298 shearing away from the surface 1300 when the desired level of torque is reached. For example, in some embodiments, the ratio can be between approximately 1 to 60 and approximately 1 to 30. In some embodiments, the ratio can be between approximately 1 to 50 and approximately 1 to 40.

Similarly, in some embodiments, as in the illustrated embodiment, where each of the one or more tabs 1298 is configured to shear away from the surface 1300 of the first end cap component 1232 when the desired level of torque is reached, the length L1 of each of the one or more tabs 1298 can be substantially smaller than the outside diameter D1 of the surface 1300 of the first end cap component 1232 upon which each of the one or more tabs 1298 can be formed or attached. The length L1 of each of the tabs 1298 can be any suitable value that results in each of the one or more tabs 1298 shearing away from the surface 1300 when the desired level of torque is reached. In some embodiments, the ratio of the aggregate length of the tabs 1298 to the outside diameter D1 can be approximately 1 to 4 or higher. In some embodiments, the ratio can be between approximately 1 to_10 and approximately 1 to 2. In some embodiments, the ratio can be between approximately 1 to 5 and approximately 1 to 3. In some embodiments, multiple tabs 1298 can be used wherein the widths W1 of each tab are different, but the aggregate widths are calculated to reach the desired level of torque to shear the tabs off.

Similarly, in some embodiments, as in the illustrated embodiment, where each of the one or more tabs 1298 is configured to shear away from the surface 1300 of the first end cap component 1232 when the desired level of torque is reached, the length L1 of each of the one or more tabs 1298 can be substantially smaller than the outside diameter D1 of the surface 1300 of the first end cap component 1232 upon which each of the one or more tabs 1298 can be formed or attached. The length L1 of each of the tabs 1298 can be any suitable value that results in each of the one or more tabs 1298 shearing away from the surface 1300 when the desired level of torque is reached. In some embodiments, the ratio of the aggregate length of the tabs 1298 to the outside diameter D1 can be approximately 1 to 4 or higher. In some embodiments, the ratio can be between approximately 1 to 10 and approximately 1 to 2. In some embodiments, the ratio can be between approximately 1 to 5 and approximately 1 to 3. In some embodiments, multiple tabs 1298 can be used wherein the widths W1 of each tab are different, but the aggregate widths are calculated to reach the desired level of torque to shear the tabs off.

In some embodiments, one or more tabs 1298 can be configured such that the approximate width W1 of each of the one or more tabs 1298 can be significantly less than the approximate width (represented by "W3" in FIG. 76) of one or more of the plurality of tabs 1308 formed on the inside surface 1310 of the second end cap component 1234 to ensure that the one or more tabs 1298 shear or break before any of the tabs 1308. Accordingly, in some embodiments, the approximate width W1 of each of the one or more tabs 1298 can be between approximately one-third or less and approximately one-half or less of the approximate width W3 of each of the plurality of tabs 1308. Moreover, in some embodiments, there are many more tabs 1308 on the second end cap component 1234 than tabs 1298 on the first end cap component 1232, thereby requiring greater torque to shear off the greater number of tabs 1308 on the second end cap component 1234.

In some embodiments, the material selected to form each of the one or more tabs 1298 can be the same as or different as compared to the material selected to form each of the one or more tabs 1308. The strength of the material chosen to form the tabs 1298, 1308 can affect the amount of torque required to shear the tabs 1298, 1308. Accordingly, in some embodiments, the tab 1298, 1308 that is desired to be sheared can be formed from a weaker, softer, or lower durometer material as compared to the material used to form the tab 1298, 1308 that is desired to remain intact. For example, in the illustrated embodiment, it is desired that the tab 1298 be sheared away from the surface 1300 on the first end cap component 1232 when the desired level of torque between the first end cap component 1232 and the second end cap component 1234 is achieved. Thus, in the illustrated embodiment, the tab 1298 can be formed from the weaker material as compared to the material used to form each of the tabs 1308. However, because the cross-sectional area of the tabs 1298, 1308 can also affect the amount of torque required to shear the tabs 1298, 1308, the material selected to form each of the tabs 1298, 1308 can be the same.

In some embodiments, as in the illustrated embodiment, as mentioned, ensuring that the one or more tabs 1298 shear or break before any of the tabs 1308 can be achieved by also configuring each of the one or more tabs 1298 such that the approximate cross-sectional area of each of the one or more tabs 1298 is less than the cross-sectional area of each of the tabs 1308 that is adjacent to and, hence, will contact each of the one or more tabs 1298. With reference to FIG. 74, the cross-sectional area of each of the tabs 1298 is based on the length (represented by "L1" in FIG. 74) and width (represented by "W1" in FIG. 74) of each of the one or more tabs 1298. Similarly, width reference to FIGS. 76 and 77, the cross-sectional area of each of the tabs 1308 is based on the length (represented by "L2" in FIG. 77) and width (represented by "W3" in FIG. 76) of each of the one or more tabs 1308.

In some embodiments, without consideration of material differences, where the one or more tabs 1298 are designed to shear before any of the tabs 1308, cross-sectional area of each of the one or more tabs 1298 can be substantially smaller than the cross-section of each of the one or more tabs 1308. The ratio of the cross-sectional area of each of the one or more tabs 1298 relative to the cross-sectional area of each of the one or more tabs 1308 can be significantly less than one. For example, in some embodiments, as in the illustrated embodiment, the ratio can be approximately 1 to 14 or higher. In some embodiments, the ratio can be between approximately 1 to 25 and approximately 1 to 10. In some embodiments, the ratio can be between approximately 1 to 16 and 1 to 12.

Further, in some embodiments, as in the illustrated embodiment, the approximate length (represented by "L1" in FIG. 74) of each of the one or more tabs 1298 is significantly less than the approximate length (represented by "L2" in FIG. 77) of each of the plurality of tabs 1308 formed on the inside surface 1310 of the second end cap component 1234. Accordingly, in some embodiments, the approximate length L1 of each of the one or more tabs 1298 can be between approximately one-third or less and approximately two-thirds of the approximate length L2 of each of the plurality of tabs 1308.

In some embodiments, the second end cap component 1234 can define depressions or channels into which each of the one or more tabs 1298 formed on the first end cap component 1232 can be inserted when the first end cap component 1232 is coupled to the second end cap component 1234. In some embodiments, the number of depressions or channels formed on the second end cap component 1234 can be equal to the number of tabs 1298 formed on the first end cap component 1232. In some embodiments, the number of depressions or channels formed on the second end cap component 1234 can be greater than the number of tabs 1298 formed on the first end cap component 1232.

Figure 78A:
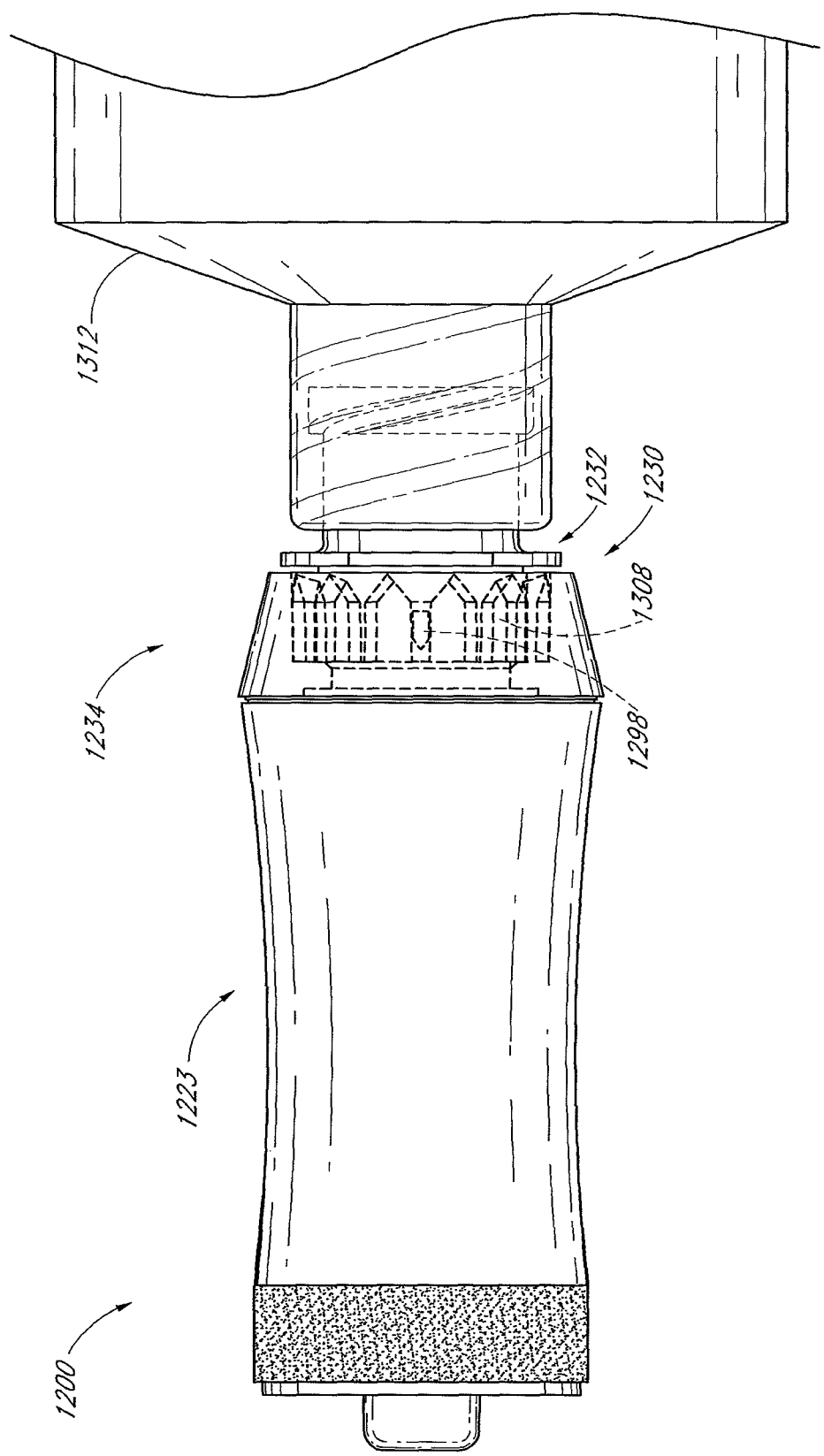
FIG. 78A is a side view of an exemplifying coupled component threadedly engaged with the embodiment of the closeable male luer connector shown in FIG. 63.

FIG. 78A is a side view of an exemplifying coupled component 1312, showing the male connecting component of the coupled component 1312 partially threadedly engaged with the first end cap component 1232 of the closeable male luer connector 1200. FIG. 78A illustrates the end cap 1230 before the one or more tabs 1298 protruding radially outwardly from the surface 1300 have been broken off. In FIG. 78A, the exemplifying coupled component 1312 is a syringe. However, the coupled component 1312 can be any suitable connector or medical instrument having a male connecting component. As illustrated therein, the coupled component 1312 is only partially threadedly engaged with the first end cap component 1232 such that the torque that is exerted on the first end cap component 1232 from threading the coupled component 1312 onto the first end cap component 1232 is less than the minimum threshold torque that is required to shear or break off each of the tabs 1298 from the first end cap component 1232. Thus, until the minimum threshold torque required to shear or break off each of the tabs 1298 is reached, the first end cap component 1232 can be rotationally fixed to the second end cap component 1234 by the abutment of each of the one or more tabs 1298 formed on the first end cap component 1232 against one or more of the plurality of tabs 1308 formed on the second end cap component 1234.

When the coupled component 1312 is substantially fully threadedly engaged with the first end cap component 1232, further twisting of the coupled component 1312 will ultimately exert a torque on the first end cap component 1232 that will exceed the minimum threshold torque required to break off the tabs 1298 from the first end cap component 1232. In some embodiments, the minimum threshold torque required to break off the tabs 1298 is approximately 4 in-lb of torque. Once the tabs 1298 have broken away from the first end cap component 1232, the first end cap component 1232 is then able to rotate substantially freely within the second end cap component 1234. However, the first end cap component 1232 can still be retained in the housing by the abutment of the side surface 1302*b* against the side surface 1314*b* of the annular protrusion 1314. Also, the o-ring 1260 can prevent fluid exchange not withstanding the ability of the first end cap component 1232 to rotate. In this way, the connector 1200 is prevented or inhibited from easily disconnecting from the coupled component 1312 because the torque needed for such disconnection would merely spin the first end cap component 1232 relative to the housing 1223 and/or the second end cap component 1234. Moreover, in some embodiments, there can be only a small amount of (or no) exposed outside surface area on the first end cap component 1232 for contact by the fingers of a user after the coupled component 1312 is attached, thereby making it difficult to apply opposing torque to the first end cap component 1232 and coupled component 1312 to enable disconnection. This can effectively "fuse" these two components together.

The use of tabs configured to be sheared off is not required. Many other structures and configurations can be used to allow threadable connection between the end of the housing and the coupled component 1312 in a first stage and then to allow rotation in a second stage to prevent or inhibit disconnection.

Figure 78B:
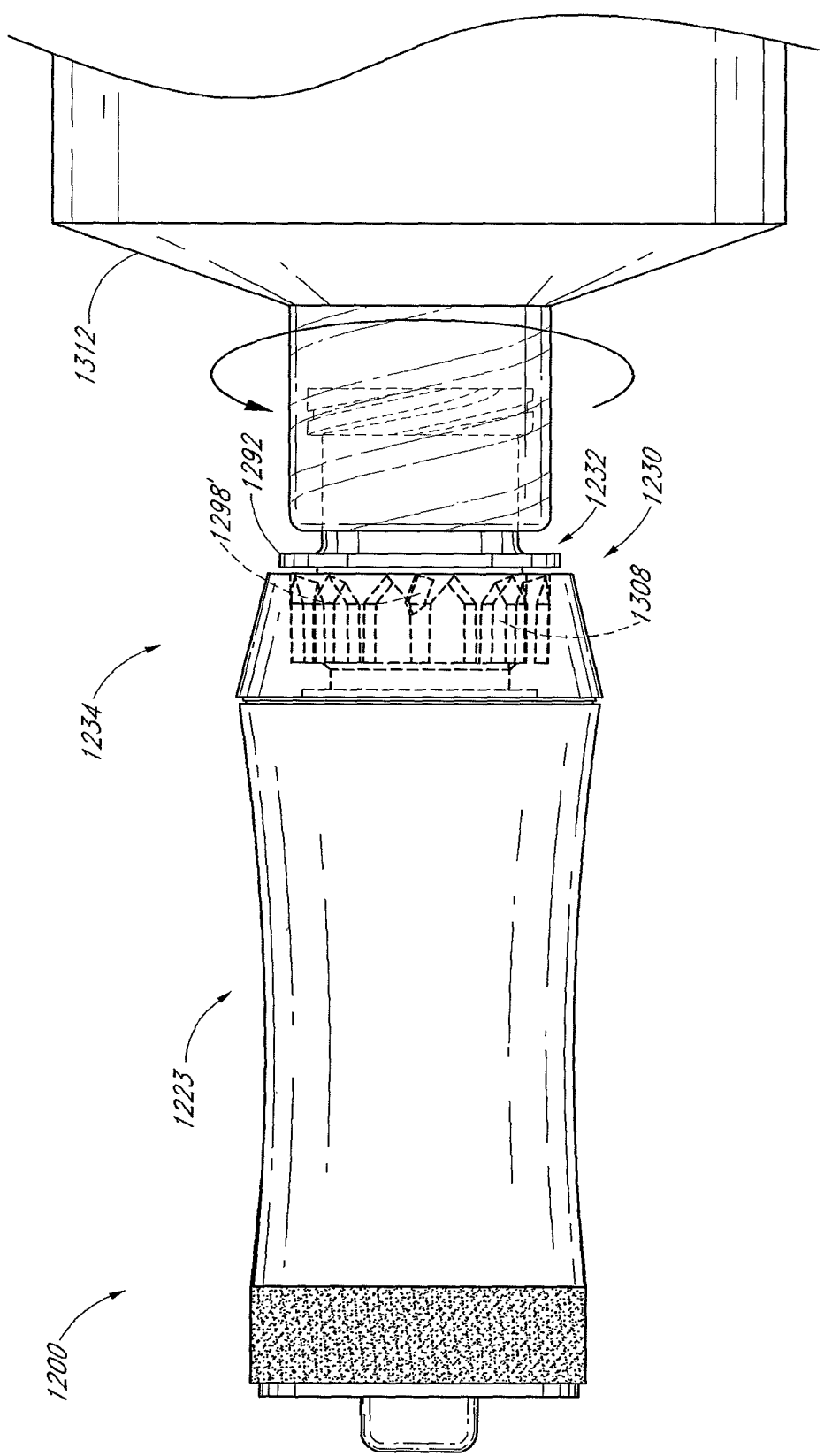
FIG. 78B is a side view of an exemplifying coupled component substantially fully threadedly engaged with the embodiment of the closeable male luer connector shown in FIG. 63.

FIG. 78B is a side view of the coupled component 1312, showing the male connecting component of the coupled component 1312 substantially fully threadedly engaged with the first end cap component 1232 of the male luer connector 1200. FIG. 78B illustrates the first end cap component 1232 after the one or more tabs 1298' have been broken off from the force exerted on each of the one or more tabs 1298 by one or more of the plurality of tabs 1308 formed on the inside surface 1310 of the second end cap component 1234 in reaction to the twisting force transferred to the first end cap component 1232 from the substantially fully threadedly engaged coupled component 1312. At this point, with each tab 1298' broken away from the outside surface 1300 of the first end cap component 1232, the first end cap component 1232 will be able to rotate substantially freely within the second end cap component 1234. Any twisting motion applied to the coupled member 1312 in either rotational direction relative to the housing 1223 in this arrangement will cause the first end cap component 1232 to rotate in unison with the coupled member 1312. The coupled member 1312 is thereby prevented from unthreading or otherwise becoming disengaged from the first end cap component 1232. Thus, in this manner, the luer connector 1200 is configured such that it cannot be removed or disengaged from the coupled member 1312 after the luer connector 1200 and the coupled member 1312 have been substantially fully coupled together.

After the one or more tabs 1298' have been sheared or broken away from the first end cap component 1232, the covering portion 1292 of the first end cap component 1232 can prevent each of the broken tabs 1298' from falling out of the luer connector 1200, as shown most clearly in FIG. 78B. Additionally, as illustrated most clearly in FIG. 68, the second end cap component 1234 can be configured to prevent the broken tab 1298' from moving into the interior space of the housing 1223. In particular, the second end cap component 1234 can be configured to define an annular protrusion 1314 that can prevent the broken tab or tabs 1298' from moving into the interior space of the housing 1223.

Figure 78C:
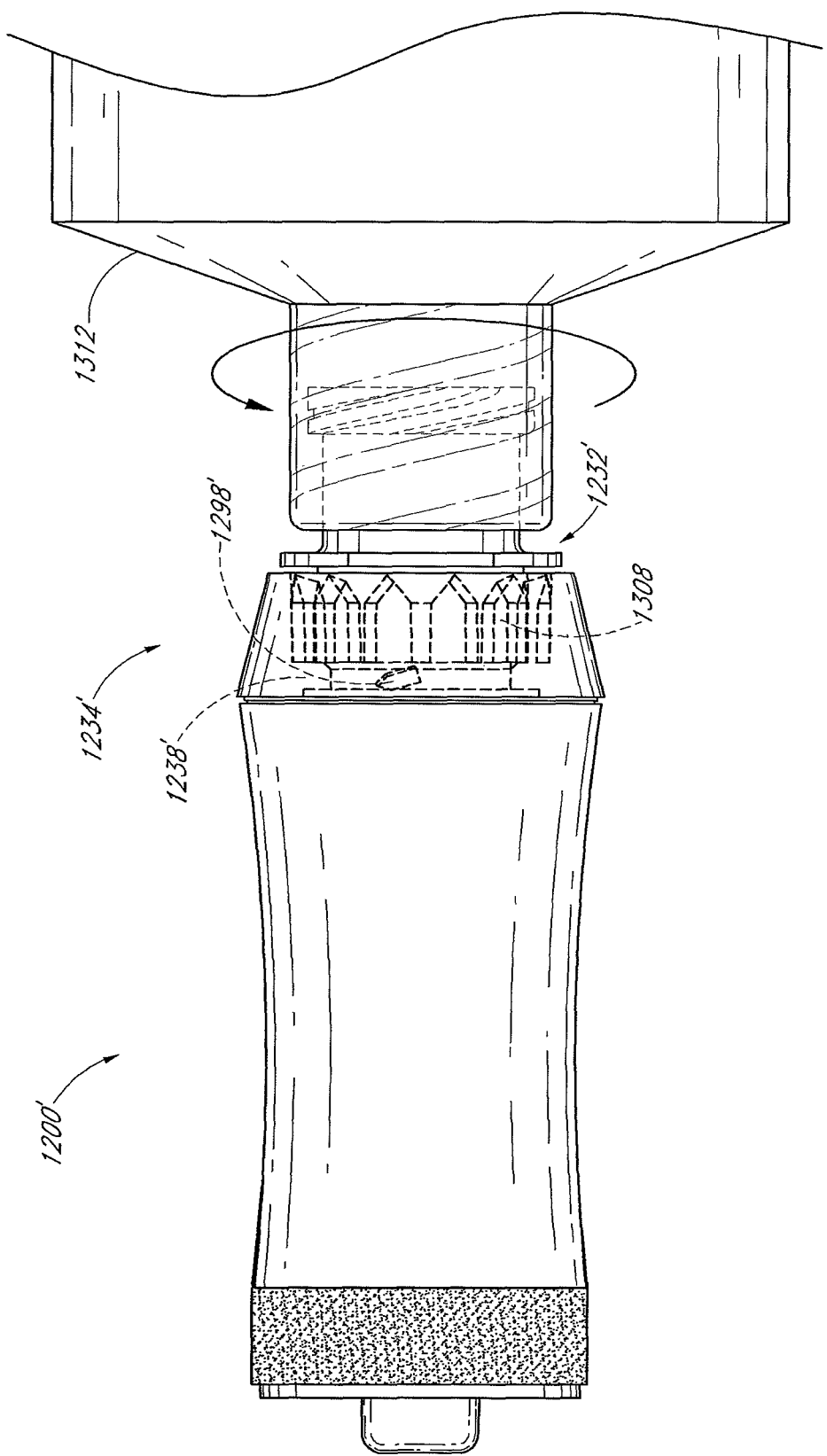
FIG. 78C is a side view of an exemplifying coupled component substantially fully threadedly engaged with another embodiment of a closeable male luer connector.

FIG. 78C is a side view of an exemplifying coupled component 1312 substantially fully threadedly engaged with another embodiment of a closeable male luer connector 1200'. In some embodiments, the closeable male luer connector 1200' can be identical to the closable male luer connector 1200 described above, except for as follows. In some embodiments, the second end cap component 1234' can be configured to define an annular space 1238' adjacent to the tabs 1308'. The annular space 1238' can be sized and configured such that, when the one or more tabs 1298' have broken away from the first end cap component 1232', the one or more tabs 1298' can fall into and become contained within the annular space 1238'.

Figure 68:
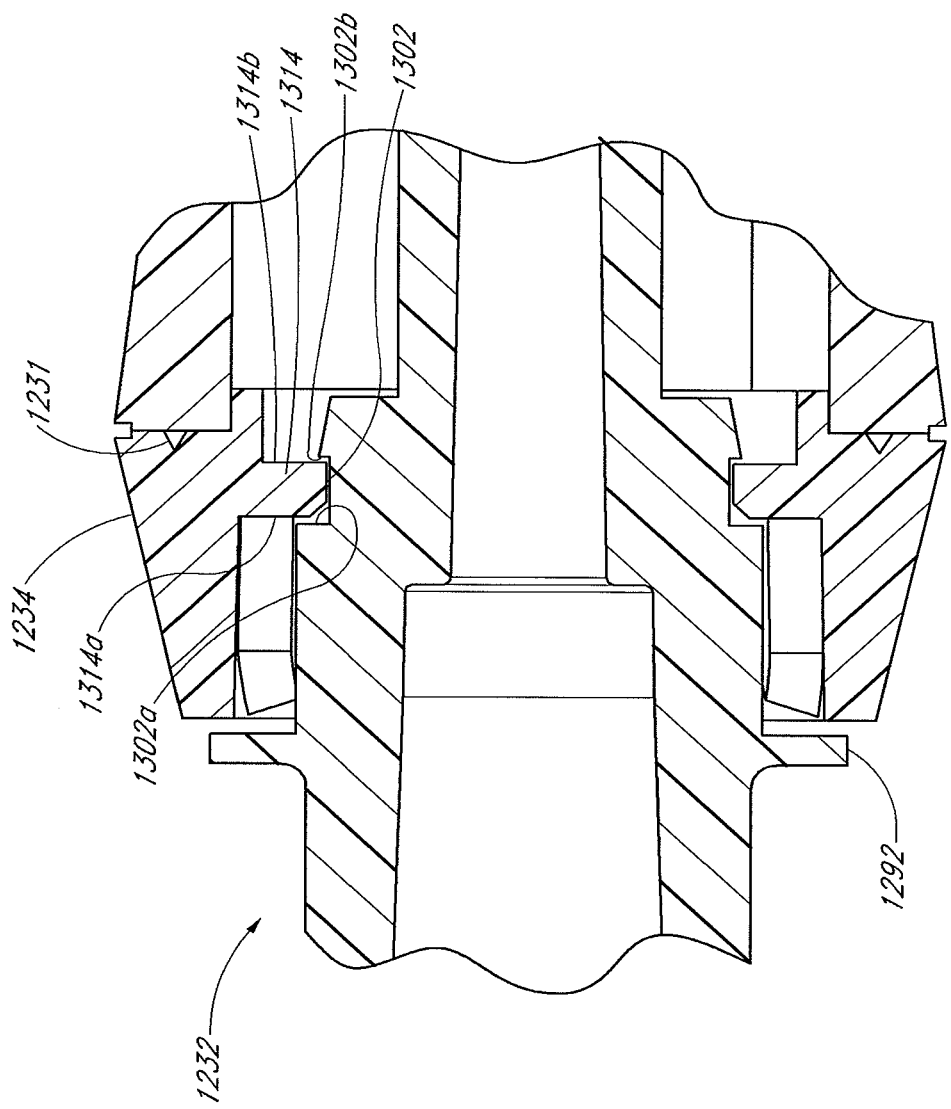
FIG. 68 is an enlarged cross-sectional view of the embodiment of the closable male luer connector shown in FIG. 63, taken along curve 68-68 in FIG. 67.
Figure 69:
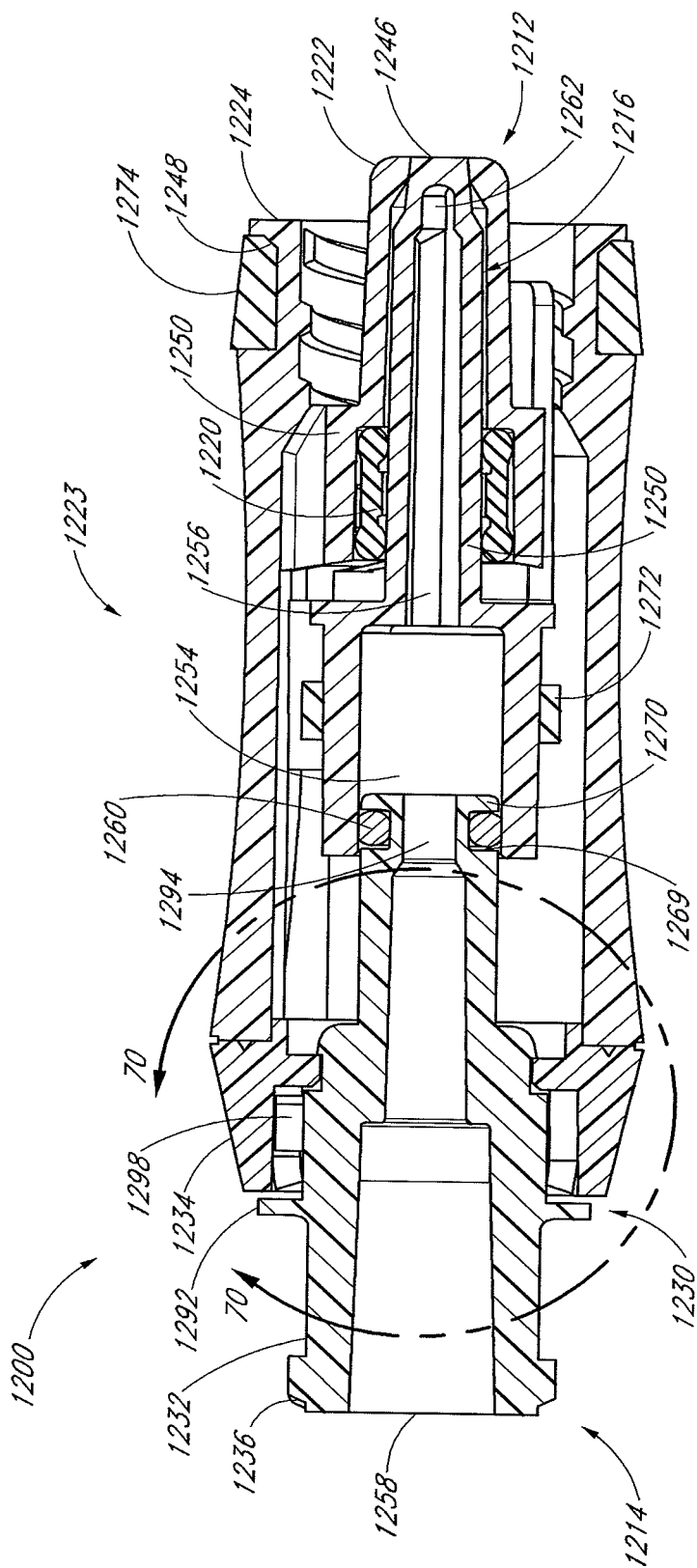
FIG. 69 is a cross-sectional view of the embodiment of the closeable male luer connector shown in FIG. 63, taken along the line 69-69 in FIG. 66.
Figure 70:
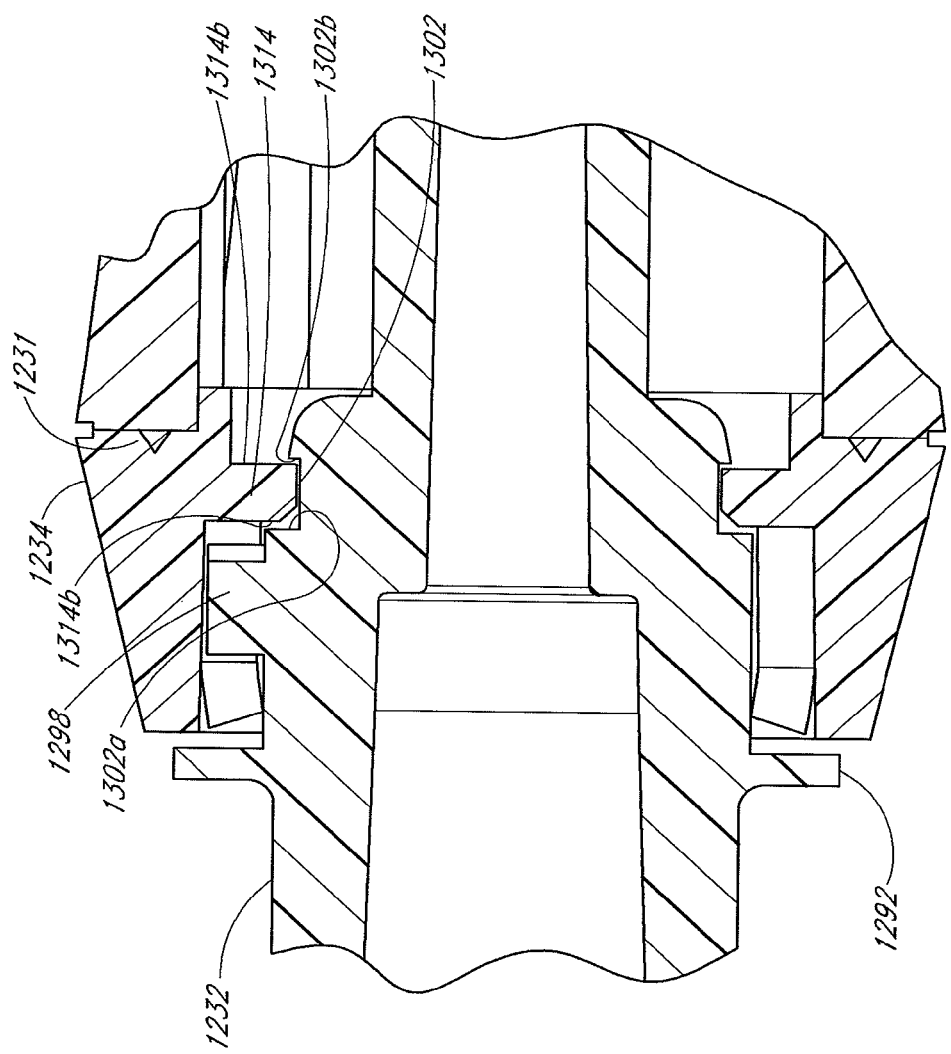
FIG. 70 is an enlarged cross-sectional view of the embodiment of the closable male luer connector shown in FIG. 63, taken along curve 70-70 in FIG. 69.

In some embodiments, the first end cap component 1232 can be coupled to the second end cap component 1234 and, hence, coupled to the luer connector 1200, as described below. After the second end cap component 1234 has been attached to the housing 1223 following any of the methods described herein or any other suitable methods, the first end cap component 1232 can then be co-axially aligned with the second end cap component 1234 and also rotationally aligned so that the each of the one or more tabs 1298 on the first end cap component 1232 is approximately aligned with the one or more spaces between the tabs 1308 formed on the second end cap component 1234. Once the first end cap component 1232 is approximately axially and rotationally aligned, the first end cap component 1232 can be inserted into the second end cap component 1234 by pushing the first end cap component 1232 against the second end cap component 1234, while maintaining the approximate axial and rotational alignment described above. With reference to FIGS. 68, 74, and 77, the first end cap component 1232 can be pushed into the inner end until the first end cap component 1232 is positioned relative to the second end cap component 1234 such that the annular protrusion 1314 formed on the second end cap component 1234 is radially adjacent to (i.e., axially aligned with) the annular groove 1302 formed on the first end cap component 1232. In particular, in this position, the opposing sides surfaces 1314a and 1314b of the annular protrusion 1314 formed in the second end cap component 1234 can be positioned between the optionally opposing side surfaces 1302a and 1302b of the annular groove 1302 formed in the second end cap component 1234.

As shown most clearly in FIG. 68, in some embodiments, the first end cap component 1232 and the second end cap component 1234 can be formed such that there will be a small gap between the generally cylindrical surface 1314c of the annular groove 1314 and the generally cylindrical surface 1302c of the annular groove 1302. This configuration can facilitate rotation of the first end cap component 1232 within the second end cap component 1234, i.e., without friction between the two optionally cylindrical surfaces 1302c and 1314c, when the one or more tabs 1298 have been sheared or broken off.

Additionally, with reference to FIG. 68, the first end cap component 1232 and the second end cap component 1234 can be sized and configured such that the side surface 1302b of the annular groove 1302 can overlap the side surface 1314b of the annular protrusion 1314 by an amount that is sufficient to prevent the first end cap component 1232 from inadvertently being pulled out of the second end cap component 1234. Additionally, the first end cap component 1232 and the second end cap component 1234 can be sized and configured such that, as described above, the first end cap component 1232 can be inserted into the second end cap component 1234 by axially aligning and pushing the first end cap component 1232 into the second end cap component 1234. Accordingly, if the side surface 1302b of the annular groove 1302 overlaps the side surface 1314b of the annular protrusion 1314 by too great of a distance, then it can be difficult in some configurations to couple the first end cap component 1232 with the second end cap component 1234 as described above.

To facilitate the insertion of the first end cap component 1232 into the second end cap component 1234, the first end cap component 1232 can be configured to have an angled or tapered annular surface 1304 and/or a rounded annular surface 1306 forward of the annular groove 1302, as shown most clearly in FIG. 74. Similarly, the second end cap component 1234 can be configured to have an angled or tapered annular surface 1316, to help align and essentially squeeze the first end cap component 1232 into the second end cap component 1234, as shown most clearly in FIG. 77.

Further, as shown in the illustrated embodiments, the one or more tabs 1298 and the plurality of tabs 1308 can comprise features and/or are configured to facilitate the insertion of the first end cap component 1232 into the second end cap component 1234. For example, in some embodiments, as illustrated most clearly in FIG. 74, each of the tabs 1298 can define angled or tapered front surfaces 1298a to help guide each of the tabs 1298 into the space between the tabs 1308 formed on the second end cap component 1234. Similarly, in some embodiments, as illustrated most clearly in FIGS. 75 and 77, the tabs 1308 on the second end cap component 1234 can define angled or tapered surfaces 1308a to help guide each of the tabs 1298 into the space between each of the tabs 1308. Additionally, in some embodiments, each of the tabs 1308 can define an angled or tapered forward edge 1308b to at least assist in axially aligning the first end cap component 1232 with the second end cap component 1234.

Any of the substantially rigid or semi-rigid components comprising the luer connecter 1200, including but not limited to the first end cap component 1232 and the second end cap component 1234, can comprise polycarbonate plastic, glass-filled polycarbonates, any other suitable water-impermeable materials, or any combinations thereof. The components comprising the luer connecter 1200 can also comprise a hydrophobic plastic. Other examples of materials suitable for construction of any of the substantially rigid or semi-rigid components comprising the luer connecter 1200 are glass-filled GE Valox 420 or polypropylene. Depending on the application, many other materials can also be used.

Figure 79A:
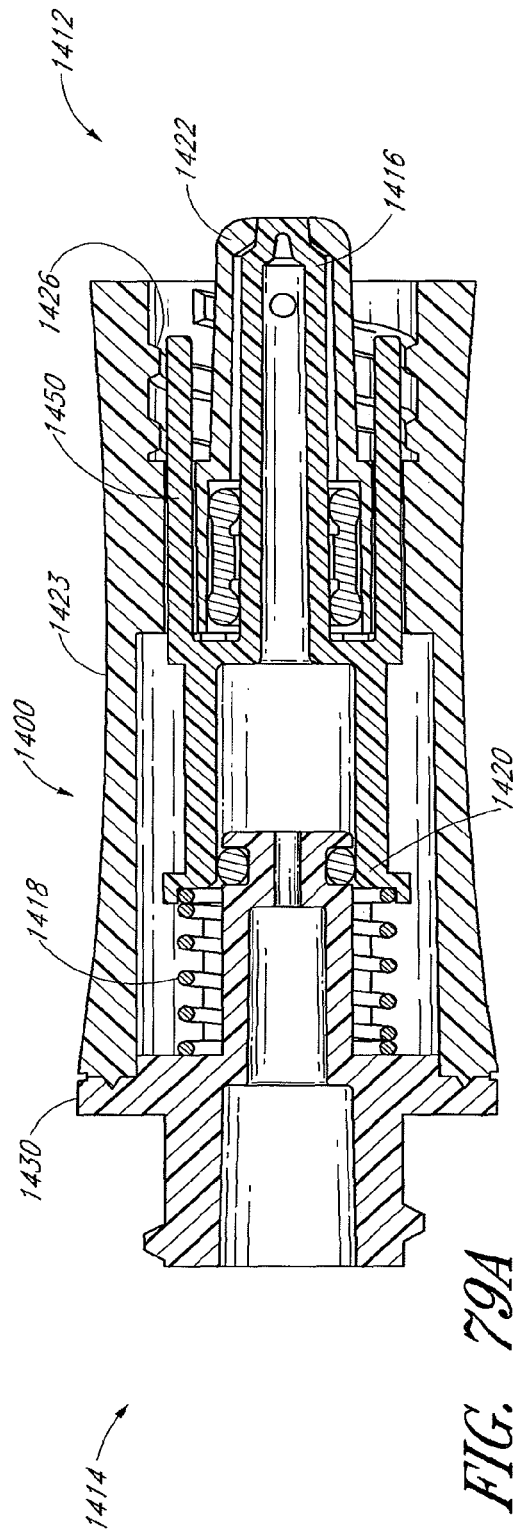
FIG. 79A is a cross-sectional view of another embodiment of a luer connector in a closed position.
Figure 79B:
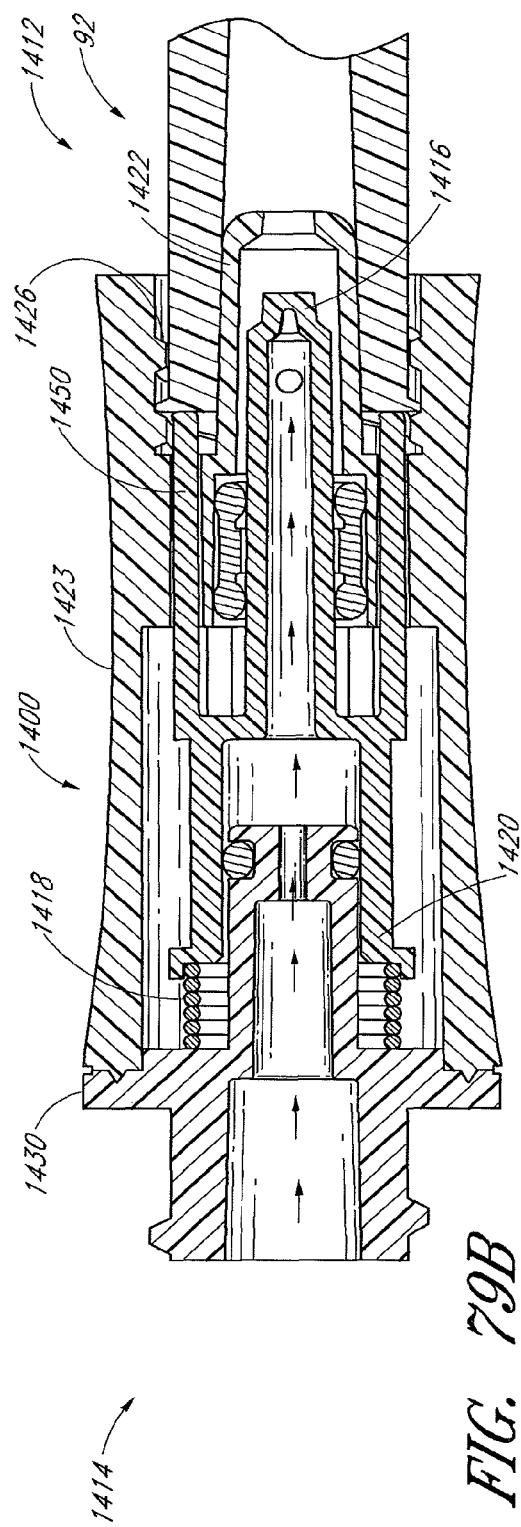
FIG. 79B is a cross-sectional view of the embodiment of the luer connector shown in FIG. 79A in an open position.

FIG. 79A is a cross-sectional view of another embodiment of a luer connector 1400 in a closed position. FIG. 79B is a cross-sectional view of the embodiment of the luer connector 1400 shown in FIG. 79A in an open position. In some embodiments, the luer connector 1400 can have any of the same features and configurations as the embodiments of the luer connector 1000 described above, and/or any of the features or configurations described herein. Additionally, the luer connector 1400 can comprise any of the features, components, or configurations of any of the other luer connectors described herein.

As with the luer connector 1000 described above, the valve member 1416 can include at least one strut 1450. In some embodiments, strut 1450 can extend from approximately the middle of the valve member 1416 toward the first end 1412. The connector 1400 can have two struts 1450, as illustrated, or the luer connector 1400 can have more or fewer as desired. The struts 1450 can be located around the luer tip 1422, but within the housing 1423, as shown. The struts 1450 can be located within the inner diameter of the inner threads 1426, and are therefore positioned to couple with at least a portion of a female luer receptacle as it engages with the luer tip 1422.

As shown in the embodiment illustrated in FIG. 79A, the resilient member 1418 can be a helical spring supported between the end cap 1430 and an aft portion of the chamber 1420. With reference to FIG. 79A, the aft portion of the chamber 1420 can define an annular protrusion, as illustrated, or can be otherwise configured to support an end portion of the resilient member 1418 in an axial and radial direction so that the end portion of the resilient member 1418 adjacent thereto remains substantially coaxially aligned with the valve member 1416. Additionally, although not illustrated, the end cap 1430 can also comprise an annular protrusion or depression, or otherwise be configured so as to provide a radial support to an end portion of the resilient member 1418, so that the resilient member 1418 remains substantially coaxially aligned with the end cap 1430.

With reference to FIGS. 79A and 79B, the resilient member 1418 can be configured to bias the valve member 1416 to the closed position, as illustrated in FIG. 79A. When the valve member 1416 is caused to be opened, the resilient member 1418 can be axially compressed between the end cap 1430 and the aft portion of the chamber 1420, as shown most clearly in FIG. 79B. The valve member 1416 can be caused to be opened when, for example, the female portion of a medical connector 92 or component is threadedly engaged with the luer connector 1400 so as to axially displace the one or more struts 1450 in the direction of the second end 1414 of the luer connector 1400. Therefore, in the embodiment of the luer connector 1400 illustrated in FIGS. 79A and 79B, the resilient member 1418 can provide the same or similar axial force to the resilient member 1018 described above with respect to the luer connector 1000.

Additionally, because the resilient member 1418 is substantially completely enclosed within the housing 1423 of the luer connector 1400, in some embodiments, the housing 1423 can be formed so as to define a continuous annular surface (i.e., formed without any slots or other openings on the exterior surface, except for openings that can be formed in either of the two axial ends). In some embodiments, the annular surface of the housing 1423 can be contoured to provide enhanced tactile feedback and control for the user. In some embodiments, the central portion of the housing 1423 can be formed with a smaller cross-sectional diameter than the first and second ends 1412, 1414.

FIG. 80A is a cross-sectional view of another embodiment of a luer connector 1400' in a closed position. FIG. 80B is a cross-sectional view of the embodiment of the luer connector 1400' shown in FIG. 80A in an open position.

With reference to FIG. 80B, the illustrated connector 1400' is threadedly engaged with a closeable female luer connector 210, which can be the same as the closeable female luer connector 210 illustrated in FIG. 10 and described above. In the embodiment illustrated in FIG. 80B, the closeable female luer connector 210 can comprise an outer housing 213, a void space 212, a fluid passageway 218, a fluid conduit 216 with one or more holes 215, a compressible seal element 214 with a proximal surface 217, and a threaded engagement region 211. The closeable female connector 210 can be positioned with its proximal end adjacent the first end 1412' of the male connector 1400'. The threaded engagement region 211 of the closeable female connector 210 can conform to standard sizing for luer connectors, such as those that meet ANSI standards. The compressible seal element 214 can be composed of water-impermeable, resilient material which can be moved into the housing 203 when a force is exerted upon it. The fluid conduit 216 can be composed of a rigid material, such as polycarbonate plastic, which is capable of resisting deformation when a force sufficient to compress the seal element 214 is exerted upon the closeable female connector 210.

The fluid passageway 218 can place the fluid conduit 216 in fluid communication with the second end 219 of the closeable female connector 210. At least one hole 215 in the fluid conduit 216 can be sealed by the compressible seal element 214 to prevent the fluid passageway 218 from being in fluid communication with the void space 212 between the compressible seal element 214 and the inner wall of the housing 213 and/or with the exterior of the housing 213. The hole or holes 215 can be appropriately sized to permit fluid to pass between the fluid passageway 218 and the void space 212 at an appropriate flow rate. One such size for the hole or holes 215 is approximately 1 mm in diameter, although irregular shapes and other sizes can be used. Holes of at least about 1 mm or approximately 1 mm-3 mm, or less than about 1 mm can also be used.

With reference to FIG. 80B, the threaded region 211 of the closeable female connector 210 can engage with the inner threads 1426' of the male connector 1400' to engage the connectors 1400', 210 as illustrated. In the illustrated engagement, the luer tip 1422' advances into the closeable female connector 210 by compressing the compressible seal element 214. As can be seen, the luer tip 1422' contacts the compressible seal element 214 on the proximal surface 217 of the compressible seal element 214. The force exerted to engage the connectors 1400', 210 and to engage the threaded regions 1426', 211 is sufficient to compress the seal element 214 to expose the holes 215 in the fluid conduit 216 and to open the valve member 1416', as will be described below. With the seal element 214 compressed, the fluid passageway 218 is in fluid communication with the interior space of the luer tip 1422'.

As the luer tip 1422' advances further into the closeable female connector 210, the fluid conduit 216 contacts the end of the valve member 1416' adjacent to the first end 1412' of the male connector 1400'. The valve member 1416' can be displaced toward the second end 1414' of the male connector 1400' by the contact and continued advancement of the luer tip 1422'. The resilient member 1418' exerts a closing force in a direction towards the first end 1412' of the male connector

1400' on the valve member 1416'. As a result, the tip of the valve member 1416' generally maintains contact with the fluid conduit 216 throughout the engagement. As the valve member 1416' is moved in a direction towards the second end 1414' of the male connector 1400', the flange section 1458' of the valve member 1416' can separate from the interior surface of the housing 1423' or luer tip 1422', thereby exposing or opening the hole 1436'. As a result, the openings 1454' are opened to fluid communication with the closeable female connector 210. The compressed seal element 214 can inhibit fluid flow into the interior of the closeable female connector 210 beyond the luer tip 1422'. In this configuration, fluid can flow from the second end 1414' of the luer connector 1400' toward the first end 1412' of the male connector 1400', through the openings 1454', out the hole 1436' in the luer tip 1422', into the interior of the outer housing 213 of the closeable female connector 210, in the holes 215 of the fluid conduit 216 and into the fluid channel 217 in the interior of the fluid conduit 216.

The connectors 1400', 210 can be threadedly disengaged. During disengagement, the force exerted by the resilient member 1418' can return the connector 1400' to its pre-engaged state by directing the valve member 1416' to engage the flange section 1458' of the end of the valve member 1416' toward the first end 1412' of the male connector 1400' with the internal surface of the luer tip 1422'. Likewise, the resilient material of which the compressible seal element 214 can be composed can cause the seal element 214 to return to its closed-position shape, and the proximal surface 217 can seal the proximal tip of the closeable female connector 210. Any of the components of the luer connector 1400 or 1400' described herein can be formed from any of the suitable materials disclosed herein, or any other materials suitable for such components.

Figure 81A:
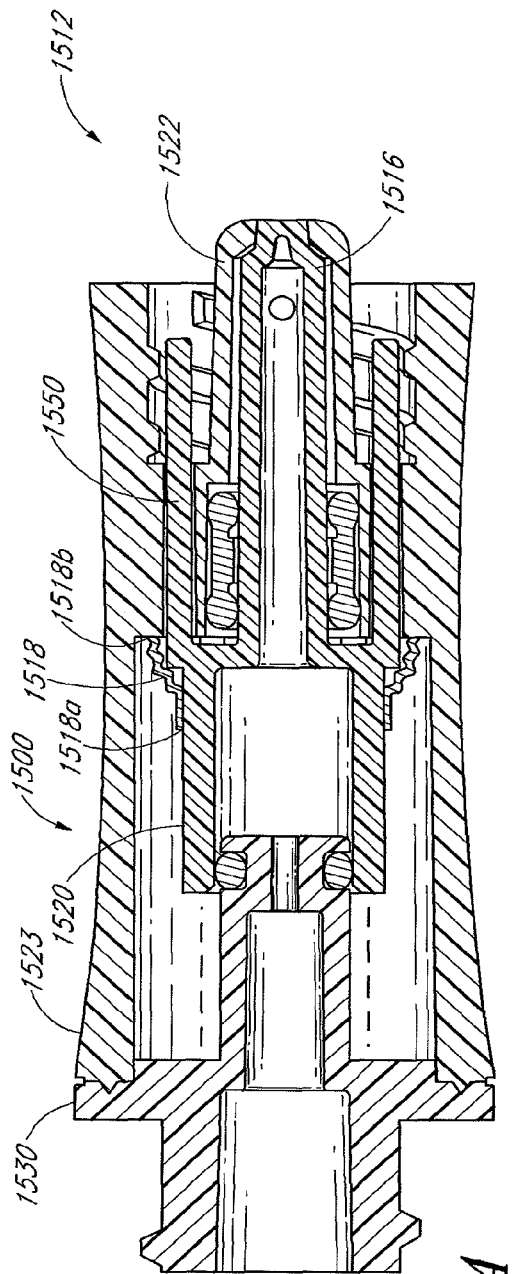
FIG. 81A is a cross-sectional view of another embodiment of a luer connector in a closed position.
Figure 81B:
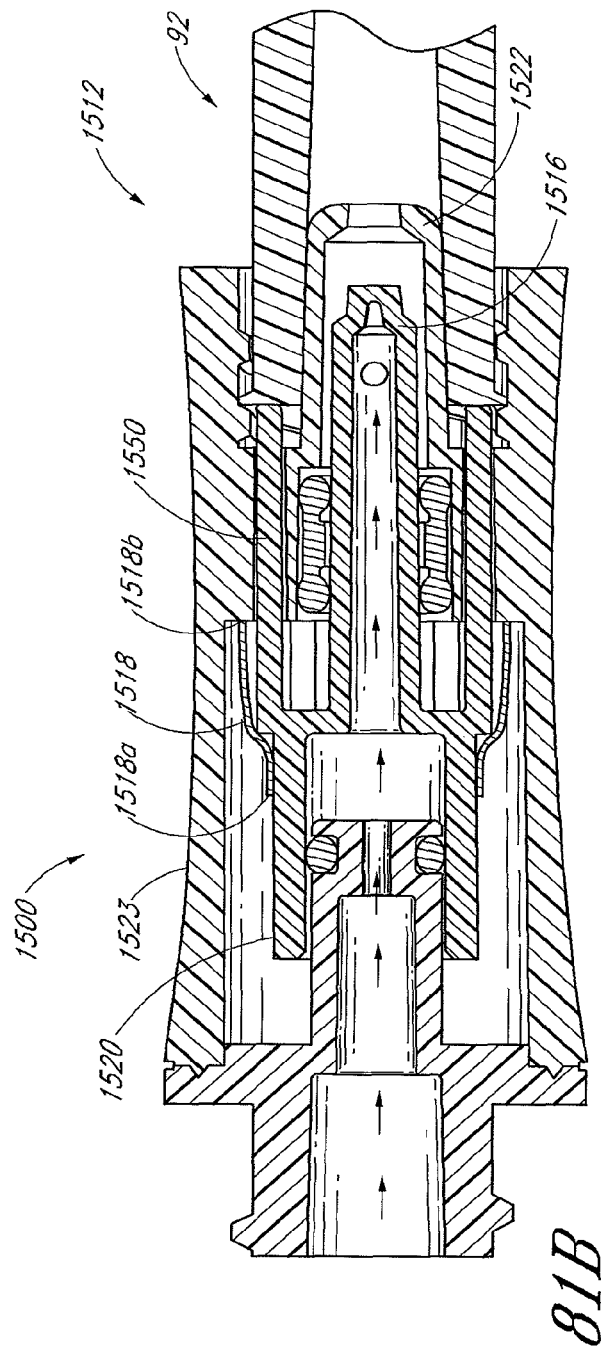
FIG. 81B is a cross-sectional view of the embodiment of the luer connector shown in FIG. 81A in an open position.

FIG. 81A is a cross-sectional view of another embodiment of a luer connector 1500 in a closed position. FIG. 81B is a cross-sectional view of the embodiment of the luer connector 1500 shown in FIG. 81A in an open position. In some embodiments, the luer connector 1500 can have any of the same features and configurations as the embodiments of the luer connector 1000 described above, and/or any of the features or configurations described herein. Additionally, the luer connector 1500 can comprise any of the features, components, or configurations of any of the other luer connectors described herein.

As with the luer connector 1000 described above, the valve member 1516 can include at least one strut 1550. In some embodiments, strut 1550 can extend from approximately the middle of the valve member 1516 toward the first end 1512. The connector 1500 can have two struts 1550, as illustrated, or the luer connector 1500 can have more or fewer as desired. The struts 1550 can be located around the luer tip 1522, but within the housing 1523, as shown. The struts 1550 can be located within the inner diameter of the inner threads 1526, and are therefore positioned to couple with at least a portion of a female luer receptacle as it engages with the luer tip 1522.

As shown in the embodiment illustrated in FIG. 81A, the resilient member 1518 can be an elastic, axially resilient material that is attached to and extends between an interior portion of the housing 1523 and an outside surface of the chamber 1520. In some embodiments, the resilient member 1518 can be conically shaped, the first end 1518*a* being attached to the outside surface of the chamber 1520 and a second end 1518*b* being attached to an inside surface of the housing 1523. In some embodiments, the resilient member 1518 can be formed of one or more generally rectangular shaped tabs that extend from an inside surface of the housing 1523 to the outside surface of the chamber 1520. In some embodiments, the resilient member 1518 can be attached to the valve member 1516 or the housing 1523 using adhesive, an annular ring that can constrict around the resilient member 1518 and the outside surface of the chamber 1520, or by any other suitable attachment means or mechanism.

With reference to FIGS. 81A and 81B, the resilient member 1518 can be configured to bias the valve member 1516 to the closed position, as illustrated in FIG. 81A. When the valve member 1516 is caused to be opened, the resilient member 1518 can be axially elongated, as shown most clearly in FIG. 81B. The valve member 1516 can be caused to be opened when, for example, the female portion of a medical connector 92 or component is threadedly engaged with the luer connector 1500 so as to axially displace the one or more struts 1550 in the direction of the second end 1514 of the luer connector 1500. Therefore, in the embodiment of the luer connector 1500 illustrated in FIGS. 81A and 81B, the resilient member 1518 provides the same or similar axial force to the valve member as compared to the resilient member 1018 described above in conjunction with the luer connector 1000.

Additionally, because the resilient member 1518 is substantially completely enclosed within the housing 1523 of the luer connector 1500, in some embodiments, the housing 1523 can be formed so as to define a continuous annular surface. In some embodiments, the annular surface is contoured to provide a recessed portion to be grasped by a user.

FIG. 82A is a cross-sectional view of another embodiment of a luer connector 1500' in a closed position. FIG. 82B is a cross-sectional view of the embodiment of the luer connector 1500' shown in FIG. 82A in an open position.

With reference to FIG. 82B, the illustrated connector 1500' is threadedly engaged with a closeable female luer connector 210, which can be the same as the closable female luer connector 210 illustrated in FIG. 10 and described above. The closeable female connector 210 can be positioned with its proximal end adjacent the first end 1512' of the male connector 1500'. The threaded region 211 of the closeable female connector 210 can engage with the inner threads 1526' of the male connector 1500' to engage the connectors 1500', 210 as illustrated. In the illustrated engagement, the luer tip 1522' can advance into the closeable female connector 210 by compressing the compressible seal element 215. As can be seen, the luer tip 1522' contacts the compressible seal element 215 on the proximal surface 217 of the compressible seal element 215. The force exerted to engage the connectors 1500', 210 and to engage the threaded regions 1526', 211 is sufficient to compress the seal element 215 to expose the holes 215 in the fluid conduit 216 and to open the valve member 1516', as will be described below. With the seal element 215 compressed, the fluid passageway 218 can be in fluid communication with the interior space of the luer tip 1522'.

As the luer tip 1522' advances further into the closeable female connector 210, the fluid conduit 216 contacts the end of the valve member 1516' adjacent to the first end 1512' of the male connector 1500'. The valve member 1516' can be displaced toward the second end 1514' of the male connector 1500' by the contact and continued advancement of the luer tip 1522'. The resilient member 1518' exerts a closing force in a direction towards the first end 1512' of the male connector 1500' on the valve member 1516'. As a result, the tip of the valve member 1516' towards the first end 1512' of the male connector 1500' generally maintains contact with the fluid conduit 216 throughout the engagement. As the valve member 1516' is moved in a direction towards the second end 1514' of the male connector 1500', the flange section 1558' of the valve member 1516' can separate from the interior surface of the housing 1523' or luer tip 1522', thereby exposing or opening the hole 1536'. As a result, the openings 1554' are opened to fluid communication with the closeable female connector 210. The compressed seal element 215 inhibits fluid flow into the interior of the closeable female connector 210 beyond the luer tip 1522'. In this configuration, fluid can flow from the second end 1514' of the luer connector 1500' toward the first end 1512' of the male connector 1500', through the openings 1554', out the hole 1536' in the luer tip 1522', into the interior of the outer housing 213 of the closeable female connector 210, in the holes 215 of the fluid conduit 216 and into the fluid channel 217 in the interior of the fluid conduit 216.

The connectors 1500', 210 can be threadedly disengaged. During disengagement, the force exerted by the resilient member 1518' can return the connector 1500' to its pre-engaged state by directing the valve member 1516' to engage the flange section 1558' of the end of the valve member 1516' with the internal surface of the luer tip 1522'. Likewise, the resilient material of which the compressible seal element 214 can be composed can cause the seal element 214 to return to its closed-position shape, and the proximal surface 217 can seal the proximal tip of the closeable female connector 210. Any of the components of the luer connector 1500 or 1500' described herein can be formed from any of the suitable materials disclosed herein, or any other materials suitable for such components.

FIG. 83A is a cross-sectional view of another embodiment of a luer connector 1600 in a closed position. FIG. 83B is a cross-sectional view of the embodiment of the luer connector 1600 shown in FIG. 83A in an open position. In some embodiments, the luer connector 1600 can have any of the same features and configurations as the embodiments of the luer connector 1000 described above, and/or any of the features or configurations described below. Additionally, the luer connector 1600 can comprise any of the features, components, or configurations of any of the other luer connectors described herein.

As with the luer connector 1000 described above, the valve member 1616 can include at least one strut 1650. In some embodiments, strut 1650 can extend from the middle portion of the valve member 1616 toward the first end 1612 of the luer connector 1600. The connector 1600 can have two struts 1650, as illustrated, or the luer connector 1600 can have more or fewer as desired. The struts 1650 can be located around the luer tip 1622, but within the housing 1623, as shown. The struts 1650 can be located within the inner diameter of the inner threads 1626, and are therefore positioned to couple with at least a portion of a female luer receptacle as it engages with the luer tip 1622.

As shown in the embodiment illustrated in FIG. 83A, the resilient member 1618 can be an elastic, axially resilient material having a first end portion 1618*a* that is attached to the valve member 1616, and a second end portion 1618*b* that is secured to the outside of the housing 1623. In this configuration, because the first portion 1618*a* of the resilient member 1618 is located inside the housing and the second portion 1618*b* is located outside the housing, the housing 1623 can define slots through which the resilient member can pass. In some embodiments, the resilient member 1618 can be completely contained within the housing 1623, with a first end portion being secured to the valve member 1616 and a second end portion being secured to the interior surface of the housing 1623.

In some embodiments, the resilient member 1618 can comprise one or more bands with annular rings at either end, similar to resilient member 18 described above. In some embodiments, the resilient member 1618 can comprise merely one or more generally rectangular shaped bands, having a first end portion that is attached to the valve member 1616 and a second end portion that is attached to the inside or outside of the housing 1623. In some embodiments, the resilient member 1618 can be attached to the valve member 1616 or the housing 1623 using adhesive, an annular ring that constricts around the resilient member 1618 and the valve member 1616, or by any other suitable attachment means or mechanism. Additionally, the valve member 1616 can define depressions, protrusions, or other features configured to axially secure a portion of the resilient member 1618 to the valve member 1616.

With reference to FIGS. 83A and 83B, the resilient member 1618 can be configured to bias the valve member 1616 to the closed position, as illustrated in FIG. 83A. When the valve member 1616 is caused to be opened, the resilient member 1618 can be axially elongated, as shown most clearly in FIG. 83B. The valve member 1616 can be caused to be opened when, for example, the female portion of a medical connector or component is threadedly engaged with the luer connector 1600 so as to axially displace the one or more struts 1650 in the direction of the second end 1614 of the luer connector 1600. Therefore, in the embodiment of the luer connector 1600 illustrated in FIGS. 83A and 83B, the resilient member 1618 provides the same or similar axial force to the valve member as compared to the resilient member 1018 described above in conjunction with the luer connector 1000.

In addition to the seal created by the end portion of the valve member 1616 adjacent to the first end 1612 of the luer connector 1600, an additional generally fluid-tight seal can also be created by an additional generally planar seal 1626, which can be supported within a cylindrical end portion 1630*a* of the end cap 1630 as illustrated in FIG. 83A. In some embodiments, the seal 1626 can be planar and disk shaped, defining a slit 1628 through the cross-section thereof, as illustrated in FIGS. 83A and 83B. In the illustrated embodiment, the slit 1628 in the seal 1626 can be opened so as to allow fluid flow through the seal 1626 when the valve member is passed through the seal 1626 and, hence, moved to the open position, as illustrated in FIG. 83B. The seal 1626 can be formed from silicone rubber or any other suitable material that can be pliable and resilient so as to be self-restoring when the valve member 1616 is no longer in contact with the seal 1626. The redundancy of having the additional seal 1626 (i.e., in addition to seal created between the valve member 1616 and the male luer tip 1622) may provide the benefit of further decreasing the risk any fluid leakage when the luer connector 1600 is in the closed position Additionally, with reference to FIGS. 83A and 83B, the luer connector 1600 can comprise a seal 1632 that can be configured to provide a seal between an outside surface of the chamber 1620 and the end cap 1630. The preferably annular seal 1632 can be configured to be sealingly attached to the interior end portion 1630*a* of the end cap 1630 and to the outside surface of the chamber 1620, so as to generally prevent any fluid leakage into the interior space of the housing 1623. In other words, the seal 1632 can be configured to generally direct the fluid or medicament passing through the end cap 1630 into the inner passage 1634 of the valve member 1616, so as to prevent leakage into the interior space of the housing 1623.

Additionally, the seal 1632 can be configured so that the volume of space V1 defined within the seal 1632 when the valve member 1616 is in the closed position (with reference to FIG. 83A) is greater than the volume of space V2 defined within the seal 1632 when the valve member 1616 is in the open position (with reference to FIG. 83B). In this configuration, as the valve member 1616 is moved toward the closed position, the volume of space within the seal 1632 can be increased from V1 to V2 so as to create a suction or negative pressure effect that can draw fluid from the inner passage 1634 into the volume of space (V) defined by the seal 1632. Accordingly, similar to other embodiments described herein, this configuration of the luer connector 1600 can eliminate or reduce the amount of the potentially harmful medicament that may otherwise leak from the luer connector 1600 as the valve member 1616 is being closed.

FIG. 84A is a cross-sectional view of another embodiment of a luer connector 1600' in a closed position. FIG. 84B is a cross-sectional view of the embodiment of the luer connector 1600' shown in FIG. 84A in an open position.

With reference to FIG. 84B, the illustrated connector 1600' is threadedly engaged with a closeable female luer connector 210, which can be the same as the closable female luer connector 210 illustrated in FIG. 10 and described above. The closeable female connector 210 can be positioned with its proximal end adjacent the first end 1612' of the male connector 1600'. The threaded region 211 of the closeable female connector 210 can engage with the inner threads 1626' of the male connector 1600' to engage the connectors 1600', 210 as illustrated. In the illustrated engagement, the luer tip 1622' can advance into the closeable female connector 210 by compressing the compressible seal element 215. As can be seen, the luer tip 1622' contacts the compressible seal element 215 on the proximal surface 217 of the compressible seal element 215. The force exerted to engage the connectors 1600', 210 and to engage the threaded regions 1626', 211 is sufficient to compress the seal element 215 to expose the holes 215 in the fluid conduit 216 and to open the valve member 1616', as will be described below. With the seal element 215 compressed, the fluid passageway 218 is in fluid communication with the interior space of the luer tip 22.

As the luer tip 1622' advances further into the closeable female connector 210, the fluid conduit 216 contacts the end of the valve member 1616' adjacent to the first end 1612' of the male connector 1600'. The valve member 1616' can be displaced toward the second end 1614' of the male connector 1600' by the contact and continued advancement of the luer tip 1622'. The resilient member 1618' can exert a closing force in a direction towards the first end 1612' of the male connector 1600' on the valve member 1616'. As a result, the tip of the valve member 1616' towards the first end 1612' of the male connector 1600' generally maintains contact with the fluid conduit 216 throughout the engagement. As the valve member 1616' is moved in a direction towards the second end 1614' of the male connector 1600', the flange section 1658' of the valve member 1616' can separate from the interior surface of the luer tip 1622'. As a result, the openings 1654' are opened to fluid communication with the closeable female connector 210. The compressed seal element 215 inhibits fluid flow into the interior of the closeable female connector 210 beyond the luer tip 1622'. In this configuration, fluid can flow from the second end 1614' of the luer connector 1600' toward the first end 1612' of the male connector 1600', through the openings 1654', out the hole 1630' in the luer tip 1622', into the interior of the outer housing 213 of the closeable female connector 210, in the holes 215 of the fluid conduit 216 and into the fluid channel 217 in the interior of the fluid conduit 216.

The connectors 1600', 210 can be threadedly disengaged. During disengagement, the force exerted by the resilient member 1618' can return the connector 1400' to its pre-engaged state by directing the valve member 1616' to engage the flange section 1658' of the end of the valve member 1616' toward the first end 1612' of the male connector 1600' with the internal surface of the luer tip 1622'. Likewise, the resilient material of which the compressible seal element 214 can be composed can cause the seal element 214 to return to its closed-position shape, and the proximal surface 217 can seal the proximal tip of the closeable female connector 210. Any of the components of the luer connector 1600 or 1600' described herein can be formed from any of the suitable materials disclosed herein, or any other materials suitable for such components.

Figure 85A:
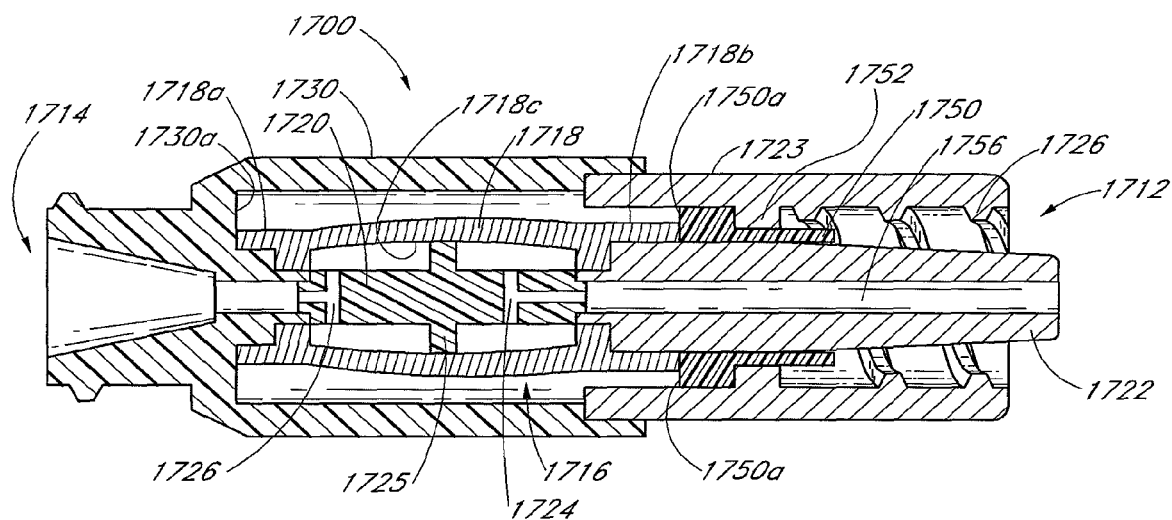
FIG. 85A is a cross-sectional view of another embodiment of a luer connector in a closed position.
Figure 85B:
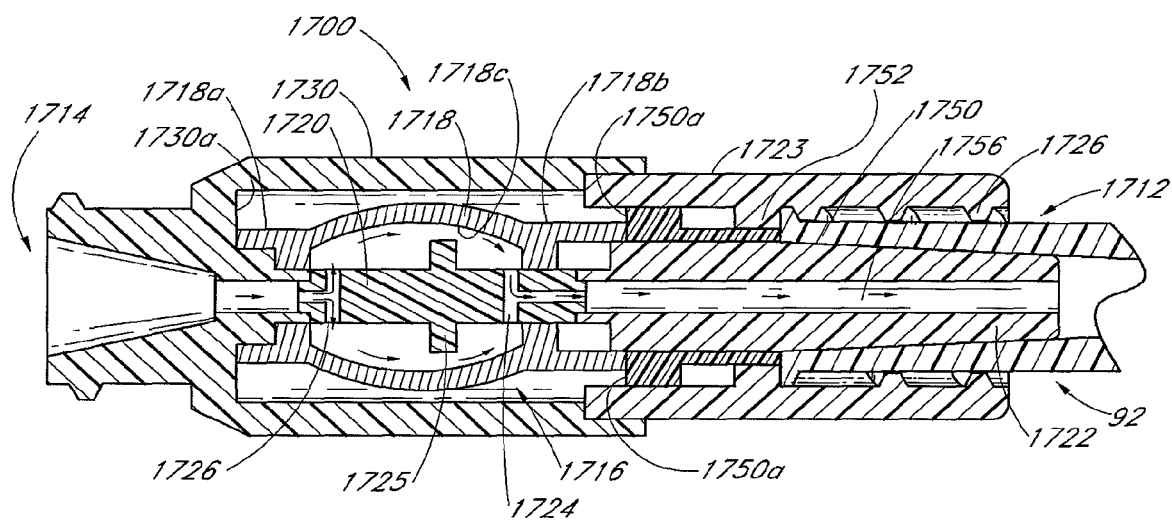
FIG. 85B is a cross-sectional view of the embodiment of the luer connector shown in FIG. 85A in an open position.

FIG. 85A is a cross-sectional view of another embodiment of a luer connector 1700 in a closed position. FIG. 85B is a cross-sectional view of the embodiment of the luer connector 1700 shown in FIG. 85A in an open position. In some embodiments, the luer connector 1700 can have any of the same features and configurations as the embodiments of the luer connector 1000 described above, and/or any of the features or configurations described below. Additionally, the luer connector 1700 can comprise any of the features, components, or configurations of any of the other luer connectors described herein.

As with the luer connector 1000 described above, the valve member 1716 can include at least one strut 1750. In some embodiments, strut 1750 can extend from approximately the middle of the valve member 1716 toward the first end 1712. The connector 1700 can have two struts 1750, as illustrated, or the luer connector 1700 can have more as desired. The struts 1750 can be located around the luer tip 1722, but within the housing 1723, as shown. The struts 1750 can be located within the inner diameter of the inner threads 1726, and are therefore positioned to couple with at least a portion of a female luer receptacle as it engages with the luer tip 1722.

As illustrated in FIG. 85A, the valve member 1716 of the luer connector 1700 can also comprise a first member 1718 (also referred to herein as a resilient member) and a second member 1720. In some embodiments, the first member 1718 can generally be tubular in shape and formed from a flexible, substantially fluid impermeable, resilient material. In the illustrated embodiment, the first member 1718 can be resilient in both the axial and radial directions. The first member 1718 can define an axial opening therethrough that, when the valve member 1716 is in the open position, permits fluid to flow through said first member 1718. In the illustrated embodiment, the first member 1718 can be concentrically positioned around the second member 1720 so as to substantially completely surround the second member 1720. The first member 1718 can be configured and positioned so that a first end portion 1718a of the first member 1718 abuts against an inside end surface 1730a of the end cap 1730. Similarly, the first member 1718 can be configured and positioned so that a second end portion 1718b of the first member 1718 abuts against the end surface 1750a of the one or more valve struts 1750 on the opposing end of the first member 1718. Additionally, in the closed position, the inside surface 1718c of the first member 1718 can abut against at least a portion of the second member 1720 so that the first member 1718 creates a substantially fluid-tight seal with the second member 1720 when the valve member 1716 is in the closed position (as shown in FIG. 85A).

The second member 1720 can be substantially rigid and, as shown in FIGS. 85A and 85B, can include one or more annular protrusions 1725 around the perimeter of a portion of the second member 1720, although only one annular protrusion 1725 is shown. In the illustrated embodiment, the annular protrusion 1725 can be configured to match the geometry of the inside of the first member 1718 so as to provide a generally fluid-tight seal against the inside surface 1718c of the first member 1718 when the valve member 1716 is in the closed position. Additionally, the second member 1720 can have a first opening 1724 that is formed in the first end portion of the second member 1720*a* (i.e., the axial end portion of the second member 1720 that is closer to the first end 1712 of the luer connector 1700). Similarly, the second member 1720 can have a second opening 1726 that is formed in the second end portion of the second member 1720*a* (i.e., the axial end portion of the second member 1720 that is closer to the second end 1714 of the luer connector 1700).

With reference to FIG. 85A, the first member 1718 can be configured to bias the valve struts 1750 toward the first end 1712 of the luer connector 1700 so that the valve struts 1750 abut against the inner wall 1752. Additionally, with reference to FIG. 85A, the first member 1718 can be configured so as to be biased to the closed position (i.e., so that the inside surface 1718*c* of the first member 1720 abuts against the annular protrusion 1725 to a sufficient degree to generally close the fluid passageway between the second end 1714 and the first end 1712 of the luer connector 1700). The amount of pressure exerted from the first member 1718 against the annular protrusion 1725 can be increased by increasing the size of the perimeter of the annular protrusion 1725 relative to the perimeter of the inside surface 1718*c* of the first member 1718, thereby increasing the sealing force between the first member 1718 and the second member 1720 while the valve member 1716 is in the closed position. Additionally, the level of the seal can be increased by, for example, increasing the thickness or resilience of the material used to form the first member 1718 or by altering its configuration.

The valve member 1717 can be caused to be opened when, for example, the female portion of a medical connector 92 (as shown in FIG. 85B) or a component is threadedly engaged with the luer connector 1700 so as to axially displace the one or more struts 1750 in the direction of the second end 1714 of the luer connector 1700. The luer connector 1700 can be configured such that, when the one or more struts 1750 are displaced toward the second end 1714 of the luer connector 1700, the struts 1750 exert an axial force on the second end portion 1718*b* of the first member 1718 that can cause the first member 1718 to decrease in length and buckle or bulge outwardly at the middle portion thereof. When the middle portion of the first member 1718 bulges outwardly, the inside surface 1718*c* can be stretched and displaced radially outward away from annular protrusion 1725. When the inside surface 1718*c* of the first member 1718 is no longer in contact with the annular protrusion 1725, the valve member is in an open position, as illustrated in FIG. 85B.

With reference to FIG. 85B, when the valve member 1716 is in the open position, a fluid or medicament flowing into the second end 1714 of the luer connector 1700 can flow through the second opening 1726, into the space between the first member 1718 and the second member 1720, around the protrusion 1725, through the first opening 1724, through the passageway 1756 and out through the end of the luer tip 1722.

Conversely, as the medical connector 92 is unthreaded or removed from the luer connector 1700, the axial bias from the first member 1718 can cause the first member 1718 to elongate to its pre-bulge arrangement, causing the struts 1750 to move toward the first end 1712 and, in some embodiments, to abut against the inner wall 1752. Similarly, as the medical connector 92 is unthreaded or removed from the luer connector 1700, the inward radial bias from the first member 1718 can cause the first member 1718 to constrict and form a seal around the annular protrusion 1725, generally preventing any further fluid from flowing through the valve member 1716.

In some embodiments, the second member 1720 can be formed separately as compared to the luer tip 1722. However, in some embodiments, the second member 1720 can be formed integrally with the luer tip 1722. Additionally, because the first member 1718 can generally be completely enclosed within the housing 1723 of the luer connector 1700, in some embodiments, the housing 1723 can be formed so as to define a continuous annular surface. Any of the components of the luer connector 1700 described herein can be formed from any of the suitable materials disclosed herein, or any other materials suitable for such components.

FIG. 86A is a cross-sectional view of another embodiment of a luer connector 1800 in a closed position. FIG. 86B is a cross-sectional view of the embodiment of the luer connector 1800 shown in FIG. 86A in an open position. In some embodiments, the luer connector 1800 can have any of the same features and configurations as the embodiments of the luer connector 1000 described above, and/or any of the features, components, or configurations of any of the other luer connectors described herein.

As illustrated in FIG. 86A, the valve member 1816 can include at least one lever arm 1850. In particular, the luer connector 1800 illustrated in FIG. 86A comprises two opposing lever arms 1850, although the luer connector 1800 can comprise any suitable any number of lever arms 1850. As illustrated therein, each lever arm 1850 can be pivotally mounted about a shaft 1852 that can be supported in a fixed position relative to the housing 1823, but that can rotate relative to the housing 1823 so as to allow the lever arm 1850 to rotate relative to the housing 1823. In some embodiments, as in the illustrated embodiments, the lever arms 1850 can extend outside of the housing 1823 through slots 1824 that can be formed in the housing 1823.

Each lever arm 1850 can be supported by the housing 1823 so that the first end portion 1850*a* of the lever arm 1850 can abut the chamber 1854, while the second end portion 1850*b* can be positioned adjacent to the luer tip 1822. In particular, in the illustrated embodiment, the lever arm 1850 can be supported by the housing 1823 so that a bottom surface 1850*c* of the first end portion 1850*a* can abut the outside surface 1854*a* of the chamber 1854. Similarly, in the illustrated embodiment, the lever arm 1850 can be supported by the housing 1823 so that a bottom surface 1850*d* of the second end portion 1850*b* of each lever arm 1850 can be positioned generally within the housing 1823 been around the luer tip 1822, as shown. The bottom surface 1850*d* of the second end portion 1850*b* of each lever arm 1850 can be located within the inner diameter of the inner threads 1826.

In this configuration, with reference to FIG. 86B, as the female portion of a medical connector 92 is threadedly engaged with the threads 1826 of the luer connector 1800 and advanced toward the second end 1814 of the luer connector 1800, as indicated by the arrows A1 in FIG. 86B, the distal tip 92*a* of the medical connector 92 can contact the bottom surface 1850*d* of the second end portion 1850*b* of each lever arm 1850. As the medical connector 92 is advanced further toward the second end 1814, the distal end to 92*a* of the medical connector 92 can force the second end portion 1850*b* of each lever arm 1850 in a radially outward direction, as indicated by the arrows A2 in FIG. 86B. Because each lever arm 1850 can rotate about the shaft 1852, as the second end portion 1850*b* of each lever arm 1850 is forced radially outward, the first end portion 1850*a* of each lever arm 1850 can rotate and move radially inward, as indicated by arrows A3 shown in FIG. 86B.

Forcing the first end portion 1850*a* of each lever arm 1850 inwardly can cause the bottom surface 1850*c* to exert a radially inward force against the outside surface 1854*a* of the chamber 1854, in the direction of the arrows A3 shown in FIG. 86B. The lever arms 1850 and the chamber 1854 can be configured such that the reaction force from the first end portion 1850a on the chamber 1854 as the first end portion 1850a is constricted inwardly against the chamber 1854 causes the chamber 1854 and, consequently, the valve member 1816 to move axially toward the second end 1814 of the luer connector 1800. As the valve member 1816 moves axially toward the second end 1814 of the luer connector 1800, the valve member is caused to be opened such that fluid or medicaments can flow through the valve member 1816 and out through the opening 1856 in the distal end of the luer tip 1822, as shown in FIG. 86B.

A resilient member 1818, which can be formed from a helical spring, can be positioned between the end cap 1830 and the chamber 1854, as illustrated in FIGS. 86A and 86B. The aft portion of the chamber 1854 can define an annular protrusion or can be otherwise configured to support an end portion of the resilient member 1818 in an axial and radial direction so that the end portion of the resilient member 1818 adjacent thereto remains substantially coaxially aligned with the valve member 1816. Additionally, the end cap 1830 can also comprise an annular protrusion or depression, or otherwise be configured so as to provide a radial support to an end portion of the resilient member 1818, so that the resilient member 1818 remains substantially coaxially aligned with the end cap 1813.

With reference to FIGS. 86A and 86B, the resilient member 1818 can be configured to bias the valve member 1816 to the closed position, as illustrated in FIG. 86A. When the valve member 1816 is caused to be opened, the resilient member 1818 can be axially compressed between the end cap 1830 and the aft portion of the chamber 1854, as shown most clearly in FIG. 86B. The resilient member 1818 can bias the chamber 1854 and the valve member 1816 toward the first end 1812 of the luer connector 1800, so as to bias the valve member 1816 toward the closed position. In this configuration, as the medical connector 92 is removed from the luer connector 1800, the resilient member 1818 can bias the valve member 1816 toward the closed position and also can bias the lever arms 1850 to rotate about the shaft 1852 so that the first end portion 1850a rotates radially outward.

A seal 1868 between the inner surface of the chamber 1854 and a portion of the end cap 1830 can prevent fluid from leaking through the space between the inner surface of the chamber 1854 and a portion of the end cap 1830. The chamber 1854 can be formed integrally with the valve member 1816, or can be formed separately and adhered, fused, or otherwise attached to the valve member 1816. Any of the components of the luer connector 1800 described herein can be formed from any of the suitable materials disclosed herein, or any other materials suitable for such components.

Some medications, including those used during chemotherapy, can be harmful to a patient in certain applications. For example, exposure to the skin can sometimes result in a chemical burn. Inhalation of aerosolized forms of some medications also can be harmful. Thus, control over the containment of the medication is highly desirable.

Some potentially harmful medications are distributed in sealed vials. The medication is removed from the vial by inserting a needle or a vial adaptor, and drawing the medication into a syringe. If a needle is used, it is withdrawn from the vial and the medication can be dispensed. However, the needle may be withdrawn with a residue of medication disposed on the outside of the needle or the vial adaptor may include a residue of medication on one or more exposed surfaces. This medication can inadvertently come in contact with the skin and cause harm. Or, if an injector is used to penetrate the vial with a withdrawal mechanism, the medication can be drawn through the mechanism and passed directly to a syringe for injection without the additional step of withdrawing the mechanism from the vial. However, even if such an injector is used, there is still the possibility of latent medication remaining on the needle used to inject the medication, on the mechanism after the vial is decoupled, or on the mechanism after the syringe is decoupled.

Any features of the embodiments shown and/or described in the Figures that have not been expressly described in this text, such as distances, proportions of components, etc. are also intended to form part of this disclosure. Additionally, although these inventions have been disclosed in the context of various embodiments, features, aspects, and examples, it will be understood by those skilled in the art that the present inventions extend beyond the specifically disclosed embodiments to other alternative embodiments and/or uses of the inventions and obvious modifications and equivalents thereof. Accordingly, it should be understood that various features and aspects of the disclosed embodiments can be combined with, or substituted for, one another in order to perform varying modes of the disclosed inventions. Moreover, any component or combination of components disclosed herein can be used in other structures of configurations of medical connectors. Thus, it is intended that the scope of the present inventions herein disclosed should not be limited by the particular disclosed embodiments described above.

As used throughout this specification, the terms "first end" and "second end" are labels of convenience that apply to a female side or a male side of a valve, or both. The labels are used interchangeably herein. By way of example, each of the structures of the embodiments disclosed herein for preventing or inhibiting disconnection of two medical connectors can be employed on either the male or female sides (or both). Any particular use of "first" or "second" with "female" or "male" should not be restricted to such end.

The following is claimed:

1. A medical fluid connector configured to inhibit disconnection, comprising:
   a proximal region comprising an end cap portion and a distally extending plunger, an inside surface of the distally extending plunger configured to be in contact with medical fluid passing through the connector when in use;
   an intermediate portion comprising a proximally extending wall, an inside surface of the proximally extending wall configured to be in contact with medical fluid passing through the connector;
   an o-ring contacting both a portion of the distally extending plunger and a portion of the proximally extending wall in a region where the distally extending plunger and the proximally extending wall overlap; and
   wherein the medical fluid connector comprises a first stage in which the plunger and the intermediate portion are not capable of rotating with respect to each other, and the medical fluid connector comprises a second stage in which the plunger and the intermediate portion are capable of rotating with respect to each other, the transition from the first stage to the second stage being configured to be actuated by advancement of a medical implement at the proximal region of the medical fluid connector; and
   wherein rotation between the plunger and the intermediate portion is configured to inhibit disconnection of the medical fluid connector from the medical implement.

2. A fluid transfer system comprising the medical fluid connector of claim 1 in combination with the medical implement.

3. The medical fluid connector of claim 1, wherein the o-ring is circular.

4. The medical fluid connector of claim 3, wherein the o-ring is resilient.

5. The medical fluid connector of claim 4, wherein the o-ring inhibits fluid leakage while permitting rotational movement.

6. The medical fluid connector of claim 1, wherein the end cap portion is located at the proximal end of the medical fluid connector.

7. The medical fluid connector of claim 6, wherein the end cap portion is generally flush with the proximal end of the medical fluid connector.

8. The medical fluid connector of claim 1, wherein a resilient seal is located between the proximal region and a distal end of the fluid connector.

9. The medical connector of claim 1, further comprising at least one actuation arm configured to be actuated by contact between the medical connector and a medical implement.

10. The medical connector of claim 9, further comprising two actuation arms.

11. The medical connector of claim 9, wherein the at least one actuation arm is configured to open the male luer portion.

12. The medical connector of claim 1, wherein the transition from the first stage to the second stage is irreversible in normal use.

13. The medical connector of claim 12, wherein the medical connector is configured to be permanently attached to the medical implement in normal use after the medical connector transitions from the first stage to the second stage.

14. The medical connector of claim 1, further comprising a distal region comprising a distally extending male luer portion configured to be in fluid communication with the proximal region.

15. The medical connector of claim 14, wherein the distally extending male luer portion comprises a first sealed stage and a second open stage.

16. The medical connector of claim 15, wherein the distally extending male luer portion is configured to transition between the first stage and the second stage upon contact or connection of the distal region of the medical connector with a medical implement.

17. The medical connector of claim 16, wherein the distally extending male luer portion in the first stage comprises an interior plug.

18. The medical connector of claim 17, wherein the interior plug in the first stage is generally flush with a distal end of the distally extending male luer portion.

19. The medical connector of claim 18, wherein the interior plug in the second stage is advanced in the proximal direction from the distal end of the distally extending male luer portion.

* * * * *